United States Patent [19]

Frank et al.

[11] Patent Number: 5,840,695

[45] Date of Patent: *Nov. 24, 1998

[54] ECTOPARASITE SALIVA PROTEINS AND APPARATUS TO COLLECT SUCH PROTEINS

[75] Inventors: Glenn R. Frank, Wellington; Shirley Wu Hunter, Ft. Collins, both of Colo.; Lynda Wallenfels, St. George, Utah

[73] Assignee: Heska Corporation, Ft. Collins, Colo.

[ * ] Notice: The term of this patent shall not extend beyond the expiration date of Pat. No. 5,646,115.

[21] Appl. No.: 630,822

[22] Filed: Apr. 10, 1996

Related U.S. Application Data

[63] Continuation-in-part of PCT/US95/13200 Oct. 6, 1995 which is a continuation-in-part of Ser. No. 487,001, Jun. 7, 1995, Pat. No. 5,795,862, which is a continuation-in-part of Ser. No. 487,608, Jun. 7, 1995, which is a continuation-in-part of Ser. No. 319,590, Oct. 7, 1994, Pat. No. 5,646,115.

[51] Int. Cl.$^6$ .......................... A61K 38/00; A01N 37/18; C07H 21/02

[52] U.S. Cl. ................. 514/12; 514/2; 536/23.1

[58] Field of Search ........................ 514/2, 12; 536/23.1; 435/252.3, 320.1

[56] References Cited

U.S. PATENT DOCUMENTS 5,356,622  10/1994  Heath et al. ......................... 424/265.1

FOREIGN PATENT DOCUMENTS

WO 93/18788  9/1993  WIPO.

OTHER PUBLICATIONS

Baker et al., 1975, *J. Small Anim. Pract.*, 16 (5):317–327.
Greene et al., 1993, *Vet. Immunol. & Immunopathol.*, 37 (1):15–23.
Halliwell, et al., 1985, *Vet. Immunol & Immunopath*, 8 (3):215–23.
Kunkle et al., 1985, *J. Amer. Vet. Medical Assn.*, 186 (7):677–80.
McKeon et al., 1994, *Int. J. Parasitol.*, 24(2):259–63.

*Primary Examiner*—Robert A. Wax
*Assistant Examiner*—Einar Stole
*Attorney, Agent, or Firm*—Sheridan Ross P.C.

[57] ABSTRACT

The present invention is directed to a novel product and method for isolating ectoparasite saliva proteins, and a novel product and method for detecting and/or treating allergic dermatitis in an animal. The present invention includes a saliva protein collection apparatus capable of collecting ectoparasite saliva proteins substantially free of contaminating material. The present invention also relates to ectoparasite saliva proteins, nucleic acid molecules having sequences that encode such proteins, and antibodies raised against such proteins. The present invention also includes methods to obtain such proteins and to use such proteins to identify animals susceptible to or having allergic dermatitis. The present invention also includes therapeutic compositions comprising such proteins and their use to treat animals susceptible to or having allergic dermatitis.

41 Claims, 16 Drawing Sheets

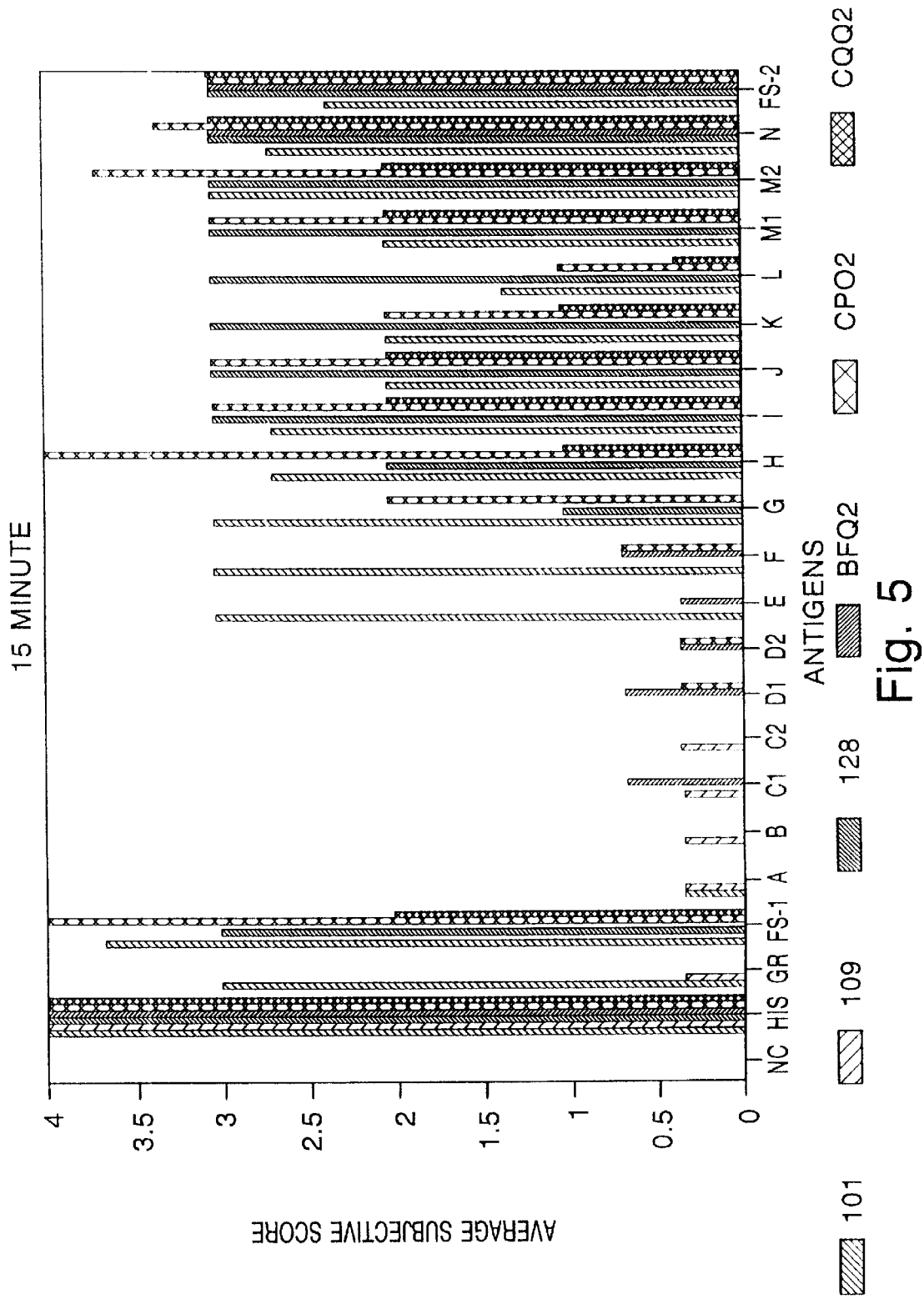

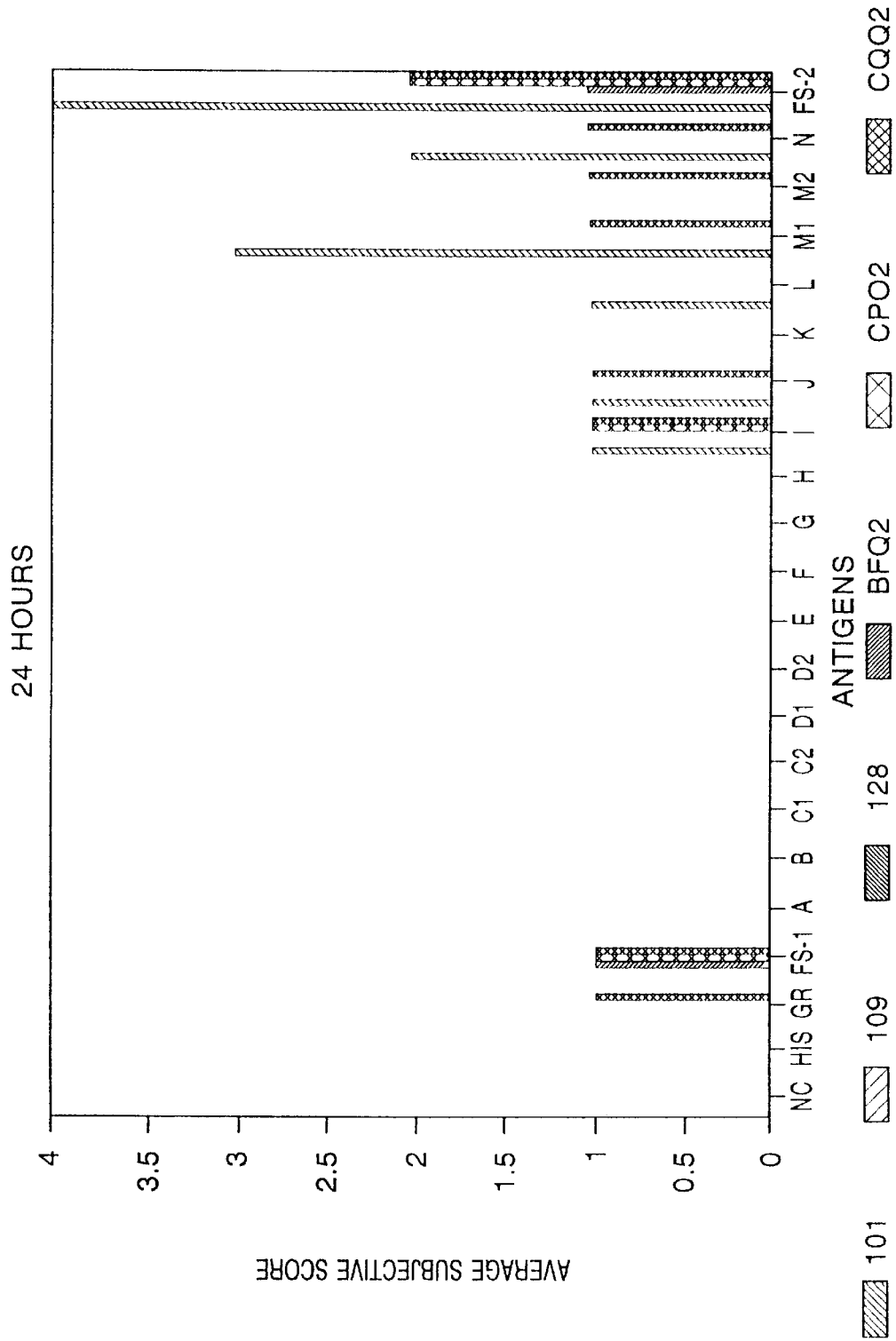

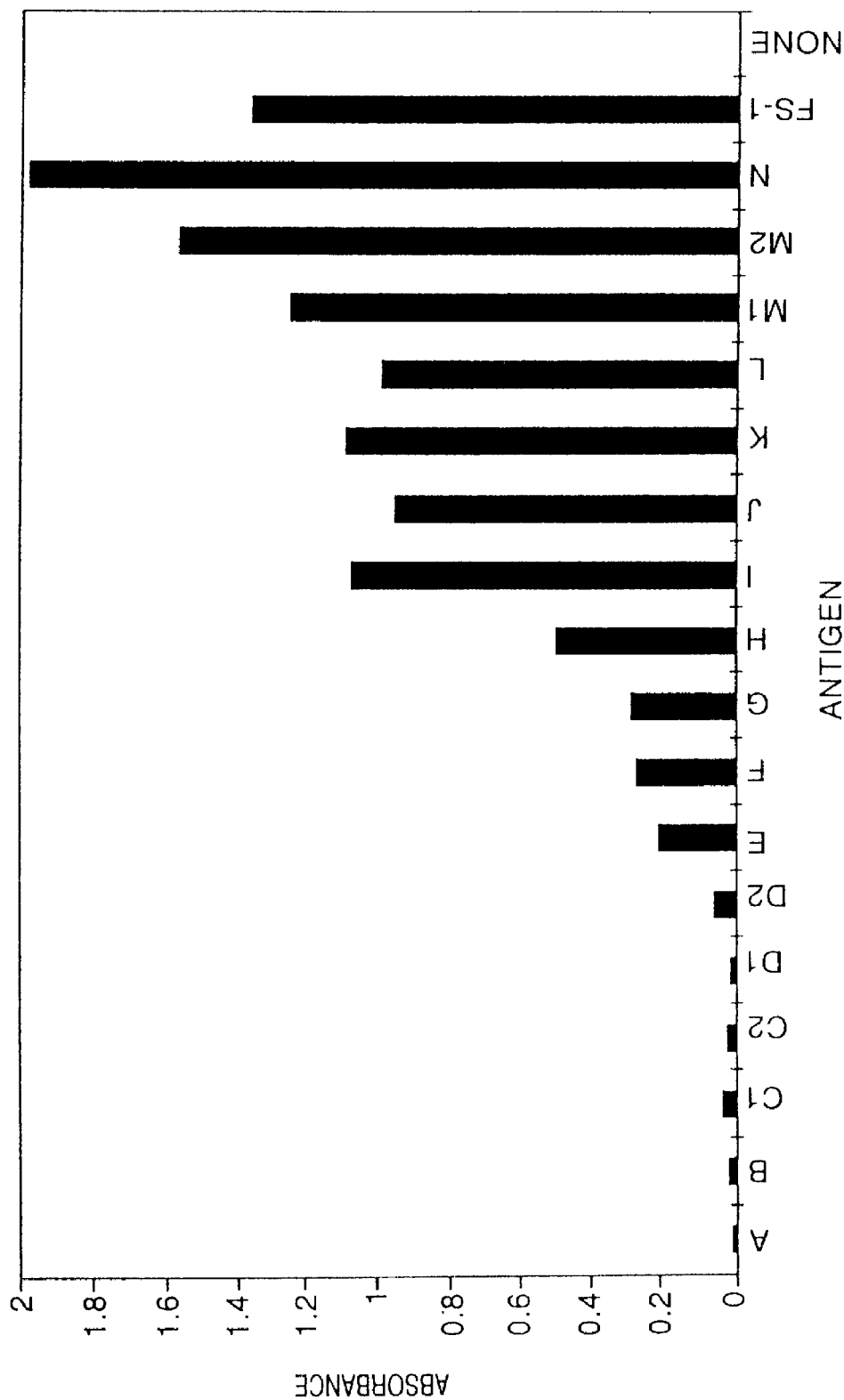

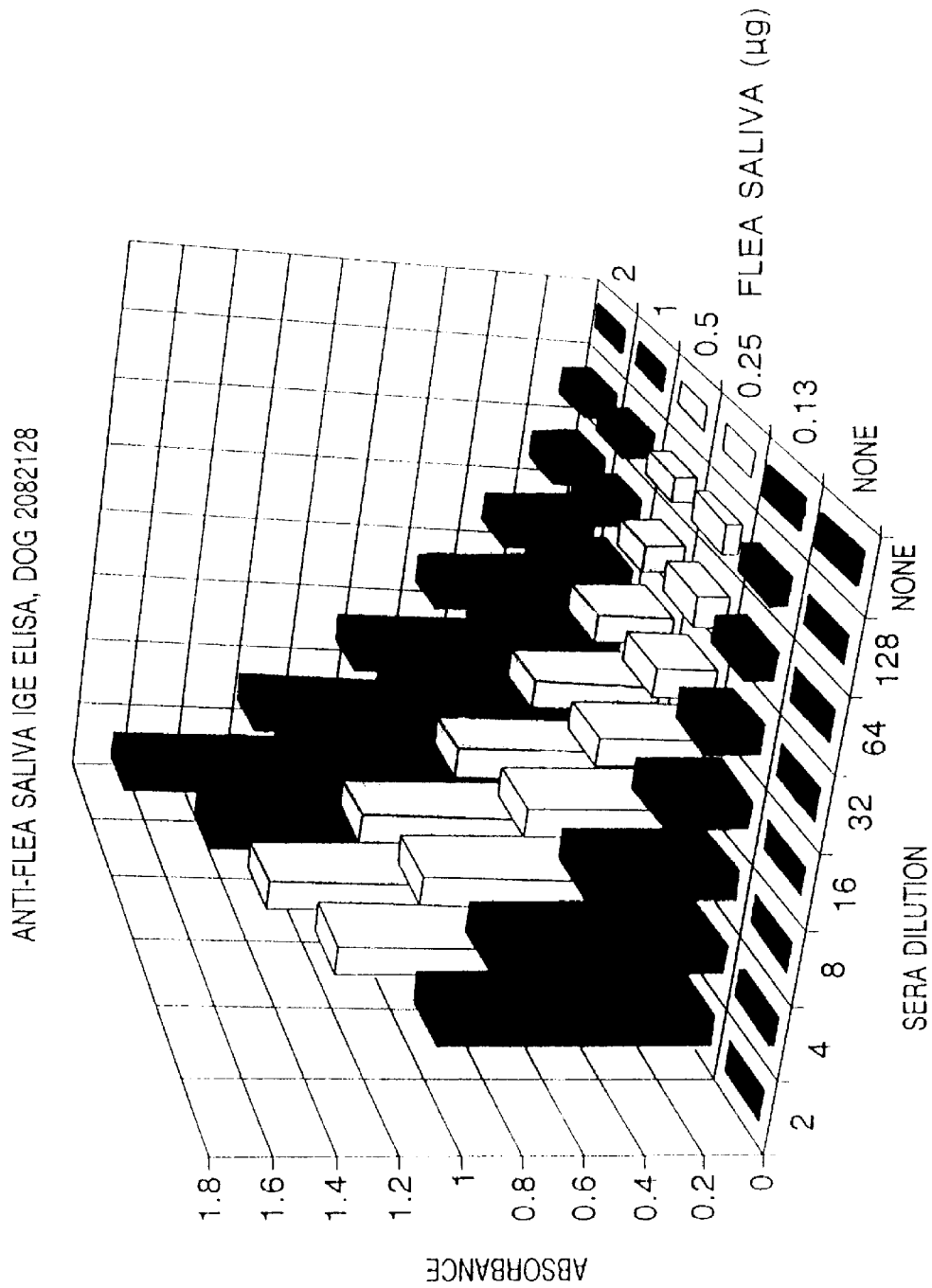

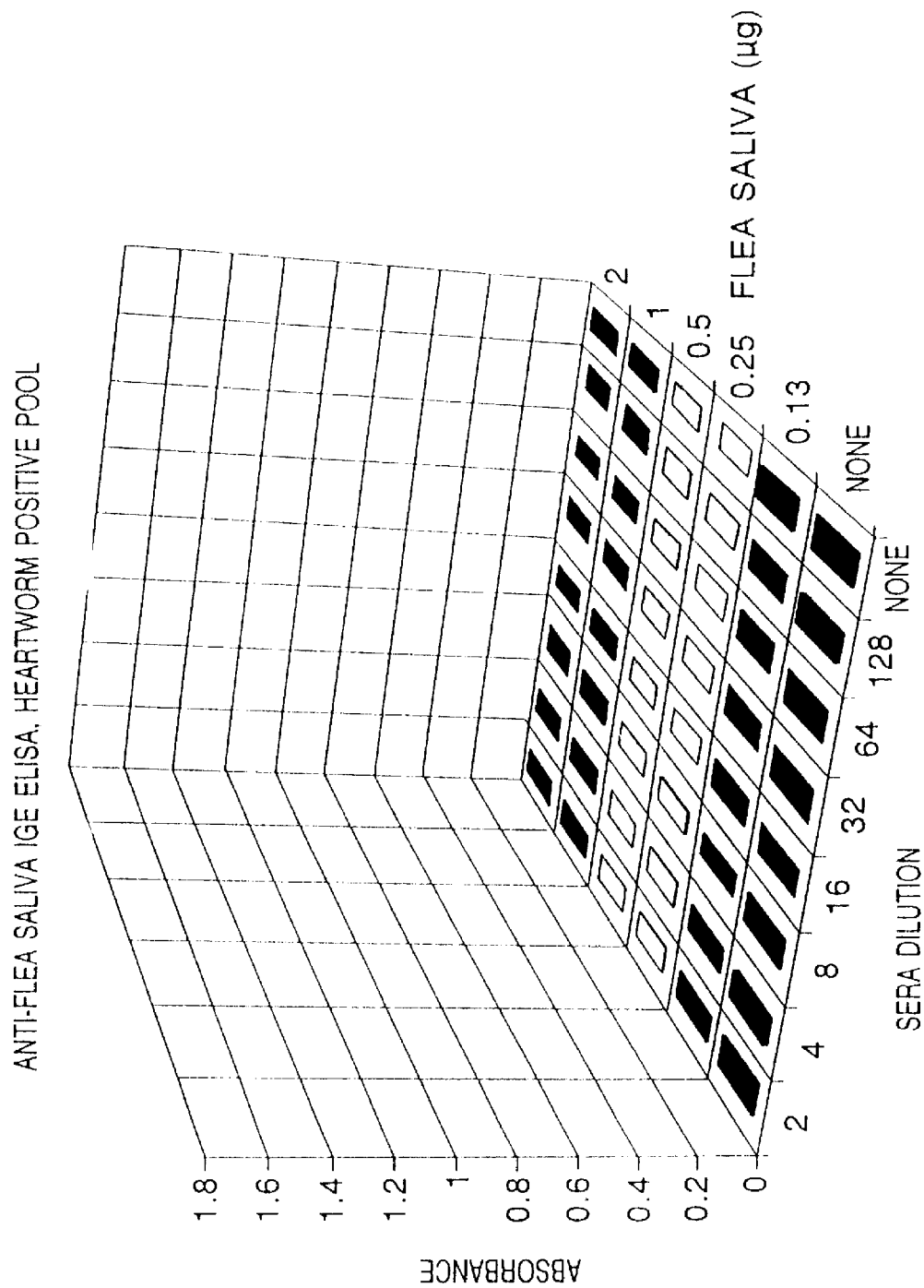

5,840,695

ECTOPARASITE SALIVA PROTEINS AND APPARATUS TO COLLECT SUCH PROTEINS

CROSS-REFERENCE TO RELATED APPLICATIONS

This application is a continuation-in-part of PCT International Application No. PCT/US95/13200, filed Oct. 6, 1995, which is a continuation-in-part application of U.S. patent application Ser. No. 08/487,001, filed Jun. 7, 1995 now U.S. Pat. No. 5,795,862 and of U.S. patent application Ser. No. 08/487,608, filed Jun. 7, 1995, which are continuation-in-part application of U.S. patent application Ser. No. 08/319,590, filed Oct. 7, 1994 now U.S. Pat. No. 5,646,115. Each of the patent applications referred to in this section is incorporated by reference herein in its entirety.

FIELD OF THE INVENTION

The present invention relates to a novel product and method for isolating ectoparasite saliva proteins, and a novel product and method for detecting and/or treating allergic dermatitis in an animal.

BACKGROUND OF THE INVENTION

Bites from ectoparasites, in particular fleas, can cause a hypersensitive response in animals. In particular, hypersensitive responses to fleabites is manifested in a disease called flea allergy dermatitis (FAD). Hypersensitivity refers to a state of altered reactivity in which an animal, having been previously exposed to a compound, exhibits an allergic response to the compound upon subsequent exposures. Hypersensitive responses include immediate and delayed-type hypersensitivity, and in particular Type I, Type II, Type III and Type IV hypersensitivities (described in detail in Janeway et al., Immunobiology, Garland Publishing, New York, 1994, which is incorporated in its entirety by this reference.).

Foreign compounds that induce symptoms of immediate and/or delayed hypersensitivity are herein referred to as allergens. The term "allergen" primarily refers to foreign compounds capable of causing an allergic response. The term can be used interchangeably with the term "antigen," especially with respect to a foreign compound capable of inducing symptoms of immediate and/or delayed hypersensitivity. Factors that influence an animal's susceptibility to an allergen can include a genetic component and/or environmental exposure to an allergen. Animals can be de-sensitized to an allergen by repeated injections of the allergen to which an animal is hypersensitive.

FAD can have manifestations of both immediate and delayed-type hypersensitivity (described in detail in Janeway et al., ibid.). Effective treatment of FAD has been difficult if not impossible to achieve. FAD afflicts about 15% of cats and dogs in flea endemic areas and the frequency is increasing each year. In a geographical area, effective flea control requires treatment of all animals. One treatment investigators have proposed includes desensitization of animals using flea allergens. However, reliable, defined preparations of flea allergens are needed for such treatments.

Until the discovery of the novel formulations of the present invention, flea allergens responsible for FAD had not been clearly defined. Whole flea antigen preparations have been used to diagnose and desensitize animals with FAD (Benjamini et al., 1960, pp. 214–222, Experimental Parasitology, Vol. 10; Keep et al., 1967, pp. 425–426, Australian Veterinary Journal, Vol. 43; Kristensen et al., 1978, pp. 414–423, Nord. Vet-Med, Vol. 30; Van Winkle, 1981, pp. 343–354, J. Amer. Animal Hosp. Assoc., Vol. 17; Haliwell et al., 1987, pp. 203–213, Veterinary Immunology and Immunopathology, Vol. 15; Greene et al., 1993, pp. 69–74, Parasite Immunology, Vol. 15); PCT Publication No. WO 93/18788 by Opdebeeck et al.; and Van Winkle, pp. 343–354, 1981, J. Am. Anim. Hosp. Assoc., vol. 32. Available commercial whole flea extracts, however, are unpredictable and, therefore, have limited usefulness.

Prior investigators have suggested that products contained in flea saliva might be involved in FAD and have also suggested methods to isolate such products: Benjamini et al., 1963, pp. 143–154, Experimental Parasitology, Vol. 13; Young et al., 1963, pp. 155–166, Experimental Parasitology 13, Vol. 13; Michaeli et al., 1965, pp. 162–170, J. Immunol., Vol. 95; and Michaeli et al., 1996, pp. 402–406, J. Immunol., Vol. 97. These investigators, however, have characterized the allergenic factors of flea saliva as being haptens having molecular weights of less than 6 kilodaltons (kD). That they are not proteins is also supported by the finding that they are not susceptible to degradation when exposed to strong acids (e.g., 6N hydrochloric acid) or heat. Some of the particular low molecular weight allergenic factors have also been characterized as being a highly fluorescent aromatic fraction (Young et al., ibid.). In addition, studies by such investigators have indicated that in order to be allergenic, such factors need to be associated with adjuvants and/or carriers, such as collagen or portions of the membrane used to collect the oral secretions. Moreover, the methods described to collect flea saliva factors were difficult and unpredictable. Furthermore the factors isolated by these methods were typically contaminated with material from the fleas, their culture medium or the skin-based membranes used to allow the fleas to feed.

Thus, there remains a need to more clearly define flea saliva allergens capable of inducing a hypersensitive response in animals. In addition, there remains a need to develop a method to collect substantially pure flea saliva allergens which provide predictable and less expensive preparations of allergens useful for desensitizing animals subject to, or having, FAD.

SUMMARY OF THE INVENTION

The present invention relates to, in one embodiment, a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein present in flea saliva extract FS-1, FS-2 and/or FS-3, i.e., the portion is encoded by a nucleic acid molecule capable of hybridizing under stringent conditions with the nucleic acid strand that is complementary to the nucleic acid strand that comprises the coding strand of the nucleic acid molecule that encodes a flea saliva protein of the present invention. Preferred flea saliva proteins include fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN (J), fspN(K), fspN(L), fspN(M), fspN(N), and/or fspN(O). In addition, the flea saliva protein of the formulation can include at least a portion of an amino acid sequence represented by SEQ ID NO:1, SEQ ID NO:2, SEQ ID NO:3, SEQ ID NO:4, SEQ ID NO:5, SEQ ID NO:6, SEQ ID NO:7, SEQ
ID NO:8, SEQ ID NO:9, SEQ ID NO:10, SEQ ID NO:11,
SEQ ID NO:12, SEQ ID NO:13, SEQ ID NO:14, SEQ ID
NO:25, SEQ ID NO:26, SEQ ID NO:27, SEQ ID NO:28,
SEQ ID NO:29, SEQ ID NO:30, SEQ ID NO:31, SEQ ID
NO:33, SEQ ID NO:35, SEQ ID NO:51, SEQ ID NO:53,
SEQ ID NO:54, SEQ ID NO:56, SEQ ID NO:58, SEQ ID
NO:60, SEQ ID NO:62, SEQ ID NO:64, SEQ ID NO:66,
SEQ ID NO:68, SEQ ID NO:70, SEQ ID NO:72, SEQ ID
NO:73, SEQ ID NO:74, SEQ ID NO:75, SEQ ID NO:76,
SEQ ID NO:77, SEQ ID NO:78, SEQ ID NO:80, SEQ ID
NO:88, SEQ ID NO:90, SEQ ID NO:100, and/or SEQ ID
NO:102.

Another embodiment of the present invention includes a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein represented as a protein peak in FIG. 2.

Another embodiment of the present invention includes a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein represented as a protein peak in FIG. 12.

One aspect of the present invention includes a formulation comprising an ectoparasite saliva product, in which the formulation, when submitted to Tris glycine SDS-PAGE, comprises a fractionation profile as depicted in a FIG. 1B, lane 13 and/or FIG. 1B, lane 14.

Yet another embodiment of the present invention includes a formulation comprising at least one isolated ectoparasite saliva product substantially free of contaminating material, the formulation being produced by a process comprising: (a) collecting ectoparasite saliva products on a collection means within a saliva collection apparatus containing ectoparasites, the apparatus comprising (i) a housing operatively connected to a chamber, the chamber having an ambient temperature warmer than the housing thereby forming a temperature differential between the housing and the chamber, the housing being capable of retaining ectoparasites, and (ii) an interface between the housing and the chamber, the interface comprising ((a)) a means capable of collecting at least a portion of saliva products deposited by ectoparasites retained in the apparatus and ((b)) a barrier means capable of substantially preventing contaminating material from contacting the collection means, in which the temperature differential attracts ectoparasites retained in the housing to attempt to feed through the barrier means and collection means and, thereby, deposit saliva products on the collection means; and (b) extracting the saliva products from the collection means to obtain the formulation. Also included in the present invention is such an apparatus and use such an apparatus to produce formulations comprising flea saliva products substantially free of contaminating material.

Another aspect of the present invention includes an isolated nucleic acid molecule capable of hybridizing under stringent conditions with a gene encoding a flea saliva protein present in flea saliva extract FS-1, FS-2 and/or FS-3, including, but not limited to fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), and/or fspN(O). In particular, the nucleic acid molecule is capable of hybridizing under stringent conditions with nucleic acid sequence SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:79; SEQ ID NO:81; SEQ ID NO:82; SEQ ID NO:83; SEQ ID NO:84; SEQ ID NO:85; SEQ ID NO:86; SEQ ID NO:87; SEQ ID NO:89; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:101; as well as with the complements of any of these sequences. In a further embodiment, a nucleic acid molecule of the present invention can include a nucleic acid molecule capable of hybridizing under stringent conditions with the complement of a nucleic acid sequence encoding a flea saliva protein having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:88, SEQ ID NO:90, SEQ ID NO:100, and SEQ ID NO:102. In a still further embodiment, a nucleic acid molecule of the present invention can include a nucleic acid molecule which comprises a nucleic acid sequence selected from the group consisting of SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71; SEQ ID NO:79; SEQ ID NO:81; SEQ ID NO:82; SEQ ID NO:83; SEQ ID NO:84; SEQ ID NO:85; SEQ ID NO:86; SEQ ID NO:87; SEQ ID NO:89; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:101, SEQ ID NO:104, a complement of any of said nucleic acid sequences, or an allelic variant of any of said nucleic acid sequences. Also included in the present invention are recombinant molecules and recombinant cells having a nucleic acid molecule of the present invention.

Also included in the present invention is a method for producing at least one ectoparasite saliva protein, comprising: (a) culturing a cell transformed with at least one nucleic acid capable of hybridizing under stringent conditions with the complement a gene encoding a flea saliva protein present in flea saliva extract FS-1, FS-2, and/or FS-3 to produce the protein; and (b) recovering the ectoparasite saliva proteins.

Another aspect of the present invention includes an antibody capable of selectively binding to an ectoparasite saliva product, or mimetope thereof.

Yet another aspect of the present invention includes a therapeutic composition for treating allergic dermatitis comprising any of the formulations disclosed herein. In particular, the therapeutic composition is useful for treating flea allergy dermatitis, mosquito allergy dermatitis and/or Culicoides allergy dermatitis. The present invention also includes a method to desensitize a host animal to allergic dermatitis, comprising administering to the animal a therapeutic composition.

The present invention further relates to an assay kit for testing if an animal is susceptible to or has allergic dermatitis, the kit comprising: (a) a formulation as disclosed herein; and (b) a means for determining if the animal is susceptible to or has allergic dermatitis, in which the means comprises use of the formulation to identify animals susceptible to or having allergic dermatitis.

According to the present invention, a method can be used to identify an animal susceptible to or having allergic dermatitis, the method comprising: (a) administering to a site on the animal a formulation of the present invention and administering to a different site on the animal a control solution selected from the group consisting of positive control solutions and negative control solutions; and (b) comparing a reaction resulting from administration of the formulation with a reaction resulting from administration of the control solution. The animal is determined to be susceptible to or to have allergic dermatitis if the reaction to the formulation is at least as large as the reaction to the positive control solution. The animal is determined not to be susceptible to or not to have allergic dermatitis if the reaction to the formulation is about the same size as the reaction to the negative control solution. In particular, the method can detect immediate hypersensitivity and/or delayed hypersensitivity.

Also according to the present invention, a method can be used to identify an animal susceptible to or having allergic dermatitis by measuring the presence of antibodies indicative of allergic dermatitis in the animal, the method comprising: (a) contacting a formulation of the present invention with a body fluid from the animal under conditions sufficient for formation of an immunocomplex between the formulation and the antibodies, if present, in the body fluid; and (b) determining the amount of immunocomplex formed, in which formation of the immunocomplex indicates that the animal is susceptible to or has allergic dermatitis. In particular, the method can be used to detect IgE antibodies as an indicator of immediate hypersensitivity in the animal.

The present invention also includes a method for prescribing treatment for allergic dermatitis, comprising: (a) identifying an animal that is susceptible to or has allergic dermatitis by an in vivo or in vitro assay comprising a formulation of the present invention; and (b) prescribing a treatment comprising administering a formulation of the present invention to the animal.

BRIEF DESCRIPTION OF THE DRAWINGS

FIG. 5 illustrates the relative size of wheals produced 15 minutes after injection of various flea saliva protein formulations into flea-sensitized dogs.

FIG. 9 illustrates the relative erythema of wheals 24 hours after injection of various flea saliva protein formulations into flea-sensitized dogs.

FIG. 10 depicts ELISA results measuring anti-flea saliva IgE antibodies in the sera of flea sensitized dogs.

FIGS. 11A and 11B depict ELISA results measuring anti-flea saliva IgE antibodies in the serum of a flea sensitized dog and the lack thereof in heartworm infected dogs.

DETAILED DESCRIPTION OF THE INVENTION

Figure 1A:
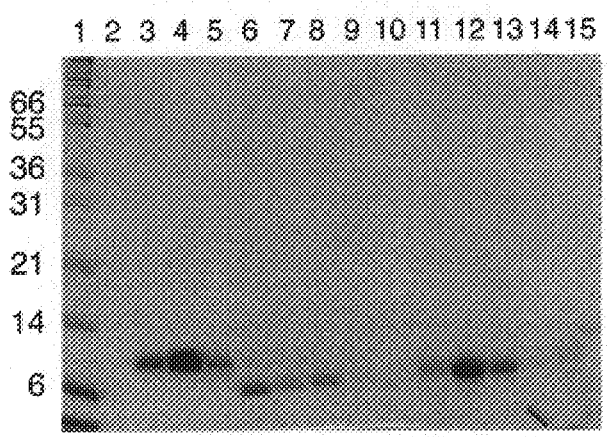
FIG. 1A illustrates the resolution of flea saliva proteins by reducing 16% Tris glycine SDS-PAGE.

The present invention includes a novel product and method for diagnosing and treating allergic dermatitis of animals to ectoparasites. The invention is particularly advantageous in that it provides for a unique formulation of ectoparasite saliva products sufficiently free of contaminants such as blood proteins, fecal material and larval culture medium, to be useful in diagnosis and therapy of allergies caused by ectoparasites. In addition, the present invention includes ectoparasite saliva products having other activities, important, for example, in a flea's ability to feed and/or counteract a host's resistance to fleas, such as products having clotting, anti-coagulant, protease, phospholipase, prostaglandin, anti-complement, other immunosuppressant, phosphatase, apyrase, vasoactive, and/or anti-inflammatory activities. Included among flea saliva products are products, such as, but not limited to, proteases, that are regurgitated by the flea that originated in other organs, such as, but not limited to, the midgut.

The invention is also particularly advantageous in that it provides an apparatus and method for reproducibly and efficiently isolating ectoparasite saliva products substantially free of contaminating material.

According to the present invention, ectoparasites are external living parasites that attach and feed through the skin of a host animal. Ectoparasites include parasites that live on a host animal and parasites that attach temporarily to an animal in order to feed. Also, according to the present invention, ectoparasite saliva refers to the material released from the mouth of an ectoparasite when the ectoparasite attempts to feed in response to a temperature differential, such as exists in an apparatus of the present invention. Ectoparasite saliva includes ectoparasite saliva products. Ectoparasite saliva products of the present invention comprise the portion of ectoparasite saliva bound to a collecting means of the present invention (described in detail below), herein referred to as ectoparasite saliva components. As such, ectoparasite saliva products also include the portion of ectoparasite saliva extracted from a collecting means of the present invention, herein referred to as ectoparasite saliva extract. Included in ectoparasite saliva extracts are ectoparasite saliva proteins which can be isolated using, for example, any method described herein. Ectoparasite saliva extracts of the present invention can also include other ectoparasite saliva products, such as, prostaglandins and other pharmacologically active molecules.

One embodiment of the present invention is a formulation that contains ectoparasite saliva products that can be used to diagnose and/or treat animals susceptible to or having (i.e., suffering from) allergic dermatitis. Preferred types of allergic dermatitis to diagnose and/or treat using ectoparasite saliva products of the present invention include flea allergy dermatitis, Culicoides allergy dermatitis and mosquito allergy dermatitis. A preferred type of allergic dermatitis to diagnose and/or treat using ectoparasite saliva products of the present invention is flea allergy dermatitis. As used herein, an animal that is susceptible to allergic dermatitis refers to an animal that is genetically predisposed to developing allergic dermatitis and/or to an animal that has been primed with an antigen in such a manner that re-exposure to the antigen results in symptoms of allergy that can be perceived by, for example, observing the animal or measuring antibody production by the animal to the antigen. As such, animals susceptible to allergic dermatitis can include animals having sub-clinical allergic dermatitis. Sub-clinical allergic dermatitis refers to a condition in which allergy symptoms cannot be detected by simply observing an animal (i.e., manifestation of the disease can include the presence of anti-ectoparasite saliva protein antibodies within an affected animal but no dermatitis). For example, subclinical allergic dermatitis can be detected using in vivo or in vitro assays of the present invention, as described in detail below. Reference to animals having allergic dermatitis includes animals that do display allergy symptoms that can be detected by simply observing an animal and/or by using in vivo or in vitro assays of the present invention, as described in detail below.

One embodiment of the present invention is a formulation that includes one or more isolated ectoparasite saliva proteins. According to the present invention, an isolated protein is a protein that has been removed from its natural milieu. An isolated ectoparasite saliva protein can, for example, be obtained from its natural source, be produced using recombinant DNA technology, or be synthesized chemically. As used herein, an isolated ectoparasite saliva protein can be a full-length ectoparasite saliva protein or any homologue of such a protein, such as an ectoparasite saliva protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol). A homologue of an ectoparasite saliva protein is a protein having an amino acid sequence that is sufficiently similar to a natural ectoparasite saliva protein amino acid sequence that a nucleic acid sequence encoding the homologue is capable of hybridizing under stringent conditions to (i.e., with) a nucleic acid molecule encoding the natural ectoparasite saliva protein (i.e., the complement of a nucleic acid sequence encoding the natural ectoparasite saliva protein amino acid sequence). A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual,* Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ectoparasite saliva protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an ectoparasite saliva protein homologue of the present invention is from about 4 to about 6 amino acids in length, with preferred sizes depending on whether a full-length, multivalent (i.e., fusion protein having more than one domain each of which has a function), or functional portions of such proteins are desired.

Ectoparasite saliva protein homologues can be the result of allelic variation of a natural gene encoding an ectoparasite saliva protein. A natural gene refers to the form of the gene found most often in nature. Ectoparasite saliva protein homologues can be produced using techniques known in the art including, but not limited to, direct modifications to a gene encoding a protein using, for example, classic or recombinant DNA techniques to effect random or targeted mutagenesis.

Preferred ectoparasite saliva proteins of the present invention, including homologues thereof, are capable of detecting and/or treating allergic dermatitis resulting from the bites of ectoparasites. A preferred ectoparasite saliva protein homologue includes at least one epitope capable of eliciting a hypersensitive response to the natural ectoparasite saliva protein counterpart. An ectoparasite saliva protein homologue can also include an epitope capable of hyposensitizing an animal to the natural form of the protein. The ability of an ectoparasite saliva protein homologue to detect and/or treat (i.e., immunomodulate or regulate by, for example, desensitizing) the hypersensitivity of an animal susceptible to or having allergic dermatitis, can be tested using techniques known to those skilled in the art. Such techniques include skin tests and immunoabsorbent assays as described in detail below. Additional preferred ectoparasite saliva proteins of the present invention have other activities that include activities important for feeding and survival of the ectoparasite.

In one embodiment, a formulation of the present invention can comprise a protein having at least a portion of an isolated ectoparasite saliva protein. According to the present invention, "at least a portion of an ectoparasite saliva protein" refers to a portion of an ectoparasite saliva protein encoded by a nucleic acid molecule that is capable of hybridizing, under stringent conditions, with a nucleic acid encoding a full-length ectoparasite saliva protein of the present invention. Preferred portions of ectoparasite saliva proteins are useful for detecting and/or treating allergic dermatitis resulting from the bites of ectoparasites. Additional preferred portions have activities important for flea feeding and survival. Suitable sizes for portions of an ectoparasite saliva protein of the present invention are as disclosed for saliva protein homologues of the present invention.

As will be apparent to one of skill in the art, the present invention is intended to apply to all ectoparasites. A formulation of the present invention can include saliva products from any ectoparasites. A preferred ectoparasite of the present invention from which to isolate saliva products (including proteins), and/or from which to identify proteins that can then be produced recombinantly or synthetically, include arachnids, insects and leeches. More preferred ectoparasites from which to obtain saliva products include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasite saliva products include those from fleas, mosquitos, midges, sandflies, blackflies, ticks and Rhodnius, with products from fleas, mosquitos and Culicoides being even more preferred.

A particularly preferred formulation of the present invention includes flea saliva proteins. Preferred flea saliva products include those from Ctenocephalides, Xenopsylla, Pulex, Tunga, Nosopsyllus, Diamanus, Ctopsyllus and Echidnophaga fleas, with saliva products from *Ctenocephalides canis* and *Ctenocephalides felis* fleas being even more preferred. For the purposes of illustration, many of the following embodiments discuss flea saliva proteins. Such discussion of flea saliva proteins is not intended, in any way, to limit the scope of the present invention.

In one embodiment, a formulation of the present invention is substantially free from contaminating material. Contaminating material can include, for example, ectoparasite fecal material, blood proteins from previous meals taken by an ectoparasite (e.g., fetuin, ferritin, albumin, hemoglobin and other large blood proteins), ectoparasite cuticular debris, and ectoparasite larval culture medium (e.g., blood, mouse food and sand). As used herein, a formulation that is substantially free of contaminants is a formulation that without further purification can be used as a diagnostic or therapeutic agent without causing undesired side effects. Preferably, a formulation substantially free from contaminating material comprises less than about 50 percent contaminating material, more preferably less than about 10 percent contaminating material, and even more preferably less than about 5 percent contaminating material. As such, a formulation of the present invention preferably comprises at least about 50 percent flea saliva products, more preferably at least about 90 percent flea saliva products, and even more preferably at least about 95 percent flea saliva products. A formulation of the present invention substantially free of contaminating material can include a formulation not having any blood contaminants or flea midgut contents. A formulation substantially free of contaminating material can be obtained using a saliva collection apparatus of the present invention as described in detail below.

A formulation that is substantially free of contaminating material can be identified by typical methods known to those of skill in the art. For example, the presence of contaminants can be identified by: (1) overloading and resolving a formulation by sodium dodecyl sulfate polyacrylamide gel electrophoresis (SDS-PAGE); (2) resolving a formulation by a variety of chromatography techniques; (3) screening a formulation with antibodies capable of binding to specific contaminants using, for example, immunoblot or enzyme-linked immunoassay techniques; (4) resolving a formulation by capillary electrophoresis; or (5) screening a formulation using an assay to detect hemoglobin.

One embodiment of a formulation of the present invention includes at least one or more flea saliva proteins having molecular weights ranging from about 6 kD to about 65 kD as determined by Tris-glycine SDS-PAGE, preferably using a 14% polyacrylamide gel and resolved using methods standard in the art. A preferred formulation includes one or more flea saliva proteins having molecular weights ranging from about 6 kD to about 55 kD. A more preferred formulation includes one or more proteins having elution (or migration) patterns as shown in FIG. 1.

In another embodiment, a formulation of the present invention includes at least one or more flea saliva proteins having molecular weights ranging from about 40 kD to about 300 kD as determined by Tris-glycine SDS-PAGE and resolved using methods standard in the art. Greater than 50% of the flea saliva proteins contained in such a formulation have a molecular weights ranging from about 40 kD to about 55 kD, and appear to be similar to fspN. A more preferred formulation includes one or more proteins having elution (or migration) patterns as shown in FIG. 1.

In another embodiment, a formulation of the present invention includes one or more flea saliva proteins having basic isoelectric points, or pI values. An isoelectric pH, or pI, value refers to the pH value at which a molecule has no net electric charge and fails to move in an electric field. A preferred formulation of the present invention includes proteins having a pI value of at least about pI 8.5, and more preferably of at least about pI 9.0. Flea saliva protein fspH, for example, has pI values ranging from about pI 8.5 to about pI 9.6, which may represent heterogeneity in the proteins due to allelic variation in the flea population from which the flea saliva proteins were collected.

In yet another embodiment, a formulation of the present invention includes at least a portion of one or more flea saliva products eluted from a collection means of the present invention. Examples of such formulations include flea extracts FS-1, FS-2, and FS-3. The FS-1, FS-2 and FS-3 fleas saliva extracts are produced according to the method described in detail in Example 2. According to the present invention, the terms FS-1 flea saliva extract, FS-2 flea saliva extract or FS-3 flea saliva extract can be used interchangeably with the terms FS-1 flea saliva product mixture, FS-2 flea saliva product mixture or FS-3 flea saliva product mixture, respectively.

Figure 1B:
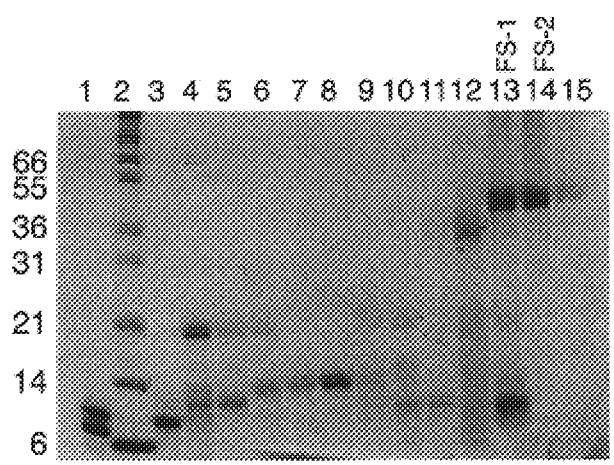
FIG. 1B illustrates the resolution of flea saliva proteins, FS-1 and FS-2 by reducing 16% Tris glycine SDS-PAGE.
Figure 2:
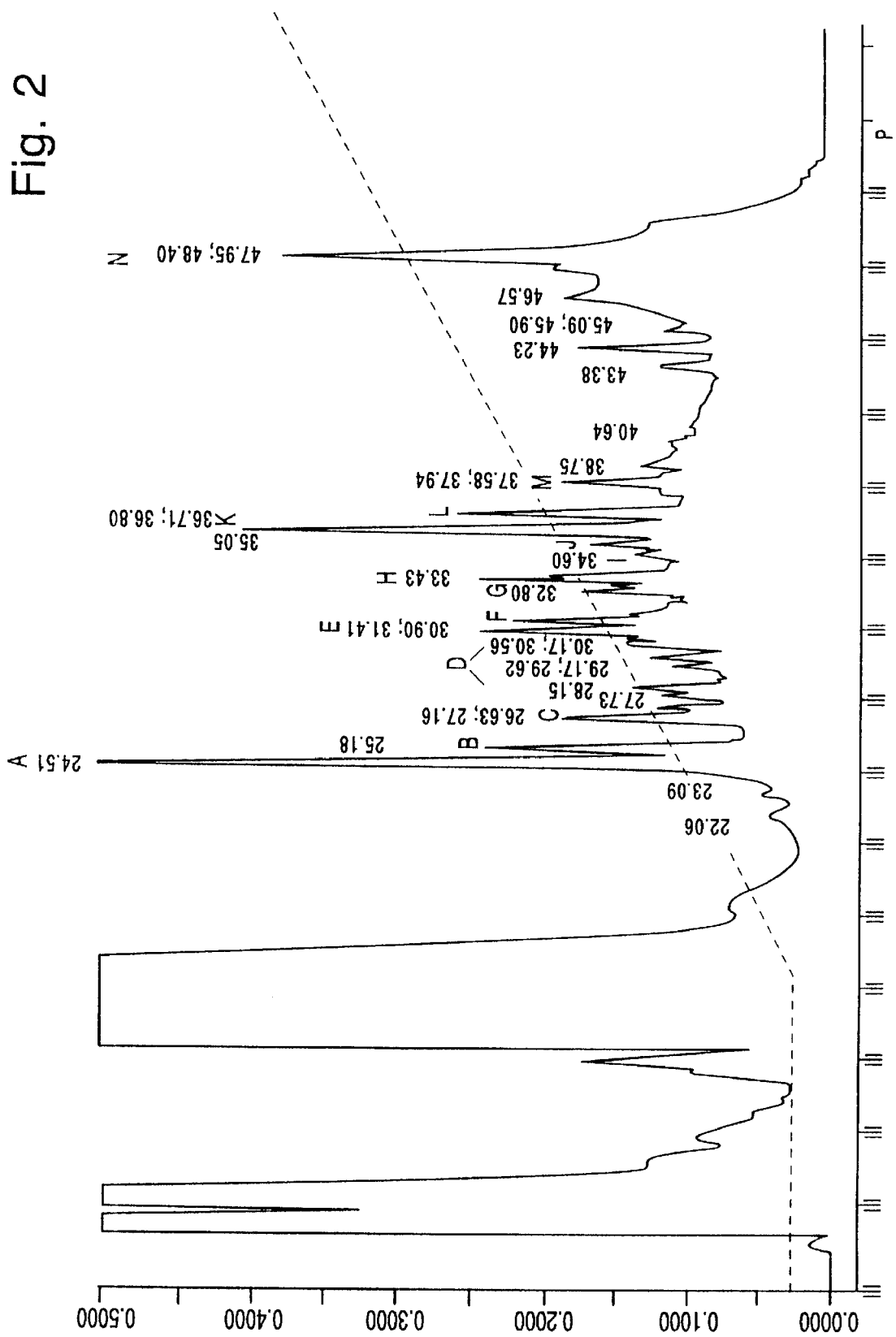
FIG. 2 illustrates the resolution of flea saliva proteins using high pressure liquid chromatography.

An FS-1 flea saliva extract includes a mixture of proteins (a) that, when submitted to reducing 16% Tris glycine SDS-PAGE, migrate as bands as are shown in FIG. 1B, lane 13; and (b) that, when submitted to reverse phase high pressure liquid chromatography (HPLC), migrate as peaks as are shown in FIG. 2. The peaks in FIG. 2 are obtained when the proteins included in FS-1 are collected using a saliva collection apparatus of the present invention as described in detail below, and further resolved into protein peaks by passing the collected proteins over a C4 HPLC column using 5% to 63% acetonitrile or 5.6% to 70% Solvent B at a flow rate of 0.8 milliliters per minute, in which Solvent A is about 0.1% TFA in water and Solvent B is about 0.085% TFA in 90% acetonitrile. Referring to FIG. 2, the peaks are referred to and depicted as peak A, peak B, peak C, peak D, peak E, peak F, peak G, peak H, peak I, peak J, peak K, peak L, peak M and peak N. Flea saliva proteins (or protein fragments) contained within such peaks are referred to as fspA, fspB, fspC, fspD, fspE, fspF, fspG, fspH, fspI, fspJ, fspK, fspL, fspM and fspN. The peaks refer to the regions marked in FIG. 2 and it is to be noted that a peak does not necessarily contain just one protein (or protein fragment). Further resolution of proteins contained within the above-referenced peaks by, for example, amino acid sequencing or SDS-PAGE gel electrophoresis, has indicated that fspC includes at least two proteins referred to as fspC1 and fspC2, fspD includes at least two proteins referred to as fspD1 and fspD2, fspG includes at least four proteins referred to as fspG1, fspG2 and fspG3, fspG4, fspJ includes at least two proteins referred to as fspJ1 and fspJ2, fspL includes at least two proteins referred to as fspL1 and fspL2, fspM includes at least two proteins referred to as fspM1 and fspM2, and fspN includes at least three proteins and/or protein fragments referred to as fspN1, fspN2 and fspN3. At least partial amino acid sequences have been obtained for a number of the flea saliva proteins as represented by SEQ ID NO:1 (a partial N- (amino-) terminal amino acid sequence of fspA), SEQ ID NO:2 (an amino acid sequence, beginning at the N-terminus, that represents most of the fspH protein), SEQ ID NO:3 (a partial N-terminal amino acid sequence of an Endoproteinase Asp-N fragment of fspH, denoted fspHe), SEQ ID NO:4 (a partial N-terminal amino acid sequence of an Endoproteinase Asp-N fragment of fspH, denoted fspHh), SEQ ID NO:5 (a partial N-terminal amino acid sequence of an Endoproteinase Asp-N fragment of fspH, denoted fspHj, which also represents a partial N-terminal amino acid sequence of fspH), SEQ ID NO:6 (a partial N-terminal amino acid sequence of fspI), SEQ ID NO:7 (a partial N-terminal amino acid sequence of fspJ1), SEQ ID NO:8 (a partial N-terminal amino acid sequence of fspJ2), SEQ ID NO:9 (a partial N-terminal amino acid sequence of fspL1), SEQ ID NO:10 (a partial N-terminal amino acid sequence of fspL2), SEQ ID NO:11 (a partial N-terminal amino acid sequence of fspN1), SEQ ID NO:12 (a partial N-terminal amino acid sequence of fspN2), SEQ ID NO:13 (a partial N-terminal amino acid sequence of fspN3), SEQ ID NO:14 (a partial N-terminal amino acid sequence of fspH), SEQ ID NO:25 (a translation of the nucleic acid sequence represented by SEQ ID NO:24, corresponding to fspI), SEQ ID NO:26 (an apparent full-length translation product of fspI), SEQ ID NO:27 (a partial N-terminal amino acid sequence of fspB), SEQ ID NO:28 (a partial N-terminal amino acid sequence of fspG1), SEQ ID NO:29 (a partial N-terminal amino acid sequence of fspG2), SEQ ID NO:30 (a partial N-terminal amino acid sequence of fspG3), SEQ ID NO:31 (a partial N-terminal amino acid sequence of an Endoproteinase Asp-N fragment of fspN, denoted fspN(100–101)), SEQ ID NO:33 (a translation product, named PfspH$_{80}$, of the partial nucleic acid sequence of nfspH$_{242}$, denoted SEQ ID NO:32), SEQ ID NO:35 (a translation product, named PfspI$_{155}$, of the partial nucleic acid sequence of nfspI$_{591}$, denoted SEQ ID NO:34), SEQ ID NO:51 (a translation product, named PfspN(A)$_{172}$, of the partial nucleic acid sequence of nfspN(A)$_{646}$, denoted SEQ ID NO:50), SEQ ID NO:53 (a translation product, named PfspN(B)$_{153}$, of the partial nucleic acid sequence of nfspN(B)$_{612}$, denoted SEQ ID NO:52), SEQ ID NO:54 (a partial apparent N-terminal amino acid sequence, named PfspN(A)$_{56}$, of PfspN(A)), SEQ ID NO:56 (an apparent full-length translation product, named PfspN(A)$_{398}$, of nfspN(A)$_{1197}$, denoted SEQ ID NO:55), SEQ ID NO:58 (an apparent full-length translation product, named PfspG4$_{90}$, of nfspG4$_{565}$, denoted SEQ ID NO:57), SEQ ID NO:60 (an apparent full-length translation product, named PfspM(A)$_{157}$, of the nucleic acid sequence of nfspM(A)$_{897}$, denoted SEQ ID NO:59), SEQ ID NO:62 (a translation product, named PfspM(B)$_{900}$, of the nucleic acid sequence of nfspM(B)$_{2706}$, denoted SEQ ID NO:61), SEQ ID NO:64 (a translation product, named PfspM(C)$_{137}$, of the nucleic acid sequence of nfspM(C)$_{414}$, denoted SEQ ID NO:63), SEQ ID NO:66 (a translation product, named PfspM(D)$_{90}$, of the nucleic acid sequence of nfspM(D)$_{273}$, denoted SEQ ID NO:65), SEQ ID NO:68 (an apparent full-length translation product, named PfspM(E)$_{461}$, of the nucleic acid sequence of nfspM(E)$_{1704}$, denoted SEQ ID NO:67), SEQ ID NO:70 (a translation product, named PfspM(F)$_{586}$, of the nucleic acid sequence of nfspM(F)$_{1758}$, denoted SEQ ID NO:69), SEQ ID NO:72 (a partial N-terminal amino acid sequence of fspM(G), denoted PfspM(G)), SEQ ID NO:73 (a partial N-terminal amino acid sequence of fspM(H), denoted PfspM(H)), SEQ ID NO:74 (a partial N-terminal amino acid sequence of fspM(I), denoted PfspM(I)), SEQ ID NO:75 (a partial N-terminal 76 acid sequence of fspM(J), denoted PfspM(J)), SEQ ID NO:76 (a partial N-terminal amino acid sequence of fspM (K), denoted PfspM(K)), SEQ ID NO:77 (a partial N-terminal amino acid sequence of fspM(L), denoted PfspM (L)) and SEQ ID NO:78 (a partial N-terminal amino acid sequence of fspM(M), denoted PfspM(M)). Details of how each protein was characterized is described in the Examples section.

An FS-2 flea saliva extract includes a mixture of proteins that, when submitted to reducing 16% Tris glycine SDS-PAGE, migrate as bands as are shown in FIG. 1B, lanes 14 and 15.

It is within the scope of the present invention that additional flea saliva products of interest remain on a collection means following the elution protocols to obtain FS-1, FS-2 and FS-3 flea saliva extracts. It is also within the scope of the invention that a formulation of the present invention can include flea saliva products removed from a collection means by eluting using other techniques, for example, by using higher concentrations of eluants.

In another embodiment, a formulation of the present invention includes at least a portion of an ectoparasite saliva protein homologue preferably having at least about 50 percent, more preferably at least about 75 percent, and even more preferably at least about 85 percent amino acid homology (identity within comparable regions) with at least a portion of at least one product contained in the saliva extracts FS-1, FS-2 or FS-3. Preferred homologues include at least a portion of an ectoparasite saliva product having at least about 50 percent, more preferably at least about 75 percent, and even more preferably at least about 85 percent amino acid homology with at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N) and/or fspN(O). As such, also included are proteins having at least a portion of one of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31 SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80 and/or other sequences disclosed herein.

In a preferred embodiment, a formulation of the present invention includes at least a portion of an ectoparasite saliva product homologue of the present invention that is encoded by a nucleic acid molecule having at least about 50 percent, more preferably at least about 75 percent, and even more preferably at least about 85 percent homology with a nucleic acid molecule encoding at least a portion of a product contained in the saliva extracts FS-1, FS-2 or FS-3. A preferred ectoparasite saliva product homologue is encoded by a nucleic acid molecule having at least about 50 percent, more preferably at least about 75 percent, and even more preferably at least about 85 percent, homology with a nucleic acid molecule encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N) or fspN(O).

Figure 3:
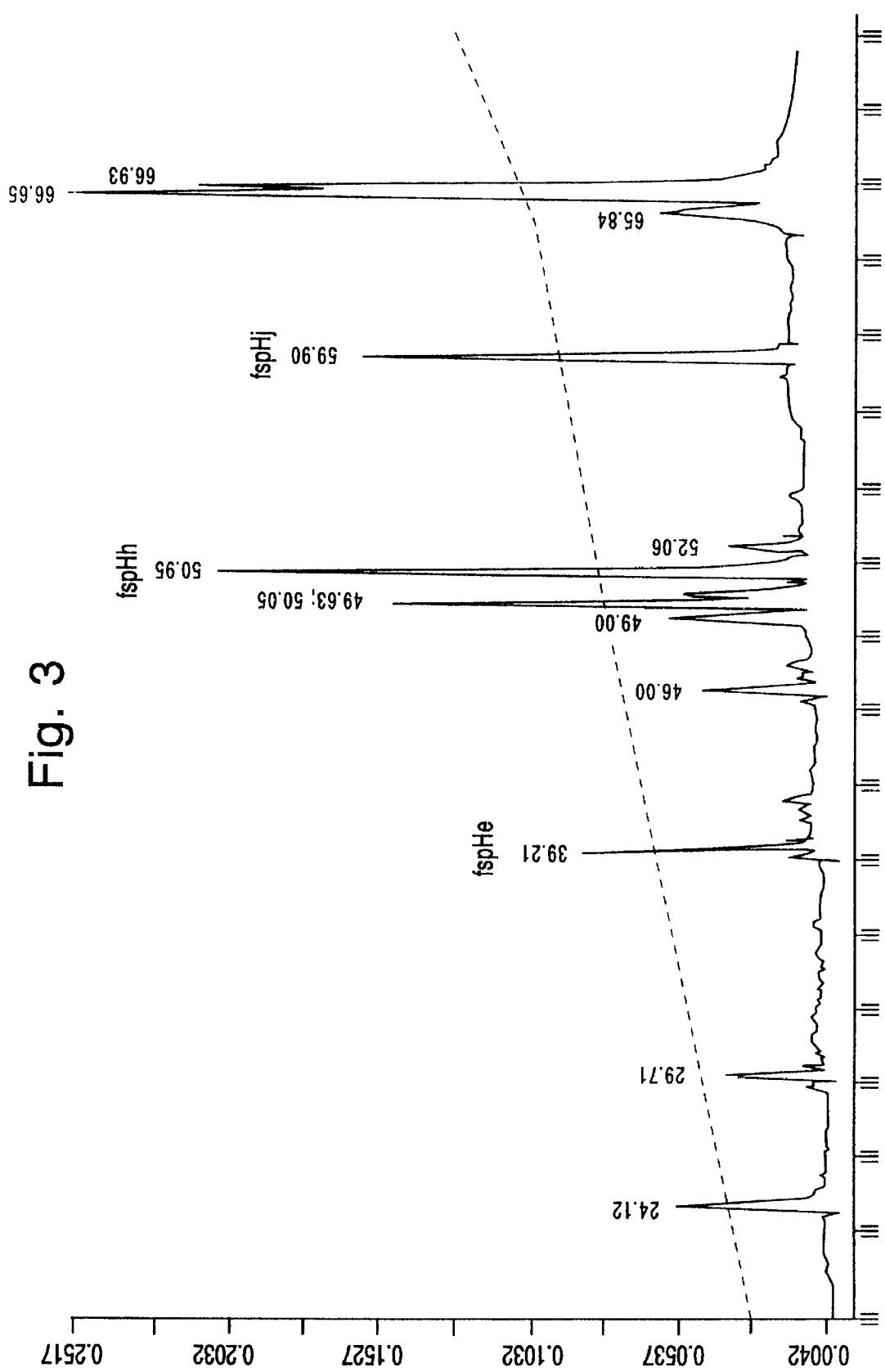
FIG. 3 illustrates the peaks obtained from reverse phase HPLC resolution of proteolytic fragments of fspH protein digested with Endoproteinase Asp-N.

In yet another embodiment, a formulation of the present invention includes a protein which, when digested with Endoproteinase Asp-N, generates proteolytic fragments that, when subjected to reverse phase HPLC, migrate with peaks as depicted in FIG. 3. The reverse phase HPLC was performed using the methods disclosed by Stone et al., Enzymatic Digestion of Proteins and HPLC Peptide Isolation, in A Practical Guide to Protein and Peptide Purification for Microsequencing, PT Matsudaira ed., Academic Press, San Diego, Calif. (i.e., Narrowbore procedure: vydac C18 reverse-phase, 300 A, 5 µm support; flow rate of 0.2 ml/min; Solvent A being 0.6% TFA in water and Solvent B being 0.052% TFA in 80% acetonitrile in water; the sample was injected at 2% B; the gradient after a hold at 2% B was 2–37.5% B over 60 min., 37.5%–75% B over 30 min., 75%–98% B over 15 min.; and detection at 214 nm). An example of such a protein is fspH, which also has the characteristics of a molecular weight of about 8613±6 daltons when determined by ESMS. A particularly preferred formulation of the present invention includes a fspH protein having the amino acid sequence represented by SEQ ID NO:2, SEQ ID NO:3, SEQ ID NO:4, SEQ ID NO:5, SEQ ID NO:14 and SEQ ID NO:33.

In preferred embodiments, formulations of the present invention can include at least one isolated protein having (i.e., including) at least a portion of one of the amino acid sequences identified in the Sequence ID Listing, and more specifically an amino acid sequence selected from the group consisting of SEQ ID NO:1; SEQ ID NO:2; SEQ ID NO:14; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:27; SEQ ID NO:28; SEQ ID NO:29; SEQ ID NO:30; SEQ ID NO:33; SEQ ID NO:25; SEQ ID NO:26; SEQ ID NO:35; SEQ ID NO:31; SEQ ID NO:51; SEQ ID NO:53; SEQ ID NO:54; SEQ ID NO:56; SEQ ID NO:58; SEQ ID NO:60; SEQ ID NO:62; SEQ ID NO:64; SEQ ID NO:66; SEQ ID NO:68; SEQ ID NO:70; SEQ ID NO:72; SEQ ID NO:73; SEQ ID NO:74; SEQ ID NO:75; SEQ ID NO:76; SEQ ID NO:77; SEQ ID NO:78; SEQ ID NO:80; SEQ ID NO:88; SEQ ID NO:90; SEQ ID NO:100; SEQ ID NO:102.

It should be noted that although fspN1 and fspN2 appear to have similar, if not identical, partial N-terminal sequences (represented, respectively by SEQ ID NOS:11 and 12), the two proteins migrate differently when submitted to Tris glycine SDS-PAGE, suggesting that they are different proteins, possibly due to a carboxyl-terminal truncation of one of the proteins and/or post-translation modification, such as glycosylation. Comparison of amino acid sequence SEQ ID NO:51 with amino acid sequences reported in GenBank indicates that SEQ ID NO:51 is about 28% identical with human prostatic acid phosphatase. Comparison of amino acid sequence SEQ ID NO:53 with amino acid sequences reported in GenBank indicates that SEQ ID NO:53 is about 30% identical with human prostatic acid phosphatase. Comparison of amino acid sequence SEQ ID NO:56 with amino acid sequences reported in GenBank indicates that SEQ ID NO:56 is about 30% identical with human prostatic acid phosphatase.

It is to be appreciated that ectoparasite saliva proteins of the present invention include, but are not limited to, full-length proteins, hybrid proteins, fusion proteins, multivalent proteins, and proteins that are truncated homologues of, or are proteolytic products of, at least a portion of a protein contained in the saliva extracts FS-1, FS-2 or FS-3; and preferably at least a portion of saliva protein fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM (G), fspM(H), fspM(I), fspM(J), fspM(K), fspM(L), fspM (M), fspN(B), fspN(C), fspN(D), fspN(E), fspN(F), fspN (G), fspN(H), fspN(I), fspN(J), fspN(K), fspN(L), fspN(M), fspN(N) and fspN(O). As such, also included are proteins having at least a portion of one of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80 and/or other sequences disclosed herein. As used herein, the term hybrid protein refers to a single protein produced from two different proteins.

The foregoing SEQ ID NO's represent amino acid sequences deduced according to methods disclosed in the Examples. It should be noted that since amino acid sequencing technology is not entirely error-free, the foregoing SEQ ID NO's, at best, represent an apparent amino acid sequence of the ectoparasite saliva proteins of the present invention. In addition, the variation seen in the foregoing SEQ ID NO's can also be due, at least in part, to allelic variation since the proteins being sequenced were derived from populations of fleas.

According to the present invention, a formulation of the present invention can include flea saliva proteins that have undergone post-translational modification. Such modification can include, for example, glycosylation. Glycosylation can include addition of N-linked and/or O-linked oligosaccharides. It is to be appreciated that post-translational modification of a protein of the present invention can contribute to an epitope's ability to induce an allergic response against the protein in an immediate or delayed hypersensitivity response.

Another embodiment of the present invention is an isolated nucleic acid molecule capable of hybridizing, under stringent conditions, with an ectoparasite saliva protein gene encoding an ectoparasite saliva protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions. An isolated nucleic acid molecule of the present invention can also be produced using recombinant DNA technology (e.g., polymerase chain reaction (PCR) amplification, cloning) or chemical synthesis. Isolated ectoparasite saliva protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an ectoparasite saliva protein of the present invention or to form stable hybrids under stringent conditions with natural nucleic acid molecule isolates.

An isolated nucleic acid molecule of the present invention can include a nucleic acid sequence that encodes at least one ectoparasite saliva protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an ectoparasite saliva protein. As heretofore disclosed, ectoparasite saliva proteins of the present invention include, but are not limited to, proteins having full-length ectoparasite saliva protein coding regions, portions thereof, and other ectoparasite saliva protein homologues.

It is to be appreciated that an ectoparasite saliva protein of the present invention can be encoded by a full-length nucleic acid sequence which encodes a polyprotein. The polyprotein can be post-translationally processed into multiple proteins which are found in saliva. As used herein, an ectoparasite saliva protein gene includes all nucleic acid sequences related to a natural ectoparasite saliva protein gene such as regulatory regions that control production of an ectoparasite saliva protein encoded by that gene (such as, but not limited to, transcription, translation or post-translation control regions) as well as the coding region itself. A nucleic acid molecule of the present invention can be an isolated natural ectoparasite saliva protein nucleic acid molecule or a homologue thereof. A nucleic acid molecule of the present invention can include one or more regulatory regions, full-length or partial coding regions, or combinations thereof. The minimal size of an ectoparasite saliva protein nucleic acid molecule of the present invention is the minimal size capable of forming a stable hybrid under stringent hybridization conditions with a corresponding natural gene.

An ectoparasite saliva protein nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an allergic response in animals having allergic dermatitis or the ability of a homologue to act as an anti-coagulant) and/or by hybridization with isolated ectoparasite saliva protein nucleic acids under stringent conditions.

One embodiment of the present invention is an ectoparasite saliva protein nucleic acid molecule capable of encoding at least a portion of a flea saliva product, or a homologue thereof (e.g., saliva products of other ectoparasites), contained in the saliva extracts FS-1, FS-2 or FS-3, wherein FS-1, when submitted to HPLC, resolves into peak A, peak B, peak C, peak D, peak E, peak F, peak G, peak H, peak I, peak J, peak K, peak L, peak M and/or peak N. A preferred nucleic acid molecule is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM (H), fspM(I), fspM(J), fspM(K), fspM(L), fspM(M), fspN (B), fspN(C), fspN(D), fspN(E), fspN(F), fspN(G), fspN(H), fspN(I), fspN(J), fspN(K), fspN(L), fspN(M), fspN(N) and/ or fspN(O), or homologues thereof. As such, preferred nucleic acid molecules include, but are not limited, nucleic acid molecules that encode proteins having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:83, SEQ ID NO:84, SEQ ID NO:85, SEQ ID NO:86, SEQ ID NO:87, SEQ ID NO:89, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:101, SEQ ID NO:104, as well as with the complements of any of these sequences or homologues thereof. Such preferred nucleic acid molecules can hybridize to the coding and/or complementary strand.

A preferred nucleic acid molecule of the present invention is capable of hybridizing under stringent conditions to a nucleic acid molecule that encodes at least a portion of a flea saliva product, or a homologue thereof (e.g., saliva products of other ectoparasites), contained in the saliva extracts FS-1, FS-2 or FS-3. Such preferred nucleic acid molecules hybridize to the coding strand and/or to the strand complementary to the coding strand of a nucleic acid molecule that encodes at least a portion of such a flea saliva product or homologue thereof. Also preferred is an ectoparasite saliva protein nucleic acid molecule that includes a nucleic acid sequence having at least about 65 percent, preferably at least about 75 percent, more preferably at least about 85 percent, and even more preferably at least about 95 percent homology with the corresponding region(s) of the nucleic acid sequence encoding at least a portion of a flea saliva product, or a homologue thereof (e.g., saliva products of other ectoparasites), contained in the saliva extracts FS-1, FS-2 or FS-3. A particularly preferred nucleic acid sequence is a nucleic acid sequence having at least about 65 percent, preferably at least about 75 percent, more preferably at least about 85 percent, and even more preferably at least about 95 percent homology with a nucleic acid sequence encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN (C), fspN(D), fspN(E), fspN(F), fspN(G), fspN(H), fspN(I), fspN(J), fspN(K), fspN(L), fspN(M), fspN(N) and fspN(O). As such, also preferred are nucleic acid molecules having at least about 65 percent, preferably at least about 75 percent, more preferably at least about 85 percent, and even more preferably at least about 95 percent homology with a nucleic acid sequence encoding at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:83, SEQ ID NO:84, SEQ ID NO:85, SEQ ID NO:86, SEQ ID NO:87, SEQ ID NO:89, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:101 and/or SEQ ID NO:104.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having a nucleic acid sequence as represented by SEQ ID NO:20, SEQ ID NO:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:79, SEQ ID NO:81, SEQ ID NO:82, or other sequences disclosed herein, or complements thereof. SEQ ID NO:20, a nucleic acid sequence that includes about 60 nucleotides of the apparent gene encoding flea saliva protein fspH, includes about 25 percent of the coding region of fspH. SEQ ID NO:24, a nucleic acid sequence that includes about 573 nucleotides of the apparent gene encoding flea saliva protein fspI, encodes a protein of about 149 amino acids, represented by SEQ ID NO:25. The entire translation product of fspI is apparently about 158 amino acids and is denoted SEQ ID NO:26. SEQ ID NO:32, a 242 bp nucleic acid sequence of the apparent gene encoding flea saliva protein fspH, encodes a protein of about 80 amino acids, which is denoted SEQ ID NO:33. SEQ ID NO:34, a 591 bp nucleic acid sequence of the apparent gene encoding flea saliva protein fspI, encodes a protein of about 155 amino acids, which is denoted SEQ ID NO:35. SEQ ID NO:50, a 646 bp nucleic acid sequence of the apparent gene encoding a fspN flea saliva protein, encodes a protein of about 172 amino acids, which is denoted SEQ ID NO:51. SEQ ID NO:52, a 612 bp nucleic acid sequence of the apparent gene encoding a fspN flea saliva protein, encodes a protein of about 153 amino acids, which is denoted SEQ ID NO:53. SEQ ID NO:55, a 1197 bp nucleic acid sequence of the apparent gene encoding fspN3, encodes a protein of about 398 amino acids, which is denoted SEQ ID NO:56. SEQ ID NO:57, a 565 bp nucleic acid sequence of the apparent gene encoding a fspG4 flea saliva protein, encodes a protein of about 90 amino acids, which is denoted SEQ ID NO:58. SEQ ID NO:59, a 897 bp nucleic acid sequence of the apparent gene encoding a fspM(A) flea saliva protein, encodes a protein of about 157 amino acids, which is denoted SEQ ID NO:60. SEQ ID NO:61, a 2706 bp nucleic acid sequence of the apparent gene encoding a fspM(B) flea saliva protein, encodes a protein of about 900 amino acids, which is denoted SEQ ID NO:62. SEQ ID NO:63, a 414 bp nucleic acid sequence of the apparent gene encoding a fspM(C) flea saliva protein, encodes a protein of about 137 amino acids, which is denoted SEQ ID NO:64. SEQ ID NO:65, a 273 bp nucleic acid sequence of the apparent gene encoding a fspM(D) flea saliva protein, encodes a protein of about 90 amino acids, which is denoted SEQ ID NO:66. SEQ ID NO:67, a 1704 bp nucleic acid sequence of the apparent gene encoding a fspM(E) flea saliva protein, encodes a protein of about 461 amino acids, which is denoted SEQ ID NO:68. SEQ ID NO:69, a 1758 bp nucleic acid sequence of the apparent gene encoding a fspM(F) flea saliva protein, encodes a protein of about 586 amino acids, which is denoted SEQ ID NO:70. SEQ ID NO:71, SEQ ID NO:79, SEQ ID NO:81, SEQ ID NO:82 include the apparent coding regions of nfspM(D), nfspG4, nfspM(A) and nfspM(E), respectively.

Knowing a nucleic acid molecule of an ectoparasite saliva protein of the present invention allows one skilled in the art to make copies of that nucleic acid molecule as well as to obtain a nucleic acid molecule including additional portions of ectoparasite saliva protein-encoding genes (e.g., nucleic acid molecules that include the translation start site and/or transcription and/or translation control regions), and/or ectoparasite saliva protein nucleic acid molecule homologues. Knowing a portion of an amino acid sequence of an ectoparasite saliva protein of the present invention allows one skilled in the art to clone nucleic acid sequences encoding such an ectoparasite saliva protein. In addition, a desired ectoparasite saliva protein nucleic acid molecule can be obtained in a variety of ways including screening appropriate expression libraries with antibodies which bind to ectoparasite saliva proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea saliva protein nucleic acid molecules, preferred cDNA libraries include cDNA libraries made from unfed whole flea, fed whole flea, fed flea midgut, unfed flea midgut, and flea salivary gland. Techniques to clone and amplify genes are disclosed, for example, in Sambrook et al., ibid. The Examples section includes examples of the isolation of cDNA sequences encoding flea saliva proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea saliva product, or a homologue thereof (e.g., saliva products of other ectoparasites), contained in the saliva extracts FS-1, FS-2 or FS-3. A preferred oligonucleotide is capable of hybridizing, under stringent conditions, with a nucleic acid molecule that is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN (C), fspN(D), fspN(E), fspN(F), fspN(G), fspN(H), fspN(I), fspN(J), fspN(K), fspN(L), fspN(M), fspN(N) and fspN(O), or homologues thereof. As such, certain preferred oligonucleotides are capable of hybridizing to a nucleic acid molecule capable of encoding a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:83, SEQ ID NO:84, SEQ ID NO:85, SEQ ID NO:86, SEQ ID NO:87, SEQ ID NO:89, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:101, SEQ ID NO:104, or homologues thereof, such oligonucleotides can hybridize to the coding or non-coding strand of a double-stranded nucleic acid molecule. Certain preferred oligonucleotides are capable of hybridizing to nucleic acid molecules including nucleic acid sequences represented by SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of saliva proteins by ectoparasites. Such therapeutic applications include the use of such oligonucleotides in, for example, antisense-, triplex formation-, ribozyme- and/or RNA drug-based technologies. The present invention, therefore, includes such oligonucleotides and methods to interfere with the production of ectoparasite saliva proteins by use of one or more of such technologies.

The present invention also includes a recombinant vector, which includes an ectoparasite saliva protein nucleic acid molecule of the present invention inserted into any vector capable of delivering the nucleic acid molecule into a host cell. Such a vector contains heterologous nucleic acid sequences, that is nucleic acid sequences that are not naturally found adjacent to ectoparasite saliva protein nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of ectoparasite saliva protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

A preferred nucleic acid molecule to include in a recombinant vector of the present invention is a nucleic acid molecule that encodes at least a portion of at least one flea saliva product, or a homologue thereof (e.g., saliva products of other ectoparasites), contained in the saliva extracts FS-1, FS-2 or FS-3. A particularly preferred nucleic acid molecule to include in a recombinant vector is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM (G), fspM(H), fspM(I), fspM(J), fspM(K), fspM(L), fspM (M), fspN(B), fspN(C), fspN(D), fspN(E), fspN(F), fspN (G), fspN(H), fspN(I), fspN(J), fspN(K), fspN(L), fspN(M), fspN(N) and fspN(O), or homologues thereof. As such, also included are nucleic acid molecules that encode a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, or other sequences disclosed herein, or homologues thereof, and nucleic acid molecules including at least a portion of a nucleic acid sequence represented by SEQ ID NO:20, SEQ ID NO:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:79, SEQ ID NO:81, SEQ ID NO:82, or other sequences disclosed herein, or complements thereof.

In one embodiment, an isolated ectoparasite saliva protein of the present invention is produced by culturing a cell capable of expressing the protein under conditions effective to produce the protein, and recovering the protein. A preferred cell to culture is a recombinant cell that is capable of expressing the ectoparasite saliva protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism.

Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell include nucleic acid molecules that encode at least a portion of a flea saliva product, or a homologue thereof (e.g., saliva products of other ectoparasites), contained in the saliva extracts FS-1, FS-2 or FS-3. Particularly preferred nucleic acid molecules with which to transform a host cell are as disclosed herein for including in recombinant vectors of the present invention.

Suitable host cells to transform include any cell that can be transformed and that can express the introduced ectoparasite saliva protein. Such cells are, therefore, capable of producing ectoparasite saliva proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., E. coli) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an ectoparasite saliva protein.

Expression vectors of the present invention may also contain secretory signals (i.e., signal segment nucleic acid sequences) to enable an expressed ectoparasite saliva protein to be secreted from the cell that produces the protein.

Suitable signal segments include an ectoparasite saliva protein signal segment or any heterologous signal segment capable of directing the secretion of an ectoparasite saliva protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of an ectoparasite nucleic acid molecule of the present invention can enhance the stability during production, storage and/or use of the protein encoded by the nucleic acid molecule. Furthermore, a fusion segment can function as a tool to simplify purification of an ectoparasite saliva protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an ectoparasite saliva protein. Linkages between fusion segments and ectoparasite saliva proteins can be constructed to be susceptible to cleavage to enable straight-forward recovery of the ectoparasite saliva proteins. Fusion proteins are preferably produced by culturing a recombinant cell transformed with a fusion nucleic acid sequence that encodes a protein including the fusion segment attached to either the carboxyl and/or amino terminal end of an ectoparasite saliva protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules that encode at least a portion of a flea saliva product, or a homologue thereof (e.g., saliva products of other ectoparasites), contained in the saliva extracts FS-1, FS-2, or FS-3. Particularly preferred nucleic acid molecules to include in a recombinant molecule are as disclosed herein for including in a recombinant vector of the present invention.

A recombinant cell of the present invention includes any cells transformed with at least one of any nucleic acid molecules of the present invention. A preferred recombinant cell is a cell transformed with at least one nucleic acid molecule that encodes at least a portion of a flea saliva product, or a homologue thereof (e.g., saliva products of other ectoparasites), contained in the saliva extracts FS-1, FS-2 and/or FS-3. A preferred recombinant cell is transformed with at least one nucleic acid molecule that is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N) and fspN(O), or homologues thereof. As such, also included are nucleic acid molecules that encode a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, or other sequences disclosed herein, or homologues thereof, and nucleic acid molecules including at least a portion of a nucleic acid sequence represented by SEQ ID NO:20, SEQ ID NO:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:79, SEQ ID NO:81, SEQ ID NO:82, or other sequences disclosed herein, or complements thereof. Particularly preferred recombinant cells include *E. coli* transformed with at least one of the aforementioned nucleic acid molecules.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce an ectoparasite saliva protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an ectoparasite saliva protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant ectoparasite saliva proteins may either remain within the recombinant cell; be secreted into the fermentation medium; be secreted into a space between two cellular membranes, such as the periplasmic space in E. coli; or be retained on the outer surface of a cell or viral membrane. The phrase "recovering the protein" refers simply to collecting the whole fermentation medium containing the protein and need not imply additional steps of separation or purification. Ectoparasite saliva proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

Ectoparasite saliva proteins are preferably retrieved in "substantially pure" form. As used herein, "substantially pure" refers to a purity that allows for the effective use of the protein as a therapeutic composition or diagnostic. For example, an animal being administered dosages of ectoparasite saliva protein isolated from a recombinant cell of the present invention should exhibit no substantial toxicity from contaminants mixed with the protein.

Ectoparasite saliva products substantially free of contaminating material can be isolated using a saliva collection apparatus of the present invention. A saliva collection apparatus of the present invention is designed to stimulate (i.e., cause) ectoparasites retained in the container to feed, and thereby to release saliva, which is collected separate from contaminating material.

Ectoparasites attach and feed from warm-blooded host animals. A host animal, as used herein, refers to an animal that ectoparasites can feed from or on. Without being bound by theory, it is believed that ectoparasites, such as fleas, possess heat receptors which enables the ectoparasite to sense a temperature differential between the warm skin of the host and the ambient air. The temperature differential stimulates (i.e., causes) the ectoparasite to feed from the warm surface (i.e., from the warm animal skin). It is also believed that motion, vibration and darkness can be sensed by ectoparasites, thereby encouraging them to feed. An ectoparasite feeds by penetrating the dermis of an animal with its mouthparts, the mouthparts remaining in that position while the ectoparasite secretes saliva to enhance feeding. During feeding, an ectoparasite can release contaminants such as blood proteins and fecal material.

A saliva collection apparatus of the present invention includes a chamber and housing such that a temperature differential between the chamber and housing of the apparatus is maintained which causes or promotes ectoparasites retained in the housing to attempt to feed from the chamber. When ectoparasites housed in such an apparatus attempt to feed in accordance with the present invention, the arthropods release saliva which is collected in such a manner that proteins, and other products, in the saliva are isolated substantially free of contaminating material. In order to collect saliva substantially free of contaminating material, an apparatus of the present invention also includes a collection means to capture saliva on a surface separate from the surface which captures the contaminating material.

A saliva collection apparatus of the present invention can be used to collect saliva from any ectoparasite such as those disclosed herein. Ectoparasites of the present invention can feed on any animal susceptible to ectoparasite infestation (i.e., a host animal), including but not limited to, a wide variety of vertebrates. Preferred host animals include mammals and birds. More preferred host animals include cats, dogs, humans, horses, rabbits, sheep, cattle, swine, goats, raccoons, ferrets, rats and opossums as well as other pets, economic food animals and animals that are hosts for fleas that infest pets and economic food animals. Particularly preferred host animals are cats and dogs.

Particularly preferred ectoparasites of the present invention from which to collect saliva include any suitable species of flea. Preferred fleas include fleas capable of infesting cats and dogs. Newly hatched fleas (i.e., recently emerged from a pupal state) that have not had a first blood meal are preferred for the following reasons: Because newly emerged fleas have not had a first blood meal, such fleas attempt to feed. Since newly emerged fleas have not had a blood meal, they also do not release as much contaminating material as do fed fleas. Newly emerged fleas live longer without a blood meal than do fleas which have had at least one blood meal. It should be noted that fed fleas can also be used with an apparatus of the present invention.

It will be obvious to one of skill in the art that a saliva collection apparatus of the present invention is useful for collecting saliva from any ectoparasite. For the purpose of illustration, a flea saliva collection apparatus of the present invention is described in detail below. Such description is not intended, in any way, to limit the scope of the present invention. It is within the skill of one in the art to collect saliva from other ectoparasites in a straightforward manner based on methods to collect saliva from fleas.

One embodiment of the present invention is a saliva collection apparatus that includes a chamber and a housing operatively connected to an interface in such a manner that a temperature differential is maintained between the chamber and the housing. The interface includes a collection means and a barrier means positioned such that, in order to attempt to feed, flea mouthparts penetrate the barrier means prior to the collection means. The temperature differential between the chamber and the housing is a difference in temperature suitable to attract fleas retained in the housing to attempt to feed through the interface and, thereby deposit saliva products on the collection means. Due to the relative positioning of the collection means and the barrier means, contaminating material is deposited on the barrier means.

A flea saliva collection apparatus of the present invention includes a housing. A housing can comprise any material capable of retaining fleas that provides structural support and that can be connected to a retaining means. The housing is preferably made of a material capable of withstanding cleaning and/or sterilization procedures commonly used by those skilled in the art. As such, the housing can be reused. Preferred housing materials of the present invention include, but are not limited to, plastic, metal, rubber, wood and glass materials and combinations of such materials. More preferred housing materials include plastic and metal materials with plastic materials being even more preferred. Preferred plastic materials include plexiglass, teflon, nylon and polycarbonate. A particularly preferred plastic material is plexiglass, or other durable, break-resistant plastic, preferably clear so as to allow viewing of fleas inside the container.

In accordance with the present invention, the size of a housing of the present invention is such that the housing can support a desired number of fleas without overcrowding. Both surface area and the volume of the housing can be important. The size of the housing can vary according to the number of fleas to be retained in the housing. Preferably, the size of the housing is sufficient to maintain from about 1,000 fleas to about 6,000 fleas per housing for about 72 hours, more preferably from about 2,000 fleas to about 5,000 fleas per housing for about 72 hours, and even more preferably from about 3,000 fleas to about 4,000 fleas per housing for about 72 hours.

A suitable height for a housing of the present invention is a height that is sufficiently high to allow room for fleas to move about while feeding. The height of a housing for fleas is preferably from about 1.0 centimeters (cm) to about 3.0 cm, more preferably from about 1.5 cm to about 2.5 cm, and even more preferably from about 1.8 cm to about 2.2 cm.

The shape of a housing of the present invention can be any shape having at least one flat surface suitable for feeding by fleas contained within the housing. A housing of the present invention is preferably shaped as a cylinder, a box having four or more sides, a half-dome, or a half cylinder. A particularly preferred shape is a short cylinder.

The diameter of a preferred housing of the present invention can vary widely. Different diameter containers can be used according to, for example, the number of fleas to be placed into the housing without overcrowding. The interior diameter of a rounded housing of the present invention is preferably from about 4.0 cm to about 5.5 cm, more preferably from about 4.5 cm to about 5.5 cm, and even more preferably about 5.0 cm.

According to the present invention, the size, shape, height, and diameter of the housing can vary for different ectoparasites depending upon the size and number of arthropods retained in the housing.

In accordance with the present invention, a housing is operatively connected to a retaining means and an exchange means. As used herein, "operatively connected" refers to combining portions of a saliva collection apparatus of the present invention in such a manner that fleas can be retained within the apparatus and can deposit saliva on the collection means. A retaining means of the present invention is penetrable by the mouthparts of fleas. A retaining means of the present invention can comprise any material or combination of materials that is suitable for retaining fleas and through which fleas can feed (i.e., the retaining means is penetrable by flea mouthparts). As such, the retaining means may comprise a material having openings sufficiently large (i.e., large enough) for flea mouthparts to penetrate, but sufficiently small (i.e., small enough) so as to effectively prevent loss of any fleas retained therein. Preferred retaining means comprise a material having openings of from about 0.25 millimeters (mm) to about 0.50 mm, more preferably having openings of from about 0.30 mm to about 0.50 mm, and even more preferably having openings of from about 0.35 mm to about 0.45 mm. One of skill in the art will recognize that the size of the openings can vary according to the type of ectoparasite retained in the housing of an apparatus. For example, maintenance of particularly small ectoparasites such as, but not limited to, lice may require retaining means having smaller openings. Conversely, a retaining means for hard ticks, which are ectoparasites that cement their mouthparts into the host animal, require larger openings, preferably in the range of about 1 mm.

Preferred materials for use as retaining means include, but are not limited to, metallic mesh, nylon mesh, plastic film, cloth and combinations of such materials. More preferred retaining means include nylon mesh and metal mesh, and an even more preferred retaining means includes nylon mesh. The collection apparatus can be retrofitted with a variety of retaining means. Preferred retaining means are reusable.

An exchange means of the present invention can comprise any material or combination of materials capable of maintaining a permissive environment for fleas within the housing by allowing the exchange of gas, humidity and heat between the interior environment of the housing and the environment exterior to the housing. The housing can be retrofitted with different exchange means having different gas, humidity and heat permeabilities. As used herein, the term gas refers to any atmospheric gases required for flea survival, including, but not limited to, carbon dioxide, oxygen, and nitrogen. Gas can also refer to gaseous products produced by fleas while maintained in a housing of the present invention, such as gaseous products of metabolism including expirations or gases from feces.

Exchange means of the present invention are comprised of materials having openings that are sufficiently large to allow gas, heat and humidity to escape, but sufficiently small so as to effectively prevent loss of fleas. Preferred exchange means comprise a material having openings of from about 0.10 millimeters (mm) to about 0.45 mm, more preferably having openings of from about 0.10 mm to about 0.30 mm, and even more preferably having openings of from about 0.13 mm to about 0.15 mm.

Preferred materials to use as an exchange means include, but are not limited to, metallic mesh, nylon mesh, plastic, cloth and combinations of such materials. More preferred exchange means include nylon mesh, metal mesh, and combinations of such materials and an even more preferred exchange means includes nylon mesh. Preferred exchange materials are reusable.

In accordance with the present invention, an apparatus includes a chamber operatively connected to a housing. A chamber of the present invention is capable of maintaining an internal temperature suitable to create a temperature differential between a housing and a chamber of an apparatus which promotes deposition of saliva by fleas retained in the housing on a collection means of an apparatus. A preferred chamber is also capable of maintaining an internal humidity level suitable for the survival of ectoparasites contained in the apparatus (e.g., suitable to prevent desiccation of the ectoparasites). A chamber of the present invention is also capable of being attached to an artificial feeding system as described in detail in the Examples. A chamber can comprise any material capable of maintaining suitable temperature and humidity levels within the chamber. A chamber is preferably made of a material capable of withstanding cleaning or sterilization procedures commonly used by those skilled in the art. As such, a chamber can be reused. Preferred chamber materials of the present invention include, but are not limited to, glass, plastic, metal, rubber, and wood materials and combinations of such materials. More preferred chamber materials include glass and plastic materials with glass materials being even more preferred.

In accordance with the present invention, the size of a chamber of the present invention is such that the chamber can maintain a suitable temperature level to stimulate fleas to deposit saliva on the collection means of the apparatus. The size of the chamber can vary according to the amount of blotting material (as described in detail below) to be placed in the chamber, the diameter of the collection means to be attached to the chamber or whether the chamber is to be attached to an artificial feeding system as described in detail in the Examples. Preferably, the height of a chamber of the present invention is high enough to allow a suitable amount of blotting material to be placed in the chamber, such that the blotting material maintains a humidity level in the chamber suitable for flea survival. The height of a chamber is preferably from about 1.0 cm to about 7.0 cm, more preferably from about 2.0 cm to about 6.0 cm, and even more preferably from about 3.0 cm to about 5.0 cm.

In accordance with the present invention, the shape of a chamber can be any shape having at least one open end to which an interface of the present invention can be attached. A chamber of the present invention is preferably shaped as a cylinder open at both ends or a cylinder open at one end. A particularly preferred shape is a cylinder open at both ends.

The diameter of a preferred chamber of the present invention can vary widely. Different diameter chambers can be used according to, for example, the diameter of the interface to be attached to the chamber or the diameter of the housing to be attached to the chamber. The interior diameter of a chamber of the present invention is preferably from about 2.0 cm to about 6.5 cm, more preferably from about 3.0 cm to about 5.5 cm, and even more preferably from about 4.0 cm to about 4.5 cm.

A chamber of the present invention can contain a blotting means suitable for maintaining a humidity level in the chamber suitable for flea survival. Methods for maintaining suitable humidity levels are described in detail below. A chamber of the present invention can contain food or water, but preferably is humid (i.e., damp but not wet) and does not contain food.

A saliva collection apparatus of the present invention includes an interface. An interface of the present invention includes means capable of collecting saliva products substantially free of contaminating material. As such, an interface of the present invention is penetrable by flea mouthparts but capable of keeping contaminating material, such as blood and fecal material, separate from flea saliva products secreted by fleas as they attempt to feed. An interface of the present invention comprises a means for collecting saliva products and a means for creating a barrier between contaminating material and collected saliva products.

A collection means of the present invention can be of any material capable of collecting (i.e., adsorbing) at least a portion of saliva proteins deposited (i.e., secreted) by retained fleas that are attempting to feed through the interface. In addition, a collection means of the present invention is capable of collecting saliva components other than saliva proteins deposited by fleas attempting to feed through the interface. The collection means is such that saliva products not only can bind to the collection means but also can be eluted (i.e., extracted) therefrom upon exposure to a suitable eluent (i.e., extractant). As such, preferred collection means materials of the present invention include materials that are hydrophobic and have a low binding capacity since saliva components are easily eluted from such material. The material of a collection means of the present invention should also be capable of being penetrated by the mouthparts of fleas.

Preferred collection means materials of the present invention include, but are not limited to, nylon, nitrocellulose, CM-derivatized, diethylaminoethyl (DEAE)-derivatized, paper, polysulfone, cellulose ester, polytetrafluoroethylene (PTFE) and polyvinylidene fluoride (PVDF) membranes. A particularly preferred anion exchange membrane collection means material includes DE-81 chromatography paper, which can be obtained from Whatman, Inc., Clifton, N.J. Particularly preferred collection means materials include PVDF. A preferred PVDF collection means material includes Durapore™.

The shape of a collection means of the present invention can vary according to the shape of the chamber to which the collection means is to be attached. A preferred shape of a collection means includes, but is not limited to, a round shape or a box-like shape having four or more sides, with a round shape being more preferred.

The size of a collection means of the present invention can also vary according to the size of the chamber to which the collection means is to be attached. The size of a collection means is preferably larger than the open end of a chamber, thereby preventing the collection means from passing into the chamber. The size of a collection means is preferably from about 2.2 cm to about 6.5 cm in diameter, more preferably from about 3.2 cm to about 5.7 cm, and even more preferably from about 4.2 cm to about 4.7 cm.

A saliva collection apparatus of the present invention provides for a novel barrier means which enables collection of ectoparasite saliva substantially free of contaminating material. A barrier means of the present invention can be any material capable of substantially preventing contaminating material from contacting the collection means (i.e., substantially prevents the passage of contaminating material such as flea fecal material and blood products through the collection means), but is also capable of being penetrated by the mouthparts of fleas and of allowing the passage of saliva through the barrier means. Preferably, the thickness of a barrier means material of the present invention is microns thick. Preferred barrier means materials of the present invention include, but are not limited to, very thin plastic, teflon, cloth, paper, paraffin and wax materials. More preferred barrier means materials of the present invention include stretched plastic, with Saran Wrap™ and particularly Parafilm™, stretched very thin (i.e., as thin as can be stretched by machine and/or hand), being even more preferred.

The size of a barrier means of the present invention can vary according to the size of the chamber to which the barrier means is to be attached. The size of the barrier means preferably is sufficiently large that the barrier means can extend up the sides of a chamber of the present invention, thereby enabling the barrier means to be secured to the chamber. The size of the barrier means is sufficiently small such that the barrier means does not interfere with, for example, the ability of the saliva collection apparatus containing the chamber to be attached to an artificial feeding system.

According to the present invention, a collection means and a barrier means are operatively connected to a chamber of a saliva collection apparatus in such a manner that fleas retained in the housing of such apparatus are capable of penetrating both the barrier means and the collection means to deposit saliva on the collection means. A collection means of the present invention preferably is removably attached to a site on a chamber by a barrier means. A preferred site of attachment of a collection means and a barrier means is the portion of a chamber designed to interface with a housing. A more preferred site of attachment of a collection means and a barrier means is the open end of a chamber.

A saliva collection apparatus of the present invention can also include a blotting means. A blotting means of the present invention is capable of maintaining a humidity within the apparatus suitable for flea survival and, as such, is capable of retaining liquid for the period of time fleas are retained in the apparatus. As such, a blotting means can be any suitable absorbent material. Preferred blotting means include natural and synthetic sponges, foam, paper, cloth, and agarose. More preferred blotting means material include sponges and paper, with filter paper being even more preferred. In a particularly preferred embodiment, one or more pieces of VWR Blotting Pads #320 (available from VWR Scientific, Denver, Colo.) comprise a blotting means.

As stated above, a saliva collection apparatus of the present invention is capable of maintaining a temperature differential between a housing and a chamber of the apparatus. A suitable temperature differential within an apparatus of the present invention includes a temperature differential which stimulates fleas retained in the apparatus to penetrate the interface of the apparatus and deposit saliva on the collecting means. Preferred temperatures in a chamber of the present invention range from about 20° C. to about 45° C., whereas preferred temperatures in a housing of the present invention range from about 5° C. to about 35° C. In a preferred embodiment, the temperature in the chamber ranges from about 35° C. to about 40° C. and the temperature in the housing ranges from about 10° C. to about 30° C. A particularly preferred chamber temperature ranges from about 35° C. to about 37° C.; and a particularly preferred housing chamber temperature is from about 20° C. to about 27° C.

The survival of ectoparasites can be affected by humidity. As such, the humidity level in a housing of an apparatus of the present invention is suitable for maintaining the survival of ectoparasites retained therein. Suitable relative humidity levels within an apparatus of the present invention can vary depending upon the ectoparasite contained within the apparatus. As used herein, relative humidity refers to the degree of atmospheric water vapor relative to the maximum degree of atmospheric water vapor that results in precipitation. Thus, relative humidity is expressed in percent humidity, wherein 100% humidity represents saturation of atmospheric water vapor. Preferred humidity levels in a chamber of the present invention range from about 50% to about 100%, whereas preferred humidity levels in a housing of the present invention range from about 40% to about 60%. In a preferred embodiment, the humidity levels in the chamber ranges from about 50% to about 94% and the humidity level in the housing is about 50%.

Another embodiment of the present invention is the use of contrasting colors to attract fleas. For example, at least one surface of a collection apparatus of the present invention can be of a color sufficiently dark to attract fleas to penetrate the interface of the apparatus. Without being bound by theory, it is believed that fleas are capable of sensing light from dark and preferably tend to feed towards a dark surface. Therefore, according to the present invention, a chamber can be darker than a housing, thereby attracting fleas to the interface between the chamber and the housing. Suitable dark colors include colors ranging from black to light brown, preferably black.

Figure 4A:
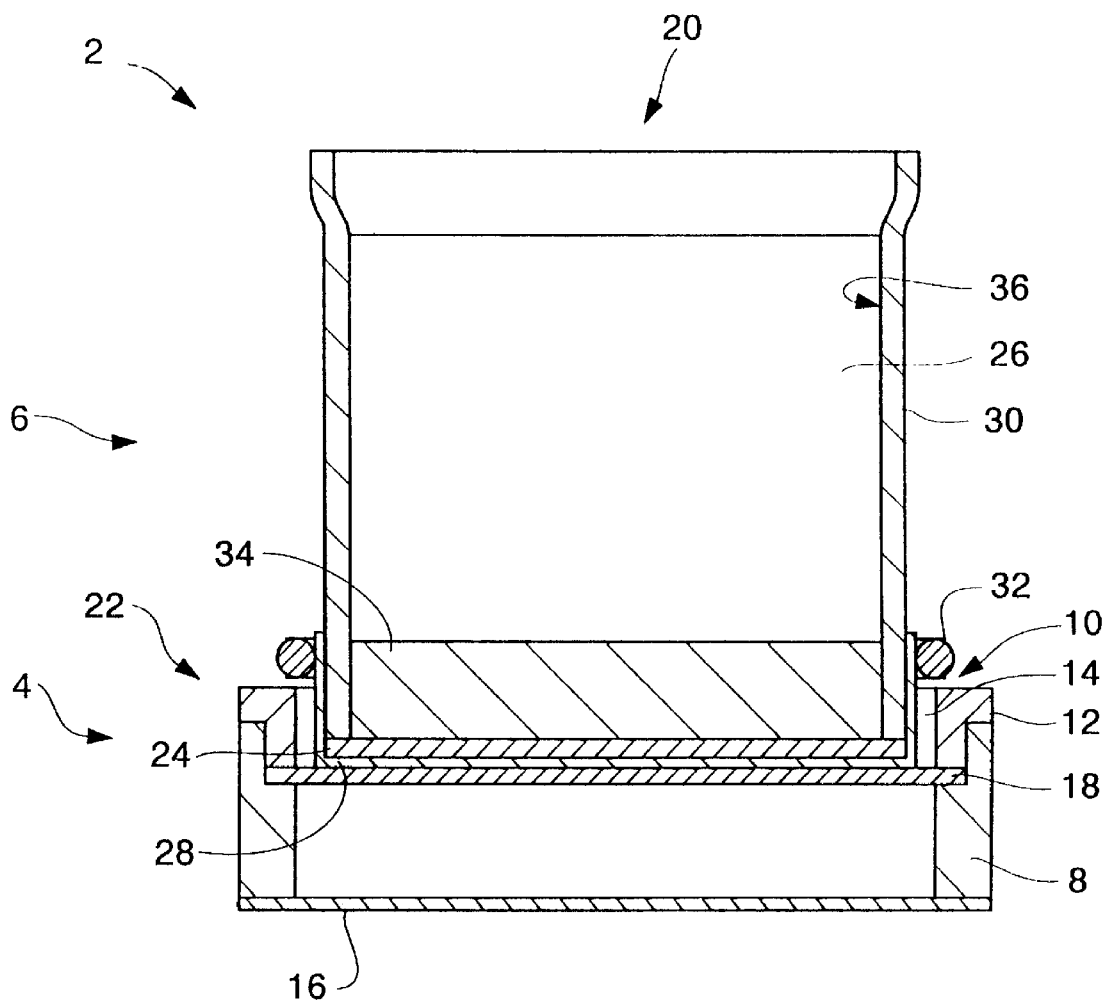
FIG. 4A illustrates a cross-section of a flea saliva collection apparatus of the present invention.
Figure 4B:
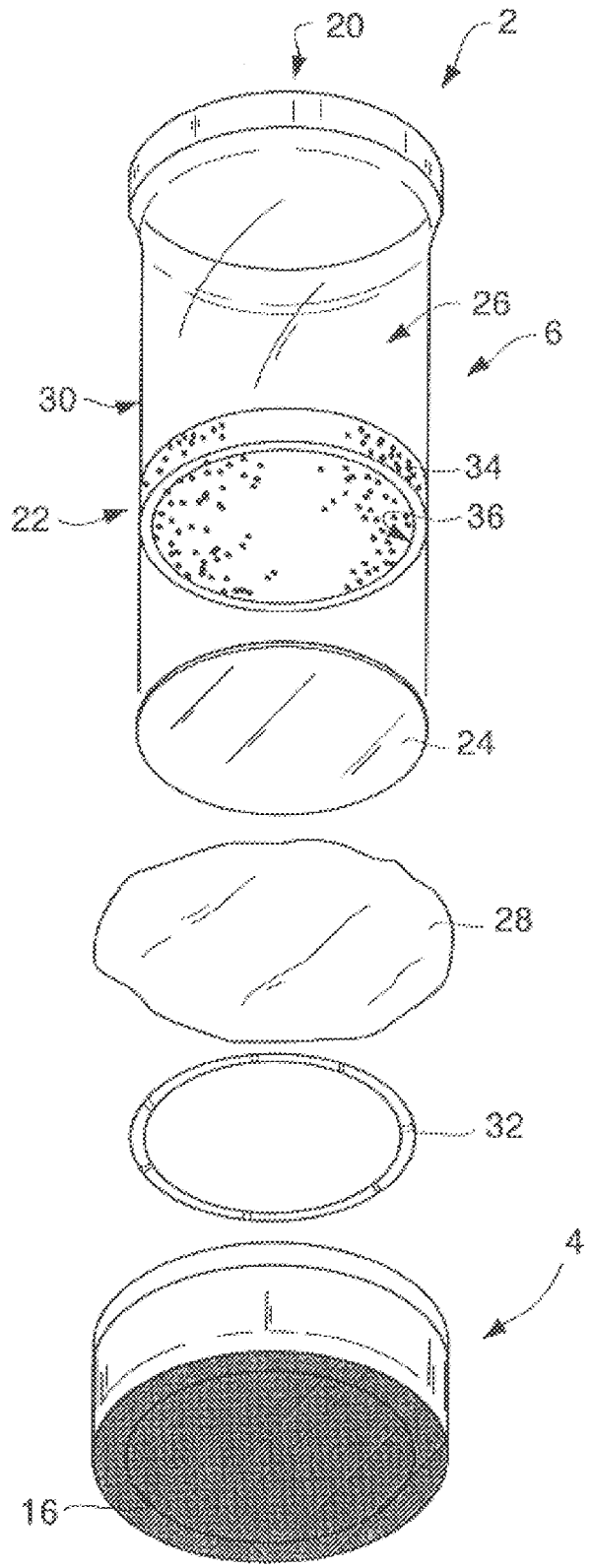
FIG. 4B illustrates a blow-out of a flea saliva collection apparatus of the present invention.

A preferred embodiment of a collection apparatus of the present invention is depicted in FIGS. 4A and 4B. A saliva collection apparatus (2) is separable into a housing (4) and a chamber (6). A cross-section of a saliva collection apparatus of the present invention (2) is shown in FIG. 4A. Referring to FIGS. 4A and 4B, the housing (4) has an open-ended cylinder having a first portion (8) and a second portion (10). The second portion (10) of the housing (4) has an outer diameter (12) and an inner diameter (14). An exchange means (16) is operatively attached to one end of the first portion (8) of the housing (4) and a retaining means (18) is attached at the opposite end of the first portion (8), between the first portion (8), and the outer diameter (12) and inner diameter (14) of the second portion (10). The exchange means (16) and retaining means (18) are attached in a manner that prevents fleas from escaping. Means of attaching an exchange means (16) and a retaining means (18) to the first portion (8) of the housing (4) include, but are not limited to, rubber cement, glue, tape, solder and araldite. A preferred means of attachment is rubber cement.

The chamber (6) of the saliva collection apparatus (2) has an open ended cylinder having a top end (20) and a bottom end (22). The top end (20) has a suitable diameter to enable the attachment of the chamber (6) to an artificial feeding system such as that described in detail in the Examples. The bottom end (22) has a suitable diameter such that the bottom end (22) can be reversibly attached to the housing (4) in such a manner as to provide a sliding fit. The bottom end (22) is covered by a collection means (24). The collection means (24) has a larger diameter than the inner circumference of the bottom end (22) of the chamber (6), thereby preventing the collection means (24) from passing into the inner space (26) of the chamber (6). Preferably, the diameter of the collection means (24) is not greater than the outer circumference of the bottom end (22) of the chamber (6). The collection means (24) can be connected to the bottom end (22) in order to provide a detachable connection, thereby facilitating removal of the collection means (24) from the saliva collecting apparatus (2) to recover saliva products from the collection means (24).

A collection means (24) attached to the bottom end (22) of a chamber (6) is covered by a barrier means (28). The barrier means (28) is operatively connected to a chamber (6) in such a manner that a seal is formed preventing contact of the collection means (24) by contaminating material deposited by fleas. The barrier means (28) can be connected to the chamber (6) in order to provide a detachable connection. Preferably, the barrier means (28) comprises a stretchable plastic material, such as Parafilm™, which is stretched as thin as possible across a collection means (24) contacting the bottom end (22) of a chamber (6) and further stretched along the sidewall (30) of the chamber (6) towards the top end (20) of the chamber (6). The barrier means (28) can be further secured to the sidewall (30) of the chamber (6) using a rubber seal (32). The rubber seal (32) detachably connects the portion of the barrier means (28) which meets the sidewall (30) of the chamber (6), thereby further securing the collection means (24) to the chamber (6) and seal in the chamber (6) environment.

Blotting (absorbent) material can be placed in the inner space (26) at the bottom end (22) of a chamber (6) to form a blotting means (34). The blotting means (34) can comprise one or more individual blotting pads (e.g., pieces of blotting material). Preferably, the blotting means (34) is from about 2.0 mm thick to about 15.0 mm thick (when dry) when placed in a 47 cm high chamber (6), more preferably is from about 2.2 mm thick to about 12.5 mm thick (when dry) when placed in a 47 mm high chamber (6), and even more preferably is from about 2.45 mm thick to about 10.0 mm thick (when dry) when placed in a 47 mm high chamber (6). In a particularly preferred embodiment, the blotting means (34) comprises from about 2 to 6 pieces of VWR Blotting Pads #320, and preferably from about 3 to 5 pieces of VWR Blotting Pads #320. The diameter of the blotting means (34) is selected to contact the inner sidewall (36) of the chamber (6). The blotting means (34) is preferably sufficiently pre-wetted to provide humidity to the chamber (6) but not so wet that liquid drips from the blotting means (34). The blotting means (34) is juxtaposed to the side of the collection means (24) facing the top end (20) of the chamber (6). The blotting means (34) can directly contact the collection means (24) in a detachable manner.

The chamber (6) is reversibly separable from the housing (4). The chamber (6) can be interconnected to the housing (4) in any reversibly secure manner such as sliding, snapping or screwing together. Preferably, the chamber (6) slides into the housing (4) and is secured using rubber bands.

The relative height dimensions of the chamber (6) can vary relative to the housing (4). Typically, the height dimension of the chamber (6) is greater than the housing (4). Preferably, the height of the chamber (6) ranges from about 1.0 cm to about 7.0 cm, more preferably from about 2.0 cm to about 6.0 cm, and even more preferably the from about 3.0 cm to about 5.0 cm. The height of the housing (4) preferably ranges from about 1.0 cm to about 3.0 cm, more preferably from about 1.5 cm to about 2.5 cm, and even more preferably from about 1.8 cm to about 2.2 cm.

One embodiment of the present invention is a method to collect saliva products from ectoparasites using an apparatus of the present invention. Such a method is particularly advantageous because it enables isolation of ectoparasite saliva, including saliva proteins, substantially free of contaminating material. As such, the method can be used, for example, to characterize ectoparasite saliva proteins and to isolate ectoparasite saliva proteins for diagnostic and therapeutic use.

One embodiment of the present method includes the steps of: (a) collecting ectoparasite saliva products on a collection means within a saliva collection apparatus which contains ectoparasites in the housing of the apparatus; and (b) extracting (i.e., eluting) the collected ectoparasite saliva products from the collection means with a solution to form an extracted product-containing solution. Such an extracted solution can be used directly as a formulation of the present invention or can be submitted to further steps of fractionation and/or purification as described in detail herein, to form additional formulations of the present invention. Examples of such extracted solutions include FS-1, FS-2 and FS-3.

In accordance with the present invention, a saliva collection apparatus containing the ectoparasites has an interface between the chamber and the housing comprising a collection means capable of collecting at least a portion of saliva products deposited by ectoparasite retained in the apparatus and a barrier means capable of substantially preventing contaminating material from contacting the collection means. The ectoparasites contained in the apparatus are maintained under conditions such that there is a temperature differential between the chamber and the housing; that is, the chamber of the apparatus has a temperature warmer than the temperature of the housing containing the ectoparasite, such that the warmer temperature in the chamber attracts the ectoparasites retained in the housing to attempt to penetrate the barrier means and collection means, thereby depositing saliva products on the collection means.

In one embodiment, the method of collecting saliva products includes pre-wetting a collection means of the present invention prior to positioning the collection means in an apparatus of the present invention. A pre-wetting solution suitable for the present invention is capable of facilitating the adsorption (i.e., collection) of saliva products in such a manner that the products can also be extracted during an extraction step (i.e., when exposed to an appropriate solvent). A suitable pre-wetting solution of the present invention includes any buffer that is non-toxic to ectoparasites and has a physiological pH. Examples of suitable buffers include, phosphate buffered saline, water, phosphate buffer, HEPES buffer (N-2-hydroxyethylpiperazine-N'2-ethanesulfonic acid buffered saline), TES buffer (Tris-EDTA buffered saline), Tris buffer and TAE buffer (Tris-acetate-EDTA). A preferred prewetting solution includes sterile water containing 50 U/ml penicillin and 50 µg/ml streptomycin.

When an apparatus used to collect saliva products includes a blotting means, that blotting means should be moistened either prior to or following placement of the blotting means into the chamber. Preferred moistening solutions include, but are not limited to, water, phosphate buffered saline, phosphate buffer, tris buffer, HEPES buffer, TEA buffer and TES buffer. More preferred moistening solutions include water and 50 U/ml penicillin and 50 µg/ml streptomycin. According to the present invention, a blotting means is sufficiently moistened to produce humidity in a chamber but not to drip liquid from which ectoparasites retained in the apparatus can drink. In a preferred embodiment, a blotting means which is about 4.0 cm in diameter and about 2.5 mm thick is moistened with about 2.3 milliliters (ml) of moistening solution.

In one embodiment, a pre-determined number of ectoparasites are introduced into the housing of an apparatus of the present invention. The number of ectoparasites to be introduced into a housing can vary with the size of the housing and should be a number that will not hinder the ability of an ectoparasite to deposit saliva on a collection means of the present invention.

In a preferred embodiment of the present invention, fleas are added to an apparatus of the present invention. Suitable and preferred numbers of fleas to introduce into a housing are heretofore disclosed. In particular, fleas newly emerged from the pupal stage are used. Such fleas can be raised as described in Wade et al., pp 186–190, 1988, *J.Med Entomol.,* vol 25. Preferably, such fleas have not had a blood meal. Fleas can be loaded into an apparatus by placing the fleas in an aquarium and aspirating them into the housing under vacuum. Additional optional components suitable for the maintenance of fleas can be added to the container, such as animal hair, and dry tissue.

In a preferred embodiment, at least one apparatus of the present invention having fleas contained in the housing of the apparatus is attached to an artificial feeding system such as disclosed herein. The apparatus can remain attached to the feeding system as long as fleas continue to release saliva while penetrating a collection means. Preferably, fleas are maintained in the apparatus attached to the feeding system from about 12 hours to about 120 hours, more preferably from about 24 hours to about 96 hours, and even more preferably for about 72 hours since fleas essentially stop secreting saliva by about that time. In accordance with the method of the present invention, preferably at least about 80 micrograms (µg), more preferably at least about 90 µg and even more preferably at least about 200 µg, of flea saliva protein can be collected from about $10^6$ flea-hour when measured using a Bio-Rad Bradford assay (available from Bio-Rad, Hercules, Calif.).

According to the present invention, ectoparasite saliva products can be extracted using a solvent capable of extracting saliva products from a collection means of the present invention, preferably in a form such that the functional activities of the eluted products are maintained. If functional activity of flea saliva proteins, for example is not maintained, it is within the scope of the invention to refold proteins to regain functionality using techniques known to those of skill in the art. Suitable extraction solvents include, but are not limited to, phosphate buffered saline, phosphate buffered saline containing sodium chloride, TFA in acetonitrile, chaotropic agents, detergents, organics, salts or combinations thereof. Preferred extraction solvents include phosphate buffered saline, phosphate buffered saline containing sodium chloride, acetonitrile and TFA in acetonitrile. More preferred extraction solvents include 1M NaCl in phosphate buffered saline, 0.1% TFA in 50% acetonitrile, 1% TFA in 50% acetonitrile, 12.8% acetonitrile and 50% acetonitrile. Suitable extraction times for eluting proteins and other products from a collection means are described in detail in the Examples.

Further purifications of saliva proteins extracted from a collection means of the present invention can be performed by fractionating the extracted product-containing solution to obtain separated peak fractions and recovering at least one of the peak fractions substantially free of the remaining fractions to obtain a formulation of ectoparasite saliva proteins. In a preferred embodiment, proteins contained in extracted saliva products of the present invention are further resolved by submitting the extract to HPLC purification to obtain peak fractions. In a particularly preferred embodiment, extracted saliva proteins of the present invention are further resolved by HPLC to obtain the peak fractions shown in FIG. 2. Details regarding the extraction and resolution of such proteins are presented in the Examples.

According to the present invention, a formulation comprising at least one ectoparasite saliva product of the present invention or a mimetope thereof, can be used to identify animals that are susceptible to or have allergic dermatitis.

In accordance with the present invention, a "mimetope" refers to any compound that is able to mimic the ability of an isolated ectoparasite saliva product of the present invention to carry out its function (e.g., anti-coagulation, anti-complement, vasodialators, proteases, acid phosphatases or detecting and/or treating the hypersensitivity of an animal susceptible to or having allergic dermatitis). A mimetope can be a peptide that has been modified to decrease its susceptibility to degradation but that still retains the desired activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. Mimetopes of the present invention can also include non-proteinaceous portions of ectoparasite saliva products having allergenic and/or antigenic activity (e.g., carbohydrate moieties associated with ectoparasite saliva proteins). A mimetope can be obtained by, for example, screening libraries of synthetic compounds for compounds capable of altering the ability of ectoparasites to feed, or of detecting and/or treating allergic dermatitis resulting from the bites of ectoparasites. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

One embodiment of the present invention is an in vivo test that is capable of detecting whether an animal is hypersensitive to ectoparasite saliva products. An in vivo test of the present invention can initially be used to determine if an animal is hypersensitive to ectoparasite saliva products and then used to determine if an animal is hypersensitive to a particular ectoparasite saliva component, in particular to an ectoparasite saliva protein. An in vivo hypersensitivity test of the present invention is particularly useful for identifying animals susceptible to or having allergic dermatitis. An in vivo hypersensitivity test of the present invention is even more useful for identifying animals susceptible to or having FAD. A suitable in vivo hypersensitivity test of the present invention can be, but is not limited to, a skin test comprising administering (e.g., intradermally injecting or superficial scratching) an effective amount of a formulation containing at least one ectoparasite saliva product, or a mimetope thereof. Methods to conduct skin tests of the present invention are known to those of skill in the art and are briefly disclosed herein.

Suitable formulations to use in an in vivo skin test include ectoparasite saliva components (i.e., saliva products collected on, and remaining absorbed to, a collection means of the present invention, ectoparasite saliva extracts, and one or more isolated ectoparasite saliva proteins). A preferred formulation includes extracts and one or more isolated proteins.

A suitable amount of ectoparasite saliva product for use in a skin test of the present invention can vary widely depending on the allergenicity of the product used in the test and on the site at which the product is delivered. Suitable amounts of ectoparasite saliva products for use in a skin test of the present invention include an amount capable of forming reaction, such as a detectable wheal or induration (hardness) resulting from an allergic reaction to the product. Preferred amounts of ectoparasite saliva extracts or proteins for use in a skin test of the present invention range from about 1 nanogram (ng) to about 500 micrograms ($\mu$g), more preferably from about 5 ng to about 300 $\mu$g, and even more preferably from about 10 ng to about 50 $\mu$g of ectoparasite saliva extracts or proteins. It is to be appreciated by those of skill in the art that such amounts will vary depending upon the allergenicity of the extracts and/or protein(s) being administered.

According to the present invention, ectoparasite saliva products of the present invention can be combined with an immunopotentiator (e.g., carriers or adjuvants of the present invention as defined in detail below). A novel aspect, however, of the present invention is that an ectoparasite saliva product of the present invention can induce a hypersensitive response in the absence of an immunopotentiator.

A skin test of the present invention further comprises administering a control solution to an animal. A control solution can include a negative control solution and/or a positive control solution. A positive control solution of the present invention contains an effective amount of at least one compound known to induce a hypersensitive response when administered to an animal. A preferred compound for use as positive control solution includes, but is not limited to, histamine. A negative control solution of the present invention can comprise a solution that is known not to induce a hypersensitive response when administered to an animal. As such, a negative control solution can comprise a solution having compounds essentially incapable of inducing a hypersensitive response or simply a buffer used to prepare the formulation, such as saline. An example of a preferred negative control solution is phenolated phosphate buffered saline (available from Greer Laboratories, Inc., Lenoir, N.C.).

Hypersensitivity of an animal to one or more formulations of the present invention can be evaluated by measuring reactions (e.g., wheal size, induration or hardness; using techniques known to those skilled in the art) resulting from administration of one or more experimental sample(s) and control sample(s) into an animal and comparing the reactions to the experimental sample(s) with reactions resulting from administration of one or more control solution. Preferred devices for intradermal injections include individual syringes. Preferred devices for scratching include devices that permit the administration of a number of samples at one time. The hypersensitivity of an animal can be evaluated by determining if the reaction resulting from administration of a formulation of the present invention is larger than the reaction resulting from administration of a negative control, and/or by determining if the reaction resulting from administration of the formulation is at least about the same size as the reaction resulting from administration of a positive control solution. As such, if an experimental sample produces a reaction greater than or equal to the size of a wheal produced by administration of a positive control sample to an animal, then that animal is hypersensitive to the experimental sample. Conversely, if an experimental sample produces a reaction similar to the reaction produced by administration of a negative control sample to an animal, then that animal is not hypersensitive to the experimental sample.

Preferred wheal sizes for evaluation of the hypersensitivity of an animal range from about 16 mm to about 8 mm, more preferably from about 15 mm to about 9 mm, and even more preferably from about 14 mm to about 10 mm in diameter.

Preferably, the ability or inability of an animal to exhibit an immediate hypersensitive response to a formulation of the present invention is determined by measuring wheal sizes from about 2 minutes to about 30 minutes after administration of a sample, more preferably from about 10 minutes to about 25 minutes after administration of a sample, and even more preferably about 15 minutes after administration of a sample.

Preferably, the ability or inability of an animal to exhibit a delayed hypersensitive response to a formulation of the present invention is determined by measuring induration and/or erythema from about 18 hours to about 30 hours after administration of a sample, more preferably from about 20 hours to about 28 hours after administration of a sample, and even more preferably at about 24 hours after administration of a sample. A delayed hypersensitivity response can also be measured using other techniques such as by determining, using techniques known to those of skill in the art, the extent of cell infiltrate at the site of administration during the time periods defined directly above.

In a preferred embodiment, a skin test of the present invention comprises intradermally injecting into an animal at a given site an effective amount of a formulation that includes flea saliva extracts (i.e., flea saliva products extracted from a collection means of the present invention) or at least one flea saliva protein of the present invention, and intradermally injecting an effective amount of a control solution into the same animal at a different site. It is within the scope of one of skill in the art to use devices capable of delivering multiple samples simultaneously at a number of sites, preferably enabling concurrent evaluation of numerous formulations. One preferred formulation comprises flea saliva products collected in accordance with the present invention. Also preferred are formulations comprising one or more recombinantly produced flea saliva proteins.

Suitable flea saliva products for use with a skin test of the present invention include FS-1, FS-2 and/or FS-3 as well as at least a portion of at least one flea saliva product that can be isolated from FS-1, FS-2 and/or FS-3. A preferred flea saliva product for use with a skin test includes FS-1, FS-2, FS-3 and/or at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N) and fspN(O), or homologues thereof. A more preferred flea saliva product for use with a skin test includes FS-1, FS-2, FS-3 and/or at least a portion of one or more of the proteins fspE, fspF, fspG1, fspG2, fspG3, fspG4, fspH, fspI, fspJ1, fspJ2, fspK, fspL1, fspL2, fspM1, fspM2, fspN1, fspN2 and fspN3. A yet more preferred flea saliva product for use with a skin test includes FS-1, FS-2, FS-3 and/or at least a portion of one or more of the proteins fspG1, fspG2, fspG3, fspG4, fspH, fspM1, fspM2, fspN1, fspN2 and fspN3. Such formulations are shown in the Examples section as being able to induce FAD in dogs. A preferred positive control sample can be a sample comprising histamine. A preferred negative control sample can be a sample comprising diluent.

Animals suitable and preferred to test for hypersensitivity to ectoparasite saliva proteins using a skin test of the present invention are disclosed herein. Particularly preferred animals to test with a skin test of the present invention include dogs, cats and horses, with dogs and cats being even more preferred.

Another embodiment of the present invention is an in vitro immunoabsorbent test that is capable of detecting the presence of an antibody capable of binding to one or more ectoparasite saliva products of the present invention by contacting a putative antibody-containing solution with a solution containing ectoparasite saliva products in such a manner that immunocomplexes can form and be detected. Thus, an in vitro immunoabsorbent test of the present invention is particularly useful for identifying animals susceptible to or having allergic dermatitis by demonstrating that an animal has been previously exposed to an ectoparasite saliva antigen and, therefore may be hypersensitive to further exposure to an ectoparasite saliva antigen.

According to the present invention, an in vitro hypersensitivity test of the present invention can be, but is not limited to, an immunoabsorbent test comprising: (a) contacting a formulation of the present invention with a body fluid from an animal under conditions sufficient for formation of an immunocomplex between the formulation and antibodies, if present, in the body fluid; and (b) determining the amount of immunocomplex formed, wherein formation of the immunocomplex indicates that the animal is susceptible to or has allergic dermatitis. The immunoabsorbent test is particularly useful for the detection of IgE antibodies in the body fluid, thereby indicating immediate hypersensitivity in the animal. Determining the amount of immunocomplex formed can include the step of separating depending on the mode of detection. Immunoabsorbent assays can be a variety of protocols and can be set-up by those of skill in the art.

A preferred immunoabsorbent test of the present invention comprises a first step of coating one or more portions of a solid substrate with a suitable amount of one or more ectoparasite saliva products of the present invention or a mimetope thereof, and of coating one or more other portions of the (or another) solid substrate with a suitable amount of positive and/or negative control solutions of the present invention. A preferred solid substrate of the present invention can include, but is not limited to, an ELISA plate, a dipstick, a radioimmunoassay plate, agarose beads, plastic beads, immunoblot membranes and paper; a more preferred solid substrate includes an ELISA plate, a dipstick or a radioimmunoassay plate, with an ELISA plate and a dipstick being even more preferred. As used herein, a dipstick refers to any solid material having a surface to which antibodies can be bound, such solid material having a stick-like shape capable if being inserted into a test tube. Suitable and preferred flea saliva products for use with an in vitro hypersensitivity test of the present invention are as disclosed for a skin test of the present invention.

A second step of a preferred in vitro hypersensitivity test of the present invention comprises contacting the coated substrate with a body fluid, such as serum, plasma or whole blood, from an animal susceptible to allergic dermatitis in such a manner as to allow antibodies contained in the body fluid that are capable of binding to ectoparasite saliva products to bind to such products bound to the substrate to form immunocomplexes. Excess body fluid and antibodies are then washed from the substrate. In a preferred embodiment in which IgE antibodies in the body fluid are to be measured, the body fluid can be pretreated to remove at least some of the other isotypes of immunoglobulin and/or other proteins, such as albumin, present in the fluid. Such removal can include, but is not limited to, contacting the body fluid with a material, such a Protein G, to remove IgG antibodies and/or affinity purifying the IgE antibodies from other components of the body fluid by exposing the fluid to, for example, Concanavalin A (Con-A).

A third step of a preferred in vitro hypersensitivity test of the present invention comprises contacting the immunocomplexes bound to the substrate with a compound capable of binding to the immunocomplexes, such as a secondary antibody or other compound that is capable of binding to the heavy chain of allergy-related antibodies produced by animals allergic to ectoparasites, in such a manner that the compound(s) can bind to the immunocomplexes. Preferred binding compounds include, but are not limited to, secondary antibodies capable of binding to the heavy chain of IgE antibodies and Fc receptors (FcR) that bind to IgE antibodies (i.e., epsilon FcR), including single chains of an FcR (e.g., the alpha chain of an epsilon FcR), as well as truncated forms with or without transmembrane domains. Preferred animals to test are disclosed herein. Compounds capable of binding to immunocomplexes are usually tagged with a label which enables the amount of compound bound to the antibody from the body fluid to be measured. Such labels include, but are not limited to, a radioactive label, an enzyme capable of producing a color reaction upon contact with a substrate, a fluorescent label, a chemiluminescent label, a chromophoric label or a compound capable of being bound by another compound. Preferred labels include, but are not limited to, fluorescein, radioisotopes, alkaline phosphatases, biotin, avidin, or peroxidases.

A fourth step of a preferred in vitro hypersensitivity test of the present invention comprises measuring the amount of detectable label bound to the solid substrate using techniques known to those of skill in the art. It is within the scope of the present invention that the amount of antibody from the body fluid bound to the substrate can be determined using one or more layers of secondary antibodies or other binding compounds. For example, an untagged secondary antibody can be bound to a serum antibody and the untagged secondary antibody can then be bound by a tagged tertiary antibody.

A hypersensitive animal is identified by comparing the level of immunocomplex formation using samples of body fluid with the level of immunocomplex formation using control samples. An immunocomplex refers to a complex comprising an antibody and its ligand (i.e., antigen). As such, immunocomplexes form using positive control samples and do not form using negative control samples. As such, if a body fluid sample results in immunocomplex formation greater than or equal to immunocomplex formation using a positive control sample, then the animal from which the fluid was taken is hypersensitive to the ectoparasite saliva product bound to the substrate. Conversely, if a body fluid sample results in immunocomplex formation similar to immunocomplex formation using a negative control sample, then the animal from which the fluid was taken is not hypersensitive to the ectoparasite saliva product bound to the substrate.

A preferred embodiment of an in vitro hypersensitivity test of the present invention comprises the steps of: (a) contacting an ELISA plate, which is coated with a suitable amount of flea saliva extract, including FS-1, FS-2, FS-3 and/or one or more flea saliva proteins, with serum, plasma or whole blood from an animal being tested for susceptibility to allergic dermatitis; and (b) identifying whether immunocomplexes are formed by step (a) by assaying for the presence of such immunocomplexes by (i) contacting the plate with an antibody that specifically binds to IgE or other compounds capable of binding to such immunocomplexes, such as an epsilon Fc receptor, and (ii) determining whether such an antibody or other compound is bound thereto. It should be noted that citing of specific embodiments does not preclude the use of a variety of other immunoassay protocols, including those in which a compound that binds IgE is coated onto a substrate; the substrate is then contacted with serum, plasma or whole blood; and binding of IgE by the compound is detected by the ability to bind flea saliva extracts or proteins of the present invention.

One embodiment of the present invention is a kit useful for identification of an animal susceptible to or having allergic dermatitis. As used herein, a suspect animal is an animal to be tested. A kit of the present invention comprises a formulation of the present invention and a means for determining if an animal is susceptible to or has allergic dermatitis, in which the formulation is used to identify animals susceptible to or having allergic dermatitis. A means for determining if an animal is susceptible to or has allergic dermatitis can include an in vivo or in vitro hypersensitivity test of the present invention as described in detail above. A kit of the present invention further comprises at least one control solution such as those disclosed herein.

A preferred kit of the present invention comprises the elements useful for performing an immunoassay. A kit of the present invention can comprise one or more experimental samples (i.e., formulations of the present invention) and one or more control samples bound to at least one pre-packed dipstick or ELISA plate, and the necessary means for detecting immunocomplex formation (e.g., labelled secondary antibodies or other binding compounds and any necessary solutions needed to resolve such labels, as described in detail above) between antibodies contained in the bodily fluid of the animal being tested and the proteins bound to the dipstick or ELISA plate. It is within the scope of the invention that the kit can comprise simply a formulation of the present invention and that the detecting means can be provided in another way.

An alternative preferred kit of the present invention comprises elements useful for performing a skin test. A kit of the present invention can comprise at least one prepacked syringe and needle apparatus containing one or more experimental samples and/or one or more control samples.

It is within the scope of the present invention that two or more different in vivo and/or in vitro tests can be used in combination for diagnostic purposes. For example, the immediate hypersensitivity of an animal to an ectoparasite saliva allergen can be tested using an in vitro immunoabsorbent test capable of detecting IgE antibodies specific for an ectoparasite saliva allergen in the animal's bodily fluid. While most animals that display delayed hypersensitivity to an ectoparasite saliva allergen also display immediate hypersensitivity to the allergen, a small number of animals that display delayed hypersensitivity to an allergen do not display immediate hypersensitivity to the allergen. In such cases, following negative results from the IgE-specific in vitro test, the delayed hypersensitivity of the animal to an ectoparasite saliva allergen can be tested using an in vivo test of the present invention.

Another aspect of the present invention includes treating animals susceptible to or having allergic dermatitis, with a formulation of the present invention. According to the present invention, the term treatment can refer to the regulation of a hypersensitive response by an animal to bites from ectoparasites. Regulation can include, for example, immunomodulation of cells involved in the animal's hypersensitive response or alteration of the ability of an ectoparasite to introduce allergens into an animal, for example by inhibiting the anti-coagulation activity of a saliva enzyme, thereby impairing the ability of the arthropod to penetrate the dermis of an animal and feed. Immunomodulation can include modulating the activity of molecules typically involved in an immune response (e.g., antibodies, antigens, major histocompatibility molecules (MHC) and molecules co-reactive with MHC molecules). In particular, immunomodulation refers to modulation of antigen:antibody interactions resulting in inflammatory responses, immunosuppression, and immunotolerization of cells involved in a hypersensitive response. Immunosuppression refers to inhibiting an immune response by, for example, killing particular cells involved in the immune response. Immunotolerization refers to inhibiting an immune response by anergizing (i.e., diminishing reactivity of a T cell to an antigen) particular cells involved in the immune response. Suitable and preferred ectoparasites against which to treat an animal are disclosed herein. A particularly preferred formulation of the present invention is used to treat FAD.

One embodiment of the present invention is a therapeutic composition that, when administered to an animal in an effective manner, is useful for immunomodulating the immune response of the animal (i.e., immunomodulating the animal) so as to block (i.e., to inhibit, reduce or substantially prevent) a hypersensitive response by the animal upon subsequent exposure to allergenic components transmitted through bites from ectoparasites. Such a therapeutic composition is useful for immunomodulating animals known to be hypersensitive to ectoparasite saliva products and animals susceptible to hypersensitive responses against ectoparasite saliva products.

One embodiment of the present invention is a therapeutic composition that includes de-sensitizing compounds capable of inhibiting an immune response to an ectoparasite saliva product of the present invention. Such de-sensitizing compounds include blocking compounds, toleragens and/or suppressor compounds. Blocking compounds comprise compounds capable of modulating antigen:antibody interactions that can result in inflammatory responses, toleragens are compounds capable of immunotolerizing an animal, and suppressor compounds are capable of immunosuppressing an animal. A desensitizing compound of the present invention can be soluble or membrane-bound. Membrane-bound de-sensitizing compounds can be associated with biomembranes, including cells, liposomes, planar membranes, cochleates or micelles. A soluble de-sensitizing compound of the present invention is useful for: (1) inhibiting a Type I hypersensitivity reaction by blocking IgE:antigen mediated de-granulation of mast cells; (2) inhibiting a Type III hypersensitivity reaction by blocking IgG:antigen complex formation leading to complement destruction of cells; and (3) inhibiting a Type IV hypersensitivity reaction by blocking T helper cell stimulation of cytokine secretion by macrophages. A membrane-bound de-sensitizing compound of the present invention is useful for: (1) inhibiting a Type II hypersensitivity reaction by blocking IgG:antigen complex formation on the surface of cells leading to complement destruction of cells; (2) inhibiting a Type II hypersensitivity reaction by blocking IgG regulated signal transduction in immune cells; and (3) inhibiting a Type IV hypersensitivity reaction by blocking T cytotoxic cell killing of antigen-bearing cells.

A de-sensitizing compound of the present invention can also be covalently linked to a ligand molecule capable of targeting the de-sensitizing compound to a specific cell involved in a hypersensitive response to ectoparasite saliva products. Appropriate ligands with which to link a desensitizing compound include, for example, at least a portion of an immunoglobulin molecule, cytokines, lectins, heterologous allergens, CD8 molecules, CD4 molecules or major histocompatibility molecules (e.g., MHC class I or MHC class II molecules). Preferred portions of immunoglobulin molecules to link to a de-sensitizing compound include variable regions capable of binding to immune cell specific surface molecules and constant regions capable of binding to Fc receptors on immune cells, in particular IgE constant regions. Preferred CD8 molecules include at least the extracellular functional domains of the β chain of CD8. Preferred CD4 molecules include at least the extracellular functional domains of CD4. An immune cell refers to a cell involved in an immune response, in particular, cells having MHC class I or MHC class II molecules. Preferred immune cells include antigen presenting cells, T cells and B cells.

In one embodiment, a therapeutic composition of the present invention includes ectoparasite saliva products of the present invention, or mimetopes thereof. Preferred therapeutic compositions include formulations comprising ectoparasite saliva extracts or at least one ectoparasite saliva product (preferably protein) of the present invention or mimetopes thereof.

Suitable therapeutic compositions of the present invention for treating flea allergy dermatitis include flea saliva extracts and other formulations including at least one flea saliva product, preferably a protein, or a mimetope thereof. Preferred therapeutic compositions include FS-1, FS-2 and/or FS-3 as well as at least a portion of at least one flea saliva product that can be isolated from FS-1, FS-2 and/or FS-3. As such, preferred formulations for use as therapeutic compositions include FS-1, FS-2, FS-3, and/or at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN (C), fspN(D), fspN(E), fspN(F), fspN(G), fspN(H), fspN(I), fspN(J), fspN(K), fspN(L), fspN(M), fspN(N) and fspN(O), or homologues thereof. A more preferred flea saliva extract for use as a therapeutic compositions includes FS-1, FS-2, FS-3, and/or at least a portion of one or more of the proteins fspE, fspF, fspG1, fspG2, fspG3, fspG4, fspH, fspI, fspJ1, fspJ2, fspK, fspL1, fspL2, fspM1, fspM2, fspN1, fspN2 and fspN3. A yet more preferred flea saliva extract for use as a therapeutic compositions includes FS-1, FS-2, and/or at least a portion of one or more of the proteins fspG1, fspG2, fspG3, fspG4, fspH, fspM1, fspM2, fspN1, fspN2 and fspN3.

In another embodiment, a therapeutic composition can include ectoparasite products of the present invention associated with a suitable excipient. A therapeutic composition of the present invention can be formulated in an excipient that the animal to be treated can tolerate. Preferred excipients are capable of maintaining a product of the present invention in a form that is capable of being bound by cells involved in an allergic response in an animal such that the cells are stimulated to initiate or enhance an immune response. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic composition of the present invention can also comprise a carrier or adjuvant, although it is to be appreciated that an advantage of saliva products of the present invention is that adjuvants and/or carriers are not required for administration. Adjuvants are typically substances that generally enhance the immune response of an animal to a specific antigen. Suitable adjuvants include, but are not limited to, cytokines, chemokines, and compounds that induce the production of cytokines and chemokines (e.g., granulocyte macrophage colony stimulating factor [GM-CSF], macrophage colony stimulating factor [M-CSF], granulocyte colony stimulating factor [G-CSF], colony stimulating factor [CSF], erythropoietin [EPO], interleukin-2 [IL-2], interleukin-3 [IL-3], interleukin-5 [IL-5], interleukin-6 [IL-6], interleukin-7 [IL-7], interleukin-8 [IL-8], interleukin-10 [IL-10], interleukin-12 [IL-12], gamma interferon [IFN-γ], interferon gamma inducing factor [IGIF], transforming growth factor beta, RANTES [regulated upon activation, normal T cell expressed and presumably secreted], macrophage inflammatory proteins [e.g., MIP1α and MIP1β], and Leishmania elongation initiating factor [LeIF]; bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant [Vaxcel™, Inc. Norcross, Ga.], Ribi adjuvants [Ribi ImmunoChem Research, Inc., Hamilton, Mont.]; and saponins and their derivatives (e.g., Quil A [Superfos Biosector A/S, Denmark]. Protein adjuvants of the present invention can be delivered in the form of the protein themselves or of nucleic acid molecules encoding such proteins using the methods described herein.

Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a therapeutic composition of the present invention into the bloodstream of an animal. Suitable controlled release formulations include, but are not limited to, biocompatible (including biodegradable) polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ.

The present invention also includes a recombinant virus particle therapeutic composition. Such a composition includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015/414, filed Feb. 8, 1993, entitled "Recombinant Virus Particle Vaccines", U.S. Pat. No. 5,266,313, by Esposito et al., issued Nov. 30, 1993 and U.S. patent application Ser. No. 08/602,010, by Haanes et al., filed Jan. 15, 1996, entitled "Recombinant Canine Herpesvirus", each of the patents and patent application referred to in this section is incorporated by reference herein in its entirety.

When administered to an animal, a recombinant virus particle therapeutic composition of the present invention infects cells within the immunized animal and directs the production of a protective protein or RNA nucleic acid molecule that is capable of protecting the animal from allergic dermatitis caused by the bites of ectoparasites. For example, a recombinant virus particle comprising a nucleic acid molecule encoding one or more ectoparasite saliva protein of the present invention is administered according to a protocol that results in the tolerization of an animal against ectoparasite saliva allergens.

According to one embodiment, a nucleic acid molecule of the present invention can be delivered to an animal as a naked (i.e., not packaged in a viral coat or cellular membrane) nucleic acid vaccine (e.g., as naked DNA or RNA molecules, such as is taught, for example in Wolff et al., 1990, *Science* 247, 1465–1468). A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a dicistronic recombinant molecule. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. An example of one embodiment is disclosed in PCT Patent Publication No. WO 95/05853, published Mar. 2, 1995. A preferred single dose of a naked nucleic acid vaccine ranges from about 1 nanogram (ng) to about 100 $\mu$g, depending on the route of administration and/or method of delivery, as can be determined by those skilled in the art. Suitable delivery methods include, for example, by injection, as drops, aerosolized, oral and/or topical. Naked DNA of the present invention can be contained in an aqueous excipient (e.g., phosphate buffered saline) alone or a carrier (e.g., lipid-based vehicles).

Therapeutic compositions of the present invention can be sterilized by conventional methods which do not result in protein degradation (e.g., filtration) and/or lyophilized.

A therapeutic composition of the present invention can be administered to any animal susceptible to ectoparasite infestation as herein described. Acceptable protocols by which to administer therapeutic compositions of the present invention in an effective manner can vary according to individual dose size, number of doses, frequency of dose administration, and mode of administration. Determination of such protocols can be accomplished by those skilled in the art. An effective dose refers to a dose capable of treating an animal against hypersensitivity to ectoparasite saliva allergens. Effective doses can vary depending upon, for example, the therapeutic composition used, the arthropod from which the composition was derived, and the size and type of the recipient animal. Effective doses to immunomodulate an animal against ectoparasite saliva allergens include doses administered over time that are capable of alleviating a hypersensitive response by an animal to ectoparasite saliva allergens. For example, a first tolerizing dose can comprise an amount of a therapeutic composition of the present invention that causes a minimal hypersensitive response when administered to a hypersensitive animal. A second tolerizing dose can comprise a greater amount of the same therapeutic composition than the first dose. Effective tolerizing doses can comprise increasing concentrations of the therapeutic composition necessary to tolerize an animal such that the animal does not have a hypersensitive response to the bite of an ectoparasite. An effective dose to desensitize an animal can comprise a concentration of a therapeutic composition of the present invention sufficient to block an animal from having a hypersensitive response to the bite of an ectoparasite. Effective desensitizing doses can include repeated doses having concentrations of a therapeutic composition that cause a minimal hypersensitive response when administered to a hypersensitive animal.

A suitable single dose is a dose that is capable of treating an animal against hypersensitivity to ectoparasite saliva allergens when administered one or more times over a suitable time period. For example, a preferred single dose of an ectoparasite saliva product, or mimetope therapeutic composition is from about 0.5 ng to about 1 g of the therapeutic composition per kilogram body weight of the animal. Further treatments with the therapeutic composition can be administered from about 1 hour to 1 year after the original administration. Further treatments with the therapeutic composition preferably are administered when the animal is no longer protected from hypersensitive responses to ectoparasite. Particular administration doses and schedules can be developed by one of skill in the art based upon the parameters discussed above. Modes of administration can include, but are not limited to, subcutaneous, intradermal, intravenous, nasal, oral, transdermal and intramuscular routes.

A therapeutic composition of the present invention can be used in conjunction with other compounds capable of modifying an animal's hypersensitivity to ectoparasite bites. For example, an animal can be treated with compounds capable of modifying the function of a cell involved in a hypersensitive response, compounds that reduce allergic reactions, such as by systemic agents or anti-inflammatory agents (e.g., anti-histamines, anti-steroid reagents, anti-inflammatory reagents and reagents that drive immunoglobulin heavy chain class switching from IgE to IgG). Suitable compounds useful for modifying the function of a cell involved in a hypersensitive response include, but are not limited to, antihistamines, cromolyn sodium, theophylline, cyclosporin A, adrenalin, cortisone, compounds capable of regulating cellular signal transduction, compounds capable of regulating adenosine 3',5'-cyclic phosphate (cAMP) activity, and compounds that block IgE activity, such as peptides from IgE or IgE specific Fc receptors, antibodies specific for peptides from IgE or IgE-specific Fc receptors, or antibodies capable of blocking binding of IgE to Fc receptors.

Another aspect of the present invention includes a method for prescribing treatment for animals susceptible to or having allergic dermatitis, using a formulation of the present invention. A preferred method for prescribing treatment for flea allergy dermatitis, for example, comprises: (1) intradermally injecting into an animal at one site an effective amount of a formulation containing at least one flea saliva antigen of the present invention, or a mimetope thereof (suitable and preferred formulations are disclosed herein); (2) intradermally injecting into the animal at a second site an effective amount of a control solution; (3) evaluating if the animal has flea allergy dermatitis by measuring and comparing the wheal size resulting from injection of the formulation with the wheal size resulting from injection of the control solution; and (4) prescribing a treatment for the flea allergy dermatitis.

An alternative preferred method for prescribing treatment for flea allergy dermatitis comprises: (1) contacting a first portion of a sample of bodily fluid obtained from an animal to be tested with an effective amount of a formulation containing at least one flea saliva antigen, or a mimetope thereof (suitable and preferred formulations are disclosed herein) to form a first immunocomplex solution; (2) contacting a positive control antibody to form a second immunocomplex solution; (3) evaluating if the animal has flea allergy dermatitis by measuring and comparing the amount of immunocomplex formation in the first and second immunocomplex solutions; and (4) prescribing a treatment for the flea allergy dermatitis. It is to be noted that similar methods can be used to prescribe treatment for allergies caused by other ectoparasites using ectoparasite saliva product formulations as disclosed herein.

Another aspect of the present invention includes a method for monitoring animals susceptible to or having allergic dermatitis, using a formulation of the present invention. In vivo and in vitro tests of the present invention can be used to test animals for allergic dermatitis prior to and following any treatment for allergic dermatitis. A preferred method to monitor treatment of flea allergy dermatitis (which can also be adapted to monitor treatment of other ectoparasite allergies) comprises: (1) intradermally injecting an animal at one site with an effective amount of a formulation containing at least one flea saliva product, or a mimetope thereof (suitable and preferred formulations are disclosed herein); (2) intradermally injecting an effective amount of a control solution into the animal at a second site; and (3) determining if the animal is desensitized to flea saliva antigens by measuring and comparing the wheal size resulting from injection of the formulation with the wheal size resulting from injection of the control solution.

An alternative preferred method to monitor treatment of flea allergy dermatitis (which can be adapted to monitor treatments of other ectoparasite allergies) comprises: (1) contacting a first portion of a sample of bodily fluid obtained from an animal to be tested with an effective amount of a formulation containing at least one flea saliva product or mimetope thereof (suitable and preferred formulations are disclosed herein) to form a first immunocomplex solution; (2) contacting a positive control antibody to form a second immunocomplex solution; and (3) determining if the animal is desensitized to flea saliva antigens by measuring and comparing the amount of immunocomplex formation in the first and second immunocomplex solutions.

The present invention also includes antibodies capable of selectively binding to an ectoparasite saliva product, or mimetope thereof. Such an antibody is herein referred to as an anti-ectoparasite saliva product antibody. As used herein, the term "selectively binds to" refers to the ability of such an antibody to preferentially bind to ectoparasite saliva products and mimetopes thereof. In particular, the present invention includes antibodies capable of selectively binding to flea saliva products. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to ectoparasite saliva proteins, or mimetopes thereof. More preferred antibodies are raised in response to at least one ectoparasite saliva protein, or mimetope thereof, having at least a portion of an ectoparasite saliva protein eluted from a collection means of the present invention. Even more preferred antibodies are raised in response to at least one flea saliva product, or homologues thereof (e.g., saliva products of other ectoparasites), contained in the saliva extracts FS-1, FS-2 and/or FS-3. More preferred ectoparasite saliva proteins against which to raise an antibody includes at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N) and fspN(O), or homologues thereof. Preferably, an antibody of the present invention has a single site binding affinity of from about $10^3$ $M^{-1}$ to about $10^{12}$ $M^{-1}$ for a flea saliva product of the present invention.

A preferred method to produce antibodies of the present invention includes administering to an animal an effective amount of an ectoparasite saliva product or mimetope thereof to produce the antibody and recovering the antibodies. Antibodies raised against defined products or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from allergic dermatitis, (b) as positive controls in test kits, and/or (c) as tools to recover desired ectoparasite saliva products from a mixture of proteins and other contaminants.

The following examples are provided for the purposes of illustration and are not intended to limit the scope of the present invention.

EXAMPLES

Example 1

This example describes the collection of flea saliva proteins using a saliva collection apparatus of the present invention.

A saliva collection apparatus was prepared as follows. Referring to FIGS. 4A and 4B, a humidifying means (34) comprising about 4 pieces of VWR blotting pads #320 (VWR, Denver, Colo.) was prepared that fit the inner diameter (about 47 mm in diameter) of a chamber (6) of a saliva collection apparatus (2). The blotting pads were pre-wetted using a sufficient amount of pre-wetting solution (sterile water containing 50 units/ml penicillin and 50 $\mu$g/ml streptomycin, available from Sigma, St. Louis, Mo.) such that the blotting pads were damp but not dripping wet. The pre-wetted filters (34) were placed inside the bottom end (22) of the chamber (6) of the saliva collection apparatus (2) such that the filter paper sat immediately inside the bottom end (22) of the chamber (6).

A collection means (24) comprising a Durapore™ membrane (available from Millipore, Bedford, Mass.) was cut to fit the outer diameter (about 48 mm in diameter) of the chamber (6) of the saliva collection apparatus (2). The Durapore™ membrane was pre-wetted using the pre-wetting solution described above. The Durapore™ membrane (24) was placed immediately outside the bottom end (22) of the chamber (6) such that the Durapore™ membrane (24) contacted the outer rim of the bottom end (22) of the chamber (6) and also contacted the damp filter paper. A barrier means comprising a piece of stretched Parafilm™ (28) (available from American National Can™, Greenwich, Conn.) was stretched over the collection means (24) and bottom end (22) of the chamber (6) and up the outer wall (30) of the chamber (6). A rubber seal (32) (i.e., an o-ring) was placed over the Parafilm™ (28) thereby further securing the Parafilm™ (28) across the collection means (24) and to the outer wall (30) and to seal in the chamber (6) environment.

The collection apparatus (2) was preassembled and then the top end (20) of the chamber (6) was attached to an artificial feeding system capable of acting as a source of heat and humidity such as that described by Wade et al., (ibid.). The artificial feeding system comprised a large plexiglass box (40 cm×40 cm×40 cm) divided horizontally into an upper compartment and a lower compartment by a plexiglass shelf having holes drilled through. A collection apparatus (2) was inserted into a hole such that the chamber (6) of the apparatus (2) was located above the shelf in the upper compartment and the housing (4) was located below the shelf in the lower compartment. The apparatus (2) was secured to the shelf by attaching a rubber band attached to metal hooks placed in the shelf. Any open holes in the shelf were closed off using rubber stoppers to isolate the environment within the upper compartment from the environment within the lower compartment. The upper compartment contained two trays of water, a fan and a heating block. The trays of water were placed such that the fan faced the trays. While the apparatus (2) was maintained in the artificial feeding system, the fan was blown continuously thereby circulating heat and humidity throughout the upper compartment and the chamber (6) of the collection apparatus (2). As such, the relative humidity within the chamber (6) was maintained at about 94% humidity and the temperature was maintained at about 37° C.

About 3,000 to 5,000 newly emerged unfed *Ctenocephalides felis* fleas were added to the housing (4) of the collection apparatus (2). The fleas were first collected in a 20 gallon glass aquarium. The fleas were then transferred to the housing (4) of a collection apparatus (2) by placing the end of the housing (4) having the nylon mesh of the exchange means (16) on top of a vacuum chamber and aspirating the fleas from the aquarium into the housing (4) through a tygon tubing. The housing (4) was then covered with the nylon mesh of the retaining means (18) to secure the fleas within the housing (4). The bottom end (22) of the chamber (6) was then placed on the housing (4) such that the Parafilm™ (28) and the nylon mesh of the retaining means (18) were juxtaposed. When the collection apparatus (2) was attached to the artificial feeding system, the ambient temperature within the housing (4) was maintained at about 27° C. while the ambient temperature of the chamber (6) was maintained at about 37° C. The relative humidity of the housing (4) was maintained at about 50% by closing the lower compartment with the plexiglass shelving.

In one experiment, flea saliva products were collected on a Durapore™ membrane (24) and visualized by immersing the membrane in 0.1% Coomassie blue stain for 20 minutes, destaining the membrane in 50% methanol and air drying the membrane. Proteins deposited on the membrane were detected by their blue color.

In another experiment, flea saliva products were collected for 0 through 24 hours, 24 through 72 hours, and 72 through 120 hours after loading fleas into the collection apparatus. At 24 hours, 72 hours and 120 hours, the Durapore™ membrane (24) attached to the collection apparatus (2) was removed and a new pre-wetted Durapore™ membrane (24) was attached to the same apparatus. The blotting pads were rewetted using the pre-wetting solution described above when the new Durapore™ membrane (24) was replaced. Flea saliva products were extracted from the Durapore™ membrane (24) by soaking each membrane from each time point separately in a solvent comprising 50% acetonitrile with 1% TFA overnight at room temperature with stirring to obtain a flea saliva product mixture comprising flea saliva products that had eluted into the solvent. The mixture containing the flea saliva products was recovered and lyophilized until dry to form a pellet. The amount and characteristics of flea saliva proteins eluted from each Durapore™ membrane from each time point was determined by reducing 14% Tris-glycine SDS-PAGE using techniques similar to those described by Sambrook et al., ibid. The resultant protein pattern was visualized by staining the gel with Coomassie blue stain using techniques as described above. The amount of saliva proteins collected on the membranes decreased when the fleas had been in the collection apparatus for more than 72 hours.

Example 2

Standard procedures to collect FS-1, FS-2 and FS-3 flea saliva extracts of the present invention were performed as follows. Flea saliva products were collected for 72 hours on collection membranes using the method described in Example 1, except that for flea saliva extract FS-3, the collection membrane was DE-81 chromatography paper, available from Whatman, Inc., Clifton, N.J.

A. Flea Saliva Extracts FS-1 and FS-2

Flea saliva products were extracted from the Durapore™ membrane (24) by soaking each membrane from each time point separately in a first solvent comprising 50% acetonitrile with 0.1% TFA for 8 hours. The first mixture containing the eluted flea saliva products was recovered and lyophilized until dry, thereby forming a first pellet. The same membranes were then soaked in a second solvent comprising 50% acetonitrile with 1% TFA overnight at room temperature with stirring to obtain a flea saliva product mixture comprising flea saliva products that had eluted into the second solvent. The second mixture was recovered from this second extraction and lyophilized until dry to form a second pellet.

The two pellets recovered from the two lyophilization steps were mixed with a third solvent comprising 12.8% acetonitrile and flea saliva products solubilized in the solvent were recovered. The non-solubilized material was mixed again with 12.8% acetonitrile and additional flea saliva products solubilized in the solvent were recovered. The two mixtures were combined to obtain the extract FS-1.

The non-solubilized material remaining after the second solubilization step was then mixed with 50% acetonitrile which solubilized the remaining material to obtain the extract FS-2.

The amount and characteristics of flea saliva proteins contained in the FS-1 and FS-2 flea saliva extracts obtained in at least one experiment were determined according to the following method. Each extract was concentrated by evaporation under vacuum and evaluated by reducing 16% Tris-glycine SDS-PAGE using techniques similar to those described by Sambrook et al., ibid. Using such standard procedures, about 10 μg of FS-1 or FS-2 eluted from the Durapore™ membrane was loaded onto a 16% Tris-glycine polyacrylamide gel and subjected to electrophoresis under reducing conditions. The gel was stained with Coomassie blue and dried.

The results are shown in FIG. 1B. FS-1 is shown in lane 13 of FIG. 1B and FS-2 is shown in lanes 14 and 15 of FIG.

1B. FS-1 was found to contain proteins estimated to have the following molecular weights: 9 kD, 11 kD, 12 kD, 15 kD, 22 kD, 48 kD, 50 kD, 53 kD, 80 kD, 124 kD, 130 kD, 189 kD and 201 kD. Those proteins of 80 kD and above were much fainter than the lower molecular weight bands. FS-2 was found to contain proteins having the following molecular weights: 47 kD, 49 kD, 52 kD, 57 kD, 64 kD, 71 kD, 88 kD, 96 kD, 97 kD, 130 kD, 161 kD, 175 kD, 189 kD, 222 kD, 235 kD and 302 kD. The bands at 47 kD, 49 kD and 52 kD were more prominent than the bands having higher molecular weights. The results suggest that a substantial portion of the protein contained in FS-2 is fspN1, fspN2 and/or fspN3.

Protein concentrations were measured using a Bio-Rad Bradford assay (available from Bio-Rad, Hercules, Calif.). The results indicate that about 750 µg of protein can be collected in about $3.66 \times 10^7$ flea hours ($5.08 \times 10^5$ fleas for 72 hours) in an FS-1 extract and about 2.35 mg of protein can be collected in about $3.66 \times 10^7$ flea hours in an FS-2 extract.

B. Flea Saliva Extract FS-3

Flea saliva products to produce FS-3 flea saliva extract were collected in a manner similar to the method by which FS-1 and FS-2 were collected, except that the collection membrane (24) was DE-81 chromatography paper. Flea saliva products were extracted from the DE-81 membrane by soaking each membrane from each time point separately in a solvent comprising 1M NaCl in phosphate buffered saline for about 8 hours. The products were recovered from the solvent using standard techniques, such as disclosed for FS-1 and FS-2.

Analysis of an FS-3 flea saliva extract indicated that FS-3 appeared to contain proteins such as those found in FS-1 and FS-2, at least based on 1-dimensional gel electrophoresis. The SDS-PAGE pattern of FS-3, for example, was very similar to that of FS-1 except that there appeared to be increased quantities of the higher molecular weight proteins in the FS-3 extract. FS-3 flea saliva extract was also shown to have anti-coagulation activity, using techniques standard in the art; see, for example, Dunwiddle et al., 1991, *Thrombosis Research* 64, 787–794; Ribeiro et al., 1990, *Comp. Biochem. Physiol.* 95, 215–218; Ribeiro et al., 1990, *Br. J. Pharmacol.* 101, 932–936; Ribeiro et al., 1987, *Exper. Parasitol.* 64, 347–353; Cupp et al., 1994, *Am. J. Trop. Med. Hyg.* 50, 241–246; Garcia et al., 1994, *Exper. Parasitol.* 78, 287–293. The FS-3 extract was also shown to exhibit acid phosphatase activity, using techniques standard in the art, such as those supplied by Sigma, St. Louis, Mo., with the Sigma acid phosphatase assay kit.

Example 3

This example describes the characterization by HPLC of flea saliva proteins collected using a saliva collection apparatus of the present invention.

An FS-1 flea saliva extract was collected as described in Example 2 from about 140,000 fleas for 72 hours. Proteins contained in FS-1 were resolved using standard procedures of high pressure liquid chromatography (HPLC). Specifically, the proteins were passed over a 15 cm×0.46 cm C4 column using a gradient from 0.1% TFA in water (Solvent A) to 0.085% TFA in 90% CH₃CN (Solvent B) at a flow rate of 0.8 ml per minute. Thus, the gradient was about 5.6% Solvent B at 15 minutes and about 100% Solvent B at 75 minutes.

The results are shown in FIG. 2. About 14 major protein fractions were resolved. The recovery for each peak was about 5 µg to 10 µg of protein per peak. The peaks were labelled peak A, peak B, peak C, peak D, peak E, peak F, peak G, peak H, peak I, peak J, peak K, peak L, peak M and peak N, as shown in FIG. 2, and represent, respectively, protein formulations fspA, fspB, fspC1 and fspC2, fspD1 and fspD2, fspE, fspF, fspG1, fspG2, fspG3, fspH, fspI, fspJ1 and fspJ2, fspK, fspL1 and fspL2, fspM1 and fspM2, and fspN1, fspN2 and fspN3.

Figure 1C:
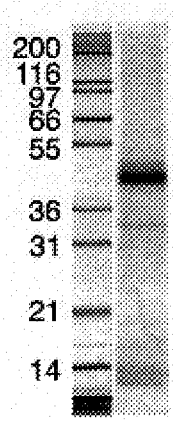
FIG. 1C illustrates the resolution of fspN by reducing 16% Tris glycine SDS-PAGE.

Samples from each HPLC peak were resolved by Tris Glycine SDS-PAGE gels using the method described in Example 1. The results are shown in FIGS. 1A, 1B and 1C. The proteins shown in FIGS. 1A and 1B were resolved on 16% Tris Glycine SDS-PAGE gels and the proteins shown in FIG. 1C were resolved on a 14% Tris Glycine SDS-PAGE gel. Protein markers are shown in lane 1 of FIG. 1A, lane 2 of FIG. 1B and lane 1 of FIG. 1C. The additional lanes show saliva formulation samples as follows:

FIG. 1A

| Lane | Fraction(s) | Fs-() |
|---|---|---|
| 1) | — | Mol. Wt. Std. |
| 2) | 10 | — |
| 3) | 11–13 | A |
| 4) | 14 | B |
| 5) | 15 | B |
| 6) | 16 | C1 |
| 7) | 17 | C2 |
| 8) | 18 | D1 |
| 9) | 19 | D1 |
| 10) | 20 | D2 |
| 11) | 21 | D2 |
| 12) | 22 | E |
| 13) | 23 | F |
| 14) | 24 | G |
| 15) | 25 | G |

FIG. 1B

| Lane | Fraction(s) | Fs-() |
|---|---|---|
| 1) | 26–27 | G |
| 2) | — | Mol. Wt. Std. |
| 3) | 28 | H |
| 4) | 29–30 | I |
| 5) | 31 | J |
| 6) | 32 | K |
| 7) | 33 | K |
| 8) | 34 | L |
| 9) | 35 | M1 |
| 10) | 36–37 | M1 |
| 11) | 38 | M1 |
| 12) | 39–50 | M2 |
| 13) | — | FS-1 |
| 14) | — | FS-2 |
| 15) | — | FS-2 |

FIG. 1C

| Lane | Fraction(s) | Fs-() |
|---|---|---|
| 1) | — | Mol. Wt. std. |
| 2) | 56–68 | N |

Referring to FIG. 1A, the following flea saliva proteins (referred to as bands) were observed: a prominent band of about 10 kD in peak A and peak B samples; a prominent band of about 6 kD and a less prominent band of 9 kD in a peak C sample referred to as C1; a prominent band of about 7 kD in a peak C sample referred to as C2; a prominent band of about 7 kD and a less prominent band of 8 kD in a peak D sample referred to as D1; a prominent band of about 8 kD and a less prominent band of 9 kD in a peak D sample referred to as D2; a prominent band of 8 kD and a less prominent band of about 7 kD in peaks E and F samples; and a prominent band of about 9 kD, and less prominent bands of about 7 kD and 10 kD in a peak G sample. Referring to FIG. 1B, the following flea saliva proteins were observed: a prominent band of about 9 kD and a less prominent band of about 12 kD in a peak H sample; a prominent band of about 21 kD, and less prominent bands of about 7 kD, 9 kD, 12 kD, 14 kD, and 70 kD in a peak I sample; prominent bands of about 14 kD and 21 kD, and less prominent bands of about 11 kD and 17 kD in a peak J sample; prominent bands of about 14 kD and 15 kD and less prominent bands of about 12 kD, 18 kD and 21 kD in a peak K sample; a prominent band of about 15 kD in a peak L sample; prominent bands of about 11 kD, 12 kD and 21 kD and less prominent bands of about 15 kD, 17 kD, 22 kD and 37 kD in a peak M sample referred to as M1; and a prominent band of about 36 kD and less prominent bands of about 11 kD, 21 kD and 22 kD in a peak M sample referred to as M2. Referring to FIG. 1C, prominent bands of about 42 kD, 43 kD and 44 kD and a less prominent band of about 32 kD were detected in a peak N sample.

Example 4

This example describes the amino acid sequence analysis of the isolated and HPLC purified flea saliva proteins.

Amino (N−) terminal amino acid sequencing analysis was performed on several of the HPLC-separated flea saliva proteins described in Example 3 using standard procedures known to those in the art (see, for example, Geisow et al., 1989, in *Protein Sequencing: A Practical Approach*, JBC Findlay and MJ Geisow (eds.), IRL Press, Oxford, England, pp. 85–98; Hewick et al., 1981, *J. Biol. Chem.*, Vol. 256, pp. 7990–7997).

The N-terminal partial amino acid sequence of flea saliva protein fspA, which migrated as Peak A in FIG. 2, was determined to be

```
Y G K Q Y S E K G G R G Q R H Q I L K K G K
  Q Y S         S K       I     L D   L
  S
  R
``` as represented in standard single letter code. This N-terminal partial amino acid sequence of fspA is denoted SEQ ID NO:1. It should be noted that there was heterogeneity in several positions which may represent sequence errors (i.e., misidentification of amino acids) or allelic variations in the flea population from which the saliva proteins were collected. There was an apparently equal likelihood of finding any one of the alternative amino acids at the indicated positions.

The N-terminal partial amino acid sequence of flea saliva protein fspB, which migrated as Peak B in FIG. 2, was determined to be S/Q G K Q Y S E X G/S K, denoted SEQ ID NO:27. This amino acid sequence was essentially the same, or at least a subset of, the N-terminal amino acid sequence obtained from flea saliva protein fspA.

Sequence analysis of Peak G proteins indicated the presence of three proteins in that peak, referred to herein as fspG1, fspG2 and fspG3. Flea saliva protein fspG1, having a molecular weight of about 9 kD, had an N-terminal partial amino acid sequence of D R R V S K, denoted SEQ ID NO:28. This N-terminal amino acid sequence is the same as that for fspH, as shown in SEQ ID NO:2, SEQ ID NO:3, SEQ ID NO:4, SEQ ID NO:5 and SEQ ID NO:14. Flea saliva protein fspG2, having a molecular weight of about 7 kD, had an N-terminal partial amino acid sequence of S K M V T E K X K S G G N N P S T K E V S I P, denoted SEQ ID NO:29. Flea saliva protein fspG3, having a molecular weight of about 6 kD, had an N-terminal partial amino acid sequence of E V S I P S G K L T I E D F X I G N H Q, denoted SEQ ID NO:30. A comparison of SEQ ID NO:30 with SEQ ID NO:29 indicates that fspG3 may be a proteolytic degradation product of fspG2, as the last five amino acids of fspG2 are identical with those at the N-terminus of fspG3.

The N-terminal partial amino acid sequence of flea saliva protein fspH, which migrated as Peak H in FIG. 2, was determined to be D R R V S K T X Q S G G K I Q S E X Q V V I K S G Q H/Y I L E N Y X S D G R, denoted herein as SEQ ID NO:14. Histidine and tyrosine were equally likely at amino acid position 27.

Flea saliva protein fspH was also subjected to proteolytic cleavage in order to obtain internal amino acid sequence data. Specifically, fspH was cleaved with Endoproteinase Asp-N (available from Boehringer Mannheim Biochemica, Indianapolis, Ind.) using methods standard in the art. The digested protein was then resolved by HPLC using the method described by Stone et al. (ibid.). The resultant HPLC profile is shown in FIG. 3. Three proteolytic fragments were isolated, that are referred to herein as fspHe, fspHh and fspHj.

The N-terminal partial amino acid sequence of fspHe was determined to be D S K H C Y C E A P Y S, also denoted SEQ ID NO:3. The N-terminal partial amino acid sequence of fspHh was determined to be D G R N N N N P C H L F C M R E C R S G N G G C G N G G R T R P D S K H C, also denoted SEQ ID NO:4. The N-terminal partial amino acid sequence of fspHj was determined to be D R R V S K T C Q S G, also denoted SEQ ID NO:5. Comparison of SEQ ID NO:5 to SEQ ID NO:14 indicated that fspHj was the N-terminal fragment of fspH.

By aligning SEQ ID NO:14, SEQ ID NO:3, SEQ ID NO:4 and SEQ ID NO:5, the following amino acid sequence was deduced, starting at the N-terminus of fspH: D R R V S K T C Q S G G K I Q S E X Q V V I K S G Q H/Y I L E N Y X S D G R N N N N P C H L F C M R E C R S G N G G C G N G G R T R P D S K H C Y C E A P Y S. This amino acid sequence is denoted SEQ ID NO:2 and is believed to represent most of fspH since the molecular weight of a protein having this sequence is about 8600 kD.

The N-terminal partial amino acid sequence of flea saliva protein fspI, which migrated as Peak I in FIG. 2, was determined to be E D I W K V N K K X T S G G K N Q D R K L D Q I I Q K G Q Q V X X Q N X X K, denoted herein as SEQ ID NO:6.

Sequence analysis of Peak J proteins indicated the presence of two proteins in that peak, referred to herein as fspJ1 and fspJ2. The N-terminal partial amino acid sequence of flea saliva protein fspJ1 was determined to be N S H E P G N T R K I R E V M D K L R K Q H P, denoted herein as SEQ ID NO:7. The N-terminal partial amino acid sequence of flea saliva protein fspJ2 was determined to be E I K R N S H E P G N T R K I R E V M D K L R K Q H P, denoted herein as SEQ ID NO:8. The proteins represented by SEQ ID NO:7 and SEQ ID NO:8 were not separately resolved by SDS-PAGE as described in Example 1. Comparison of SEQ ID NO:7 and SEQ ID NO:8 suggest that fspJ1 may be a truncated version of fspJ2, in that the N-terminal partial amino acid sequence of fspJ1 appears to be very similar to that of fspJ2 except that fspJ1 lacks the first 4 amino acids found at the N-terminus of fspJ2.

Sequence analysis of Peak L proteins indicated the presence of two proteins in that peak, referred to herein as fspL1 and fspL2. That there were two proteins, namely fspL1 and fspL2, was shown by subjecting peak L to C4 reverse phase chromatography using 0.13% heptafluorobutyric acid (Solvent A) and 0.1% heptafluorobutyric acid in 90% acetonitrile (Solvent B) in the following gradient format: an 80 minute gradient from 30% Solvent B to 70% Solvent B. The N-terminal partial amino acid sequence of the HPLC-separated fspL1 was determined to be N D K E P G N T R K I R E V M D K L R K Q A Q P R T D G Q R P K T X I M, also denoted SEQ ID NO:9. The N-terminal partial amino acid sequence for fspL2 was determined to be X L X R N D K E P G N T R K I R E V M D K, also denoted SEQ ID NO:10. A comparison of SEQ ID NO:9 and SEQ ID NO:10 indicates that fspL1 and fspL2 are similar proteins, except that fspL1 is 4 amino acids shorter than fspL2 at the N-terminus.

Resolution of proteins contained in Peak N by SDS-PAGE as described in Example 3 revealed 3 distinct bands. The bands were denoted flea saliva proteins fspN1, fspN2 and fspN3. The N-terminal partial amino acid sequence of fspN1 was determined to be N D E L K F V F V M A K, also denoted SEQ ID NO:11. The N-terminal partial amino acid sequence of fspN2 was determined to be X D E L K F V F V M A K G P S X Q A X D Y P C, also denoted SEQ ID NO:12. The N-terminal partial amino acid sequence of fspN3 was determined to be E L K F V F A T A R G M S H T P C D Y P, also denoted SEQ ID NO:13. Comparison of SEQ ID NO:11 and SEQ ID NO:12 suggests that fspN1 and fspN2 share the same N-terminal sequence. Since fspN1 and fspN2 migrate differently when subjected to SDS-PAGE, however, the two proteins are likely to be different homologues, possibly due to one protein having a longer C-terminal domain and/or due to post-translational modification(s). Comparison of SEQ ID NO:13 to SEQ ID NO:11 and SEQ ID NO:12 suggests that fspN3 may be a homologue of fspN1 and fspN2 with internal sequence variations.

Flea saliva proteins in Peak N were also subjected to proteolytic cleavage in order to obtain internal amino acid sequence data. Specifically, the proteins in Peak N were cleaved with Endoproteinase Asp-N (available from Boehringer Mannheim Biochemica, Indianapolis, Ind.) using methods standard in the art. The digested protein was then resolved by HPLC using the method described by Stone et al. (ibid.) and sequenced as previously described. A partial amino acid sequence of flea saliva proteins in Peak N, named fragment pfspN(100–101), was determined to be D I E N I K K G E G Q P G A P G G K E N N L S/L V L, denoted herein as SEQ ID NO:31.

Example 5

This example describes the further characterization of proteins contained in Peak H.

To determine the isoelectric pH of the proteins contained in Peak H, proteins present in that peak were resolved using standard isoelectric focusing techniques known to those of skill in the art; see, for example, O'Farrell, 1975, *J. Biol. Chem.*, Vol. 250, pp. 4007–4021. The pI value for proteins contained in Peak H is about pI 9, ranging from about pI 8.5 to about pI 9.6.

The molecular weight of proteins contained in Peak H was determined by ESMS. The ESMS procedure was performed on a Fisons VG quattro-SQ mass spectrometer. The mass range was calibrated for 100–2000 m/z. The injection rate was performed at 4 µl per minute. The cone voltage was set at 45 volts. The injection sample contained 0.1% formic acid in 50% acetonitrile at a protein concentration of about 100 pmole per µl. The results indicate that Peak H apparently contains a population of proteins all having a molecular weight of 8613±6 daltons.

Example 6

This example describes the isolation of nucleic acid sequences encoding at least portions of flea saliva proteins fspH and fspI.

A. Description of Flea Libraries

Fed flea and unfed flea cDNA libraries were prepared using standard procedures. Briefly, about 3000 to 4000 fed fleas and about the same number of unfed fleas were collected separately, placed into a dry-ice cooled mortar/pestle and ground to a fine powder. RNA from the ground-up fleas was prepared by direct extraction using the guanidinium thiocyanate procedure followed by centrifugation in cesium chloride gradients (see, for example, Sambrook et al., ibid.). Cesium chloride-purified gelatinous RNA pellets were collected and dissolved in sterile TE buffer (10 mM Tris-HCl, pH 7.6 and 1 mM EDTA) containing 0.1% sodium dodecyl sulfate. The dissolved pellet was precipitated with addition of 3 M sodium acetate, pH 5.2 to a final concentration of 0.2 mM and two volumes of absolute ethanol to remove residual CsCl. Total RNA was fractionated for enrichment of the mRNA fraction using a FastTrack™ kit (available, with procedures, from InVitrogen Corp., San Diego, Calif.).

Isolated whole flea mRNA was used directly for cDNA synthesis and molecular cloning. The methods of cDNA synthesis and molecular cloning were those provided with the Lambda Zap-cDNA synthesis kit™ (available from Stratagene, Inc., La Jolla, Calif.). Following is a list of flea cDNA libraries prepared having the indicated number of total plaque forming units (PFU) packaged: (a) two whole fed flea cDNA expression libraries referred to as Library C (about $2.5 \times 10^6$ PFU) and Library H (about $1.3 \times 10^6$ PFU); (b) a whole unfed flea cDNA expression library (about $1.3 \times 10^6$ PFU); (c) a flea salivary gland cDNA expression library prepared from approximately 6000 salivary glands collected from fed and unfed fleas (about $1.5 \times 10^6$ PFU); and (d) a flea fed midgut cDNA expression library prepared from approximately 5000 isolated midguts (about $2.3 \times 10^6$ PFU).

B. Isolation of a Nucleic Acid Molecule encoding fspH

A nucleic acid molecule encoding a portion of flea saliva protein fspH was identified using the flea salivary gland cDNA expression library described in Example 6A.

Degenerate synthetic oligonucleotide primers were designed from the amino acid sequence deduced for fspH (see Example 4). Three synthetic oligonucleotides were synthesized that corresponded to the region of fspH spanning from about residues 38 through 51 of SEQ ID NO:2: Primer 1, a "sense" primer corresponding to amino acid residues from about 38 through about 44 of SEQ ID NO:2, has the nucleic acid sequence 5' AAT(C) AAT(C) AAT(C) AAT(C) CCT(GAC) TGT(C) CA 3', and is denoted SEQ ID NO:15. Primer 2, an "antisense" primer corresponding to amino acid residues from about 46 through about 51 of SEQ ID NO:2, has the nucleic acid sequence 5' CA C(T)TC C(TAG)CT(G) CAT G(A)CA G(A)AA 3' and is denoted SEQ ID NO:16. Primer 3, a sense primer corresponding to amino acid residues from about 43 through about 48 of SEQ ID NO:2, has the nucleic acid sequence 5' TGT(C) CAT(C) T(C)TG(ATC) TTT(C) TGC(T) ATG-3' and is denoted SEQ ID NO:17. A fourth primer, Primer 4, was synthesized that corresponded to the carboxyl region of fspH, namely spanning from about amino residue 69 through 76 of SEQ ID NO:2. Primer 4, an antisense primer, has the nucleic acid sequence 5' GGA(CGA) GCT(C) TCA(G) CAA(G) TAA (G) CAA(G) TGT(C) TT' 3', denoted SEQ ID NO:18.

PCR amplification of fragments from the flea salivary gland library was conducted using standard techniques. PCR amplification products were generated using the combination of Primer 1 and the M13 forward universal standard primer 5' GTAAAACGACGGCCAGT 3', denoted SEQ ID NO:19. The resultant PCR amplification products were used for a nested PCR amplification using Primer 3 and Primer 4. The resultant PCR product, a fragment of 101 nucleotides denoted nfspH$_{101}$, was cloned into the InVitrogen, Corp., TA™ cloning vector (procedures provided by InVitrogen, Corp.) and subjected to DNA sequence analysis using standard techniques. The resulting nucleic acid sequence is presented as SEQ ID NO:20: T TGT CAC TTT TTT TGT ATG AGA GAA TGC AGG TCA GGA AAC GGC GGT TGC GGA AAC GGA GGA AGG ACA AGA CCT GAT TCG AAG CAC TGC TAT GC (primer-derived sequences are in bold). The 60 nucleotides of internal non-primer-derived sequence codes for 20 amino acids of fspH, spanning from residue about 48 through about 68, as numbered in SEQ ID NO:2.

Using standard techniques, nucleic acid molecule nfspH$_{101}$ can be used as a probe to isolate a nucleic acid molecule that encodes a protein corresponding to a full-length, or larger partial, fspH protein.

C. Isolation of a Nucleic Acid Molecule Encoding fspI

The amino acid sequence for fspI (SEQ ID NO:6) disclosed in Example 4 was used to design a set of synthetic degenerate oligonucleotide PCR amplification primers. Degenerate Primer 5, a sense primer corresponding to residues from about 1 through about 8 of SEQ ID NO:6, has the nucleic acid sequence 5' GAA(G) GAT(C) ATT(CA) TGG AAA(G) GTT(CAG) AAT(C) AA 3', denoted SEQ ID NO:21. Degenerate Primer 6, a sense primer corresponding to residues from about 11 through about 18 of SEQ ID NO:6, has the nucleic acid sequence 5' ACT(CGA) TCT(CGA) GGT(CGA) GGT(CGA) AAA(G) AAT(C) CAA(G) GA 3', denoted SEQ ID NO:22.

Primers 5 and 6 were used in combination with the vector primers BSKX (5' TTGGGTACCGGGCCCCCCCT 3', SEQ ID NO:23) and the M13 primer denoted by SEQ ID NO:19 in order to generate PCR amplification products. The PCR products were cloned into the InVitrogen TA™ vector and subjected to DNA sequence analysis. One cloned product analyzed, called nfspI$_{573}$ contained a 573-nucleotide product that corresponded, at least in part, to the partial amino acid sequence determined for fspI. The nucleotide sequence of nfspI$_{573}$ is presented as SEQ ID NO:24. Translation of SEQ ID NO:24 yields the following longest open reading frame, denoted as SEQ ID NO:25.

By combining the partial N-terminal sequence of fspI (SEQ ID NO:6) with the protein sequence SEQ ID NO:25 deduced from the nucleic acid sequence SEQ ID NO:24, it is possible to obtain an apparent full-length amino acid sequence for fspI, denoted SEQ ID NO:26.

Example 7

This example further describes the isolation of nucleic acid sequences encoding at least portions of flea saliva proteins fspH and fspI.

A. Amplification of a Nucleic Acid Molecule Encoding fspH

The DNA sequence determined from the carboxyl-terminal PCR product (SEQ ID NO:20) in Example 6B was used to synthesize two non-degenerate synthetic homologous primers: Primer 7, 5' CCT GAC CTG CAT TCT CTC ATA C 3', denoted SEQ ID NO:38, and Primer 8, 5' AGG TCT TGT CCT TCC TCC GTT TCC GCA 3', denoted SEQ ID NO:39. Primer 8 was used in combination with the M13 reverse primer 5' GGAAACAGCTATGACCATG 3', denoted SEQ ID NO:40, to amplify the 5'-terminal portion of the fspH gene from a fraction of the salivary gland cDNA expression library described above in Example 6A using standard techniques. The resultant PCR product, although not clearly visible on a gel, was identified as a single product by Southern hybridization using Primer 7 as a [$^{32}$P]-radiolabeled probe. A clearly visible ethidium bromide stained PCR product was obtained by performing a nested PCR reaction utilizing Primer 7 and the vector T3 primer, 5' ATTAACCCTCACTAAAG 3', denoted SEQ ID NO:41. The approximately 400-bp product was clearly visible on a 1% agarose gel and was hybridization-positive with [$^{32}$P]-labeled degenerate Primer 1 (SEQ ID NO:15).

A partial, 242-bp, nucleotide sequence of the 400-bp product of fspH, named nfspH$_{242}$ is presented as SEQ ID NO:32. Translation of SEQ ID NO:32 yields the amino acid sequence, named PfspH$_{80}$ denoted as SEQ ID NO:33.

B. Amplification of a Nucleic Acid Molecule Encoding fspI

Two additional primers were made for isolating the fspI protein cDNA sequence from the flea salivary gland library prepared as described in Example 6A. The isolation procedure used PCR reiteration of the flea salivary gland library and probe hybridization to the PCR generated products. Repeating the PCR on fractions of the flea salivary gland library (mini-libraries) narrowed the occurrence frequency of the cloned fspI protein cDNA to approximately 1 in 200 plaque forming units (PFU) before a final plaque lift and identification by hybridization with a [$^{32}$P]-labeled probe.

Two primers based on SEQ ID NO:24 were used: Primer 9, 5' GCA AAG GTT ATA GAG GAG CTT G 3', denoted as SEQ ID NO:42, and Primer 10, 5' AGC TTT CCA TCA CAT CCA GC 3', denoted as SEQ ID NO:43. The primers generated an internal PCR DNA sequence of 268 bp (including primers) which was used as a marker sequence for screening the salivary gland mini-libraries. The final screening of the salivary gland mini-libraries was done with a pool of the four [$^{32}$P]-labeled primers; Primer 5, SEQ ID NO:21, Primer 6, SEQ ID NO:22, Primer 8, SEQ ID NO:42 and Primer 10, SEQ ID NO:43, using standard techniques. A nucleic acid molecule, named nfspI$_{591}$, identified by this technique was sequenced using standard techniques to give SEQ ID NO:34. The translation of SEQ ID NO:34 yielded yields the amino acid sequence, denoted as SEQ ID NO:35, for a protein named PfspI$_{155}$. This amino acid sequence is similar to SEQ ID NO:26, except that SEQ ID NO:35 does not contain the amino acid sequence E D I at the amino terminus, and SEQ ID NO:35 contains a "C" at position 7, whereas SEQ ID NO:26 has an "L" at the corresponding position.

Example 8

This example demonstrates the ability of a formulation of the present invention to induce flea allergy dermatitis in an animal susceptible to flea allergy dermatitis.

To determine whether the isolated flea saliva proteins described in Examples 2 and 3 were capable of inducing an allergic response in animals susceptible to flea allergy dermatitis, skin tests were performed on sensitized dogs. Six dogs were sensitized to fleas using the method of Gross, et al., 1985, *Veterinary Pathology,* Vol. 22, pp. 78–71. Briefly, each dog was exposed to about 25 *C. felis* fleas contained in chambers by allowing the contained fleas to feed on the experimental dogs for about 15-minute periods at weekly intervals. The six dogs were sensitized over the following periods: Dog 2080109 was exposed to fleas 38 times over a period spanning Aug. 31, 1993 through Jun. 7, 1994. Dog 2082101 was exposed to fleas 22 times over a period spanning Dec. 14, 1993 through Jun. 7, 1994. Dog 2082128 was exposed to fleas 20 times over a period spanning Aug. 31, 1993 through May 24, 1994. Dog BFQ2 was exposed to fleas 17 times over a period spanning Mar. 15, 1994 through Jul. 12, 1994. Dog CPO2 was exposed to fleas 12 times over a period spanning Mar. 15, 1994 through Jun. 7, 1994. Dog CQQ2 was exposed to fleas 1 time on Mar. 15, 1994.

Skin testing was performed the morning of Jul. 21, 1994. The dogs were shaved in the lateral thorax/abdominal area and intradermally injected in that area with a variety of formulations of the present invention as well as with control solutions. The total volume per injection was 50 microliters ($\mu$l), with the formulations and controls being diluted in phenolated saline. Each dog received the injections listed in Table 1.

TABLE 1

Samples administered to dogs.

| SAMPLE | REPLICATES | µg/inj | FLEA-HOUR |
|---|---|---|---|
| DILUENT | 2 | N/A* | N/A |
| HISTAMINE | 2 | 1.38 | N/A |
| GREER | 3 | 50 (w/v) | N/A |
| FS-1 | 3 | 1.88 | 4,660 |
| A | 3 | 0.23 | 23,000 |
| B | 3 | 0.32 | 23,000 |
| C1 | 3 | 1.10** | 23,000 |
| C2 | 3 | 0.42 | 23,000 |
| D1 | 3 | 0.24 | 23,000 |
| D2 | 3 | 0.29 | 23,000 |
| E | 3 | 0.16 | 23,000 |
| F | 3 | 0.10 | 23,000 |
| G | 3 | 0.21 | 23,000 |
| H | 3 | 0.20 | 23,000 |
| I | 3 | 0.12 | 23,000 |
| J | 3 | 0.08 | 23,000 |
| K | 3 | 0.12 | 23,000 |
| L | 3 | 0.08 | 23,000 |
| M1 | 3 | 0.16 | 23,000 |
| M2 | 3 | 0.27 | 23,000 |
| N | 3 | 0.20 | 23,000 |
| FS-2 | 3 | 0.71 | 4,660 |

*N/A is not applicable
**Apparent amount, probably artificially high due to assay interference Note that in these studies, fspJ1 and fspJ2 were administered together as fspJ; fspL1 and fspL2 were administered together as fspL; fspN1, fspN2 and fspN3 were administered together as fspN. It is also to be noted that A, B, C1, C2, D1, D2, E, F, G, H, I, J, K, L, M1, M2 and N refer, respectively to flea saliva proteins fspA, fspB, fspC1, fspC2, fspD1, fspD2, fspE, fspF, fspG, fspH, fspI, fspJ, fspK, fspL, fspM1, fspM2 and fspN. The negative control comprised diluent (NC) and the positive controls comprised Greer antigen (GR) and histamine (HIS). The amount of Greer antigen used was determined by weight per volume (w/v) according to the information provided by the manufacturers (Greer Laboratories, Inc., Lenoir, N.C.). The amount of histamine used was determined by information provided on the supplier's label (available from Greer Laboratories, Inc., Lenoir, N.C.).

A. Comparison of Wheal Sizes at Sites of Injection

All injection sites were objectively (Obj) measured in millimeters (mm) at 15 min and subjectively (Sub) scored on a scale of 0 to 4. The subjective scoring was performed by Kenneth W. Kwochka, D.V.M., Diplomat ACVD, (American College of Veterinary Dermatologists) at Ohio State University, Columbus, Ohio. Tables 2 through 7 indicate the results obtained for each dog. # refers to the number designation given to each sample; antigen refers to the sample. Inj 1, Inj 2 and Inj 3 refer to triplicate injections and NA refers to "not applicable."

TABLE 2

DOG ID: 2082101

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 3 | 10 | 3 | 10 | 3 | 10 |
| 4 | FS-1 | 3 | 10 | 4 | 12 | 4 | 12 |
| 5 | A | 1 | 8 | 0 | 8 | 0 | 8 |
| 6 | B | 0 | 6 | 0 | 6 | 0 | 6 |
| 7 | C1 | 0 | 6 | 0 | 6 | 0 | 6 |
| 8 | C2 | 0 | 6 | 0 | 6 | 0 | 6 |
| 9 | D1 | 0 | 8 | 0 | 8 | 0 | 6 |
| 10 | D2 | 0 | 6 | 0 | 6 | 0 | 8 |
| 11 | E | 3 | 12 | 3 | 12 | 3 | 12 |
| 12 | F | 3 | 14 | 3 | 12 | 3 | 12 |
| 13 | G | 3 | 12 | 3 | 12 | 3 | 12 |
| 14 | H | 3 | 11 | 2 | 12 | 3 | 12 |
| 15 | I | 3 | 12 | 2 | 12 | 3 | 11 |
| 16 | J | 2 | 10 | 2 | 11 | 2 | 10 |
| 17 | K | 2 | 11 | 2 | 10 | 2 | 9 |
| 18 | L | 2 | 9 | 1 | 10 | 1 | 10 |
| 19 | M1 | 2 | 12 | 2 | 11 | 2 | 11 |
| 20 | M2 | 3 | 12 | 3 | 11 | 3 | 12 |
| 21 | N | 3 | 11 | 3 | 10 | 2 | 11 |
| 22 | FS-2 | 2 | 11 | 3 | 12 | 2 | 10 |
| 23 | Neg Cntl | 0 | 8 | NA | NA | NA | NA |
| 24 | Histamine | 4 | 14 | NA | NA | NA | NA |

TABLE 3

DOG ID: 2080109

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 7 | NA | NA | NA | NA |
| 2 | Histamine | 4 | 14 | NA | NA | NA | NA |
| 3 | Greer | 0 | 8 | 0 | 8 | 0 | 8 |
| 4 | FS-1 | 4 | 13 | 4 | 13 | 4 | 13 |
| 5 | A | 0 | 9 | 0 | 8 | 0 | 8 |
| 6 | B | 0 | 7 | 0 | 7 | 0 | 7 |
| 7 | C1 | 0 | 8 | 0 | 7 | 0 | 7 |
| 8 | C2 | 0 | 8 | 0 | 7 | 0 | 8 |
| 9 | D1 | 1 | 9 | 1 | 9 | 1 | 9 |
| 10 | D2 | 1 | 9 | 1 | 8 | 1 | 8 |
| 11 | E | 3 | 11 | 3 | 11 | 2 | 10 |
| 12 | F | 3 | 11 | 3 | 13 | 4 | 13 |
| 13 | G | 3 | 14 | 3 | 13 | 3 | 13 |
| 14 | H | 2 | 12 | 2 | 11 | 2 | 10 |
| 15 | I | 2 | 10 | 3 | 10 | 3 | 10 |
| 16 | J | 2 | 10 | 3 | 10 | 3 | 10 |
| 17 | K | 2 | 9 | 2 | 9 | 2 | 9 |
| 18 | L | 1 | 9 | 1 | 6 | 1 | 7 |
| 19 | M1 | 3 | 11 | 3 | 13 | 3 | 13 |
| 20 | M2 | 3 | 14 | 3 | 13 | 3 | 14 |
| 21 | N | 3 | 13 | 3 | 14 | 2 | 10 |
| 22 | FS-2 | 2 | 9 | 1 | 7 | 1 | 8 |
| 23 | Neg Cntl | 0 | 6 | NA | NA | NA | NA |
| 24 | Histamine | 4 | 16 | NA | NA | NA | NA |

TABLE 4

DOG ID: 2082128

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 0 | 6 | 0 | 6 | 0 | 6 |
| 4 | FS-1 | 3 | 12 | 3 | 12 | 3 | 12 |
| 5 | A | 0 | 7 | 0 | 7 | 0 | 6 |
| 6 | B | 0 | 7 | 0 | 7 | 0 | 6 |
| 7 | C1 | 0 | 7 | 0 | 6 | 0 | 7 |
| 8 | C2 | 0 | 6 | 0 | 7 | 0 | 7 |
| 9 | D1 | 0 | 7 | 0 | 7 | 0 | 7 |
| 10 | D2 | 0 | 7 | 0 | 7 | 0 | 7 |
| 11 | E | 0 | 7 | 0 | 6 | 0 | 7 |
| 12 | F | 0 | 6 | 0 | 6 | 0 | 6 |
| 13 | G | 1 | 10 | 1 | 9 | 1 | 9 |
| 14 | H | 2 | 10 | 2 | 10 | 2 | 11 |
| 15 | I | 3 | 12 | 3 | 12 | 3 | 11 |
| 16 | J | 3 | 12 | 3 | 11 | 3 | 11 |
| 17 | K | 3 | 11 | 3 | 12 | 3 | 12 |
| 18 | L | 3 | 11 | 3 | 10 | 3 | 11 |
| 19 | M1 | 3 | 11 | 3 | 11 | 3 | 12 |
| 20 | M2 | 3 | 12 | 3 | 12 | 3 | 12 |
| 21 | N | 3 | 12 | 3 | 12 | 3 | 12 |
| 22 | FS-2 | 3 | 12 | 3 | 11 | 3 | 12 |
| 23 | Neg Cntl | 0 | 6 | NA | NA | NA | NA |
| 24 | Histamine | 4 | 14 | NA | NA | NA | NA |

TABLE 5

DOG ID: BFQ2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 0 | 6 | 0 | 6 | 0 | 6 |
| 4 | FS-1 | 1 | 9 | 1 | 9 | 1 | 9 |
| 5 | A | 0 | 7 | 0 | 7 | 0 | 7 |
| 6 | B | 0 | 7 | 0 | 7 | 0 | 7 |
| 7 | C1 | 0 | 7 | 1 | 7 | 1 | 7 |
| 8 | C2 | 0 | 7 | 0 | 7 | 0 | 6 |
| 9 | D1 | 0 | 8 | 1 | 7 | 1 | 8 |
| 10 | D2 | 0 | 7 | 0 | 6 | 1 | 7 |
| 11 | E | 1 | 7 | 0 | 6 | 0 | 6 |
| 12 | F | 1 | 6 | 1 | 7 | 0 | 7 |
| 13 | G | 0 | 8 | 1 | 8 | 1 | 8 |
| 14 | H | 0 | 8 | 0 | 7 | 0 | 7 |
| 15 | I | 1 | 7 | 0 | 7 | 0 | 8 |
| 16 | J | 0 | 7 | 0 | 7 | 0 | 7 |
| 17 | K | 0 | 7 | 0 | 7 | 0 | 6 |
| 18 | L | 0 | 8 | 0 | 7 | 0 | 7 |
| 19 | M1 | 0 | 7 | 0 | 7 | 0 | 7 |
| 20 | M2 | 0 | 7 | 0 | 7 | 1 | 8 |
| 21 | N | 3 | 12 | 3 | 11 | 3 | 11 |
| 22 | FS-2 | 3 | 11 | 3 | 11 | 3 | 11 |
| 23 | Neg Cntl | 0 | 7 | NA | NA | NA | NA |
| 24 | Histamine | 4 | 15 | NA | NA | NA | NA |

TABLE 6

DOG ID: CPO2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 3 | NA | NA | NA | NA |
| 2 | Histamine | 4 | 13 | NA | NA | NA | NA |
| 3 | Greer | 0 | 7 | 0 | 7 | 0 | 6 |
| 4 | FS-1 | 4 | 12 | 4 | 12 | 4 | 12 |
| 5 | A | 0 | 7 | 0 | 6 | 0 | 6 |

TABLE 6-continued

DOG ID: CPO2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 6 | B | 0 | 6 | 0 | 7 | 0 | 7 |
| 7 | C1 | 0 | 7 | 0 | 6 | 0 | 7 |
| 8 | C2 | 0 | 6 | 0 | 6 | 0 | 6 |
| 9 | D1 | 0 | 7 | 1 | 7 | 0 | 7 |
| 10 | D2 | 1 | 6 | 0 | 6 | 0 | 5 |
| 11 | E | 0 | 6 | 0 | 6 | 0 | 6 |
| 12 | F | 0 | 6 | 0 | 6 | 2 | 7 |
| 13 | G | 2 | 9 | 2 | 8 | 2 | 8 |
| 14 | H | 4 | 11 | 4 | 12 | 4 | 11 |
| 15 | I | 3 | 12 | 3 | 11 | 3 | 10 |
| 16 | J | 3 | 10 | 3 | 11 | 3 | 10 |
| 17 | K | 2 | 8 | 2 | 8 | 2 | 8 |
| 18 | L | 1 | 8 | 1 | 7 | 1 | 7 |
| 19 | M1 | 3 | 11 | 3 | 11 | 3 | 11 |
| 20 | M2 | 3 | 11 | 4 | 12 | 4 | 12 |
| 21 | N | 4 | 12 | 3 | 10 | 3 | 11 |
| 22 | FS-2 | 3 | 11 | 3 | 12 | 3 | 12 |
| 23 | Neg Cntl | 0 | 6 | NA | NA | NA | NA |
| 24 | Histamine | 4 | 13 | NA | NA | NA | NA |

TABLE 7

DOG ID: CQQ2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 13 | NA | NA | NA | NA |
| 3 | Greer | 0 | 7 | 0 | 7 | 0 | 7 |
| 4 | FS-1 | 2 | 8 | 2 | 8 | 2 | 8 |
| 5 | A | 0 | 6 | 0 | 6 | 0 | 7 |
| 6 | B | 0 | 7 | 0 | 7 | 0 | 6 |
| 7 | C1 | 0 | 7 | 0 | 6 | 0 | 6 |
| 8 | C2 | 0 | 7 | 0 | 7 | 0 | 6 |
| 9 | D1 | 0 | 6 | 0 | 6 | 0 | 6 |
| 10 | D2 | 0 | 6 | 0 | 6 | 0 | 7 |
| 11 | E | 0 | 6 | 0 | 6 | 0 | 6 |
| 12 | F | 0 | 6 | 0 | 7 | 0 | 7 |
| 13 | G | 0 | 7 | 0 | 7 | 0 | 6 |
| 14 | H | 1 | 7 | 1 | 7 | 1 | 7 |
| 15 | I | 2 | 8 | 2 | 9 | 2 | 8 |
| 16 | J | 2 | 8 | 2 | 8 | 2 | 8 |
| 17 | K | 1 | 7 | 1 | 7 | 1 | 7 |
| 18 | L | 1 | 6 | 0 | 6 | 0 | 6 |
| 19 | M1 | 2 | 7 | 2 | 8 | 2 | 8 |
| 20 | M2 | 2 | 8 | 2 | 8 | 2 | 9 |
| 21 | N | 3 | 11 | 3 | 12 | 3 | 11 |
| 22 | FS-2 | 3 | 11 | 3 | 11 | 3 | 10 |
| 23 | Neg Cntl | 0 | 7 | NA | NA | NA | NA |
| 24 | Histamine | 4 | 14 | NA | NA | NA | NA |

As a control, 2 flea naive dogs (i.e., dogs that had never been exposed to fleas) were also tested with single replicates of the same samples that were injected into the sensitized dogs. These dogs are referred to as WANU and WBCE. Objective and subjective wheal size measurements 15 minutes after injection of the samples are shown in Tables 8 and 9.

TABLE 8

DOG ID: WANU

| # | Antigen | Inj 1 Sub | Inj 1 Obj |
|---|---|---|---|
| 1 | Neg Cntl | 0 | 7 |
| 2 | Histamine | 4 | 10 |
| 3 | Greer | 0 | 6 |
| 4 | FS-1 | 0 | 6 |
| 5 | A | 0 | 7 |
| 6 | B | 0 | 6 |
| 7 | C1 | 0 | 6 |
| 8 | C2 | 0 | 6 |
| 9 | D1 | 0 | 7 |
| 10 | D2 | 0 | 6 |
| 11 | E | 0 | 6 |
| 12 | F | 0 | 6 |
| 13 | G | 0 | 7 |
| 14 | H | 0 | 7 |
| 15 | I | 0 | 7 |
| 16 | J | 0 | 7 |
| 17 | K | 0 | 6 |
| 18 | L | 0 | 7 |
| 19 | M1 | 0 | 6 |
| 20 | M2 | 0 | 6 |
| 21 | N | 1 | 8 |
| 22 | FS-2 | 1 | 8 |
| 23 | Neg Cntl | NA | NA |
| 24 | Histamine | NA | NA |

TABLE 9

DOG ID: WBCE

| # | Antigen | Inj 1 Sub | Inj 1 Obj |
|---|---|---|---|
| 1 | Neg Cntl | 0 | 6 |
| 2 | Histamine | 4 | 12 |
| 3 | Greer | 0 | 7 |
| 4 | FS-1 | 0 | 7 |
| 5 | A | 0 | 7 |
| 6 | B | 0 | 7 |
| 7 | C1 | 0 | 7 |
| 8 | C2 | 0 | 7 |
| 9 | D1 | 0 | 7 |
| 10 | D2 | 0 | 6 |
| 11 | E | 0 | 7 |
| 12 | F | 0 | 7 |
| 13 | G | 0 | 8 |
| 14 | H | 0 | 7 |
| 15 | I | 0 | 7 |
| 16 | J | 0 | 7 |
| 17 | K | 0 | 7 |
| 18 | L | 0 | 6 |
| 19 | M1 | 0 | 7 |
| 20 | M2 | 0 | 7 |
| 21 | N | 0 | 7 |
| 22 | FS-2 | 0 | 7 |
| 23 | Neg Cntl | NA | NA |
| 24 | Histamine | NA | NA |

The average subjective score obtained for each flea saliva antigen from the 6 sensitized dogs tested was calculated and is summarized in FIG. 5. The results indicate that the flea saliva products produced as described in Examples 2 and 3 include at least one allergenic protein capable of inducing an immediate hypersensitive response in a sensitized dog. In particular, injection of the mixtures of flea saliva antigens referred to as FS-1 and FS-2 resulted in substantial wheal formation. Flea saliva proteins fspE, fspF, fspG, fspH, fspi, fspJ, fspK, fspL, fspM1, fspM2 and fspN also resulted in substantial wheal formation. Flea saliva proteins fspA, fspB, fspC1, fspC2, fspD1 and fspD2 produced minimal, if any, allergic response, depending on the dog being tested. The sample containing fspH produced the largest wheal formation when compared with the other flea saliva proteins.

B. Comparison of Levels of Induration and Erythema at the Injection Sites

In addition to wheal size, the amount of induration and erythema were also measured at each site of injection. Induration produced by the injection of the flea saliva antigens was measured at 6 hours and 24 hours by subjective scoring. Such subjective induration measurements were performed by Kenneth W. Kwochka, D.V.M. In addition, the amount of erythema at each site of injection were subjectively scored by Kenneth W. Kwochka, D.V.M.

The amounts of induration and erythema measured by subjective scoring at 6 hours were negative for each of the sensitized and control dogs except for the following formulations in the following sensitized dogs. Administration of FS-1 to Dog 2082101 produced an average induration score of 1 at 2 sites of injection but no erythema score. Administration of fspL to Dog 2082101 produced no induration but an erythema score of 1 at 1 site of injection. Administration of fspM1 to Dog 2082101 produced no induration but an erythema score of 3 at 1 site of injection. Administration of FS-2 to Dog 2082101 produced no induration but an average erythema score of 1.33 at 3 sites of injection.

Administration of fspH to Dog 2082128 produced no induration but an average erythema score of 2 at 3 sites of injection. Administration of fspI to Dog 2082128 produced an average induration score of 1 and an average erythema score of 1 at 2 sites of injection. Administration of fspJ to Dog 2082128 produced an average induration score of 1 and an average erythema score of 1 at 3 sites of injection. Administration of FS-2 to Dog 2082128 produced no induration but an average erythema score of 2 at 3 sites of injection.

Administration of FS-1 to Dog BFQ2 produced an average induration score of 2 and an average erythema score of 2 at 3 sites of injection. Administration of fspN to Dog BFQ2 produced an average induration score of 1 and an average erythema score of 2 at 2 sites of injection. Administration of FS-2 to Dog BFQ2 produced an average induration score of 1 and an average erythema score of 2 at 2 sites of injection. Administration of FS-1 to Dog CPO2 produced an average induration score of 2.5 but no erythema at 2 sites of injection. Administration of fspG to Dog CPO2 produced no induration but an average erythema score of 2 at 3 sites of injection. Administration of fspH to Dog CPO2 produced no induration but an average erythema score of 1 at 2 sites of injection. Administration of FS-2 to Dog CPO2 produced no induration but an average erythema score of 2 at 3 sites of injection.

Figure 6:
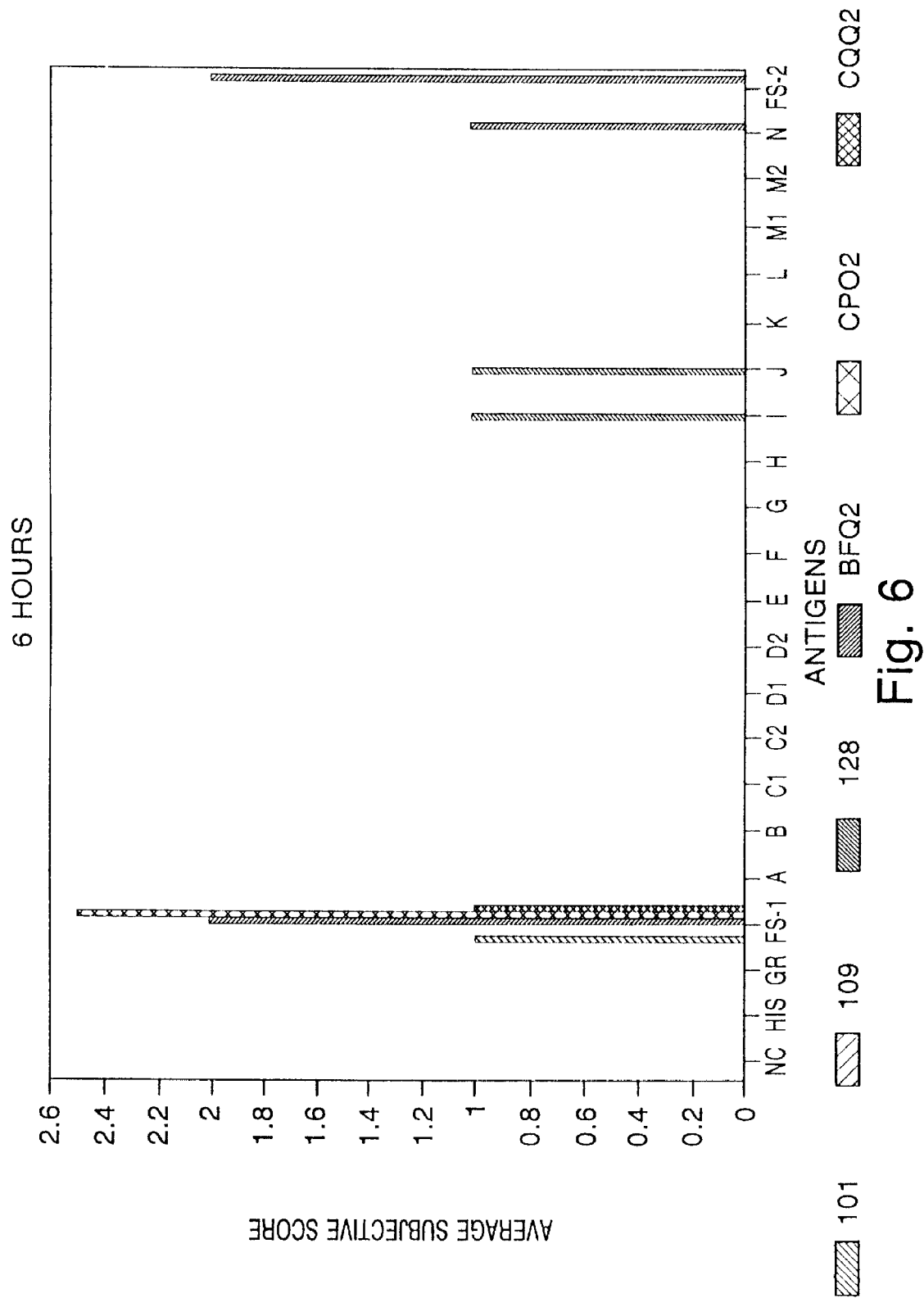
FIG. 6 illustrates the relative induration of wheals 6 hours after injection of various flea saliva protein formulations into flea-sensitized dogs.
Figure 7:
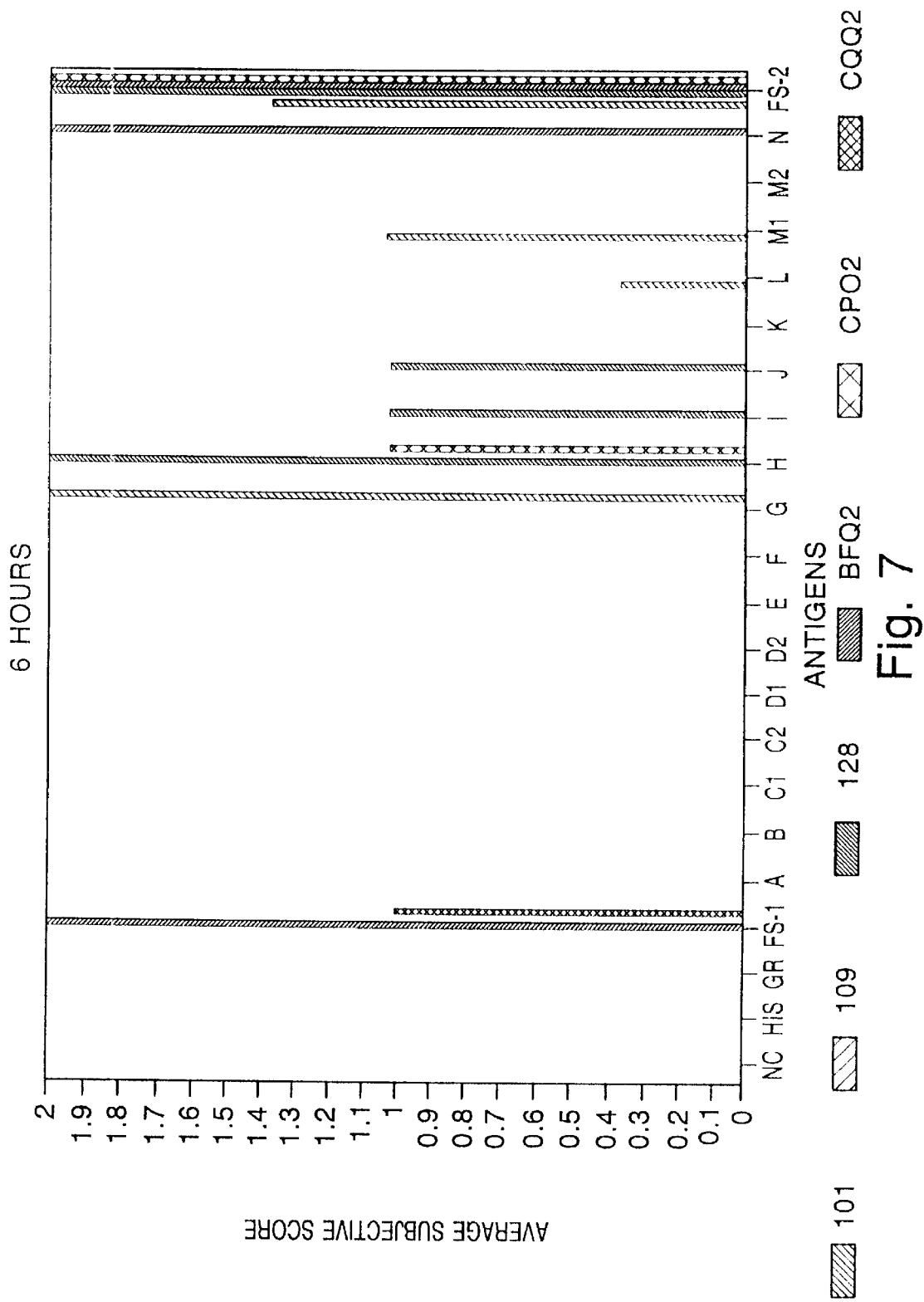
FIG. 7 illustrates the relative erythema of wheals 6 hours after injection of various flea saliva protein formulations into flea-sensitized dogs.

The average subjective score for induration obtained for each flea saliva antigen from the 6 sensitized dogs tested was calculated and is summarized in FIG. 6. The average subjective score for erythema obtained for each flea saliva antigen from the 6 sensitized dogs tested was calculated and is summarized in FIG. 7.

The amounts of induration and erythema measured by subjective scoring at 24 hours results for five of the flea-sensitized dogs and the two control dogs were negative except for the following formulations in the following sensitized dogs.

Administration of fspi to Dog 2082101 produced an average induration score of 1 and an average erythema score of 1 at 3 sites of injection. Administration of fspJ to Dog 2082101 produced an average induration score of 1 and an average erythema score of 1 at 3 sites of injection. Administration of fspM1 to Dog 2082101 produced an average induration score of 1 and an average erythema score of 3 at 3 sites of injection. Administration of fspN to Dog 2082101 produced an average induration score of 1 and an average erythema score of 2 at 3 sites of injection. Administration of FS-2 to Dog 2082101 produced an average induration score of 3 and an average erythema score of 4 at 3 sites of injection.

Administration of FS-1 to Dog BFQ2 produced an average induration score of 1 and an average erythema score of 1 at 3 sites of injection. Administration of FS-2 to Dog BFQ2 produced an induration score of 1 and an erythema score of 1 at 1 site of injection.

Administration of FS-1 to Dog CPO2 produced an induration score of 2 and an erythema score of 1 at 1 site of injection. Administration of fspI to Dog CPO2 produced an average induration score of 1 and an average erythema score of 1 at 3 sites of injection. Administration of FS-2 to Dog CPO2 produced an average induration score of 1 and an average erythema score of 2 at 3 sites of injection.

Administration of Greer antigen to Dog CQQ2 produced no induration but an average erythema score of 1 at 3 sites of injection. Administration of FS-1 to Dog CQQ2 produced an induration score of 1 and an erythema score of 1 at 1 site of injection. Administration of fspI, fspJ, fspM1 or fspM2 to Dog CQQ2 produced no induration but an average erythema score of 1 at 3 sites of injection. Administration of fspN to Dog CQQ2 produced an induration score of 1 and an erythema score of 1 at 1 site of injection. Administration of FS-2 to Dog CQQ2 produced an average induration score of 1 and an average erythema score of 2 at 3 sites of injection.

Figure 8:
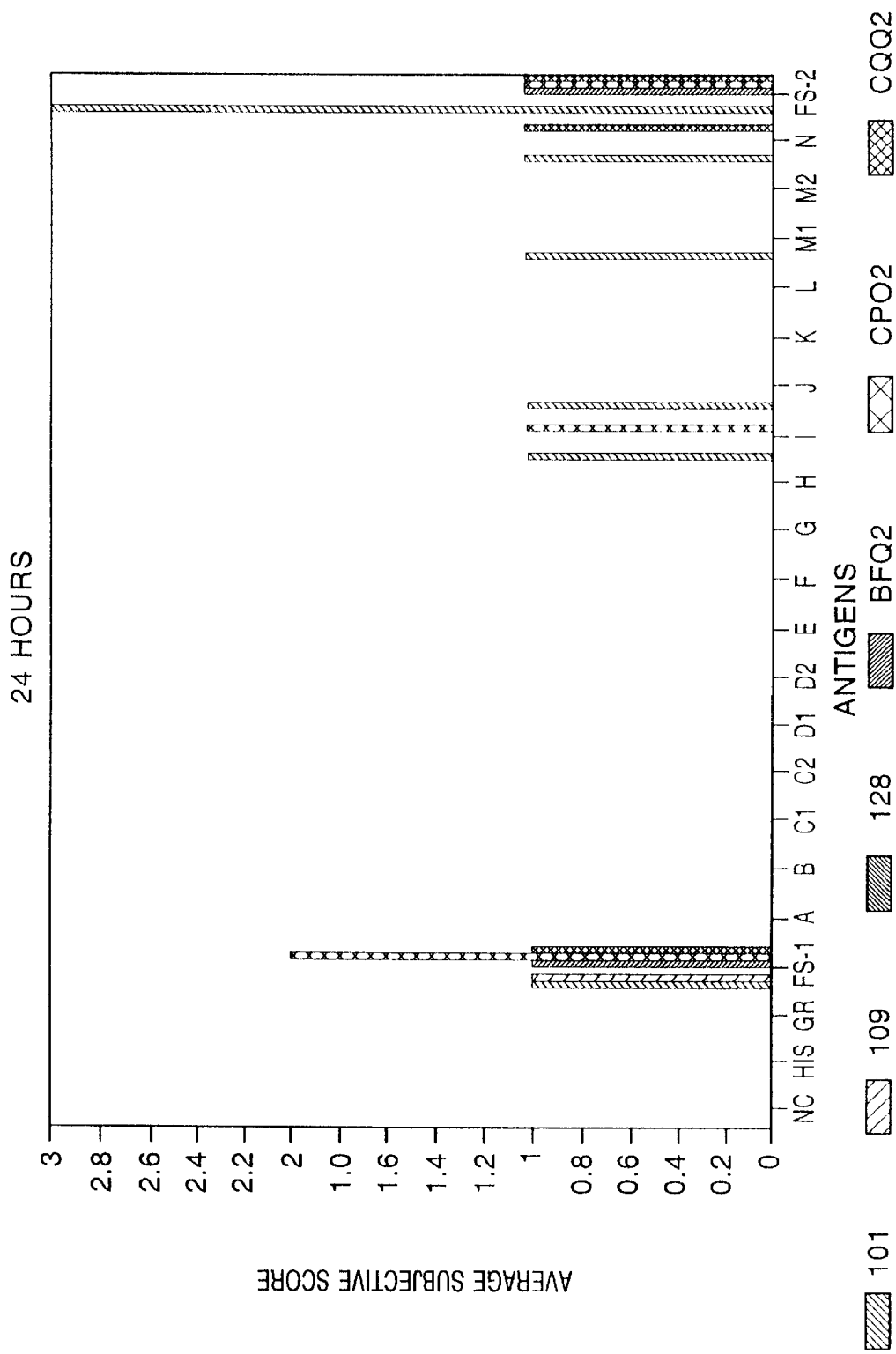
FIG. 8 illustrates the relative induration of wheals 24 hours after injection of various flea saliva protein formulations into flea-sensitized dogs.
Figure 12:
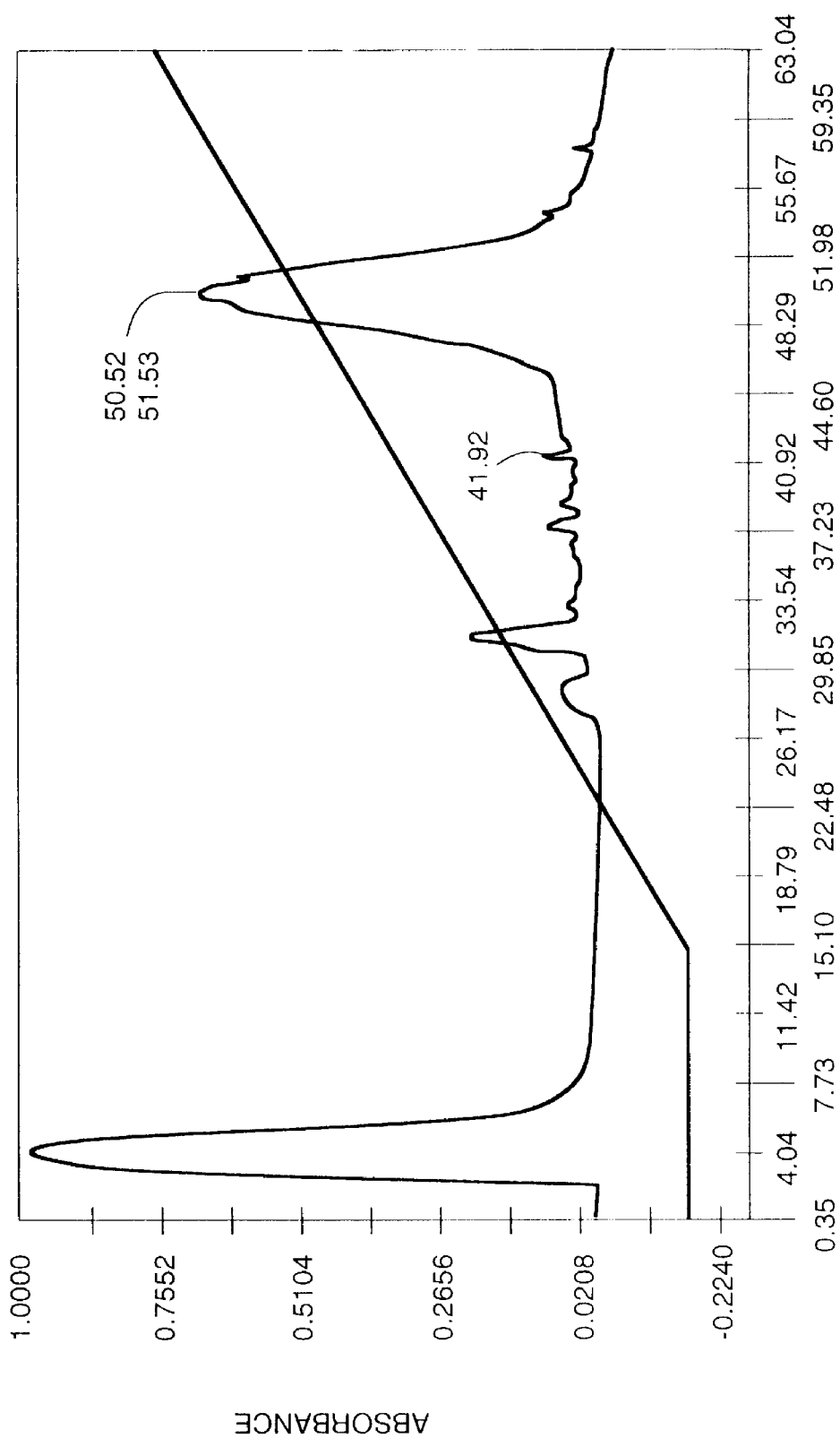
FIG. 12 illustrates the resolution of a FS-2 extract using high pressure liquid chromatography.

The average subjective score for induration obtained for each flea saliva antigen from the 6 sensitized dogs tested was calculated and is summarized in FIG. 8. The average subjective score for erythema obtained for each flea saliva antigen from the 6 sensitized dogs tested was calculated and is summarized in FIG. 9.

The results indicate that at least some of the flea saliva protein formulations produced as described in Examples 2 and 3 include at least one allergenic protein capable of inducing a delayed hypersensitive response in a sensitized dog. Injection of the mixtures of flea saliva proteins referred to as FS-1 and FS-2 induced substantial induration and erythema for at least 24 hours. In addition, the flea saliva protein samples fspI, fspJ, M1 and fspN were sufficiently allergenic to induce induration and erythema for at least 24 hours. The flea saliva protein sample fspL and fspM2 induced substantial levels of induration but not substantial levels of erythema at 24 hours.

Taken together, the results shown indicated above and shown in FIGS. 5 through 9, indicate that saliva protein formulations of the present invention are sufficiently allergenic to induce a hypersensitive response in a sensitized dog. Numerous samples induced both an immediate hypersensitive response and a delayed hypersensitive response.

Example 9

This example demonstrates the ability of numerous flea saliva protein samples isolated in Examples 2 and 3 to induce a hypersensitive response by histopathology of tissue removed from selected lesions on the dogs described in Example 8.

Two tissue samples per dog were removed from each sensitized dog described in Example 8. No biopsies were taken from the two naive dogs. The selected sites from which the tissue samples were removed are indicated in Table 10 below. Biopsies were taken with a 4 mm biopsy punch after subcutaneous injections of Lidocaine. Biopsies were processed and read by Dr. David M. Getzy, DVM, Diplomat ACVP (American College of Veterinary Pathologists) at the Colorado Veterinary Diagnostic Laboratory (College of Veterinary Medicine and Biomedical Sciences, Colorado State University, Fort Collins, Colo.).

TABLE 10

Histopathology

| Dog | Antigen | Time | No. | Slide | Lesion Type | Grade |
|---|---|---|---|---|---|---|
| 101 | FS-1 | 15 min. | 1 | A | A | 1 |
|  |  | 6 hr. | 2 | B | A | 2.5 |
|  |  | 24 hr. | 3 | C | A | 3 |
| 109 | FS-1 | 15 min. | 4 | D | A | 1 |
|  |  | 6 hr. | 5 | E | C | 2 |
|  |  | 24 hr. | 6 | F | C | 3 |
| 128 | FS-1 | 15 min. | 7 | G | A | 1.5 |
|  |  | 6 hr. | 8 | H | C | 1.5 |
|  |  | 24 hr. | 9 | I | C | 3 |
| CPO2 | FS-1 | 15 min. | 10 | J | A | 1.5 |
|  |  | 6 hr. | 11 | K | C | 3 |
|  |  | 24 hr. | 12 | L | C | 4 |
| CQQ2 | FS-1 | 15 min. | 13 | M | A | 1.5 |
|  |  | 6 hr. | 14 | N | C | 2.5 |
|  |  | 24 hr. | 15 | O | C | 2.5 |
| 101 | fspE | 15 min. | 16 | P | A | 1 |
|  |  | 6 hr. | 17 | Q | C | 1.5 |
|  |  | 24 hr. | 18 | R | A | 1.5 |
| 109 | fspF | 15 min. | 19 | S | A | 1 |
|  |  | 6 hr. | 20 | T | A | 1.5 |
|  |  | 24 hr. | 21 | U | A | 1.5 |
| 128 | fspI | 15 min. | 22 | V | A | 1 |
|  |  | 6 hr. | 23 | W | C | 2.5 |
|  |  | 24 hr. | 24 | X | C | 2.5 |
| BFQ2 | fspN | 15 min. | 25 | Y | A | 1.5 |
|  |  | 6 hr. | 26 | Z | C | 2 |
|  |  | 24 hr. | 27 | AA | C | 3.5 |
| BFQ2 | fspo | 15 min. | 28 | BB | A | 1 |
|  |  | 6 hr. | 29 | CC | C | 3 |
|  |  | 24 hr. | 30 | DD | C | 2.5 |
| CPO2 | fspH | 15 min. | 31 | EE | A | 1.5 |
|  |  | 6 hr. | 32 | FF | C | 1.5 |
|  |  | 24 hr. | 33 | GG | A | 1.5 |
| CQQ2 | fspN | 15 min. | 34 | HH | A | 1 |
|  |  | 6 hr. | 35 | II | C | 2.5 |
|  |  | 24 hr. | 36 | JJ | C | 2.5 |

Two types of lesions were found in the tissue samples tested. Lesion Type A refers to a moderate superficial dermal edema having mild numbers of mast cells in a perivascular orientation within the superficial dermis. Vascular endothelium exhibited mild reactive hypertrophy. Minimal numbers of neutrophils were noted in this region as well. Lesion Type C refers to lesions that were similar to those described in Lesion Type A except that the eosinophils were mild to moderate in severity, while neutrophils and mast cells were mild in severity.

On a scale of 0 to 5, lesions ranged from grade 1 to grade 4 in severity. Some of the specimens had predominantly mastocytic inflammatory perivascular infiltrates, edema, and minimal numbers of other cellular components. Other sections showed a predominance of eosinophilic inflammatory infiltrates, with lesser numbers of mast cells and neutrophils. The severity of these lesions was variable, however, in some areas, it progressed to intraepidermal eosinophilic pustulation and collagen necrobiosis within the superficial dermis.

Taken together, the tissue samples indicated the presence of superficial perivascular/periadnexal, mastocytic and eosinophilic, subacute dermatitis. Lesions noted in all the slide specimens examined are consistent with an allergic Type I hypersensitivity reaction.

Example 10

This example further demonstrates the ability of proteins described in Examples 2 and 3 to induce an allergic response in animals naturally susceptible to flea allergy dermatitis through skin tests performed on dogs. These reactions were compared to those obtained using the current standard for diagnosis of flea allergy dermatitis, Greer Whole Flea Extract (Greer Laboratories, Inc., Lenoir, N.C.). In addition, in order to determine specificity of the reactions, test results were compared to those obtained from a population of control dogs with normal skin and a population of dogs with pruritic skin disorders other than flea allergy dermatitis.

Three groups of dogs were used in the study: (1) 10 dogs with naturally occurring flea allergy dermatitis as determined by clinical signs, presence of fleas at the time of diagnosis, and a positive immediate or delayed reaction to Greer Whole Flea Extract; (2) 10 dogs with non-flea-related pruritic dermatoses including, but not limited to, atopy, food allergy dermatitis, pyoderma, seborrhea, and other parasitic hypersensitivity reactions; and (3) 10 dogs with normal skin and no history of chronic skin diseases. The dogs were of any breed, age or sex. They were recruited from the hospital population of the Ohio State University Veterinary Teaching Hospital, Columbus, Ohio. All dogs had written owner consent to participate in the study.

All tests and subjective scoring were performed by Kenneth W. Kwochka, D.V.M., Diplomat ACVD, (American College of Veterinary Dermatologists), in the Dermatology Examination Room at the Veterinary Teaching Hospital, College of Veterinary Medicine, The Ohio State University, Columbus, Ohio. All dogs were tested on the anterior-ventral-lateral aspect of the chest on the left side. Dogs were sedated for testing using standard dosages of xylazine and atropine administered intravenously immediately before the skin test. No glucocorticoids, antihistamines, or other non-steroidal antiinflamatory medications were allowed for at least 3 weeks prior to testing. The area for testing was gently clipped with a #40 electric clipper blade and the injection sites marked with an indelible black felt-tipped marking pen. Twenty-two sites were marked: two rows of ten dots and one row of two dots. Intradermal injections were placed both above and below each mark for a total of forty-four injections that were administered in the following order:

Row 1: Neg. cont.-Histamine-Greer-Greer-Flea saliva-Flea saliva-A-A-B-B
Row 2: C1-C1-C2-C2-D1-D1-D2-D2-E-E
Row 3: F-F-G-G-H-H-I-I-J-J
Row 4: K-K-L-L-M1-M1-M2-M2-N-N
Row 5: FS2-FS2
Row 6: Neg. cont.-Histamine Each site was injected intradermally with 50 $\mu$l of sterile diluent (Neg. cont.), 1/100,000 w/v histamine phosphate (Histamine), Greer Whole Flea Extract (Greer), whole flea saliva (Flea saliva), or individual salivary protein fractions (fspA,(A); fspB, (B); fspC1, (C1); fspC2, (C2); fspD1, (D1); fspD2, (D2); fspE, (E); fspF, (F); fspG, (G); fspH, (H); fspI, (I); fspJ, (J); fspK, (K); fspL, (L); fspM1, (M1); fspM2, (M2); fspN, (N); and FS-2 (FS2). All injections were diluted in the same sterile diluent as the Neg. cont.

Skin reactions were read subjectively and objectively at 15 minutes and 24 hours after injections. Owners were required to return their dogs to the Veterinary Teaching Hospital for the 24 hour readings. Subjective assessments were basted on a scale of 0, 1+, 2+, 3+ and 4+ based on wheal size, amount of erythema and amount of induration. Objective assessment was based on wheal diameter measured in millimeters.

Comparison of Skin Reactions

A. FAD Dogs

Of the 10 dogs positive to Greer, 7 (70%) were positive the Flea Saliva (FS). None of the 3 FS-negative dogs reacted to any of the salivary protein fractions. Additionally, the 3 dogs negative to FS at 15 minutes were negative to everything at 24 hours. The 7 FS-positive dogs were used to summarize the 15 minute reactions, shown below in Table 11.

TABLE 11

| Immediate (15 min) subjective scores of 7 FS-positive dogs to test antigens | | |
|---|---|---|
| % Positive | Scores $\geq$2+ | Scores $\geq$3+ |
| 0 | | I |
| 14 | B, I, J, L | B, D1, J, L |
| 29 | A, C1, C2, D1 | A, C1, C2, K |
| 43 | E, F, K | D2, E, F, H, M2 |
| 57 | D2, H, M2 | G, N, FS2 |
| 71 | G, M1 | M1 |
| 86 | N, FS2 | Greer |
| 100 | Greer, FS | FS |

Four of the 7 FS-positive dogs could not be evaluated at 24 hours because the severity of the immediate reactions warranted antiinflammatory therapy. The remaining 3 FS-positive dogs were used to summarize the 24 hour reactions, shown below in Table 12.

TABLE 12

| Delayed (24 hr) subjective scores of 3 FS-positive dogs to test antigens | | |
|---|---|---|
| % Positive | Scores $\geq$2+ | Scores $\geq$3+ |
| 0 | | |
| 33 | M2 | |
| 67 | Greer, FS, N, FS2 | FS, N, FS2 |
| 100 | | |

B. Normal Dogs

Three dogs had an immediate reaction to the skin test antigens to some extent. None had a positive delayed reaction at 24 hours. A summary of the immediate (15 min) subjective results is shown below in Table 13.

TABLE 13

| Immediate (15 min) subjective scores of 10 normal dogs to test antigens | | |
|---|---|---|
| % Positive | Scores $\geq$2+ | Scores $\geq$3+ |
| 0 | | |
| 10 | N, FS2 | FS2 |
| 20 | Greer, FS | Greer, FS |
| 30 | | |
| 40 | | |
| 50 | | |
| 60 | | |
| 70 | | |
| 80 | | |
| 90 | | |
| 100 | | |

Individual Dog Comments
Dog #1: Greer 3+, FS 3+, N 2+, FS2 4+
Dog #2: Greer 3+
Dog #3: FS 3+

C. Non-FAD Pruritis Dogs

Six dogs had an immediate reaction to the skin test antigens to some extent. A summary of the immediate (15 min) subjective results is shown below in Table 14.

TABLE 14

Immediate (15 min) subjective scores of 10 Non-FAD pruritis dogs to test antigens

| % Positive | Scores ≥2+ | Scores ≥3+ |
|---|---|---|
| 0 | | |
| 10 | G, 0 | G, 0 |
| 20 | Greer, M1 | Greer, FS, M11 M2 |
| 30 | FS, M2, N | N |
| 40 | | |
| 50 | | |
| 60 | | |
| 70 | | |
| 80 | | |
| 90 | | |
| 100 | | |

Individual Dog Comments
Dog #1: FS 2+, M1 3+, M2 3+, N 3+, FS2 3+
  Atopic dog under chronic flea exposure
Dog #2: FS 4+, G 4+, M1 4+, M2 3+, N 3+
  Atopic dog under chronic flea exposure
Dog #3: FS 4+, M2 2+
  Atopic dog under chronic flea exposure
Dog #4: N 3+
  Atopic dog under chronic flea exposure
Dog #5: Greer 4+
  Chronic *otitis externa*
Dog #6: Greer 4+
  Generalized demodicosis (mange)
  Dogs #1, #2 and #3 all came back to the clinic subsequently and were diagnosed with FAD and were Greer positive.

Three dogs had a delayed reaction to the skin test antigens to some extent. A summary of the delayed (24 hr) subjective results is shown below in Table 15.

TABLE 15

Delayed (24 hr) subjective scores of 10 Non-FAD pruritis dogs to test antigens

| % Positive | Scores ≥2+ | Scores ≥3+ |
|---|---|---|
| 0 | | |
| 10 | FS, N, FS2 | Greer, FS, N, FS2 |
| 20 | | |
| 30 | Greer | |
| 40 | | |
| 50 | | |
| 60 | | |
| 70 | | |
| 80 | | |
| 90 | | |
| 100 | | |

Individual Dog Comments
Dog #3: Greer 2+
  Atopic dog under chronic flea exposure
Dog #4: Greer 2+
  Atopic dog under chronic flea exposure
Dog #6: Greer 3+, FS 3+, N 3+, FS2 3+
  Generalized demodicosis (mange)

As an aid in determining the fraction(s) of flea saliva that correlate best with a positive skin test result, all the data for the artificially sensitized and clinically diagnosed FAD dogs that were 2+ or greater to FS (12 dogs total; 5 artificially sensitized and 7 clinically diagnosed as FAD positive) were tabulated according to the responses to the test antigens. The immediate (15 min) subjective results are shown below in Table 16, and the delayed (24 h) subjective results are shown below in Table 17.

TABLE 16

PERCENT RESPONDING (15 min subjective score)

| Antigen | Artificially Sensitized (5) | | Clinical Diagnosis (7) | | Combined (12) | |
|---|---|---|---|---|---|---|
| | Score ≥2+ | Score ≥3+ | Score ≥2+ | Score ≥3+ | Score ≥2+ | Score ≥3+ |
| Greer | 20 | 20 | 100 | 86 | 67 | 58 |
| FS | 100 | 80 | 100 | 100 | 100 | 92 |
| A | 0 | 0 | 29 | 29 | 17 | 17 |
| B | 0 | 0 | 14 | 14 | 8 | 8 |
| C | 0 | 0 | 29 | 29 | 17 | 17 |
| D1 | 0 | 0 | 29 | 14 | 17 | 8 |
| D2 | 0 | 0 | 57 | 43 | 33 | 25 |
| E | 40 | 20 | 43 | 43 | 42 | 33 |
| F | 40 | 40 | 43 | 43 | 42 | 42 |
| G | 60 | 40 | 71 | 57 | 67 | 50 |
| H | 80 | 20 | 57 | 43 | 67 | 33 |
| I | 100 | 40 | 14 | 0 | 50 | 17 |
| J | 100 | 40 | 14 | 14 | 50 | 25 |
| K | 80 | 20 | 43 | 29 | 58 | 25 |
| L | 20 | 20 | 14 | 14 | 17 | 17 |
| M1 | 100 | 60 | 71 | 71 | 83 | 67 |
| N2 | 100 | 80 | 57 | 43 | 75 | 58 |
| N | 100 | 60 | 86 | 57 | 92 | 58 |
| FS2 | 80 | 60 | 86 | 57 | 83 | 58 |

TABLE 17

PERCENT RESPONDING (24 hr subjective score)

| Antigen | Artificially Sensitized (5) | | Clinical Diagnosis (7) | | Combined (12) | |
|---|---|---|---|---|---|---|
| | Score ≥2+ | Score ≥3+ | Score ≥2+ | Score ≥3+ | Score ≥2+ | Score ≥3+ |
| Greer | 0 | 0 | 67 | 0 | 25 | 0 |
| FS | 0 | 0 | 67 | 67 | 25 | 25 |
| A | 0 | 0 | 0 | 0 | 0 | 0 |
| B | 0 | 0 | 0 | 0 | 0 | 0 |
| C | 0 | 0 | 0 | 0 | 0 | 0 |
| D1 | 0 | 0 | 0 | 0 | 0 | 0 |
| D2 | 0 | 0 | 0 | 0 | 0 | 0 |
| E | 0 | 0 | 0 | 0 | 0 | 0 |
| F | 0 | 0 | 0 | 0 | 0 | 0 |
| G | 0 | 0 | 0 | 0 | 0 | 0 |
| H | 0 | 0 | 0 | 0 | 0 | 0 |
| I | 0 | 0 | 0 | 0 | 0 | 0 |
| J | 0 | 0 | 0 | 0 | 0 | 0 |
| K | 0 | 0 | 0 | 0 | 0 | 0 |
| L | 0 | 0 | 0 | 0 | 0 | 0 |
| M1 | 20 | 0 | 0 | 0 | 13 | 0 |
| M2 | 0 | 0 | 33 | 0 | 13 | 0 |
| N | 20 | 0 | 67 | 67 | 38 | 25 |
| FS2 | 60 | 20 | 67 | 67 | 63 | 38 |

The results of these studies indicate that the most substantial responses were obtained for fractions fspG, fspH, fspM1, fspM2 and fspN.

Example 11

The following example illustrates the expression of fspI proteins in bacteria and in insect cells.
A. Expression of Flea Protein fspI in *E. coli*
A 500 bp DNA fragment of fspI was PCR amplified from nucleic acid molecule nfspI$_{591}$, using: Primer 11, a sense primer having the nucleic acid sequence 5' ATTCGGATC-CATGGAAAGTTAATAAAAAATGTAC 3' (BamHI site in bold), denoted as SEQ ID NO:36; and Primer 12, an antisense primer having the nucleic acid sequence 5' TAATGGATCCTTATTTTTTGGTCGACAATAAC 3', denoted SEQ ID NO:37. The PCR product, a fragment of about 535 nucleotides, denoted nfspI$_{535}$, was digested with BamHI restriction endonuclease, gel purified, and subcloned into expression vector pTrcHisB (available from InVitrogen Corp.) that had been digested with BamHI and CIP treated to produce recombinant molecule pHis-nfspI$_{535}$.

The recombinant molecule was transformed into both HB101 (available from BRL, Gaithersburg, Md.) and BL21 (available from Novagen, Madison, Wis.) competent cells to form recombinant cells E.coliHB:pHis-nfspI$_{535}$ and E.coliBL:pHis-nfspI$_{535}$. The recombinant cells were cultured in an enriched bacterial growth medium containing 0.1 mg/ml ampicillin and 0.1% glucose at 32° C. When the cells reached an OD$_{600}$ of about 0.4–0.5, expression was induced by the addition of 0.5 mM isopropyl BD-thiogalactoside (IPTG), and the cells were cultured for 2 hours at 32° C.

SDS-polyacrylamide gel electrophoresis and western immunoblot analyses of recombinant cell lysates containing the fusion protein PHIS-PfspI$_{155}$ were accomplished by standard procedures using either a T7 Tag monoclonal antibody (available from InVitrogen Corp.) or rabbit anti-FAD antiserum (#A3381) generated by Paravax, Inc. in Fort Collins, Colo., produced by immunizing rabbits with nitrocellulose membranes containing flea saliva, produced as described in Example 2. Antigen/antibody reactions were detected by colorimetric enzyme reactions using alkaline phosphatase-conjugated anti-mouse or anti-rabbit antibodies. A 28 kD protein was detected on the immunoblots of induced lysates with both primary antibodies.

B. Expression of Flea Protein fsPI in Insect Cells

Nucleic acid molecule nfspI$_{475}$ was PCR amplified from an fspI nucleic acid molecule using the following primers, which were designed to facilitate expression in insect cells using a baculovirus vector: sense Primer 13, with the BamHI site in bold, is 5' CGC GGA TCC TAT AAA TAT GGA GGA CAT CTG GAA AGT TAA TAA AAA ATG TAC ATC 3', denoted as SEQ ID NO:44; and antisense Primer 14, with the XbaI site in bold, is 5' GCT CTA GAG CAT TTA TTT TTT GGT CGA CAA TAA CAA AAC 3', denoted as SEQ ID NO:45. The PCR product was digested with BamHI and XbaI and an about 475 bp DNA fragment was excised and purified from an agarose gel.

Nucleic acid molecule nfspI$_{475}$ was ligated into a pVL1393 vector (available from InVitrogen Corp.) digested with BamHI and XbaI to produce recombinant molecule pVL-nfspI$_{475}$.

The recombinant molecule was transfected into S. frugiperda Sf9 cells with linearized Baculovirus DNA to form recombinant cell S. frugiperda:pVL-nfspI$_{475}$. The recombinant cells were cultured using standard conditions to produce recombinant virus. The transfection supernatant was also found to contain a 23 kD protein which reacted with a rabbit anti-FAD antiserum (#A3381) by Western blot analysis.

Example 12

This example describes the isolation of nucleic acid sequences encoding at least portions of flea saliva proteins in fspN, and their characterization relative to human prostatic acid phosphatase.

The flea salivary gland and the whole fed flea cDNA libraries described previously in Example 6A were immunoscreened using New Zealand White rabbit antiserum developed against a collected mixture of flea salivary proteins (e.g., the rabbit was immunized one or more times with a ground up nitrocellulose filter used as collection membrane to collect flea saliva proteins, followed by one or more immunization with a flea saliva protein extract eluted from a Duropore filter). The immunoscreening protocols used are those described in the picoBlue™ Immunoscreening Kit instruction manual, available from Stratagene, Inc. The methods for preparation of the cDNA expression libraries for immunoscreening, i.e., expression of the cDNA clones and procedures for transferring lambda phage plaques to membranes for immunoscreening, are described in the ZAP-CDNA Synthesis Kit instruction manual, also available from Stratagene, Inc., La Jolla, Calif.

Forty immunopositive clones were selected from the screening. One immunopositive clone was derived from the salivary gland cDNA library and 39 other immunopositive clones were derived from the whole fed flea cDNA library. The initial fspN-protein CDNA sequences, termed nfspN(A) and nfspN(B) were isolated from the whole fed flea cDNA library and came from this initial immunoscreening.

Partial nucleotide sequences for nfspN(A) and nfspN(B) are represented by SEQ ID NO's. Each sequence represents approximately the carboxyl terminal half of the cDNA gene coding region as well as the 3' untranslated region through the poly (A) region. The nucleotide sequence for a nfspN(A) nucleic acid molecule named nfspN(A)$_{646}$ is denoted as SEQ ID NO:50. Translation of SEQ ID NO:50 yields a protein named PfspN(A)$_{172}$ having an amino acid sequence denoted SEQ ID NO:51. The nucleotide sequences for a nfspN(B) nucleic acid molecule named nfspN(B)$_{612}$ is denoted SEQ ID NO:52. Translation of SEQ ID NO:52 yields a protein named PfspN(B)$_{153}$ having an amino acid sequence denoted SEQ ID NO:53.

In addition, an apparent N-terminal amino acid sequence deduced from nucleic acid sequence of nfspN(A), named PfspN(A)$_{56}$ and denoted SEQ ID NO:54, was determined. The amino acid sequence of PfspN(A)$_{56}$ (i.e., SEQ ID NO:54) is similar, but not identical, to the N-terminal amino acid sequences obtained for fspN1 (SEQ ID NO:11), fspN2 (SEQ ID NO:12) and fspN3 (SEQ ID NO:13). While not being bound by theory, it is believed that there is a family of fspN proteins that are found in flea saliva, which may be due to allelic variation or multiple genes in the flea genome. Nucleic acid molecules nfspN(A)$_{646}$ and nfspN(B)$_{612}$ are about 76% identical, and the translated products are about 65% identical.

In a second immunoscreening experiment in which antiserum collected from a rabbit that was immunized with the proteins in peak N of the HPLC separation of flea saliva extract described in Example 4 (i.e., fspN proteins) was used to probe a flea salivary gland cDNA library (prepared as described in Example 6), approximately 20 positive clones were isolated. The nucleic acid sequence of one of the recovered nucleic acid molecules appears to be identical to that of nfspN(A). At least two of the other nucleic acid molecules have nucleic acid sequences that are similar, but not identical, to that of nfspN(A), again supporting the likelihood of a family of fspN proteins in flea saliva. Yet another nucleic acid molecule appears to have a nucleic acid sequence that is similar to myosin gene sequences.

The nucleic acid and amino acid sequences of the fspN(A) and fspN(B) nucleic acid molecules and proteins, respectively, were compared to known nucleic acid and amino acid sequences using a Genbank homology search.

Both nucleic acid sequences were found to be similar to the corresponding (i.e., carboxyl-terminal) region of the nucleic acid sequence of human prostatic acid phosphatase. The most highly conserved region of continuous similarity between flea and human amino acid sequences spans from about amino acid 272 through about amino acid 333 of the human enzyme. Comparison of the nucleic acid sequence encoding amino acids from about 268 through about 333 of the human enzyme with the corresponding regions of nfspN(A) and nfspN(B) nucleic acid sequences indicate that nfspN(A) is about 40% identical, and nfspN(B) is about 43% identical, to that region of the human prostatic acid phosphatase gene. Comparison of the region spanning from about amino acid 268 through about amino acid 333 of the human enzyme with the corresponding regions of PfspN(A) and PfspN(B) indicate that PfspN(A) is about 28% identical, and PfspN(B) is about 30% identical, to that region of the human prostatic acid phosphatase gene. The possibility that at least some fspN proteins encode an active acid phosphatase is supported by the finding that flea saliva extract FS-3 has been shown to have acid phosphatase activity, as described in Example 3.

The apparent complete nucleic acid sequence of the coding region of nucleic acid molecule nfspN(A), referred to herein as $nfspN(A)_{1197}$, is denoted herein as SEQ ID NO:55. Translation of SEQ ID NO:55 yields an apparent full-length fspN protein named $PfspN(A)_{398}$ having an amino acid sequence denoted herein as SEQ ID NO:56. (It should be noted that although nucleic acid sequence SEQ ID NO:55 and amino acid sequence SEQ ID NO:56 do not exactly match nucleic acid sequence SEQ ID NO:50 or amino acid sequences SEQ ID NO:51 or SEQ ID NO:54 in the corresponding regions, the mismatches are likely due to sequencing errors in SEQ ID NO:50, SEQ ID NO:51 and SEQ ID NO:54.)

Comparison of SEQ ID NO:56 with the N-terminal amino acid sequences obtained for fspN1 (SEQ ID NO:11), fspN2 (SEQ ID NO:12) and fspN3 (SEQ ID NO:13) indicates that the amino terminal amino acids of fspN1 and fspN2 correspond to amino acid position 18 of SEQ ID NO:56, while the amino terminal amino acid of fspN3 corresponds to amino acid position 20 of SEQ ID NO:56. SEQ ID NO:13 appears to be identical to the region of SEQ ID NO:56 spanning amino acid positions from 20 through 39, suggesting that nfspN(A) encodes fspN3. SEQ ID NO:11 is about 67% identical to the corresponding region of SEQ ID NO:56, and SEQ ID NO:12 is about 60% identical (discounting the 3 unknown amino acids in SEQ ID NO:12) to the corresponding region of SEQ ID NO:56, supporting the suggestion that fspN1 and fspN2 are members of the same flea saliva protein family as fspN3.

Comparison of SEQ ID NO:56 with the amino acid sequence of human prostatic acid phosphatase indicates that the two sequences share about 30% identity at the amino acid level.

Example 13

This Example demonstrates the production of a bacterial recombinant cell including an fspN protein and use of that cell to produce the fspN protein.

An about 1000 bp DNA fragment, denoted $nfspN_{1000}$, was PCR amplified from a nucleic acid molecule encoding an fspN protein using the following primers: F7 sense, having nucleic acid sequence 5' GGCGTCTCGAGAGAAT-TGAAATTTGTGTTTGCG 3' (XhoI site in bold), denoted SEQ ID NO:46; and F7 antisense, having nucleic acid sequence 5' AGACGAGAATTCCAATTTATCAT-GAGCGG 3' (EcoRI site in bold), denoted SEQ ID NO:47. The PCR product was digested with XhoI and EcoRI restriction endonucleases, gel purified and subcloned into expression vector pTrcHisB (available from InVitrogen, Corp.) that had been digested with XhoI and EcoRI to form recombinant molecule $pHis-nfspN_{1000}$. The recombinant molecule was transformed into E. coli BL21 competent cells (available from Novagen) to form recombinant cell E. coli:$pHis-nfspN_{1000}$.

Recombinant cell E. coli:$pHis-nfspN_{1000}$ was cultured and induced as described in Example 11A to produce fusion protein PHIS-PfspN3. The recombinant fusion protein was detected by immunoblot analysis using the T7 Tag monoclonal antibody as described in Example 11A. PHIS-PfspN3 was Ni purified using Ni-NTA spin kit (available from Qiagen, Chatsworth, Calif.) and the purification verified using T7 Tag monoclonal antibody as described above.

Example 14

The Example demonstrates the expression of an fspN protein in insect cells.

Recombinant molecule $pVL-nfspN_{1000}$ containing the $nfspN_{1000}$ nucleic acid molecule operatively linked to baculovirus polyhedrin transcription control sequences was produced in the following manner. An about 1000 bp DNA fragment, denoted $nfspN_{1000}$, was PCR amplified from a nucleic acid molecule encoding an fspN protein using the following primers: sense primer 17, having nucleic acid sequence 5' CCG GAA TTC CGG TAT AAA TAT GTG GCG TCT ACT G 3' (EcoRI site in bold), denoted SEQ ID NO:48, and designed to enhance expression in insect cells; and antisense primer 18, having nucleic acid sequence 5' CCG GAA TTC TTA AGA CGA TTT ACA CAA TTT ATC 3' (EcoRI site in bold), denoted SEQ ID NO:49. The PCR product was digested with EcoRI and non-directionally cloned into the baculovirus shuttle vector pVL1393 (available from InVitrogen, Corp.). Orientation was determined by restriction digest with the enzyme EcoRV. The resultant recombinant molecule, i.e., $pVL-nfspN_{1000}$, was co-transfected into S. frugiperda cells (donated by the Colorado Bioprocessing Center, Fort Collins, Colo.) with wild type linear baculovirus DNA (AcMNPV) and insectin cationic liposome according to manufacturer's specifications (available from InVitrogen Corp.) to produce recombinant cell S. frugiperda:$pVL-nfspN_{1000}$. The supernatant was tested five days post-transfection by Western blot analysis using rabbit antiserum against flea fspN proteins (as described in Example 12; denoted B2237) and a protein approximately 40 kD was detected. The recombinant virus, $vBV-nfspN_{1000}$ was recovered from the supernatant and plaque purified.

Example 15

This Example demonstrates that use of ELISAs to detect anti-flea saliva IgE antibodies in the sera of dogs sensitized to fleas or flea saliva.
A. In a first study, sera collected from three dogs that had been artificially sensitized to flea bites were pooled and pretreated by contacting the pooled sera with Protein G to remove at least some of the non-IgE immunoglobulins present in the sera. IgE antibodies were then affinity-purified from the pretreated sera using Con-A chromatography.

The affinity-purified IgE antibodies were exposed to the following flea saliva products and proteins: FS-1 saliva extract at 2 mg/ml (23,300 flea-hours per $\mu$l); fspA, fspB, fspC1, fspC2, fspD1, fspD2, fspE, fspF, fspG, fspH, fspI, fspJ, fspK, fspL, fspM1, fspM2, and fspN (from a 233,000 fleahours per μl sample applied to HPLC chromatography as described in Example 3). The flea saliva products and proteins were suspended in 0.1M sodium carbonate, pH 9.6, and 100 μl samples of each were placed in microtiter dish wells. The samples were incubated overnight at room temperature, washed 5 times with PBS/Tween, blocked with a solution of PBS, 2% BSA, 0.02% NaN$_3$, for 1 hour at 37° C., and washed 5 times with PBS/Tween. The washed wells were each exposed to 100 μl aliquots of the affinity-purified dog IgE antibodies for 1 hour at 37° C. The wells were washed 5 times with PBS/Tween and exposed for 1 hour, at 37° C., to 100 μl of a monoclonal mouse anti-canine IgE antibody preparation diluted 1:000 in PBS, 2% BSA, 0.05% Triton X-100. The wells were washed 5 times with PBS/Tween, exposed for 1 hour, at 37° C., to 100 μl donkey anti-mouse IgG (H+L)-HRP, and washed 5 times with PBS/Tween. The wells were developed with 100 μl KPL TMB:H$_2$O$_2$, 1:1, for 10 minutes, the reaction being stopped with 50 μl 2.5N hydrogen sulfate. The wells were read at 450 nm.

The results, shown in Table 18 and FIG. 10, indicate that FAD+ dogs have in their sera IgE antibodies that react in a sensitive and specific manner with FS-1 flea saliva extract as well as with flea saliva proteins fspE, fspF, fspG, fspH, fspI, fspJ, fspK, fspL, fspM1, fspM2 and fspN. The IgE antibody preparation reacted minimally, if at all, with flea saliva proteins fspA, fspB, fspC1, fspC2, fspD1 and fspD2. Thus, the IgE reactivity closely followed the skin test results of Example 8 in the artificially sensitized dogs with the same flea saliva products and proteins.

TABLE 18

| Fraction | Volume of Antigen | | | |
|---|---|---|---|---|
| | 0.5 μl | 0.25 μl | 0.125 μl | 0.063 μl |
| A | 0.007 | 0.008 | 0.012 | 0.018 |
| B | 0.016 | 0.010 | 0.013 | 0.052 |
| C1 | 0.035 | 0.008 | 0.035 | 0.020 |
| C2 | 0.022 | 0.009 | 0.002 | 0.005 |
| D1 | 0.013 | 0.025 | 0.004 | 0.005 |
| D2 | 0.059 | 0.018 | 0.017 | 0.012 |
| E | 0.214 | 0.263 | 0.206 | 0.092 |
| F | 0.276 | 0.393 | 0.217 | 0.114 |
| G | 0.288 | 0.217 | −0.010 | −0.010 |
| H | 0.503 | 0.336 | 0.203 | 0.062 |
| I | 1.076 | 0.997 | 0.917 | 0.637 |
| J | 0.955 | 0.816 | 0.673 | 0.456 |
| K | 1.095 | 0.898 | 0.815 | 0.690 |
| L | 0.991 | 0.721 | 0.465 | 0.162 |
| M1 | 1.251 | 1.190 | 0.840 | 0.454 |
| M2 | 1.561 | 1.105 | 0.902 | 0.558 |
| N | 1.989 | 1.887 | 1.819 | 1.435 |
| FS-1 | 1.367 | 1.246 | 0.982 | 0.604 |
| none | 0.002 | 0.005 | 0.008 | 0.121 |

B. In a second study, serum collected from a dog that had been artificially sensitized to flea bites was pretreated by contacting the serum with Protein G to remove at least some of the non-IgE immunoglobulins present in the serum. The reactivity of the pretreated serum to FS-1 flea saliva extract was determined as described in Example 15A. Also tested was the reactivity to FS-1 flea saliva extract of sera collected from dogs infected with heartworm, pooled and pretreated by contacting the serum with Protein G. The results, shown in Table 19 and FIGS. 11A and 11B, demonstrate a dose dependent reactivity of IgE from the FAD+ dog while IgE from heartworm infected dogs had no reactivity against FS-1 flea saliva extract.

TABLE 19

| | Sera dil. | | | | | | | |
|---|---|---|---|---|---|---|---|---|
| | 1:2 | 1:4 | 1:8 | 1:16 | 1:32 | 1:64 | 1:128 | none |
| DOG 2082128 | | | | | | | | |
| 2 μg | 1.67 | 1.20 | 0.85 | 0.57 | 0.34 | 0.19 | 0.11 | 0.01 |
| 1 g | 1.43 | 1.16 | 0.80 | 0.49 | 0.30 | 0.17 | 0.10 | 0.00 |
| 0.5 μg | 1.32 | 1.02 | 0.71 | 0.46 | 0.28 | 0.14 | 0.08 | 0.00 |
| 0.25 μg | 1.18 | 0.92 | 0.59 | 0.38 | 0.22 | 0.12 | 0.06 | 0.00 |
| 0.13 μg | 0.95 | 0.80 | 0.52 | 0.30 | 0.19 | 0.11 | 0.06 | 0.00 |
| none | 0.00 | 0.01 | 0.00 | 0.00 | 0.00 | 0.00 | 0.00 | 0.01 |
| HEARTWORM POOL | | | | | | | | |
| 2 μg | 0.00 | 0.00 | 0.00 | 0.00 | 0.00 | 0.00 | 0.00 | 0.00 |
| 1 μg | 0.00 | 0.00 | 0.00 | 0.00 | 0.00 | 0.00 | 0.00 | 0.00 |
| 0.5 μg | 0.00 | 0.00 | 0.00 | 0.00 | 0.00 | 0.00 | 0.00 | 0.00 |
| 0.25 μg | 0.00 | 0.01 | 0.01 | 0.00 | 0.00 | 0.00 | 0.00 | 0.00 |
| 0.13 μg | 0.01 | 0.00 | 0.00 | 0.00 | 0.00 | 0.00 | 0.00 | 0.00 |
| none | 0.01 | 0.01 | 0.01 | 0.00 | 0.00 | 0.00 | 0.01 | 0.00 |

Example 16

This example demonstrates the ability of formulations of the present invention, including formulations comprising flea saliva extract FS-1, E. coli-produced fsph, E. coli-produced fspN3 or insect cell S. frugiperda-produced fspN3 to identify animals susceptible to flea allergy dermatitis (i.e., to induce flea allergy dermatitis in an animal susceptible to flea allergy dermatitis).

The formulations were produced as follows. FS-1 was produced as described in Example 2. E. coli-produced fspH was produced by an E. coli cell transformed with a nucleic acid molecule encoding fspH operatively linked to expression vector λP$_R$/T$^2$ori/S10HIS-RSET-A9, the production of which is described in PCT/US95/02941, Example 7; the resultant PHIS-fspH fusion protein was purified as described in Example 13. E. coli-produced fspN3 and S. frugiperda-produced fspN3 were produced as described in Examples 13 and 14, respectively; E. coli produced fspN3 was purified as described in Example 11A; S. frugiperda-produced fspN3 was purified by anion/cation exchange chromatography.

The formulations were tested in artificially sensitized dogs 2080109, 2082101, 2082128, BFQ2, CPO2, CQQ2, as described in Example 8. The injected samples were as follows: (a) saline negative control; (b) histamine positive control; (c) 2 μg FS-1; (d) 0.1 μg E. coli-produced fspH; (e) 1.0 μg E. coli-produced fspH; (f) 0.2 μg E. coli-produced fspN3; (g) 2.0 μg E. coli-produced fspN3; (h) 0.2 μg S. frugiperda-produced fspN3; and (i) 2.0 μg S. frugiperda-produced fspN3. The immediate hypersensitivity results are shown in Table 20, and the delayed hypersensitivity results are shown in Table 21. Scoring was as described in Example 8; NA indicates a bad injection.

TABLE 20 a) Immediate (15 min.) subjective score (1–4+) (NA was a bad injection)

| | | | | E. coli FS-H | | E. coli fspN3 | | S. frugiperda fspN3 | |
|---|---|---|---|---|---|---|---|---|---|
| Dog | Saline | Histamine | FS-1 | 0.1 | 1.0 | 0.2 | 2.0 | 0.2 | 2.0 |
| 109 | 0 | 4 | 4 | NA | 4 | 1 | 1 | 1 | 1 |
| 101 | 0 | 4 | 4 | 4 | 4 | 1 | 2 | 0 | 1 |
| 128 | 0 | 4 | 4 | 2 | 4 | 1 | 2 | 1 | 3 |
| BFQ2 | 0 | 4 | 3 | 0 | 3 | 0 | 0 | 0 | 2 |

TABLE 20-continued a) Immediate (15 min.) subjective score (1–4+) (NA was a bad injection)

| Dog | Saline | Histamine | FS-1 | E. coli FS-H 0.1 | E. coli FS-H 1.0 | E. coli fspN3 0.2 | E. coli fspN3 2.0 | S. frugiperda fspN3 0.2 | S. frugiperda fspN3 2.0 |
|---|---|---|---|---|---|---|---|---|---|
| CPO2 | 0 | 4 | 4 | 4 | 4 | 1 | 4 | 1 | 2 |
| CQQ2 | 0 | 4 | 4 | 4 | 4 | 0 | 0 | 0 | 2 |

TABLE 21 b) Delayed (24 hr.) subjective score (1–4+) (NA was a bad injection)

| Dog | Saline | Histamine | FS-1 | E. coli FS-H 0.1 | E. coli FS-H 1.0 | E. coli fspN3 0.2 | E. coli fspN3 2.0 | S. frugiperda fspN3 0.2 | S. frugiperda fspN3 2.0 |
|---|---|---|---|---|---|---|---|---|---|
| 109 | 0 | 0 | 0 | NA | 0 | 0 | 0 | 0 | 0 |
| 101 | 0 | 0 | 3 | 0 | 2 | 2 | 3 | 2 | 3 |
| 128 | 0 | 0 | 3 | 0 | 2 | 2 | 2 | 2 | 3 |
| BFQ2 | 0 | 0 | 1 | 0 | 0 | 0 | 0 | 0 | 0 |
| CPO2 | 0 | 0 | 0 | 0 | 0 | 0 | 0 | 0 | 0 |
| CQQ2 | 0 | 0 | 0 | 0 | 0 | 0 | 0 | 0 | 0 |

In summary, these results indicate that *E. coli*-produced fspH exhibited a strong positive immediate reaction in all dogs, the reaction being proportional to the dogs' reaction to flea saliva. *E. coli*-produced and *S. frugiperda*-produced fspN3 proteins also exhibited a positive immediate reaction in 4 and all dogs, respectively. The two dogs that showed a strong delayed hypersensitive response reaction to FS-1 showed similar delayed hypersensitive response reactions to recombinantly produced fspH and fspN3.

Example 17

This example describes the amino acid sequence analysis of additional isolated flea saliva proteins from FS-1 extract and eluted from DE-81 filters.

FS-1 flea saliva extract and flea saliva product eluted from DE-81 filters were collected using standard techniques. Using standard purification techniques (e.g., C4 reverse phase chromatography; SDS-PAGE gel electrophoresis and blotting; and/or flow through electrophoresis), several proteins were isolated from peak M and partial amino acid sequences were determined as described in Example 4. Partial N-terminal amino acid sequencing indicated that peak M contained fspJ, fspL and fspN proteins as well as newly identified proteins referred to herein as fspM(G), fspM(H), fspM(I), fspM(J), fspM(K), fspM(L) and fspM (M). Flea saliva protein fspM(G), having a molecular weight of about 37 kD, had an N-terminal partial amino acid sequence of M R G N H V F L E D G M A D M T G G Q Q M G R D L Y, denoted SEQ ID NO:72. Flea saliva protein fspM(H), having a molecular weight of about 34 kD, had an N-terminal partial amino acid sequence of K Y R N (Y/D) X T N D P Q Y, denoted SEQ ID NO:73. Flea saliva protein fspM(I), having a molecular weight of about 10 kD had an N-terminal partial amino acid sequence of E I K R N D R E P G N L S K I R T V M D K V I K Q T Q, denoted SEQ ID NO:74. Flea saliva protein fspM(J), having a molecular weight of about 25 kD, had an N-terminal partial amino acid sequence of L K D N D I Y (A/H) (A/H) R D I N E I L R V L D P S K, denoted SEQ ID NO:75. Flea saliva protein fspM(K), having a molecular weight of about 30 kD, had an N-terminal partial amino acid sequence of N Y G R V Q I E D Y T X S N H K D X E E K D Q I N G L, denoted SEQ ID NO:76. Flea saliva protein fspM(L), having a molecular weight of about 37 kD, had an N-terminal partial amino acid sequence of K Y R N X Y T N D P Q L K L L D E G, denoted SEQ ID NO:77. Flea saliva protein fspM(M) was recovered from peak M and subjected to amino acid sequence analysis as described in Example 4. Flea saliva protein fsp(M), having a molecular weight of about 31 kD, had an N-terminal partial amino acid sequence of Y F N D Q I K S V M E P X V F K Y P X A X L, denoted SEQ ID NO:78. A Genbank homology search revealed no significant homology between known amino acid sequences and those determined for fspM(G), fspM(H), fspM(I), fspM(J), fspM(K), fspM(L) and fspM(M).

Example 18

This example describes the isolation of nucleic acid molecules encoding at least a portion of a fspG flea saliva protein. This example also describes expression of a fspG protein by bacteria.

A. Isolation of fspG4 Nucleic Acid Molecules

The partial N-terminal amino acid sequence of fspG2 (i.e., SEQ ID NO:29) was used to synthesize degenerate antisense Primer G2-2, having the nucleic acid sequence 5' TGR TTT CCW ATR AAR TCT TC 3', denoted SEQ ID NO:103. Primer G2-2 was used in combination with the M13 reverse primer (SEQ ID NO:40), to PCR amplify, using standard techniques, the 5'-terminal portion of the fspG4 gene from a salivary gland cDNA expression library as described above in Example 6A. The resulting PCR product was approximately 225-bp when visualized on a 1% agarose gel. The nucleotide sequence of the 225-bp PCR fragment was obtained, named nfspG4$_{225}$ is presented as SEQ ID NO:104.

The nucleic acid sequence of nfspG4$_{225}$ was used to synthesize sense Primer G5, having nucleic acid sequence 5' AAT TCG GCA CGA GTG 3', denoted SEQ ID NO:105. Primer G5 was used in combination with the M13 universal primer (SEQ ID NO:19), to PCR amplify, as described above, the 3'-terminal portion of the fspG4 gene from the salivary gland cDNA expression library described above in Example 6A. The resulting PCR product, denoted nfspG4$_{610}$, was approximately 610-bp when visualized on a 1% agarose gel. The nucleotide sequence of the 610-bp PCR fragment was obtained, 565 nucleotides of which are presented as SEQ ID NO:57. The nucleic acid molecule containing nucleic acid sequence SEQ ID NO:57 is referred to herein as nfspG4$_{565}$. Translation of SEQ ID NO:57 suggests that nucleic acid molecule nfspG4$_{565}$ encodes a full-length fspG protein of about 90 amino acids, referred to herein as PfspG4$_{90}$, assuming an open reading frame having a start codon spanning from about nucleotide 45 through about nucleotide 47 of SEQ ID NO:57 and a stop codon spanning from about nucleotide 315 through about nucleotide 317 of SEQ ID NO:57. This open reading frame, excluding the stop codon, comprises nucleic acid molecule nfspG4$_{270}$ of the present invention, the nucleic acid sequence of which is represented herein by SEQ ID NO:79. PfspG4$_{90}$ is denoted herein as SEQ ID NO:58. Residues 20–42 of SEQ ID NO:58 appear to be identical to SEQ ID NO:29 (N-terminal partial amino acid sequence of fspG2), except that residue 37 of SEQ ID NO:58 is a glutamic acid rather than a lysine. In addition, residues 38–57 of SEQ ID NO:58 appear to be identical to SEQ ID NO:30 (N-terminal partial amino acid sequence of fspG3). These similarities support the likelihood of a family of fspG proteins in flea saliva.

Analysis of SEQ ID NO:57 suggests that the sequence includes a leader segment of about 19 amino acids followed by a mature protein. The leader sequence is apparently cleaved to form a mature protein termed PfspG4$_{711}$ denoted SEQ ID NO:80. PfspG4$_{71}$ has a calculated molecular weight of 7536 daltons and calculated pI of about 9.0. PfspG4$_{90}$ has a calculated molecular weight of 9657 daltons and calculated pI of about 9.26. A Genbank homology search revealed no significant homology between SEQ ID NO:57 or SEQ ID NO:58 and known nucleic acid sequences or known amino acid sequences, respectively.

B. Expression

An about 216-bp DNA fragment of nfspG4 was PCR amplified from nucleic acid molecule nfspG4, using: Primer G7: a sense primer having the nucleic acid sequence 5' AGT GGA TCC GTC AAA AAT GGT CAC TG 3', denoted as SEQ ID NO:106 (BamHI site in bold); and Primer G8, an antisense primer having the nucleic acid sequence 5' CCG GAA TTC GGT TAT TCG CAA TAA CAG T 3' (EcoRI site in bold), denoted SEQ ID NO:107. The PCR product, a fragment of about 216 nucleotides, denoted nfspG4$_{216}$, was digested with BamHI and EcoRI restriction endonucleases, gel purified, and subcloned into expression vector $\lambda P_R$/T$^2$ori/S10HIS-RSET-A9 (described in Example 16) that had been digested with BamHI and EcoRI to produce recombinant molecule pHis-nfspG4$_{216}$.

The recombinant molecule was transformed into *E. coli* to form recombinant cell *E.coli*:pHis-nfspG4$_{216}$. The recombinant cell was cultured and induced as described in Example 11A to produce fusion protein PHIS-fspG4$_{72}$. The recombinant fusion protein was detected by immunoblot analysis using the T7 Tag monoclonal antibody as described in Example 11A.

Example 19

This example describes the isolation of nucleic acid sequences encoding at least a portion of flea saliva proteins fspM(A), fspM(B), fspM(C), fspM(D), fspM(E), and fspM (F).

A. nfspM(A)$_{897}$ and nfspM(B)$_{2706}$

A flea salivary gland cDNA library (prepared as described in Example 6) was immunoscreened with antiserum collected from a rabbit that was immunized with the proteins in peak M2 of the HPLC separation of flea saliva extract described in Example 3 (i.e., fspM2 proteins). Immunoscreening was performed as described in Example 12.

A nucleotide sequence for a nfspM nucleic acid molecule named nfspM(A)$_{897}$ is denoted as SEQ ID NO:59. Translation of SEQ ID NO:59 suggests that nucleic acid molecule nfspM(A)$_{897}$ encodes a full-length fspM protein of about 157 amino acids, referred to herein as PfspM(A)$_{157}$, assuming an open reading frame having a start codon spanning from about nucleotide 97 through about nucleotide 99 of SEQ ID NO:59 and a stop codon spanning from about nucleotide 568 through about nucleotide 570 of SEQ ID NO:59. This open reading frame, excluding the stop codon, comprises nucleic acid molecule nfspM(A)$_{471}$ of the present invention, the nucleic acid sequence of which is represented herein by SEQ ID NO:81. The amino acid sequence of PfspM(A)$_{157}$ is denoted SEQ ID NO:60. PfspM(A)$_{157}$ has a calculated molecular weight of about 18,291.68 daltons and calculated pI of about 10.3. A Genbank homology search revealed no significant homology between SEQ ID NO:59 or SEQ ID NO:60 and known nucleic acid or amino acid sequences, respectively.

A nucleotide sequence for another nfspM nucleic acid molecule named nfspM(B)$_{2706}$ is denoted as SEQ ID NO:61. Translation of SEQ ID NO:61 suggests that nucleic acid molecule nfspM(B)$_{2706}$ encodes a non-full-length fspM protein of about 900 amino acids, referred to herein as PfspM(B)$_{900}$, assuming an open reading frame having a start codon spanning from about nucleotide 5 through about nucleotide 7 of SEQ ID NO:61. The amino acid sequence of PfspM(B)$_{900}$ is denoted SEQ ID NO:62. PfspM(B)$_{900}$ has a calculated molecular weight of about 104,647 daltons and calculated pI of about 5.8.

The nucleic acid and amino acid sequences of the nfspM (B)$_{2706}$ nucleic acid molecule and PfspM(B)$_{900}$ protein, respectively, were compared to known nucleic acid and amino acid sequences using a Genbank homology search. SEQ ID NO:62 was found to be similar to the amino acid sequence of RhoA-binding alpha kinase (ROK). The most highly conserved region of continuous similarity between SEQ ID NO:62 and ROK amino acid sequences spans from about amino acid 32 through about amino acid 351 of SEQ ID NO:62 and from about amino acid 1 through about amino acid 900 of the ROK, there being about 75% identity between the two regions. Comparison of the nucleic acid sequence encoding amino acids from about 326 through about 1285 of the ROK kinase with the corresponding regions, spanning nucleotides from about 98 through about 1075 of nfspM(B)$_{2706}$ indicate that those regions are about 71% identical.

B. nfspM(C)$_{414}$ and nfspM(D)$_{273}$

A flea salivary gland cDNA library (prepared as described in Example 6) was immunoscreened with antiserum collected from a rabbit that was immunized with the proteins in peak M1 of the HPLC separation of flea saliva extract described in Example 3 (i.e., fspM1 proteins). Immunoscreening was performed as described in Example 12.

Nucleotide sequence for a nfspM nucleic acid molecule named nfspM(C)$_{414}$ is denoted as SEQ ID NO:63. Translation of SEQ ID NO:63 suggests that nucleic acid molecule nfspM(C)$_{414}$ encodes a non-full-length fspM protein of about 137 amino acids, referred to herein as PfspM(C)$_{137}$, assuming the first residue spans from about nucleotide 2 through about nucleotide 4 of SEQ ID NO:64. The amino acid sequence of PfspM(C)$_{138}$ is denoted SEQ ID NO:64. PfspM(C)$_{137}$ has a calculated molecular weight of about 14,452 daltons and calculated pI of about 2.81. A Genbank homology search revealed no significant homology between SEQ ID NO:63 or SEQ ID NO:64 and known nucleic acid sequences or known amino acid sequences, respectively.

A nucleotide sequence for another nfspM nucleic acid molecule named nfspM(D)273 is denoted as SEQ ID NO:65. Translation of SEQ ID NO:65 suggests that nucleic acid molecule nfspM(D)$_{273}$ encodes a non-full-length fspM protein of about 90 amino acids, referred to herein as PfspM(D)$_{90}$, assuming the first residue spans from about nucleotide 3 through about nucleotide 5 of SEQ ID NO:65. The amino acid sequence of PfspM(D)$_{90}$ is denoted SEQ ID NO:66. PfspM(D) has a calculated molecular weight of about 9,503 daltons and calculated pI of about 3.01. SEQ ID NO:65 and SEQ ID NO:66 appear to be substantially similar to SEQ ID NO:63 and SEQ ID NO:64, respectively, suggesting a family of fspM proteins in flea saliva.

C. nfspM(E) $_{1704}$ and nfspM(F) 1758

A flea salivary gland cDNA library (prepared as described in Example 6) was immunoscreened with antiserum collected from a rabbit that was immunized with the proteins in peak M2 of the HPLC separation of flea saliva extract described in Example 3 (i.e., fspM2 proteins). Immunoscreening was performed as described in Example 12.

A nucleotide sequence for another nfspM nucleic acid molecule named nfspM(E)$_{1704}$ is denoted as SEQ ID NO:67.

Translation of SEQ ID NO:67 suggests that nucleic acid molecule nfspM(E)$_{1704}$ encodes a full-length fspM protein of about 461 amino acids, referred to herein as PfspM(E)$_{461}$, assuming the first residue spans from about nucleotide 24 through about nucleotide 26 of SEQ ID NO:67 and a stop codon spanning from about nucleotide 1407 through about nucleotide 1409 of SEQ ID NO:67. This open reading frame, excluding the stop codon, comprises nucleic acid molecule nfspM(E)$_{1383}$ of the present invention, the nucleic acid sequence of which is represented herein by SEQ ID NO:82. The amino acid sequence of PfspM(E)$_{461}$ is denoted SEQ ID NO:68. PfspM(E)$_{461}$ has a calculated molecular weight of about 54,139 daltons and calculated pI of about 7.00. A Genbank homology search revealed no significant homology between SEQ ID NO:67 or SEQ ID NO:68 and known nucleic acid sequences or known amino acid sequences, respectively.

A nucleotide sequence for another nfspM nucleic acid molecule named nfspM(F)$_{1758}$ is denoted as SEQ ID NO:69. Translation of SEQ ID NO:69 suggests that nucleic acid molecule nfspM(F)$_{1758}$ encodes a non-full-length fspM protein of about 586 amino acids, referred to herein as PfspM (F)$_{586}$, assuming an open reading frame having a start codon spanning from about nucleotide 1 through about nucleotide 3 of SEQ ID NO:69. The amino acid sequence of PfspM (F)$_{586}$ is denoted SEQ ID NO:70. PfspM(F)$_{586}$ has a calculated molecular weight of about 66,547 daltons and calculated pI of about 4.80. A Genbank homology search revealed no significant homology between SEQ ID NO:69 or SEQ ID NO:70 and known nucleic acid sequences or known amino acid sequences, respectively.

Example 20

This Example demonstrates the expression of a fspM protein in *E. Coli* cells.

Flea saliva protein PHIS-PfspM(D)$_{90}$ fusion protein was produced in the following manner. An about 305-bp DNA fragment, referred to herein as nfspM(D)$_{305}$ (denoted SEQ ID NO:71), was isolated from nfspM(D)$_{273}$ subcloned into pBluescript plasmid by digesting the nfspM(D)-containing plasmid with BamHl and XhoI restriction endonucleases. The digestion product was gel purified and subcloned into expression vector pTrcHisB that had been digested with BamHl and XhoI, and dephosphorylated. The resultant recombinant molecule, referred to herein as pHis-nfspM(D)$_{305}$, was transformed into *E. coli* HB101 competent cells (available from Gibco BRL, Gaithersburg, Md.) to form recombinant cell *E. coli*:pHis-nfspM(D)$_{305}$. The recombinant cell was cultured and expression of nfspM$_{305}$ induced using conditions described in Example 11. Immunoblot analysis of recombinant cell *E. coli*:pHis-nfspM(D)$_{305}$ lysates using a T7 tag monoclonal antibody (Novagen, Inc) directed against the fusion portion of the recombinant PHis-nfspM(D)$_{305}$ fusion protein identified a protein of the appropriate size, namely an about 15,851 kD protein.

Example 21

This example describes the isolation of nucleic acid sequences encoding at least a portion of flea saliva proteins fspN(C), fspN(D), fspN(E), fspN(F), fspN(G), fspN(H), fspN(I), fspN(J), fspN(K), fspN(L), fspN(M), fspN(N) and fspN(O).

A. Preparation of IgE Enriched Antiserum

Serum was obtained from the artificially sensitized dog CQQ2 (described in Example 8). About 10 ml of antiserum was incubated with protein G-Sepharose (5 ml) over night at 4° C.

B. Immunoscreening with IgE Enriched Antiserum

About 2.4 ml of *Escherichia coli* (XL1 Blue, O.D.$_{600}$= 0.5) was incubated with 6.48×10$^5$ pfu of phage from a flea salivary gland ZAP-cDNA library (1.8×10$^7$pfu/ml), at 37° C. for 15 min and plated in 12 Luria-Bertani (LB) medium agar plates (150 mm). The plates were incubated at 37° C. over night. Each plate was then overlaid with an IPTG (10 mM) treated nitrocellulose filters for about 4 hours at 37° C. The filters were then removed and washed with TBST (20 mM Tris-HCl pH 7.5, 150 mM NaCl, 0.05% Tween-20). The filters were blocked with 5% dry milk in TBST for 2 hours at room temperature. Different filters were then incubated first with either IgE enriched CQQ2 antiserum or antiserum obtained from dogs infected with *Dirofilaria immitis*) at 4° C., overnight, then with a monoclonal anti-canine IgE antibody (D-9; gift from the laboratory of Dr. D. J. DeBoer, School of Veterinary Medicine, University of Wisconsin, Madison, Wis.), and then with a donkey anti-mouse IgG antibody conjugated to horseradish peroxidase (obtained from Jackson ImmunoResearch, West Grove, Pa.) for 2 hours at room temperature at each step. All of the filters were washed with TBST (3×15 min/wash) between each incubation. All of the filters were then treated to a final wash in TBS. Immunocomplexed plaques were identified by immersing the filters into the developing solution (TMB Peroxidase Substrate/TMB Peroxidase Solution/TMB Membrane Enhancer from Kirkegaard & Perry Laboratories) at 1/1/0.1 volume ratio to produce a color reaction. Eighteen plaques were identified and further plaque purified under the same immunoscreening condition as described above.

C. nfspN(C)$_{335}$, nfspN(D)$_{396}$, nfspN(E)$_{285}$, nfspN(F)$_{228}$, nfspN(G)$_{339}$, nfspN(G)$_{493}$ Single plaque of purified positive clones were isolated and stored in SM phage buffer (50 mM Tris, pH 7.4, 0.58% NaCl, 0.2% MgCl$_2$.7H$_2$O and 0.01% Gelatin). The in vivo excision of the pBluescript phagemid from each positive clone was prepared by using ExAssist™/SOLR™ system (Stratagene). The pBluescript plasmid was purified by plasmid midi kit (Qiagen), and denatured with NaOH (0.4N) at 37° C. for 15 min. The denatured plasmid was precipitated by ethanol and nucleic acid sequence obtained.

A nucleotide sequence for a nfspN nucleic acid molecule named nfspN(C)$_{335}$ is denoted as SEQ ID NO:83. A Genbank homology search revealed some similarity between SEQ ID NO:83 and ribosomal protein S6.

A nucleotide sequence for another nfspN nucleic acid molecule named nfspN(D)$_{396}$ is denoted as SEQ ID NO:84. A Genbank homology search revealed some similarity between SEQ ID NO:84 and erythropoietin.

A nucleotide sequence for another nfspN nucleic acid molecule named nfspN(E)$_{285}$ is denoted as SEQ ID NO:85. A Genbank homology search revealed some similarity between SEQ ID NO:85 and glutamic acid-rich protein or heat-shock protein, HSP81.

A nucleotide sequence for another nfspN nucleic acid molecule named nfspN(F)$_{228}$ is denoted as SEQ ID NO:86.

Nucleic acid sequence for portions of another nfspN nucleic acid molecule, denoted herein as nfspN(G), were obtained. The nucleic acid molecule representing a 5' portion of nfspN(G) named nfspN(G)$_{339}$ is denoted as SEQ ID NO:87. Translation of SEQ ID NO:87 suggests that nucleic acid molecule nfspN(G)$_{339}$encodes a non-full-length fspN (G) protein of about 113 amino acids, referred to herein as PfspN(G)$_{113}$, assuming the first residue spans from about nucleotide 1 through about nucleotide 3 of SEQ ID NO:87. The amino acid sequence of PfspN(G)$_{113}$ is denoted SEQ ID NO:88.

The nucleic acid molecule representing a 3' portion of nfspN(G) named nfspN(G)$_{493}$ is denoted as SEQ ID NO:89. Translation of SEQ ID NO:89 suggests that nucleic acid molecule nfspN(G)$_{493}$ encodes a non-full-length fspN(G) protein of about 130 amino acids, referred to herein as PfspN(G)$_{130}$, assuming the first residue spans from about nucleotide 1 through about nucleotide 3 of SEQ ID NO:89 and a stop codon spanning from about nucleotide 391 through about nucleotide 393 of SEQ ID NO:89. The amino acid sequence of PfspN(G)$_{130}$ is denoted SEQ ID NO:90. A Genbank homology search revealed some similarity between SEQ ID NO:87 and SEQ ID NO:89 and vitellogenin.

A nucleotide sequence for another nfspN nucleic acid molecule named nfspN(H)$_{306}$ is denoted as SEQ ID NO:91.

A nucleotide sequence for another nfspN nucleic acid molecule named nfspN(I)$_{490}$ is denoted as SEQ ID NO:92.

A nucleotide sequence for another nfspN nucleic acid molecule named nfspN(J)$_{616}$ is denoted as SEQ ID NO:93.

A nucleotide sequence for another nfspN nucleic acid molecule named nfspN(K)$_{475}$ is denoted as SEQ ID NO:94.

A nucleotide sequence for another nfspN nucleic acid molecule named nfspN(L)$_{295}$ is denoted as SEQ ID NO:95.

A nucleotide sequence for another nfspN nucleic acid molecule named nfspN(M)$_{372}$ is denoted as SEQ ID NO:96.

Nucleic acid sequence for portions of another nfspN nucleic acid molecule, denoted herein as nfspN(N), were obtained. The nucleic acid molecule representing a 5' portion of nfspN(N) named nfspN(N)$_{252}$ is denoted as SEQ ID NO:97. The nucleic acid molecule representing a 3' portion of nfspN(N) named nfspN(N)$_{613}$ is denoted as SEQ ID NO:98.

Nucleic acid sequence for portions of another nfspN nucleic acid molecule, denoted herein as nfspN(O), were obtained. The nucleic acid molecule representing a 5' portion of nfspN(O) named nfspN(O)$_{538}$ is denoted as SEQ ID NO:99. Translation of SEQ ID NO:99 suggests that nucleic acid molecule nfspN(O)$_{538}$ encodes a non-full-length fspN(O) protein of about 178 amino acids, referred to herein as PfspN(O)$_{178}$, assuming the first residue spans from about nucleotide 1 through about nucleotide 3 of SEQ ID NO:99. The amino acid sequence of PfspN(N)$_{178}$ is denoted SEQ ID NO:100.

The nucleic acid molecule representing a 3' portion of nfspN(O) named nfspN(O)$_{432}$ is denoted as SEQ ID NO:101. Translation of SEQ ID NO:101 suggests that nucleic acid molecule nfspN(O)$_{432}$ encodes a non-full-length fspN(O) protein of about 129 amino acids, referred to herein as PfspN(O)$_{129}$, assuming the first residue spans from about nucleotide 1 through about nucleotide 3 of SEQ ID NO:101 and a stop codon spanning from about nucleotide 388 through about nucleotide 390 of SEQ ID NO:101. The amino acid sequence of PfspN(0)$_{129}$ is denoted SEQ ID NO:102.

Example 22

This example describes studies confirming the specificity of IgE enriched antiserum from CQQ2 to fspN protein.

Three different petri dishes (100 mm) were overlaid with 300 microliter per plate of *E.coli* (XL1 Blue, O.D.$_{600}$=500). A drop (about 100 pfu/drop) of each of the eighteen isolated phage clones was dropped onto each plate (18 phage clones/plate). Using the methods described in Example 22, the plates were incubated, filter lifted and the filters immunoscreened with IgE enriched antiserum from CQQ2, antiserum from a *D. Immitis* infected dog and antiserum from rabbits injected with flea saliva product from peak N.

The results of the experiment indicate that both the IgE enriched CQQ2 antiserum and the antiserum specific for peak N flea saliva product bind to the products of the purified phage clones significantly better than the antiserum from a *D. Immitis* infected dog.

SEQUENCE LISTING ( 1 ) GENERAL INFORMATION:

( i i i ) NUMBER OF SEQUENCES: 107

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( i x ) FEATURE:
        ( A ) NAME/KEY: Xaa = Tyr, Gln, Ser or Arg
        ( B ) LOCATION: 1

( i x ) FEATURE:
        ( A ) NAME/KEY: Xaa = Gly or Tyr
        ( B ) LOCATION: 2

( i x ) FEATURE:
        ( A ) NAME/KEY: Xaa = Lys or Ser
        ( B ) LOCATION: 3

( i x ) FEATURE:
        ( A ) NAME/KEY: Xaa = Gly or Ser
        ( B ) LOCATION: 9

(ix) FEATURE:
  (A) NAME/KEY: Xaa = Gly or Lys
  (B) LOCATION: 10

(ix) FEATURE:
  (A) NAME/KEY: Xaa = Arg or Ile
  (B) LOCATION: 14

(ix) FEATURE:
  (A) NAME/KEY: Xaa = Ile or Leu
  (B) LOCATION: 17

(ix) FEATURE:
  (A) NAME/KEY: Xaa = Lys or Asp
  (B) LOCATION: 19

(ix) FEATURE:
  (A) NAME/KEY: Xaa = Gly or Leu
  (B) LOCATION: 21

(xi) SEQUENCE DESCRIPTION: SEQ ID NO:1:

```
Xaa Xaa Xaa Gln Tyr Ser Glu Lys Xaa Xaa Arg Gly Gln Xaa His Gln
1               5                   10                  15
Xaa Leu Xaa Lys Xaa Lys
            20
```

(2) INFORMATION FOR SEQ ID NO:2:

(i) SEQUENCE CHARACTERISTICS:
    (A) LENGTH: 78 amino acids
    (B) TYPE: amino acid
    (D) TOPOLOGY: linear (ii) MOLECULE TYPE: protein (ix) FEATURE:
    (A) NAME/KEY: Xaa = His or Tyr
    (B) LOCATION: 27

(xi) SEQUENCE DESCRIPTION: SEQ ID NO:2:

```
Asp Arg Arg Val Ser Lys Thr Cys Gln Ser Gly Gly Lys Ile Gln Ser
1               5                   10                  15
Glu Xaa Gln Val Val Ile Lys Ser Gln Xaa Ile Leu Glu Asn Tyr
                20                  25                  30
Xaa Ser Asp Gly Arg Asn Asn Asn Pro Cys His Leu Phe Cys Met
        35                  40                  45
Arg Glu Cys Arg Ser Gly Asn Gly Gly Cys Gly Asn Gly Gly Arg Thr
        50                  55                  60
Arg Pro Asp Ser Lys His Cys Tyr Cys Glu Ala Pro Tyr Ser
65                  70                  75
```

(2) INFORMATION FOR SEQ ID NO:3:

(i) SEQUENCE CHARACTERISTICS:
    (A) LENGTH: 12 amino acids
    (B) TYPE: amino acid
    (D) TOPOLOGY: linear (ii) MOLECULE TYPE: protein (xi) SEQUENCE DESCRIPTION: SEQ ID NO:3:

```
Asp Ser Lys His Cys Tyr Cys Glu Ala Pro Tyr Ser
1               5                   10
```

(2) INFORMATION FOR SEQ ID NO:4:

(i) SEQUENCE CHARACTERISTICS:
    (A) LENGTH: 37 amino acids (B) TYPE: amino acid
(D) TOPOLOGY: linear (i i) MOLECULE TYPE: protein (x i) SEQUENCE DESCRIPTION: SEQ ID NO:4:

```
Asp Gly Arg Asn Asn Asn Asn Pro Cys His Leu Phe Cys Met Arg Glu
1               5                   10                  15
Cys Arg Ser Gly Asn Gly Gly Cys Gly Asn Gly Gly Arg Thr Arg Pro
            20              25                  30
Asp Ser Lys His Cys
            35
```

(2) INFORMATION FOR SEQ ID NO:5:

(i) SEQUENCE CHARACTERISTICS:
(A) LENGTH: 11 amino acids
(B) TYPE: amino acid
(D) TOPOLOGY: linear (i i) MOLECULE TYPE: protein (x i) SEQUENCE DESCRIPTION: SEQ ID NO:5:

```
Asp Arg Arg Val Ser Lys Thr Cys Gln Ser Gly
1               5                   10
```

(2) INFORMATION FOR SEQ ID NO:6:

(i) SEQUENCE CHARACTERISTICS:
(A) LENGTH: 38 amino acids
(B) TYPE: amino acid
(D) TOPOLOGY: linear (i i) MOLECULE TYPE: protein (x i) SEQUENCE DESCRIPTION: SEQ ID NO:6:

```
Glu Asp Ile Trp Lys Val Asn Lys Lys Xaa Thr Ser Gly Gly Lys Asn
1               5                   10                  15
Gln Asp Arg Lys Leu Asp Gln Ile Ile Gln Lys Gly Gln Gln Val Xaa
            20              25                  30
Xaa Gln Asn Xaa Xaa Lys
            35
```

(2) INFORMATION FOR SEQ ID NO:7:

(i) SEQUENCE CHARACTERISTICS:
(A) LENGTH: 23 amino acids
(B) TYPE: amino acid
(D) TOPOLOGY: linear (i i) MOLECULE TYPE: protein (x i) SEQUENCE DESCRIPTION: SEQ ID NO:7:

```
Asn Ser His Glu Pro Gly Asn Thr Arg Lys Ile Arg Glu Val Met Asp
1               5                   10                  15
Lys Leu Arg Lys Gln His Pro
            20
```

(2) INFORMATION FOR SEQ ID NO:8:

(i) SEQUENCE CHARACTERISTICS:
(A) LENGTH: 27 amino acids
(B) TYPE: amino acid
(D) TOPOLOGY: linear (i i) MOLECULE TYPE: protein ( x i ) SEQUENCE DESCRIPTION: SEQ ID NO:8:

Glu Ile Lys Arg Asn Ser His Glu Pro Gly Asn Thr Arg Lys Ile Arg
1               5                   10                  15

Glu Val Met Asp Lys Leu Arg Lys Gln His Pro
            20                  25

( 2 ) INFORMATION FOR SEQ ID NO:9:

( i ) SEQUENCE CHARACTERISTICS:
( A ) LENGTH: 36 amino acids
( B ) TYPE: amino acid
( D ) TOPOLOGY: linear ( i i ) MOLECULE TYPE: protein ( x i ) SEQUENCE DESCRIPTION: SEQ ID NO:9:

Asn Asp Lys Glu Pro Gly Asn Thr Arg Lys Ile Arg Glu Val Met Asp
1               5                   10                  15

Lys Leu Arg Lys Gln Ala Gln Pro Arg Thr Asp Gly Gln Arg Pro Lys
            20                  25                  30

Thr Xaa Ile Met
        35

( 2 ) INFORMATION FOR SEQ ID NO:10:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( x i ) SEQUENCE DESCRIPTION: SEQ ID NO:10:

Xaa Leu Xaa Arg Asn Asp Lys Glu Pro Gly Asn Thr Arg Lys Ile Arg
1               5                   10                  15

Glu Val Met Asp Lys
            20

( 2 ) INFORMATION FOR SEQ ID NO:11:

( i ) SEQUENCE CHARACTERISTICS:
( A ) LENGTH: 12 amino acids
( B ) TYPE: amino acid
( D ) TOPOLOGY: linear ( i i ) MOLECULE TYPE: DNA (genomic)

( x i ) SEQUENCE DESCRIPTION: SEQ ID NO:11:

Asn Asp Glu Leu Lys Phe Val Phe Val Met Ala Lys
1               5                   10

( 2 ) INFORMATION FOR SEQ ID NO:12:

( i ) SEQUENCE CHARACTERISTICS:
( A ) LENGTH: 23 amino acids
( B ) TYPE: amino acid
( D ) TOPOLOGY: linear ( i i ) MOLECULE TYPE: protein ( x i ) SEQUENCE DESCRIPTION: SEQ ID NO:12:

Xaa Asp Glu Leu Lys Phe Val Phe Val Met Ala Lys Gly Pro Ser Xaa
1               5                   10                  15

Gln Ala Xaa Asp Tyr Pro Cys
            20

( 2 ) INFORMATION FOR SEQ ID NO:13:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Glu Leu Lys Phe Val Phe Ala Thr Ala Arg Gly Met Ser His Thr Pro
1               5                   10                  15
Cys Asp Tyr Pro
            20
```

( 2 ) INFORMATION FOR SEQ ID NO:14:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i x ) FEATURE:
        ( A ) NAME/KEY: Xaa = His or Tyr
        ( B ) LOCATION: 27

( x i ) SEQUENCE DESCRIPTION: SEQ ID NO:14:

```
Asp Arg Arg Val Ser Lys Thr Xaa Gln Ser Gly Gly Lys Ile Gln Ser
1               5                   10                  15
Glu Xaa Gln Val Val Ile Lys Ser Gly Gln Xaa Ile Leu Glu Asn Tyr
                20              25                  30
Xaa Ser Asp Gly Arg
        35
```

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:15:

```
AAYAAYAAYA AYCCNTGYCA                                          20
```

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:16:

```
CAYTCNCKCA TRCARAA                                             17
```

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single ( D ) TOPOLOGY: linear ( i i ) MOLECULE TYPE: DNA (primer)

( x i ) SEQUENCE DESCRIPTION: SEQ ID NO:17:

TGYCAYYTNT TYTGYATG                                                                                     18

( 2 ) INFORMATION FOR SEQ ID NO:18:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA (primer)

( x i ) SEQUENCE DESCRIPTION: SEQ ID NO:18:

GGNGCYTCRC ARTARCARTG YTT                                                                               23

( 2 ) INFORMATION FOR SEQ ID NO:19:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( i i ) MOLECULE TYPE: DNA (primer)

( x i ) SEQUENCE DESCRIPTION: SEQ ID NO:19:

GTAAAACGAC GGCCAGT                                                                                      17

( 2 ) INFORMATION FOR SEQ ID NO:20:

( i ) SEQUENCE CHARACTERISTICS:
                ( A ) LENGTH: 93 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:20:

TTGTCACTTT TTTTGTATGA GAGAATGCAG GTCAGGAAAC GGCGGTTGCG GAAACGGAGG                                        60

AAGGACAAGA CCTGATTCGA AGCACTGCTA TGC                                                                    93

( 2 ) INFORMATION FOR SEQ ID NO:21:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA (primer)

( x i ) SEQUENCE DESCRIPTION: SEQ ID NO:21:

GARGAYATHT GGAARGTNAA YAA                                                                               23

( 2 ) INFORMATION FOR SEQ ID NO:22:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA (primer)

( x i ) SEQUENCE DESCRIPTION: SEQ ID NO:22:

ACNTCNGGNG GNAARAAYCA RGA    23

( 2 ) INFORMATION FOR SEQ ID NO:23:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:23:

TTGGGTACCG GGCCCCCCCT    20

( 2 ) INFORMATION FOR SEQ ID NO:24:

( i ) SEQUENCE CHARACTERISTICS:
( A ) LENGTH: 573 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:24:

```
CTTACGTCCG GGGGTAAGAA TCAGGATAGA AAACTCGATC AAATAATTCA AAAAGGCCAA    60
CAAGTTAAAA TCCAAAATAT TTGCAAATTA ATACGAGATA AACCACATAC AAATCAAGAG   120
AAAGAAAAAT GTATGAAATT TTGCACAAAA AACGTTTGCA AAGGTTATAG AGGAGCTTGT   180
GATGGCAATA TTTGCTACTG CAGCAGGCCA AGTAATTTAG GTCCTGATTG GAAAGTCAAC   240
GAAAGAATCG AAAGACTCCC AATAACAAAG ATTCTCGTCT CAGGAAATAG TTCCATATCG   300
ACAACAATTA CGAATTCCAA ATATTTCGAA ACTAAAAATT CAGAGACCAA TGAAGATTCC   360
AAATCGAAAA AACATTCGAA AGAAAAATGT CGTGGTGGAA ATGATGCTGG ATGTGATGGA   420
AACGTTTTGT TATTGTCGAC CAAAAAATAA ATAATAATTA TAATAAATAA ATTGTTATAG   480
TTATTAGTTA TCCCGTCACA TATTAGAAAA GTGGCTTATA ATTTATGAAC AATATAACAC   540
ATAAATTAGT TGTGTAAAAA AAAAAAAAAA AAA                                573
```

( 2 ) INFORMATION FOR SEQ ID NO:25:

( i ) SEQUENCE CHARACTERISTICS:
( A ) LENGTH: 149 amino acids
( B ) TYPE: amino acid
( D ) TOPOLOGY: linear ( i i ) MOLECULE TYPE: protein ( x i ) SEQUENCE DESCRIPTION: SEQ ID NO:25:

```
Leu Thr Ser Gly Gly Lys Asn Gln Asp Arg Lys Leu Asp Gln Ile Ile
 1               5                  10                  15
Gln Lys Gly Gln Gln Val Lys Ile Gln Asn Ile Cys Lys Leu Ile Arg
            20                  25                  30
Asp Lys Pro His Thr Asn Gln Glu Lys Glu Lys Cys Met Lys Phe Cys
        35                  40                  45
Thr Lys Asn Val Cys Lys Gly Tyr Arg Gly Ala Cys Asp Gly Asn Ile
    50                  55                  60
Cys Tyr Cys Ser Arg Pro Ser Asn Leu Gly Pro Asp Trp Lys Val Asn
65                  70                  75                  80
```

|     |     |     |     |     |     |     |     |     |     |     |     |     |     |     |
|---|---|---|---|---|---|---|---|---|---|---|---|---|---|---|
| Glu | Arg | Ile | Glu | Arg<br>85 | Leu | Pro | Ile | Thr | Lys<br>90 | Ile | Leu | Val | Ser | Gly<br>95 | Asn |
| Ser | Ser | Ile | Ser<br>100 | Thr | Thr | Ile | Thr | Asn<br>105 | Ser | Lys | Tyr | Phe | Glu<br>110 | Thr | Lys |
| Asn | Ser | Glu<br>115 | Thr | Asn | Glu | Asp | Ser<br>120 | Lys | Ser | Lys | Lys | His<br>125 | Ser | Lys | Glu |
| Lys | Cys<br>130 | Arg | Gly | Gly | Asn | Asp<br>135 | Arg | Gly | Cys | Asp | Gly<br>140 | Asn | Val | Leu | Leu |
| Leu | Ser | Thr | Lys | Lys |
| 145 |

(2) INFORMATION FOR SEQ ID NO:26:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:26:

| Glu<br>1 | Asp | Ile | Trp | Lys<br>5 | Val | Asn | Lys | Lys | Leu<br>10 | Thr | Ser | Gly | Gly | Lys<br>15 | Asn |
|---|---|---|---|---|---|---|---|---|---|---|---|---|---|---|---|
| Gln | Asp | Arg | Lys<br>20 | Leu | Asp | Gln | Ile | Ile<br>25 | Gln | Lys | Gly | Gln | Gln<br>30 | Val | Lys |
| Ile | Gln | Asn<br>35 | Ile | Cys | Lys | Leu | Ile<br>40 | Arg | Asp | Lys | Pro | His<br>45 | Thr | Asn | Gln |
| Glu | Lys<br>50 | Glu | Lys | Cys | Met | Lys<br>55 | Phe | Cys | Thr | Lys | Asn<br>60 | Val | Cys | Lys | Gly |
| Tyr<br>65 | Arg | Gly | Ala | Cys | Asp<br>70 | Gly | Asn | Ile | Cys | Tyr<br>75 | Cys | Ser | Arg | Pro | Ser<br>80 |
| Asn | Leu | Gly | Pro | Asp<br>85 | Trp | Lys | Val | Asn | Glu<br>90 | Arg | Ile | Glu | Arg | Leu<br>95 | Pro |
| Ile | Thr | Lys | Ile | Leu<br>100 | Val | Ser | Gly | Asn<br>105 | Ser | Ser | Ile | Ser | Thr<br>110 | Thr | Ile |
| Thr | Asn | Ser<br>115 | Lys | Tyr | Phe | Glu | Thr<br>120 | Lys | Asn | Ser | Glu | Thr<br>125 | Asn | Glu | Asp |
| Ser | Lys<br>130 | Ser | Lys | Lys | His | Ser<br>135 | Lys | Glu | Lys | Cys | Arg<br>140 | Gly | Gly | Asn | Asp |
| Arg<br>145 | Gly | Cys | Asp | Gly | Asn<br>150 | Val | Leu | Leu | Leu | Ser<br>155 | Thr | Lys | Lys |

(2) INFORMATION FOR SEQ ID NO:27:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: Xaa = Ser or Gln
        (B) LOCATION: 1

(ix) FEATURE:
        (A) NAME/KEY: Xaa = any amino acid
        (B) LOCATION: 8

(ix) FEATURE:
        (A) NAME/KEY: Xaa = Gly or Lys
        (B) LOCATION: 9

(xi) SEQUENCE DESCRIPTION: SEQ ID NO:27:

```
        Xaa  Gly  Lys  Gln  Tyr  Ser  Glu  Xaa  Xaa  Lys
        1              5                        10
```

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
        Asp  Arg  Arg  Val  Ser  Lys
        1              5
```

( 2 ) INFORMATION FOR SEQ ID NO:29:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( i x ) FEATURE:
        ( A ) NAME/KEY: Xaa = any amino acid
        ( B ) LOCATION: 8

( x i ) SEQUENCE DESCRIPTION: SEQ ID NO:29:

```
        Ser  Lys  Met  Val  Thr  Glu  Lys  Xaa  Lys  Ser  Gly  Gly  Asn  Asn  Pro  Ser
        1              5                        10                       15
        Thr  Lys  Glu  Val  Ser  Ile  Pro
                       20
```

( 2 ) INFORMATION FOR SEQ ID NO:30:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( i x ) FEATURE:
        ( A ) NAME/KEY: Xaa = any amino acid
        ( B ) LOCATION: 15

( x i ) SEQUENCE DESCRIPTION: SEQ ID NO:30:

```
        Glu  Val  Ser  Ile  Pro  Ser  Gly  Lys  Leu  Thr  Ile  Glu  Asp  Phe  Xaa  Ile
        1              5                        10                       15
        Gly  Asn  His  Gln
                       20
```

( 2 ) INFORMATION FOR SEQ ID NO:31:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
        Asp  Ile  Glu  Asn  Ile  Lys  Lys  Gly  Glu  Gly  Gln  Pro  Gly  Ala  Pro  Gly
        1              5                        10                       15
        Gly  Lys  Glu  Asn  Asn  Leu  Ser  Val  Leu
                       20                       25
```

( 2 ) INFORMATION FOR SEQ ID NO:32:

( i ) SEQUENCE CHARACTERISTICS:
        ( A ) LENGTH: 242 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..242

( x i ) SEQUENCE DESCRIPTION: SEQ ID NO:32:

```
AT TTT TCC CTT TGT GTT TTA TAC CAA ATT GTG GTT GCT GAT AGA AGA       47
   Phe Ser Leu Cys Val Leu Tyr Gln Ile Val Val Ala Asp Arg Arg
   1               5                   10                  15

GTT TCC AAA ACA TGT CAA AGT GGA GGA AAG ATA CAA AGT GAG GAG CAA       95
Val Ser Lys Thr Cys Gln Ser Gly Gly Lys Ile Gln Ser Glu Glu Gln
                20                  25                  30

GTG GTA ATT AAA TCT GGA CAA CAT ATT CTT GAA AAT TAT TGC TCA GAT      143
Val Val Ile Lys Ser Gly Gln His Ile Leu Glu Asn Tyr Cys Ser Asp
            35                  40                  45

GGG AGA AAT AAT AAT AAT CCA TGC CAC TTG TTT TGT ATG AGA GAA TGC      191
Gly Arg Asn Asn Asn Asn Pro Cys His Leu Phe Cys Met Arg Glu Cys
        50                  55                  60

AGG TCA GGA AAC GGC GGT TGC GGA AAC GGA GGA AGG ACA AGA CCT GAT      239
Arg Ser Gly Asn Gly Gly Cys Gly Asn Gly Gly Arg Thr Arg Pro Asp
    65                  70                  75

TCG                                                                   242
Ser
80
```

( 2 ) INFORMATION FOR SEQ ID NO:33:

( i ) SEQUENCE CHARACTERISTICS:
        ( A ) LENGTH: 80 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Phe Ser Leu Cys Val Leu Tyr Gln Ile Val Val Ala Asp Arg Arg Val
1               5                   10                  15

Ser Lys Thr Cys Gln Ser Gly Gly Lys Ile Gln Ser Glu Glu Gln Val
            20                  25                  30

Val Ile Lys Ser Gly Gln His Ile Leu Glu Asn Tyr Cys Ser Asp Gly
        35                  40                  45

Arg Asn Asn Asn Asn Pro Cys His Leu Phe Cys Met Arg Glu Cys Arg
    50                  55                  60

Ser Gly Asn Gly Gly Cys Gly Asn Gly Gly Arg Thr Arg Pro Asp Ser
65                  70                  75                  80
```

( 2 ) INFORMATION FOR SEQ ID NO:34:

( i ) SEQUENCE CHARACTERISTICS:
        ( A ) LENGTH: 591 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..466

( x i ) SEQUENCE DESCRIPTION: SEQ ID NO:34:

```
TGG  AAA  GTT  AAT  AAA  AAA  TGT  ACA  TCA  GGT  GGA  AAA  AAT  CAA  GAT  AGA     48
Trp  Lys  Val  Asn  Lys  Lys  Cys  Thr  Ser  Gly  Gly  Lys  Asn  Gln  Asp  Arg
 1              5                        10                       15

AAA  CTC  GAT  CAA  ATA  ATT  CAA  AAA  GGC  CAA  CAA  GTT  AAA  ATC  CAA  AAT     96
Lys  Leu  Asp  Gln  Ile  Ile  Gln  Lys  Gly  Gln  Gln  Val  Lys  Ile  Gln  Asn
               20                        25                       30

ATT  TGC  AAA  TTA  ATA  CGA  GAT  AAA  CCA  CAT  ACA  AAT  CAA  GAG  AAA  GAA    144
Ile  Cys  Lys  Leu  Ile  Arg  Asp  Lys  Pro  His  Thr  Asn  Gln  Glu  Lys  Glu
          35                        40                        45

AAA  TGT  ATG  AAA  TTT  TGC  ACA  AAA  AAC  GTT  TGC  AAA  GGT  TAT  AGA  GGA    192
Lys  Cys  Met  Lys  Phe  Cys  Thr  Lys  Asn  Val  Cys  Lys  Gly  Tyr  Arg  Gly
     50                        55                        60

GCT  TGT  GAT  GGC  AAT  ATT  TGC  TAC  TGC  AGC  AGG  CCA  AGT  AAT  TTA  GGT    240
Ala  Cys  Asp  Gly  Asn  Ile  Cys  Tyr  Cys  Ser  Arg  Pro  Ser  Asn  Leu  Gly
 65                       70                        75                       80

CCT  GAT  TGG  AAA  GTC  AAC  GAA  AGA  ATC  GAA  AGA  CTC  CCA  ATA  ACA  AAG    288
Pro  Asp  Trp  Lys  Val  Asn  Glu  Arg  Ile  Glu  Arg  Leu  Pro  Ile  Thr  Lys
                    85                        90                       95

ATT  CTC  GTC  TCA  GGA  AAT  AGT  TCC  ATA  TCG  ACA  ACA  ATT  ACG  AAT  TCC    336
Ile  Leu  Val  Ser  Gly  Asn  Ser  Ser  Ile  Ser  Thr  Thr  Ile  Thr  Asn  Ser
               100                       105                       110

AAA  TAT  TTC  GAA  ACT  AAA  AAT  TCA  GAG  ACC  AAT  GAA  GAT  TCC  AAA  TCG    384
Lys  Tyr  Phe  Glu  Thr  Lys  Asn  Ser  Glu  Thr  Asn  Glu  Asp  Ser  Lys  Ser
          115                       120                       125

AAA  AAA  CAT  TCG  AAA  GAA  AAA  TGT  CGT  GGT  GGA  AAT  GAT  CGT  GGA  TGT    432
Lys  Lys  His  Ser  Lys  Glu  Lys  Cys  Arg  Gly  Gly  Asn  Asp  Arg  Gly  Cys
     130                       135                       140

GAT  GGA  AAC  GTT  TTG  TTA  TTG  TCG  ACC  AAA  AAA  T AAATAATAAT                476
Asp  Gly  Asn  Val  Leu  Leu  Leu  Ser  Thr  Lys  Lys
145                       150                       155

TATAATAAAT  AAATTGTTAT  AGTTATTAGT  TATCCCGTCA  CATATTAGAA  AAGTGGCTTA            536

TAATTTATGA  ACAATATAAC  ACATAAATTA  GTTGTGTAAA  AAAAAAAAAA  AAAAA                591
```

( 2 ) INFORMATION FOR SEQ ID NO:35:

( i ) SEQUENCE CHARACTERISTICS:
        ( A ) LENGTH: 155 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

```
Trp  Lys  Val  Asn  Lys  Lys  Cys  Thr  Ser  Gly  Gly  Lys  Asn  Gln  Asp  Arg
 1              5                        10                       15

Lys  Leu  Asp  Gln  Ile  Ile  Gln  Lys  Gly  Gln  Gln  Val  Lys  Ile  Gln  Asn
               20                        25                       30

Ile  Cys  Lys  Leu  Ile  Arg  Asp  Lys  Pro  His  Thr  Asn  Gln  Glu  Lys  Glu
          35                        40                        45

Lys  Cys  Met  Lys  Phe  Cys  Thr  Lys  Asn  Val  Cys  Lys  Gly  Tyr  Arg  Gly
     50                        55                        60

Ala  Cys  Asp  Gly  Asn  Ile  Cys  Tyr  Cys  Ser  Arg  Pro  Ser  Asn  Leu  Gly
 65                       70                        75                       80

Pro  Asp  Trp  Lys  Val  Asn  Glu  Arg  Ile  Glu  Arg  Leu  Pro  Ile  Thr  Lys
                    85                        90                       95
```

| Ile | Leu | Val | Ser | Gly | Asn | Ser | Ser | Ile | Ser | Thr | Thr | Ile | Thr | Asn | Ser |
|---|---|---|---|---|---|---|---|---|---|---|---|---|---|---|---|
| | | | 100 | | | | | 105 | | | | | 110 | | |

| Lys | Tyr | Phe | Glu | Thr | Lys | Asn | Ser | Glu | Thr | Asn | Glu | Asp | Ser | Lys | Ser |
|---|---|---|---|---|---|---|---|---|---|---|---|---|---|---|---|
| | | | 115 | | | | 120 | | | | | 125 | | | |

| Lys | Lys | His | Ser | Lys | Glu | Lys | Cys | Arg | Gly | Gly | Asn | Asp | Arg | Gly | Cys |
|---|---|---|---|---|---|---|---|---|---|---|---|---|---|---|---|
| | 130 | | | | | 135 | | | | | 140 | | | | |

| Asp | Gly | Asn | Val | Leu | Leu | Leu | Ser | Thr | Lys | Lys |
|---|---|---|---|---|---|---|---|---|---|---|
| 145 | | | | | 150 | | | | | 155 |

( 2 ) INFORMATION FOR SEQ ID NO:36:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:36:

ATTCGGATCC ATGGAAAGTT AATAAAAAAT GTAC      34

( 2 ) INFORMATION FOR SEQ ID NO:37:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:37:

TAATGGATCC TTATTTTTTG GTCGACAATA AC      32

( 2 ) INFORMATION FOR SEQ ID NO:38:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:38:

CCTGACCTGC ATTCTCTCAT AC      22

( 2 ) INFORMATION FOR SEQ ID NO:39:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:39:

AGGTCTTGTC CTTCCTCCGT TTCCGCA      27

( 2 ) INFORMATION FOR SEQ ID NO:40:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:40:

GGAAACAGCT ATGACCATG                                                                 19

( 2 ) INFORMATION FOR SEQ ID NO:41:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:41:

ATTAACCCTC ACTAAAG                                                                   17

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:42:

GCAAAGGTTA TAGAGGAGCT TG                                                             22

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:43:

AGCTTTCCAT CACATCCAGC                                                                20

( 2 ) INFORMATION FOR SEQ ID NO:44:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:44:

CGCGGATCCT ATAAATATGG AGGACATCTG GAAAGTTAAT AAAAAATGTA CATC                          54

( 2 ) INFORMATION FOR SEQ ID NO:45:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:45:

GCTCTAGAGC ATTTATTTTT TGGTCGACAA TAACAAAAC                       39

( 2 ) INFORMATION FOR SEQ ID NO:46:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:46:

GGCGTCTCGA GAGAATTGAA ATTTGTGTTT GCG                             33

( 2 ) INFORMATION FOR SEQ ID NO:47:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:47:

AGACGAGAAT TCCAATTTAT CATGAGCGG                                  29

( 2 ) INFORMATION FOR SEQ ID NO:48:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:48:

CCGGAATTCC GGTATAAATA TGTGGCGTCT ACTG                            34

( 2 ) INFORMATION FOR SEQ ID NO:49:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:49:

CCGGAATTCT TAAGACGATT TACACAATTT ATC                             33

( 2 ) INFORMATION FOR SEQ ID NO:50:

( i ) SEQUENCE CHARACTERISTICS:
        ( A ) LENGTH: 646 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..519

( x i ) SEQUENCE DESCRIPTION: SEQ ID NO:50:

CG GCA CGA GCT CGG TCT GTT GGA AGT ATG AAA AAC AAA TTG AAA AGT    47

```
        Ala  Arg  Ala  Arg  Ser  Val  Gly  Ser  Met  Lys  Asn  Lys  Leu  Lys  Ser
         1              5                        10                        15

TTT  TCC  GAG  AAA  TAT  GTA  TGG  GCG  GCT  TTA  ACT  TCT  AAC  GAC  AAT  CTT      95
Phe  Ser  Glu  Lys  Tyr  Val  Trp  Ala  Ala  Leu  Thr  Ser  Asn  Asp  Asn  Leu
                    20                       25                       30

AGG  AAA  ATG  TCT  GGA  GGT  CGT  ATG  ATT  AAC  GAT  ATA  TTG  AAC  GAT  ATC     143
Arg  Lys  Met  Ser  Gly  Gly  Arg  Met  Ile  Asn  Asp  Ile  Leu  Asn  Asp  Ile
               35                       40                       45

GAT  AAT  ATA  AAG  AAA  GGA  AAT  GGA  CAA  CCG  AAT  GCT  CCT  GGA  AAA  ACT     191
Asp  Asn  Ile  Lys  Lys  Gly  Asn  Gly  Gln  Pro  Asn  Ala  Pro  Gly  Lys  Thr
               50                       55                       60

GAA  AAT  AAA  TTA  TCG  GTG  TCT  GAC  CGT  TCC  TCA  AGG  TAT  CTT  AGC  AGC     239
Glu  Asn  Lys  Leu  Ser  Val  Ser  Asp  Arg  Ser  Ser  Arg  Tyr  Leu  Ser  Ser
          65                       70                       75

ATT  CGT  TTC  AGC  CTT  TTT  CGT  CCA  AGG  TAC  AAA  ATT  GAA  AAT  CAG  GAC     287
Ile  Arg  Phe  Ser  Leu  Phe  Arg  Pro  Arg  Tyr  Lys  Ile  Glu  Asn  Gln  Asp
 80                       85                       90                       95

CTT  GAA  CCG  TCT  AGT  TTA  TAT  CCT  GGC  CAA  GGA  GCC  CTC  CAT  GTT  ATT     335
Leu  Glu  Pro  Ser  Ser  Leu  Tyr  Pro  Gly  Gln  Gly  Ala  Leu  His  Val  Ile
                    100                      105                      110

GAA  CTG  CAC  AAA  GAT  AAG  AAT  CAG  TGG  AAT  GTA  AAA  ACC  CTC  TAT  AGA     383
Glu  Leu  His  Lys  Asp  Lys  Asn  Gln  Trp  Asn  Val  Lys  Thr  Leu  Tyr  Arg
               115                      120                      125

AAC  AAT  GAC  CAA  CAG  GAA  CTC  AAA  CCT  ATG  AAA  CTT  GCA  AAA  TGC  GGT     431
Asn  Asn  Asp  Gln  Gln  Glu  Leu  Lys  Pro  Met  Lys  Leu  Ala  Lys  Cys  Gly
               130                      135                      140

GAC  ACA  TGT  TCT  TAT  GAA  ACT  TTC  AAA  TCA  ACT  CTA  CAA  TCC  TAT  AAC     479
Asp  Thr  Cys  Ser  Tyr  Glu  Thr  Phe  Lys  Ser  Thr  Leu  Gln  Ser  Tyr  Asn
          145                      150                      155

ATG  GAT  AAG  ACC  GCT  CAT  GAT  AAA  TTG  TGT  AAA  TCG  TCT  T AAAAATTATT      529
Met  Asp  Lys  Thr  Ala  His  Asp  Lys  Leu  Cys  Lys  Ser  Ser
160                      165                      170

CGTGAAAAAT  AGAATTTTAT  TGCTATTTTC  TGTAAAACCA  TATAAAGCTA  TTTTAATACT             589

TTGTACAGTA  TATACATAAT  AAATTGCTAC  ATTTGCTCTA  AAAAAAAAAA  AAAAAA                 646
```

( 2 ) INFORMATION FOR SEQ ID NO:51:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Ala  Arg  Ala  Arg  Ser  Val  Gly  Ser  Met  Lys  Asn  Lys  Leu  Lys  Ser  Phe
 1              5                        10                       15

Ser  Glu  Lys  Tyr  Val  Trp  Ala  Ala  Leu  Thr  Ser  Asn  Asp  Asn  Leu  Arg
               20                       25                       30

Lys  Met  Ser  Gly  Gly  Arg  Met  Ile  Asn  Asp  Ile  Leu  Asn  Asp  Ile  Asp
          35                       40                       45

Asn  Ile  Lys  Lys  Gly  Asn  Gly  Gln  Pro  Asn  Ala  Pro  Gly  Lys  Thr  Glu
     50                       55                       60

Asn  Lys  Leu  Ser  Val  Ser  Asp  Arg  Ser  Ser  Arg  Tyr  Leu  Ser  Ser  Ile
 65                       70                       75                       80

Arg  Phe  Ser  Leu  Phe  Arg  Pro  Arg  Tyr  Lys  Ile  Glu  Asn  Gln  Asp  Leu
               85                       90                       95

Glu  Pro  Ser  Ser  Leu  Tyr  Pro  Gly  Gln  Gly  Ala  Leu  His  Val  Ile  Glu
               100                      105                      110
```

| | | | | | | | | | | | | | | |
|---|---|---|---|---|---|---|---|---|---|---|---|---|---|---|
|Leu|His|Lys|Asp|Lys|Asn|Gln|Trp|Asn|Val|Lys|Thr|Leu|Tyr|Arg|Asn|
| | |115| | | |120| | | | |125| | | |
|Asn|Asp|Gln|Gln|Glu|Leu|Lys|Pro|Met|Lys|Leu|Ala|Lys|Cys|Gly|Asp|
| |130| | | | |135| | | |140| | | | |
|Thr|Cys|Ser|Tyr|Glu|Thr|Phe|Lys|Ser|Thr|Leu|Gln|Ser|Tyr|Asn|Met|
|145| | | | |150| | | | |155| | | | |160|
|Asp|Lys|Thr|Ala|His|Asp|Lys|Leu|Cys|Lys|Ser|Ser|
| | | | |165| | | |170| | | |

( 2 ) INFORMATION FOR SEQ ID NO:52:

( i ) SEQUENCE CHARACTERISTICS:
        ( A ) LENGTH: 612 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..461

( x i ) SEQUENCE DESCRIPTION: SEQ ID NO:52:

```
C GGC ACG AGG AAA AAC GAG CTG AAA AGT TTT TCC GAA GAA TAT TTA          46
  Gly Thr Arg Lys Asn Glu Leu Lys Ser Phe Ser Glu Glu Tyr Leu
   1               5                  10                  15

TGG AGG GCT CTA ACT TCT AAT GAG AAT CTT AGA AAG ATG TCA GGA GGC        94
Trp Arg Ala Leu Thr Ser Asn Glu Asn Leu Arg Lys Met Ser Gly Gly
                 20                  25                  30

CGT ATG ATT AAC GAT ATA TTG AAC GAT ATC GAT AGT ATA AAA GAA GAA       142
Arg Met Ile Asn Asp Ile Leu Asn Asp Ile Asp Ser Ile Lys Glu Glu
             35                  40                  45

AGG GAC AAC CGG GTG CTC CTG GAA AAA CAG GAA ATT AAA TTA TCA ATG       190
Arg Asp Asn Arg Val Leu Leu Glu Lys Gln Glu Ile Lys Leu Ser Met
         50                  55                  60

CTG ACC GTT CCT CAA GCT ATC TTA GCA GCA TTT GTT TCA GCT TTT GCT       238
Leu Thr Val Pro Gln Ala Ile Leu Ala Ala Phe Val Ser Ala Phe Ala
     65                  70                  75

CCC AAA GGT ACA AAA ATT GAA AAT CAG GAC CTT GGT CCG TCT AGT TTA       286
Pro Lys Gly Thr Lys Ile Glu Asn Gln Asp Leu Gly Pro Ser Ser Leu
 80                  85                  90                  95

TAT CCT GGC CAA GGA GCA CTC CAC GTT ATT GAA CTG CAC AAG GAT AAC       334
Tyr Pro Gly Gln Gly Ala Leu His Val Ile Glu Leu His Lys Asp Asn
                100                 105                 110

AAC CAA TGG AGT GTG AAA GTT CTC TAT AGA AAC AAT GAC AAA ATG GAA       382
Asn Gln Trp Ser Val Lys Val Leu Tyr Arg Asn Asn Asp Lys Met Glu
             115                 120                 125

CTG GAA CCT ATG AAA CTT CCA TCA TGC GAT GAC AAA TGT CCT TGT GAA       430
Leu Glu Pro Met Lys Leu Pro Ser Cys Asp Asp Lys Cys Pro Cys Glu
         130                 135                 140

CTT TTA AAT CAA CTC TAC AAT CCT ATG ATA T GAAAAGCAG TCATGTAAAT        481
Leu Leu Asn Gln Leu Tyr Asn Pro Met Ile
     145                 150

TATGTAAAAA GCAATAAAAC TGTTGGCAAA ACATACACTT GAACATATTC TGCAAAATTA     541

TATGACGTTA TTTTTAATAT CACGAAATAA ACTACAAACA AACATATACA AATAAAAAAA     601

AAAAAAAAAA A                                                          612
```

( 2 ) INFORMATION FOR SEQ ID NO:53:

( i ) SEQUENCE CHARACTERISTICS:
        ( A ) LENGTH: 153 amino acids (B) TYPE: amino acid
(D) TOPOLOGY: linear (i i) MOLECULE TYPE: protein (x i) SEQUENCE DESCRIPTION: SEQ ID NO:53:

| Gly | Thr | Arg | Lys | Asn | Glu | Leu | Lys | Ser | Phe | Ser | Glu | Glu | Tyr | Leu | Trp |
|---|---|---|---|---|---|---|---|---|---|---|---|---|---|---|---|
| 1 | | | | 5 | | | | | 10 | | | | | 15 | |
| Arg | Ala | Leu | Thr | Ser | Asn | Glu | Asn | Leu | Arg | Lys | Met | Ser | Gly | Gly | Arg |
| | | | 20 | | | | | 25 | | | | | 30 | | |
| Met | Ile | Asn | Asp | Ile | Leu | Asn | Asp | Ile | Asp | Ser | Ile | Lys | Glu | Glu | Arg |
| | | 35 | | | | | 40 | | | | | 45 | | | |
| Asp | Asn | Arg | Val | Leu | Leu | Glu | Lys | Gln | Glu | Ile | Lys | Leu | Ser | Met | Leu |
| | 50 | | | | | 55 | | | | | 60 | | | | |
| Thr | Val | Pro | Gln | Ala | Ile | Leu | Ala | Ala | Phe | Val | Ser | Ala | Phe | Ala | Pro |
| 65 | | | | | 70 | | | | | 75 | | | | | 80 |
| Lys | Gly | Thr | Lys | Ile | Glu | Asn | Gln | Asp | Leu | Gly | Pro | Ser | Ser | Leu | Tyr |
| | | | | 85 | | | | | 90 | | | | | 95 | |
| Pro | Gly | Gln | Gly | Ala | Leu | His | Val | Ile | Glu | Leu | His | Lys | Asp | Asn | Asn |
| | | | 100 | | | | | 105 | | | | | 110 | | |
| Gln | Trp | Ser | Val | Lys | Val | Leu | Tyr | Arg | Asn | Asn | Asp | Lys | Met | Glu | Leu |
| | | 115 | | | | | 120 | | | | | 125 | | | |
| Glu | Pro | Met | Lys | Leu | Pro | Ser | Cys | Asp | Asp | Lys | Cys | Pro | Cys | Glu | Leu |
| | 130 | | | | | 135 | | | | | 140 | | | | |
| Leu | Asn | Gln | Leu | Tyr | Asn | Pro | Met | Ile | | | | | | | |
| 145 | | | | | 150 | | | | | | | | | | |

(2) INFORMATION FOR SEQ ID NO:54:

(i) SEQUENCE CHARACTERISTICS:
(A) LENGTH: 56 amino acids
(B) TYPE: amino acid
(D) TOPOLOGY: linear (i i) MOLECULE TYPE: protein (x i) SEQUENCE DESCRIPTION: SEQ ID NO:54:

| Met | Trp | Arg | Leu | Leu | Leu | Val | Ile | Ser | Ser | Ala | Leu | Ile | Ile | Gln | Asn |
|---|---|---|---|---|---|---|---|---|---|---|---|---|---|---|---|
| 1 | | | | 5 | | | | | 10 | | | | | 15 | |
| Val | Asn | Ala | Glu | Leu | Lys | Phe | Val | Phe | Ala | Thr | Ala | Thr | Arg | Tyr | Val |
| | | | 20 | | | | | 25 | | | | | 30 | | |
| Ser | His | Thr | Pro | Ser | Pro | Cys | Asp | Pro | Gly | Gly | Pro | Lys | Ile | Thr | Asn |
| | | 35 | | | | | 40 | | | | | 45 | | | |
| Lys | Pro | Gly | Asp | Phe | Gln | Arg | Val | | | | | | | | |
| | 50 | | | | | 55 | | | | | | | | | |

(2) INFORMATION FOR SEQ ID NO:55:

(i) SEQUENCE CHARACTERISTICS:
(A) LENGTH: 1197 base pairs
(B) TYPE: nucleic acid
(C) STRANDEDNESS: single
(D) TOPOLOGY: linear (i i) MOLECULE TYPE: cDNA (i x) FEATURE:
(A) NAME/KEY: CDS
(B) LOCATION: 1..1196

(x i) SEQUENCE DESCRIPTION: SEQ ID NO:55:

| | | | | | | | | | | | | | | | | |
|---|---|---|---|---|---|---|---|---|---|---|---|---|---|---|---|---|
| ATG | TGG | CGT | CTA | CTG | TTA | GTT | ATT | TCA | AGT | GCA | CTT | ATC | ATT | CAA | AAT | 48 |
| Met | Trp | Arg | Leu | Leu | Leu | Val | Ile | Ser | Ser | Ala | Leu | Ile | Ile | Gln | Asn | |
| 1 | | | | 5 | | | | | 10 | | | | | 15 | | |
| GTT | AAT | GCA | GAA | TTG | AAA | TTT | GTG | TTT | GCG | ACT | GCA | CGA | GGT | ATG | TCA | 96 |
| Val | Asn | Ala | Glu | Leu | Lys | Phe | Val | Phe | Ala | Thr | Ala | Arg | Gly | Met | Ser | |
| | | | 20 | | | | 25 | | | | | 30 | | | | |
| CAT | ACA | CCT | TGT | GAT | TAT | CCA | GGC | GGT | CCA | AAA | ATT | ACT | AAC | AAG | CCT | 144 |
| His | Thr | Pro | Cys | Asp | Tyr | Pro | Gly | Gly | Pro | Lys | Ile | Thr | Asn | Lys | Pro | |
| | | 35 | | | | | 40 | | | | | 45 | | | | |
| GAG | ACT | TCA | AGC | GTG | TTG | ACA | ACA | GCT | GGT | AAA | AAT | GAG | GCA | CTA | GAA | 192 |
| Glu | Thr | Ser | Ser | Val | Leu | Thr | Thr | Ala | Gly | Lys | Asn | Glu | Ala | Leu | Glu | |
| | 50 | | | | | 55 | | | | | 60 | | | | | |
| ATT | GGC | AAA | CTA | TTA | TCT | GAC | CAT | TAC | AAA | AGT | AAT | TTA | ACA | GTT | AAG | 240 |
| Ile | Gly | Lys | Leu | Leu | Ser | Asp | His | Tyr | Lys | Ser | Asn | Leu | Thr | Val | Lys | |
| 65 | | | | | 70 | | | | | 75 | | | | | 80 | |
| GAA | TGG | GAC | TCA | AGT | AAA | AAT | TAT | TGG | ACA | TTA | GCT | AGT | AAT | ACA | AGA | 288 |
| Glu | Trp | Asp | Ser | Ser | Lys | Asn | Tyr | Trp | Thr | Leu | Ala | Ser | Asn | Thr | Arg | |
| | | | | 85 | | | | | 90 | | | | | 95 | | |
| AGA | TCT | CAA | GAA | GGA | ACA | CTT | ATT | ATT | GGT | TCT | GGA | CTA | GAA | GGA | AAG | 336 |
| Arg | Ser | Gln | Glu | Gly | Thr | Leu | Ile | Ile | Gly | Ser | Gly | Leu | Glu | Gly | Lys | |
| | | | 100 | | | | | 105 | | | | | 110 | | | |
| AGT | AGA | GCA | GCA | GAG | TGG | TCA | CAA | GAG | ATA | GGA | AAG | AAA | ACC | ACA | TTT | 384 |
| Ser | Arg | Ala | Ala | Glu | Trp | Ser | Gln | Glu | Ile | Gly | Lys | Lys | Thr | Thr | Phe | |
| | | 115 | | | | | 120 | | | | | 125 | | | | |
| TCA | GGA | TTT | TCT | GAG | TAT | GCT | AAA | TTT | TAT | AGT | CAA | AAA | GAA | TGC | CCA | 432 |
| Ser | Gly | Phe | Ser | Glu | Tyr | Ala | Lys | Phe | Tyr | Ser | Gln | Lys | Glu | Cys | Pro | |
| | 130 | | | | | 135 | | | | | 140 | | | | | |
| AAC | TTC | ATA | AAA | CAA | CAG | TTG | GAT | GCA | GTG | AAG | GAC | TTG | TTA | AAG | AGT | 480 |
| Asn | Phe | Ile | Lys | Gln | Gln | Leu | Asp | Ala | Val | Lys | Asp | Leu | Leu | Lys | Ser | |
| 145 | | | | | 150 | | | | | 155 | | | | | 160 | |
| GCA | AAA | GAA | TAT | AAT | ACA | GAA | TTT | GAC | AAA | TTA | AAG | AAA | GTG | TAT | AAT | 528 |
| Ala | Lys | Glu | Tyr | Asn | Thr | Glu | Phe | Asp | Lys | Leu | Lys | Lys | Val | Tyr | Asn | |
| | | | | 165 | | | | | 170 | | | | | 175 | | |
| ATT | GAT | GCA | ATG | AAG | GGC | CCA | CAA | AAT | GTT | TGG | CTG | GCA | TAC | GAG | ACT | 576 |
| Ile | Asp | Ala | Met | Lys | Gly | Pro | Gln | Asn | Val | Trp | Leu | Ala | Tyr | Glu | Thr | |
| | | | 180 | | | | | 185 | | | | | 190 | | | |
| TTA | AAT | TTA | CAA | AGC | AAG | CTC | GAT | CAG | ATT | GGT | TTG | GGA | AGT | ATG | AAA | 624 |
| Leu | Asn | Leu | Gln | Ser | Lys | Leu | Asp | Gln | Ile | Gly | Leu | Gly | Ser | Met | Lys | |
| | | 195 | | | | | 200 | | | | | 205 | | | | |
| AAC | AAA | TTG | AAA | AGT | TTT | TCC | GAG | AAA | TAT | GTA | TGG | GCG | GGT | TTA | ACT | 672 |
| Asn | Lys | Leu | Lys | Ser | Phe | Ser | Glu | Lys | Tyr | Val | Trp | Ala | Gly | Leu | Thr | |
| | 210 | | | | | 215 | | | | | 220 | | | | | |
| TCT | AAC | GAC | AAT | CTT | AGG | AAA | ATG | TCT | GGA | GGT | CGT | ATG | ATT | AAC | GAT | 720 |
| Ser | Asn | Asp | Asn | Leu | Arg | Lys | Met | Ser | Gly | Gly | Arg | Met | Ile | Asn | Asp | |
| 225 | | | | | 230 | | | | | 235 | | | | | 240 | |
| ATA | TTG | AAC | GAT | ATC | GAT | AAT | ATA | AAG | AAA | GGA | AAT | GGA | CAA | CCG | AAT | 768 |
| Ile | Leu | Asn | Asp | Ile | Asp | Asn | Ile | Lys | Lys | Gly | Asn | Gly | Gln | Pro | Asn | |
| | | | | 245 | | | | | 250 | | | | | 255 | | |
| GCT | CCT | GGA | AAA | CTG | AAA | ATA | ATT | ATC | GGG | CTG | ACC | GCC | CCA | AGG | TTC | 816 |
| Ala | Pro | Gly | Lys | Leu | Lys | Ile | Ile | Ile | Gly | Leu | Thr | Ala | Pro | Arg | Phe | |
| | | | 260 | | | | | 265 | | | | | 270 | | | |
| TTA | GCA | GAA | TCC | GTT | CAG | CTT | GGG | TCC | AAG | GGT | ACA | AAA | TTG | AAT | CAG | 864 |
| Leu | Ala | Glu | Ser | Val | Gln | Leu | Gly | Ser | Lys | Gly | Thr | Lys | Leu | Asn | Gln | |
| | | 275 | | | | | 280 | | | | | 285 | | | | |
| GAC | CAA | AAT | AAA | TTA | TCG | GTG | CTG | ACC | GTT | CCT | CAA | GGT | ATC | TTA | GCA | 912 |
| Asp | Gln | Asn | Lys | Leu | Ser | Val | Leu | Thr | Val | Pro | Gln | Gly | Ile | Leu | Ala | |
| | 290 | | | | | 295 | | | | | 300 | | | | | |
| GCA | TTC | GTT | TCA | GCT | TTT | GCT | CCC | AAA | GGT | ACA | AAA | ATT | GAA | AAT | CAG | 960 |
| Ala | Phe | Val | Ser | Ala | Phe | Ala | Pro | Lys | Gly | Thr | Lys | Ile | Glu | Asn | Gln | |
| 305 | | | | | 310 | | | | | 315 | | | | | 320 | |

| | | | | | | | | | | | | | | | |
|---|---|---|---|---|---|---|---|---|---|---|---|---|---|---|---|
| GAC | CTT | GAT | CCG | TCT | AGT | TTA | TAT | CCT | GGC | CAA | GGA | GCA | CTC | CAT | GTT | 1008
| Asp | Leu | Asp | Pro | Ser | Ser | Leu | Tyr | Pro | Gly | Gln | Gly | Ala | Leu | His | Val |
| | | | 325 | | | | | 330 | | | | | 335 | | |
| ATT | GAA | CTG | CAC | AAA | GAT | AAG | AAC | CAG | TGG | AAT | GTA | AAA | ATC | CTC | TAT | 1056
| Ile | Glu | Leu | His | Lys | Asp | Lys | Asn | Gln | Trp | Asn | Val | Lys | Ile | Leu | Tyr |
| | | | 340 | | | | | 345 | | | | | 350 | | |
| AGA | AAC | AAT | GAC | CAA | TCG | GAA | CTC | AAA | CCT | ATG | AAA | CTT | GCA | AAA | TGC | 1104
| Arg | Asn | Asn | Asp | Gln | Ser | Glu | Leu | Lys | Pro | Met | Lys | Leu | Ala | Lys | Cys |
| | | 355 | | | | | 360 | | | | | 365 | | | |
| GGT | GAC | ACA | TGT | TCT | TAT | GAA | ACT | TTC | AAA | TCA | ACT | CTA | CAA | TCC | TAT | 1152
| Gly | Asp | Thr | Cys | Ser | Tyr | Glu | Thr | Phe | Lys | Ser | Thr | Leu | Gln | Ser | Tyr |
| | 370 | | | | | 375 | | | | | 380 | | | | |
| AAC | ATG | GAT | AAG | ACC | GCT | CAT | GAT | AAA | TTG | TGT | AAA | TCG | TCT | TAA | | 1197
| Asn | Met | Asp | Lys | Thr | Ala | His | Asp | Lys | Leu | Cys | Lys | Ser | Ser | | |
| 385 | | | | | 390 | | | | | 395 | | | | | |

(2) INFORMATION FOR SEQ ID NO:56:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO:56:

| | | | | | | | | | | | | | | |
|---|---|---|---|---|---|---|---|---|---|---|---|---|---|---|
| Met | Trp | Arg | Leu | Leu | Leu | Val | Ile | Ser | Ser | Ala | Leu | Ile | Ile | Gln | Asn |
| 1 | | | | 5 | | | | | 10 | | | | | 15 |
| Val | Asn | Ala | Glu | Leu | Lys | Phe | Val | Phe | Ala | Thr | Ala | Arg | Gly | Met | Ser |
| | | | 20 | | | | | 25 | | | | | 30 | | |
| His | Thr | Pro | Cys | Asp | Tyr | Pro | Gly | Gly | Pro | Lys | Ile | Thr | Asn | Lys | Pro |
| | | 35 | | | | | 40 | | | | | 45 | | | |
| Glu | Thr | Ser | Ser | Val | Leu | Thr | Thr | Ala | Gly | Lys | Asn | Glu | Ala | Leu | Glu |
| | 50 | | | | | 55 | | | | | 60 | | | | |
| Ile | Gly | Lys | Leu | Leu | Ser | Asp | His | Tyr | Lys | Ser | Asn | Leu | Thr | Val | Lys |
| 65 | | | | | 70 | | | | | 75 | | | | | 80 |
| Glu | Trp | Asp | Ser | Ser | Lys | Asn | Tyr | Trp | Thr | Leu | Ala | Ser | Asn | Thr | Arg |
| | | | | 85 | | | | | 90 | | | | | 95 | |
| Arg | Ser | Gln | Glu | Gly | Thr | Leu | Ile | Ile | Gly | Ser | Gly | Leu | Glu | Gly | Lys |
| | | | | 100 | | | | | 105 | | | | | 110 | |
| Ser | Arg | Ala | Ala | Glu | Trp | Ser | Gln | Glu | Ile | Gly | Lys | Lys | Thr | Thr | Phe |
| | | | 115 | | | | | 120 | | | | | 125 | | |
| Ser | Gly | Phe | Ser | Glu | Tyr | Ala | Lys | Phe | Tyr | Ser | Gln | Lys | Glu | Cys | Pro |
| | | 130 | | | | | 135 | | | | | 140 | | | |
| Asn | Phe | Ile | Lys | Gln | Gln | Leu | Asp | Ala | Val | Lys | Asp | Leu | Leu | Lys | Ser |
| 145 | | | | | 150 | | | | | 155 | | | | | 160 |
| Ala | Lys | Glu | Tyr | Asn | Thr | Glu | Phe | Asp | Lys | Leu | Lys | Lys | Val | Tyr | Asn |
| | | | | 165 | | | | | 170 | | | | | 175 | |
| Ile | Asp | Ala | Met | Lys | Gly | Pro | Gln | Asn | Val | Trp | Leu | Ala | Tyr | Glu | Thr |
| | | | 180 | | | | | 185 | | | | | 190 | | |
| Leu | Asn | Leu | Gln | Ser | Lys | Leu | Asp | Gln | Ile | Gly | Leu | Gly | Ser | Met | Lys |
| | | | 195 | | | | | 200 | | | | | 205 | | |
| Asn | Lys | Leu | Lys | Ser | Phe | Ser | Glu | Lys | Tyr | Val | Trp | Ala | Gly | Leu | Thr |
| | | 210 | | | | | 215 | | | | | 220 | | | |
| Ser | Asn | Asp | Asn | Leu | Arg | Lys | Met | Ser | Gly | Gly | Arg | Met | Ile | Asn | Asp |
| 225 | | | | | 230 | | | | | 235 | | | | | 240 |
| Ile | Leu | Asn | Asp | Ile | Asp | Asn | Ile | Lys | Lys | Gly | Asn | Gly | Gln | Pro | Asn |
| | | | | 245 | | | | | 250 | | | | | 255 | |

| | | | | | | | | | | | | | | |
|---|---|---|---|---|---|---|---|---|---|---|---|---|---|---|
| Ala | Pro | Gly | Lys 260 | Leu | Lys | Ile | Ile 265 | Gly | Leu | Thr | Ala | Pro 270 | Arg | Phe |
| Leu | Ala | Glu 275 | Ser | Val | Gln | Leu 280 | Ser | Lys | Gly | Thr | Lys 285 | Leu | Asn | Gln |
| Asp | Gln 290 | Asn | Lys | Leu | Ser | Val 295 | Leu | Thr | Val | Pro | Gln 300 | Gly | Ile | Leu | Ala |
| Ala 305 | Phe | Val | Ser | Ala | Phe 310 | Ala | Pro | Lys | Gly | Thr 315 | Lys | Ile | Glu | Asn | Gln 320 |
| Asp | Leu | Asp | Pro | Ser 325 | Ser | Leu | Tyr | Pro | Gly 330 | Gln | Gly | Ala | Leu | His 335 | Val |
| Ile | Glu | Leu | His 340 | Lys | Asp | Lys | Asn | Gln 345 | Trp | Asn | Val | Lys | Ile 350 | Leu | Tyr |
| Arg | Asn | Asn 355 | Asp | Gln | Ser | Glu | Leu 360 | Lys | Pro | Met | Lys | Leu 365 | Ala | Lys | Cys |
| Gly | Asp 370 | Thr | Cys | Ser | Tyr | Glu 375 | Thr | Phe | Lys | Ser | Thr 380 | Leu | Gln | Ser | Tyr |
| Asn 385 | Met | Asp | Lys | Thr | Ala 390 | His | Asp | Lys | Leu | Cys 395 | Lys | Ser | Ser |

(2) INFORMATION FOR SEQ ID NO:57:

(i) SEQUENCE CHARACTERISTICS:
        (A) LENGTH: 565 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 45..317

(xi) SEQUENCE DESCRIPTION: SEQ ID NO:57:

```
TGAAATTCAA TATTTTGTTT TACATTAAAT TTTTCAAATT CGAT ATG AAA TTT TTA          56
                                                 Met Lys Phe Leu
                                                   1

CTG GCA ATT TGC GTG TTG TGT GTT TTA TTA AAT CAA GTA TCT ATG TCA          104
Leu Ala Ile Cys Val Leu Cys Val Leu Leu Asn Gln Val Ser Met Ser
  5              10                  15                  20

AAA ATG GTC ACT GAA AAG TGT AAG TCA GGT GGA AAT AAT CCA AGT ACA          152
Lys Met Val Thr Glu Lys Cys Lys Ser Gly Gly Asn Asn Pro Ser Thr
             25                  30                  35

GAA GAG GTG TCA ATA CCA TCT GGG AAG CTT ACT ATT GAA GAT TTT TGT          200
Glu Glu Val Ser Ile Pro Ser Gly Lys Leu Thr Ile Glu Asp Phe Cys
         40                  45                  50

ATT GGA AAT CAT CAA AGT TGC AAA ATA TTT TAC AAA AGT CAA TGT GGA          248
Ile Gly Asn His Gln Ser Cys Lys Ile Phe Tyr Lys Ser Gln Cys Gly
             55                  60                  65

TTT GGA GGT GGT GCT TGT GGA AAC GGT GGT TCA ACA CGA CCA AAT CAA          296
Phe Gly Gly Gly Ala Cys Gly Asn Gly Gly Ser Thr Arg Pro Asn Gln
     70                  75                  80

AAA CAC TGT TAT TGC GAA TAACCATATT CCGGATGAAA GACCAAATTG                 344
Lys His Cys Tyr Cys Glu
 85              90

ATATAAATTA CTAAAATTAT GCTAGATAGC AATCATAAAA TTTTGAAGTT TTCAATGATC        404

CTAACATGTT TTGCCTCCAA TTTATTTTAA CAGCAAATTG CTGGAACTTA CCGTACCGTA        464

ACTAAATGTT CAAGAAATAC TGAATGTTTA CAAATAGATT ATTATAAATA TTGTAACATT        524

GTCTAATATT TATAAGAATT ATATAAACTG AATTGCAAAA A                            565
```

(2) INFORMATION FOR SEQ ID NO:58:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO:58:

```
Met Lys Phe Leu Leu Ala Ile Cys Val Leu Cys Val Leu Leu Asn Gln
 1               5                  10                  15
Val Ser Met Ser Lys Met Val Thr Glu Lys Cys Lys Ser Gly Gly Asn
            20                  25                  30
Asn Pro Ser Thr Glu Glu Val Ser Ile Pro Ser Gly Lys Leu Thr Ile
        35                  40                  45
Glu Asp Phe Cys Ile Gly Asn His Gln Ser Cys Lys Ile Phe Tyr Lys
    50                  55                  60
Ser Gln Cys Gly Phe Gly Gly Gly Ala Cys Gly Asn Gly Gly Ser Thr
65                  70                  75                  80
Arg Pro Asn Gln Lys His Cys Tyr Cys Glu
            85                  90
```

(2) INFORMATION FOR SEQ ID NO:59:

(i) SEQUENCE CHARACTERISTICS:
        (A) LENGTH: 897 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 97..568

(xi) SEQUENCE DESCRIPTION: SEQ ID NO:59:

```
CCGAAATCTC CTATCACAGT GTACGGAGTG TAAAATATTG TTGAAGTATT TTGAAATTTA      60

TTAATTTATT CGAAAGGAG ATTTCATTAA ATAAAA ATG GTT TAC GAA AGT GAC        114
                                       Met Val Tyr Glu Ser Asp
                                        1               5

TTT TAC ACG ACC CGT CGG CCC TAC AGT CGT CCG GCT TTG TCT TCA TAC      162
Phe Tyr Thr Thr Arg Arg Pro Tyr Ser Arg Pro Ala Leu Ser Ser Tyr
            10                  15                  20

TCC GTA ACG GCA CGT CCA GAG CCG GTT CCT TGG GAC AAA TTG CCG TTC      210
Ser Val Thr Ala Arg Pro Glu Pro Val Pro Trp Asp Lys Leu Pro Phe
        25                  30                  35

GTC CCC CGT CCA AGT TTG GTA GCA GAT CCC ATA ACA GCA TTT TGC AAG      258
Val Pro Arg Pro Ser Leu Val Ala Asp Pro Ile Thr Ala Phe Cys Lys
    40                  45                  50

CGA AAA CCT CGC CGA GAA GAA GTT GTT CAA AAA GAG TCC ATT GTT CGA      306
Arg Lys Pro Arg Arg Glu Glu Val Val Gln Lys Glu Ser Ile Val Arg
55                  60                  65                  70

AGG ATC AAT TCT GCA GGA ATT AAA CCC AGC CAG AGA GTT TTA TCG GCT      354
Arg Ile Asn Ser Ala Gly Ile Lys Pro Ser Gln Arg Val Leu Ser Ala
            75                  80                  85

CCA ATA AGA GAA TAC GAA TCC CCA AGG GAC CAG ACC AGG CGT AAA GTT      402
Pro Ile Arg Glu Tyr Glu Ser Pro Arg Asp Gln Thr Arg Arg Lys Val
        90                  95                  100

TTG GAA AGC GTC AGA AGA CAA GAA GCT TTT CTG AAC CAA GGA GGA ATT      450
Leu Glu Ser Val Arg Arg Gln Glu Ala Phe Leu Asn Gln Gly Gly Ile
    105                 110                 115
```

```
TGT CCA TTG ACC ACC AGA AAT GAT GAC ATG GAT AGA CTT CTA CCC CGT        498
Cys Pro Leu Thr Thr Arg Asn Asp Asp Met Asp Arg Leu Leu Pro Arg
    120                     125                 130

CTC CAC AGT TCA CAC ACA ACA CCT TCT GCG GAT AGG AAA GTT TTG TTG        546
Leu His Ser Ser His Thr Thr Pro Ser Ala Asp Arg Lys Val Leu Leu
135                     140                 145                 150

ACC ACT TTT CAC AGA AGA TAC T GATTAAAAAT GAAAGTTAAG AAATTTGTTG         598
Thr Thr Phe His Arg Arg Tyr
                    155

AAGTCATGTG GTGTTTTTA TACATTCTTT ATTAATCGAT ATTCCTAACG AACGATACGA       658

TAACTTTCGA TAACTTTTTC TGGTTAATTT TGACAAAATA TGCATTTGCA AGCATAACAT      718

TCATTTTCAA GGCAAACGCT TTCTGATGAT TATCTTGTTA AAAGTGTGGA AACAAGCGTA      778

GTGTTAACAA ATGCATTGCT TGTTTTGATT ATTTATTTAT CTATTATATA TTCCATATTG      838

TATTGTAGGT GGTGTACTTG GTATTACTAA TACACGTACT TTGTGAAAAA AAAAAAAAA       897
```

(2) INFORMATION FOR SEQ ID NO:60:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO:60:

```
Met Val Tyr Glu Ser Asp Phe Tyr Thr Thr Arg Arg Pro Tyr Ser Arg
 1               5                  10                  15

Pro Ala Leu Ser Ser Tyr Ser Val Thr Ala Arg Pro Glu Pro Val Pro
            20                  25                  30

Trp Asp Lys Leu Pro Phe Val Pro Arg Pro Ser Leu Val Ala Asp Pro
            35                  40                  45

Ile Thr Ala Phe Cys Lys Arg Lys Pro Arg Arg Glu Glu Val Val Gln
        50                  55                  60

Lys Glu Ser Ile Val Arg Arg Ile Asn Ser Ala Gly Ile Lys Pro Ser
 65                  70                  75                  80

Gln Arg Val Leu Ser Ala Pro Ile Arg Glu Tyr Glu Ser Pro Arg Asp
                85                  90                  95

Gln Thr Arg Arg Lys Val Leu Glu Ser Val Arg Arg Gln Glu Ala Phe
            100                 105                 110

Leu Asn Gln Gly Gly Ile Cys Pro Leu Thr Thr Arg Asn Asp Asp Met
            115                 120                 125

Asp Arg Leu Leu Pro Arg Leu His Ser Ser His Thr Thr Pro Ser Ala
        130                 135                 140

Asp Arg Lys Val Leu Leu Thr Thr Phe His Arg Arg Tyr
145                 150                 155
```

(2) INFORMATION FOR SEQ ID NO:61:

(i) SEQUENCE CHARACTERISTICS:
        (A) LENGTH: 2706 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 5..2706

( x i ) SEQUENCE DESCRIPTION: SEQ ID NO:61:

```
GCGG ATG AAG AGC ATC GAG GCT TAT ACA AAC AGA TAT GAA ATC ATA GCT        49
     Met Lys Ser Ile Glu Ala Tyr Thr Asn Arg Tyr Glu Ile Ile Ala
      1           5                  10                      15

TCT GAA ATA GTT AAT CTT CGA ATG AAA CCA GAT GAT TTT AAT TTA ATA         97
Ser Glu Ile Val Asn Leu Arg Met Lys Pro Asp Asp Phe Asn Leu Ile
                 20                  25                  30

AAA GTT ATT GGT CGA GGA GCA TTT GGT GAA GTA CAG TTA GTG CGA CAC        145
Lys Val Ile Gly Arg Gly Ala Phe Gly Glu Val Gln Leu Val Arg His
             35                  40                  45

AAA TCA ACT GCA CAA GTT TTT GCT ATG AAA CGC CTA TCA AAA TTT GAA        193
Lys Ser Thr Ala Gln Val Phe Ala Met Lys Arg Leu Ser Lys Phe Glu
         50                  55                  60

ATG ATT AAG AGA CCA GAC TCT GCA TTT TTT TGG GAA GAA CGT CAT ATA        241
Met Ile Lys Arg Pro Asp Ser Ala Phe Phe Trp Glu Glu Arg His Ile
     65                  70                  75

ATG GCT CAT GCA AAA TCA GAA TGG ATT GTA CAA TTA CAT TTT GCT TTT        289
Met Ala His Ala Lys Ser Glu Trp Ile Val Gln Leu His Phe Ala Phe
 80                  85                  90                      95

CAA GAT CAA AAA TAT CTT TAT ATG GTC ATG GAT TAT ATG CCG GGG GGT        337
Gln Asp Gln Lys Tyr Leu Tyr Met Val Met Asp Tyr Met Pro Gly Gly
                100                 105                 110

GAC TTG GTG AGT CTT ATG TCC GAT TAT GAA ATT CCA GAA AAA TGG GCA        385
Asp Leu Val Ser Leu Met Ser Asp Tyr Glu Ile Pro Glu Lys Trp Ala
            115                 120                 125

ATG TTC TAT ACA ATG GAA GTG GTG CTA GCA CTT GAT ACA ATT CAC TCC        433
Met Phe Tyr Thr Met Glu Val Val Leu Ala Leu Asp Thr Ile His Ser
        130                 135                 140

ATG GGA TTT GTA CAT CGT GAT GTT AAA CCT GAT AAT ATG CTT CTA GAC        481
Met Gly Phe Val His Arg Asp Val Lys Pro Asp Asn Met Leu Leu Asp
145                 150                 155

AAA TAT GGT CAT TTA AAG TTA GCT GAC TTT GGA ACC TGT ATG AAA ATG        529
Lys Tyr Gly His Leu Lys Leu Ala Asp Phe Gly Thr Cys Met Lys Met
160                 165                 170                 175

GAT ACA GAT GGT TTG GTA CGT TCT AAT AAT GCT GTT GGA ACG CCT GAT        577
Asp Thr Asp Gly Leu Val Arg Ser Asn Asn Ala Val Gly Thr Pro Asp
                180                 185                 190

TAC ATT TCT CCC GAA GTT TTG CAG TCC CAA GGT GGT GAA GGA GTT TAC        625
Tyr Ile Ser Pro Glu Val Leu Gln Ser Gln Gly Gly Glu Gly Val Tyr
            195                 200                 205

GGT CGT GAA TGC GAT TGG TGG TCT GTG GGA ATT TTT TTG TAT GAA ATG        673
Gly Arg Glu Cys Asp Trp Trp Ser Val Gly Ile Phe Leu Tyr Glu Met
        210                 215                 220

TTA TTT GGA GAA ACA CCT TTT TAT GCA GAC AGT TTG GTT GGA ACT TAC        721
Leu Phe Gly Glu Thr Pro Phe Tyr Ala Asp Ser Leu Val Gly Thr Tyr
225                 230                 235

AGT AAA ATT ATG GAT CAC AGA AAC TCA TTA ACT TTT CCT CCA GAA GTG        769
Ser Lys Ile Met Asp His Arg Asn Ser Leu Thr Phe Pro Pro Glu Val
240                 245                 250                 255

GAA ATA AGC CAA TAT GCC CGA TCT TTG ATA CAA GGA TTT TTA ACA GAC        817
Glu Ile Ser Gln Tyr Ala Arg Ser Leu Ile Gln Gly Phe Leu Thr Asp
                260                 265                 270

AGA ACA CAG CGT TTA GGC AGA AAT GAA GTG GAA GAA ATT AAA CGA CAT        865
Arg Thr Gln Arg Leu Gly Arg Asn Glu Val Glu Glu Ile Lys Arg His
            275                 280                 285

CCA TTT TTC ATA AAT GAT CAA TGG ACT TTT GAC AAT TTA AGA GAC TCT        913
Pro Phe Phe Ile Asn Asp Gln Trp Thr Phe Asp Asn Leu Arg Asp Ser
        290                 295                 300
```

| | | | | | | | | | | | | | | | |
|---|---|---|---|---|---|---|---|---|---|---|---|---|---|---|---|
| GCC | CCA | CCT | GTA | GTG | CCA | GAG | CTG | AGT | GGT | GAT | GAT | GAT | ACA | AGG | AAC | 961 |
| Ala | Pro | Pro | Val | Val | Pro | Glu | Leu | Ser | Gly | Asp | Asp | Asp | Thr | Arg | Asn | |
| 305 | | | | | 310 | | | | | | | 315 | | | | |
| TTT | GAT | GAT | ATT | GAA | CGT | GAT | GAA | ACA | CCT | GAA | GAG | AAT | TTT | CCT | ATA | 1009 |
| Phe | Asp | Asp | Ile | Glu | Arg | Asp | Glu | Thr | Pro | Glu | Glu | Asn | Phe | Pro | Ile | |
| 320 | | | | | 325 | | | | | 330 | | | | | 335 | |
| CCA | AAA | ACT | TTT | GCT | GGT | AAT | CAT | CTG | CCA | TTT | GTT | GGA | TTC | ACA | TAT | 1057 |
| Pro | Lys | Thr | Phe | Ala | Gly | Asn | His | Leu | Pro | Phe | Val | Gly | Phe | Thr | Tyr | |
| | | | | 340 | | | | | 345 | | | | | 350 | | |
| AAT | GGT | GAT | TAC | CAA | TTA | TTA | ACA | AAT | GGA | GGT | GTT | AGA | AAT | AGT | GAT | 1105 |
| Asn | Gly | Asp | Tyr | Gln | Leu | Leu | Thr | Asn | Gly | Gly | Val | Arg | Asn | Ser | Asp | |
| | | | 355 | | | | | 360 | | | | | 365 | | | |
| ATG | GTT | GAT | ACA | AAA | TTA | AAC | AAC | ATT | TGT | GTT | TCA | AGT | AAG | GAT | GAT | 1153 |
| Met | Val | Asp | Thr | Lys | Leu | Asn | Asn | Ile | Cys | Val | Ser | Ser | Lys | Asp | Asp | |
| | | 370 | | | | | 375 | | | | | 380 | | | | |
| GTG | TTA | AAT | TTA | CAA | AAT | TTA | TTA | GAA | CAA | GAG | AAA | GGT | AAC | AGT | GAA | 1201 |
| Val | Leu | Asn | Leu | Gln | Asn | Leu | Leu | Glu | Gln | Glu | Lys | Gly | Asn | Ser | Glu | |
| | 385 | | | | | 390 | | | | | | 395 | | | | |
| AAT | TTG | AAA | ACA | AAC | ACC | CAA | TTA | TTA | AGT | AAT | AAA | TTA | GAT | GAA | CTA | 1249 |
| Asn | Leu | Lys | Thr | Asn | Thr | Gln | Leu | Leu | Ser | Asn | Lys | Leu | Asp | Glu | Leu | |
| 400 | | | | | 405 | | | | | 410 | | | | | 415 | |
| GGT | CAG | AGA | GAA | TGT | GAA | TTA | AGG | AAT | CAG | GCT | GGA | GAT | TAT | GAG | AAA | 1297 |
| Gly | Gln | Arg | Glu | Cys | Glu | Leu | Arg | Asn | Gln | Ala | Gly | Asp | Tyr | Glu | Lys | |
| | | | | 420 | | | | | 425 | | | | | 430 | | |
| GAA | TTG | ACT | AAA | TTC | AAA | TTA | TCG | TGC | AAA | GAA | TTA | CAA | CGT | AAG | GCA | 1345 |
| Glu | Leu | Thr | Lys | Phe | Lys | Leu | Ser | Cys | Lys | Glu | Leu | Gln | Arg | Lys | Ala | |
| | | | 435 | | | | | 440 | | | | | 445 | | | |
| GAA | TTT | GAG | AAT | GAA | TTA | CGG | CGT | AAA | ACT | GAG | TCC | TTA | CTA | GTT | GAA | 1393 |
| Glu | Phe | Glu | Asn | Glu | Leu | Arg | Arg | Lys | Thr | Glu | Ser | Leu | Leu | Val | Glu | |
| | | 450 | | | | | 455 | | | | | 460 | | | | |
| ACA | AAG | AAA | AGA | CTA | GAC | GAA | GAG | CAG | AAT | AAA | AGA | ACT | AGA | GAA | ATG | 1441 |
| Thr | Lys | Lys | Arg | Leu | Asp | Glu | Glu | Gln | Asn | Lys | Arg | Thr | Arg | Glu | Met | |
| | 465 | | | | | 470 | | | | | 475 | | | | | |
| AAT | AAT | AAT | CAA | CAG | CAC | AAT | GAC | AAA | ATA | AAT | ATG | TTA | GAA | AAA | CAA | 1489 |
| Asn | Asn | Asn | Gln | Gln | His | Asn | Asp | Lys | Ile | Asn | Met | Leu | Glu | Lys | Gln | |
| 480 | | | | | 485 | | | | | 490 | | | | | 495 | |
| ATT | AAT | GAT | TTA | CAA | GAA | AAA | TTG | AAA | GGT | GAA | TTA | GAG | CAC | AAT | CAG | 1537 |
| Ile | Asn | Asp | Leu | Gln | Glu | Lys | Leu | Lys | Gly | Glu | Leu | Glu | His | Asn | Gln | |
| | | | | 500 | | | | | 505 | | | | | 510 | | |
| AAA | TTA | AAG | AAG | CAA | GCT | GTT | GAG | CTT | AGA | GTT | GCT | CAG | TCT | GCT | ACT | 1585 |
| Lys | Leu | Lys | Lys | Gln | Ala | Val | Glu | Leu | Arg | Val | Ala | Gln | Ser | Ala | Thr | |
| | | | 515 | | | | | 520 | | | | | 525 | | | |
| GAA | CAA | CTG | AAT | AAT | GAA | TTA | CAG | GAA | ACT | ATG | CAG | GGT | TTA | CAA | ACA | 1633 |
| Glu | Gln | Leu | Asn | Asn | Glu | Leu | Gln | Glu | Thr | Met | Gln | Gly | Leu | Gln | Thr | |
| | | 530 | | | | | 535 | | | | | 540 | | | | |
| CAA | AGA | GAT | GCT | TTA | CAA | CAA | GAA | GTA | GCA | TCT | CTC | CAA | GGC | AAA | CTT | 1681 |
| Gln | Arg | Asp | Ala | Leu | Gln | Gln | Glu | Val | Ala | Ser | Leu | Gln | Gly | Lys | Leu | |
| | 545 | | | | | 550 | | | | | 555 | | | | | |
| TCT | CAA | GAG | AGG | AGC | TCT | AGA | TCA | CAG | GCT | TCT | GAT | ATG | CAG | ATA | GAA | 1729 |
| Ser | Gln | Glu | Arg | Ser | Ser | Arg | Ser | Gln | Ala | Ser | Asp | Met | Gln | Ile | Glu | |
| 560 | | | | | 565 | | | | | 570 | | | | | 575 | |
| CTA | GAA | GCA | AAA | TTG | CAG | GCT | CTC | CAT | ATT | GAA | CTG | GAG | CAT | GTC | AGA | 1777 |
| Leu | Glu | Ala | Lys | Leu | Gln | Ala | Leu | His | Ile | Glu | Leu | Glu | His | Val | Arg | |
| | | | | 580 | | | | | 585 | | | | | 590 | | |
| AAT | TGT | GAA | GAC | AAA | GTT | ACC | CAA | GAC | AAC | AGA | CAA | CTA | TTG | GAA | AGG | 1825 |
| Asn | Cys | Glu | Asp | Lys | Val | Thr | Gln | Asp | Asn | Arg | Gln | Leu | Leu | Glu | Arg | |
| | | | 595 | | | | | 600 | | | | | 605 | | | |
| ATA | TCA | ACA | TTG | GAG | AAA | GAA | TGT | GCT | TCT | CTA | GAA | TTA | GAA | TTG | AAA | 1873 |
| Ile | Ser | Thr | Leu | Glu | Lys | Glu | Cys | Ala | Ser | Leu | Glu | Leu | Glu | Leu | Lys | |
| | | 610 | | | | | 615 | | | | | 620 | | | | |

| | | | | | | | | | | | | | | | |
|---|---|---|---|---|---|---|---|---|---|---|---|---|---|---|---|
| GCA | ACA | CAA | AAC | AAA | TAT | GAG | CAA | GAG | GTC | AAA | GCA | CAT | CGC | GAA | ACT | 1921
| Ala | Thr | Gln | Asn | Lys | Tyr | Glu | Gln | Glu | Val | Lys | Ala | His | Arg | Glu | Thr |
| | | | | 625 | | | 630 | | | | | 635 | | | |
| GAA | AAA | TCA | AGA | CTG | GTC | AGT | AAA | GAA | GAA | GCA | AAT | ATG | GAG | GAA | GTT | 1969
| Glu | Lys | Ser | Arg | Leu | Val | Ser | Lys | Glu | Glu | Ala | Asn | Met | Glu | Glu | Val |
| 640 | | | | | 645 | | | | 650 | | | | | | 655 |
| AAA | GCA | CTC | CAA | ATA | AAA | TTA | AAT | GAA | GAG | AAA | TCT | GCT | CGA | CAG | AAA | 2017
| Lys | Ala | Leu | Gln | Ile | Lys | Leu | Asn | Glu | Glu | Lys | Ser | Ala | Arg | Gln | Lys |
| | | | | 660 | | | | | 665 | | | | | 670 | |
| TCT | GAT | CAG | AAT | TCT | CAA | GAA | AAG | GAA | CGA | CAA | ATT | TCT | ATG | TTA | TCT | 2065
| Ser | Asp | Gln | Asn | Ser | Gln | Glu | Lys | Glu | Arg | Gln | Ile | Ser | Met | Leu | Ser |
| | | | 675 | | | | | 680 | | | | | 685 | | |
| GTG | GAT | TAT | CGT | CAA | ATC | CAA | CAG | CGT | TTG | CAA | AAG | CTA | GAA | GGA | GAA | 2113
| Val | Asp | Tyr | Arg | Gln | Ile | Gln | Gln | Arg | Leu | Gln | Lys | Leu | Glu | Gly | Glu |
| | | 690 | | | | | 695 | | | | | 700 | | | |
| TAT | AGG | CAA | GAG | AGT | GAA | AAA | GTT | AAA | GCT | CTC | CAC | AGT | CAG | ATT | GAG | 2161
| Tyr | Arg | Gln | Glu | Ser | Glu | Lys | Val | Lys | Ala | Leu | His | Ser | Gln | Ile | Glu |
| | 705 | | | | | 710 | | | | | 715 | | | | |
| CAA | GAG | CAA | CTA | AAA | AAA | TCA | CAA | TTA | CAA | AGC | GAA | TTG | GGT | GTT | CAA | 2209
| Gln | Glu | Gln | Leu | Lys | Lys | Ser | Gln | Leu | Gln | Ser | Glu | Leu | Gly | Val | Gln |
| 720 | | | | | 725 | | | | | 730 | | | | | 735 |
| AGG | TCT | CAG | ACT | GCA | CAT | TTA | ACA | GCC | AGG | GAA | GCT | CAG | CTA | GTT | GGA | 2257
| Arg | Ser | Gln | Thr | Ala | His | Leu | Thr | Ala | Arg | Glu | Ala | Gln | Leu | Val | Gly |
| | | | | 740 | | | | | 745 | | | | | 750 | |
| GAA | GTT | GCT | CAT | CTT | AGA | GAT | GCT | AAA | AGA | AAT | GTT | GAA | GAA | GAG | TTA | 2305
| Glu | Val | Ala | His | Leu | Arg | Asp | Ala | Lys | Arg | Asn | Val | Glu | Glu | Glu | Leu |
| | | | | 755 | | | | | 760 | | | | | 765 | |
| CAC | AAG | TTA | AAA | ACT | GCT | CGA | TCA | GTG | GAT | AAT | GCT | CAG | ATG | AAA | GAG | 2353
| His | Lys | Leu | Lys | Thr | Ala | Arg | Ser | Val | Asp | Asn | Ala | Gln | Met | Lys | Glu |
| | | 770 | | | | | 775 | | | | | 780 | | | |
| CTT | CAA | GAA | CAA | GTT | GAA | GCC | GAG | CAA | GTT | TTC | TCG | ACT | CTT | TAT | AAA | 2401
| Leu | Gln | Glu | Gln | Val | Glu | Ala | Glu | Gln | Val | Phe | Ser | Thr | Leu | Tyr | Lys |
| | 785 | | | | | 790 | | | | | 795 | | | | |
| ACA | CAT | TCT | AAT | GAA | CTT | AAG | GAA | GAA | CTT | GAG | GAA | AAA | TCT | CGT | CAT | 2449
| Thr | His | Ser | Asn | Glu | Leu | Lys | Glu | Glu | Leu | Glu | Glu | Lys | Ser | Arg | His |
| 800 | | | | | 805 | | | | | 810 | | | | | 815 |
| ATT | CAA | GAA | ATG | GAA | GAA | GAA | AGA | GAA | AGT | TTG | GTT | CAT | CAG | CTA | CAA | 2497
| Ile | Gln | Glu | Met | Glu | Glu | Glu | Arg | Glu | Ser | Leu | Val | His | Gln | Leu | Gln |
| | | | | 820 | | | | | 825 | | | | | 830 | |
| ATT | GCA | TTA | GCT | AGA | GCT | GAT | TCA | GAG | GCA | TTG | GCG | AGA | TCA | ATA | GCT | 2545
| Ile | Ala | Leu | Ala | Arg | Ala | Asp | Ser | Glu | Ala | Leu | Ala | Arg | Ser | Ile | Ala |
| | | | 835 | | | | | 840 | | | | | 845 | | |
| GAT | GAA | AGT | ATA | GCT | GAT | TTA | GAA | AAG | GAA | AAG | ACT | ATG | AAG | GAA | TTA | 2593
| Asp | Glu | Ser | Ile | Ala | Asp | Leu | Glu | Lys | Glu | Lys | Thr | Met | Lys | Glu | Leu |
| | | 850 | | | | | 855 | | | | | 860 | | | |
| GAA | CTA | AAA | GAA | TTA | TTA | AAC | AAA | AAT | CGT | ACT | GAA | CTT | TCC | CAG | AAA | 2641
| Glu | Leu | Lys | Glu | Leu | Leu | Asn | Lys | Asn | Arg | Thr | Glu | Leu | Ser | Gln | Lys |
| | 865 | | | | | 870 | | | | | 875 | | | | |
| GAC | ATT | TCA | ATA | AGT | GCA | TTG | CGT | GAA | CGA | GAA | AAT | GAA | CAG | AAG | AAA | 2689
| Asp | Ile | Ser | Ile | Ser | Ala | Leu | Arg | Glu | Arg | Glu | Asn | Glu | Gln | Lys | Lys |
| 880 | | | | | 885 | | | | | 890 | | | | | 895 |
| CTT | TTA | GAA | CAA | ATC | TC | | | | | | | | | | | 2706
| Leu | Leu | Glu | Gln | Ile | | | | | | | | | | | |
| | | | | 900 | | | | | | | | | | | |

( 2 ) INFORMATION FOR SEQ ID NO:62:

( i ) SEQUENCE CHARACTERISTICS:
        ( A ) LENGTH: 900 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

| Met | Lys | Ser | Ile | Glu | Ala | Tyr | Thr | Asn | Arg | Tyr | Glu | Ile | Ile | Ala | Ser |
|---|---|---|---|---|---|---|---|---|---|---|---|---|---|---|---|
| 1 | | | | 5 | | | | | 10 | | | | | 15 | |

| Glu | Ile | Val | Asn | Leu | Arg | Met | Lys | Pro | Asp | Asp | Phe | Asn | Leu | Ile | Lys |
|---|---|---|---|---|---|---|---|---|---|---|---|---|---|---|---|
| | | | 20 | | | | | 25 | | | | | 30 | | |

| Val | Ile | Gly | Arg | Gly | Ala | Phe | Gly | Glu | Val | Gln | Leu | Val | Arg | His | Lys |
|---|---|---|---|---|---|---|---|---|---|---|---|---|---|---|---|
| | | | 35 | | | | | 40 | | | | | 45 | | |

| Ser | Thr | Ala | Gln | Val | Phe | Ala | Met | Lys | Arg | Leu | Ser | Lys | Phe | Glu | Met |
|---|---|---|---|---|---|---|---|---|---|---|---|---|---|---|---|
| | | 50 | | | | | 55 | | | | | 60 | | | |

| Ile | Lys | Arg | Pro | Asp | Ser | Ala | Phe | Phe | Trp | Glu | Glu | Arg | His | Ile | Met |
|---|---|---|---|---|---|---|---|---|---|---|---|---|---|---|---|
| 65 | | | | | 70 | | | | | 75 | | | | | 80 |

| Ala | His | Ala | Lys | Ser | Glu | Trp | Ile | Val | Gln | Leu | His | Phe | Ala | Phe | Gln |
|---|---|---|---|---|---|---|---|---|---|---|---|---|---|---|---|
| | | | | 85 | | | | | 90 | | | | | 95 | |

| Asp | Gln | Lys | Tyr | Leu | Tyr | Met | Val | Met | Asp | Tyr | Met | Pro | Gly | Gly | Asp |
|---|---|---|---|---|---|---|---|---|---|---|---|---|---|---|---|
| | | | 100 | | | | | 105 | | | | | 110 | | |

| Leu | Val | Ser | Leu | Met | Ser | Asp | Tyr | Glu | Ile | Pro | Glu | Lys | Trp | Ala | Met |
|---|---|---|---|---|---|---|---|---|---|---|---|---|---|---|---|
| | | 115 | | | | | 120 | | | | | 125 | | | |

| Phe | Tyr | Thr | Met | Glu | Val | Val | Leu | Ala | Leu | Asp | Thr | Ile | His | Ser | Met |
|---|---|---|---|---|---|---|---|---|---|---|---|---|---|---|---|
| | 130 | | | | | 135 | | | | | 140 | | | | |

| Gly | Phe | Val | His | Arg | Asp | Val | Lys | Pro | Asp | Asn | Met | Leu | Leu | Asp | Lys |
|---|---|---|---|---|---|---|---|---|---|---|---|---|---|---|---|
| 145 | | | | | 150 | | | | | 155 | | | | | 160 |

| Tyr | Gly | His | Leu | Lys | Leu | Ala | Asp | Phe | Gly | Thr | Cys | Met | Lys | Met | Asp |
|---|---|---|---|---|---|---|---|---|---|---|---|---|---|---|---|
| | | | | 165 | | | | | 170 | | | | | 175 | |

| Thr | Asp | Gly | Leu | Val | Arg | Ser | Asn | Asn | Ala | Val | Gly | Thr | Pro | Asp | Tyr |
|---|---|---|---|---|---|---|---|---|---|---|---|---|---|---|---|
| | | | 180 | | | | | 185 | | | | | 190 | | |

| Ile | Ser | Pro | Glu | Val | Leu | Gln | Ser | Gln | Gly | Gly | Glu | Gly | Val | Tyr | Gly |
|---|---|---|---|---|---|---|---|---|---|---|---|---|---|---|---|
| | | 195 | | | | | 200 | | | | | 205 | | | |

| Arg | Glu | Cys | Asp | Trp | Trp | Ser | Val | Gly | Ile | Phe | Leu | Tyr | Glu | Met | Leu |
|---|---|---|---|---|---|---|---|---|---|---|---|---|---|---|---|
| | 210 | | | | | 215 | | | | | 220 | | | | |

| Phe | Gly | Glu | Thr | Pro | Phe | Tyr | Ala | Asp | Ser | Leu | Val | Gly | Thr | Tyr | Ser |
|---|---|---|---|---|---|---|---|---|---|---|---|---|---|---|---|
| 225 | | | | | 230 | | | | | 235 | | | | | 240 |

| Lys | Ile | Met | Asp | His | Arg | Asn | Ser | Leu | Thr | Phe | Pro | Pro | Glu | Val | Glu |
|---|---|---|---|---|---|---|---|---|---|---|---|---|---|---|---|
| | | | | 245 | | | | | 250 | | | | | 255 | |

| Ile | Ser | Gln | Tyr | Ala | Arg | Ser | Leu | Ile | Gln | Gly | Phe | Leu | Thr | Asp | Arg |
|---|---|---|---|---|---|---|---|---|---|---|---|---|---|---|---|
| | | | 260 | | | | | 265 | | | | | 270 | | |

| Thr | Gln | Arg | Leu | Gly | Arg | Asn | Glu | Val | Glu | Glu | Ile | Lys | Arg | His | Pro |
|---|---|---|---|---|---|---|---|---|---|---|---|---|---|---|---|
| | | 275 | | | | | 280 | | | | | 285 | | | |

| Phe | Phe | Ile | Asn | Asp | Gln | Trp | Thr | Phe | Asp | Asn | Leu | Arg | Asp | Ser | Ala |
|---|---|---|---|---|---|---|---|---|---|---|---|---|---|---|---|
| | 290 | | | | | 295 | | | | | 300 | | | | |

| Pro | Pro | Val | Val | Pro | Glu | Leu | Ser | Gly | Asp | Asp | Asp | Thr | Arg | Asn | Phe |
|---|---|---|---|---|---|---|---|---|---|---|---|---|---|---|---|
| 305 | | | | | 310 | | | | | 315 | | | | | 320 |

| Asp | Asp | Ile | Glu | Arg | Asp | Glu | Thr | Pro | Glu | Glu | Asn | Phe | Pro | Ile | Pro |
|---|---|---|---|---|---|---|---|---|---|---|---|---|---|---|---|
| | | | | 325 | | | | | 330 | | | | | 335 | |

| Lys | Thr | Phe | Ala | Gly | Asn | His | Leu | Pro | Phe | Val | Gly | Phe | Thr | Tyr | Asn |
|---|---|---|---|---|---|---|---|---|---|---|---|---|---|---|---|
| | | | 340 | | | | | 345 | | | | | 350 | | |

| Gly | Asp | Tyr | Gln | Leu | Leu | Thr | Asn | Gly | Gly | Val | Arg | Asn | Ser | Asp | Met |
|---|---|---|---|---|---|---|---|---|---|---|---|---|---|---|---|
| | | 355 | | | | | 360 | | | | | 365 | | | |

| Val | Asp | Thr | Lys | Leu | Asn | Asn | Ile | Cys | Val | Ser | Ser | Lys | Asp | Asp | Val |
|---|---|---|---|---|---|---|---|---|---|---|---|---|---|---|---|
| | 370 | | | | | 375 | | | | | 380 | | | | |

| Leu | Asn | Leu | Gln | Asn | Leu | Leu | Glu | Gln | Glu | Lys | Gly | Asn | Ser | Glu | Asn |
|---|---|---|---|---|---|---|---|---|---|---|---|---|---|---|---|
| 385 | | | | | 390 | | | | | 395 | | | | | 400 |

```
Leu  Lys  Thr  Asn  Thr  Gln  Leu  Leu  Ser  Asn  Lys  Leu  Asp  Glu  Leu  Gly
               405                 410                 415

Gln  Arg  Glu  Cys  Glu  Leu  Arg  Asn  Gln  Ala  Gly  Asp  Tyr  Glu  Lys  Glu
               420                 425                 430

Leu  Thr  Lys  Phe  Lys  Leu  Ser  Cys  Lys  Glu  Leu  Gln  Arg  Lys  Ala  Glu
               435                 440                 445

Phe  Glu  Asn  Glu  Leu  Arg  Arg  Lys  Thr  Glu  Ser  Leu  Leu  Val  Glu  Thr
     450                 455                 460

Lys  Lys  Arg  Leu  Asp  Glu  Glu  Asn  Lys  Arg  Thr  Arg  Glu  Met  Asn
465                 470                 475                      480

Asn  Asn  Gln  Gln  His  Asn  Asp  Lys  Ile  Asn  Met  Leu  Glu  Lys  Gln  Ile
               485                 490                 495

Asn  Asp  Leu  Gln  Glu  Lys  Leu  Lys  Gly  Glu  Leu  Glu  His  Asn  Gln  Lys
               500                 505                 510

Leu  Lys  Lys  Gln  Ala  Val  Glu  Leu  Arg  Val  Ala  Gln  Ser  Ala  Thr  Glu
               515                 520                 525

Gln  Leu  Asn  Asn  Glu  Leu  Gln  Glu  Thr  Met  Gln  Gly  Leu  Gln  Thr  Gln
     530                 535                 540

Arg  Asp  Ala  Leu  Gln  Gln  Glu  Val  Ala  Ser  Leu  Gln  Gly  Lys  Leu  Ser
545                 550                 555                      560

Gln  Glu  Arg  Ser  Ser  Arg  Ser  Gln  Ala  Ser  Asp  Met  Gln  Ile  Glu  Leu
               565                 570                 575

Glu  Ala  Lys  Leu  Gln  Ala  Leu  His  Ile  Glu  Leu  Glu  His  Val  Arg  Asn
               580                 585                 590

Cys  Glu  Asp  Lys  Val  Thr  Gln  Asp  Asn  Arg  Gln  Leu  Leu  Glu  Arg  Ile
               595                 600                 605

Ser  Thr  Leu  Glu  Lys  Glu  Cys  Ala  Ser  Leu  Glu  Leu  Glu  Leu  Lys  Ala
     610                 615                 620

Thr  Gln  Asn  Lys  Tyr  Glu  Gln  Glu  Val  Lys  Ala  His  Arg  Glu  Thr  Glu
625                 630                 635                      640

Lys  Ser  Arg  Leu  Val  Ser  Lys  Glu  Glu  Ala  Asn  Met  Glu  Glu  Val  Lys
               645                 650                 655

Ala  Leu  Gln  Ile  Lys  Leu  Asn  Glu  Glu  Lys  Ser  Ala  Arg  Gln  Lys  Ser
               660                 665                 670

Asp  Gln  Asn  Ser  Gln  Glu  Lys  Glu  Arg  Gln  Ile  Ser  Met  Leu  Ser  Val
               675                 680                 685

Asp  Tyr  Arg  Gln  Ile  Gln  Gln  Arg  Leu  Gln  Lys  Leu  Glu  Gly  Glu  Tyr
     690                 695                 700

Arg  Gln  Glu  Ser  Glu  Lys  Val  Lys  Ala  Leu  His  Ser  Gln  Ile  Glu  Gln
705                 710                 715                      720

Glu  Gln  Leu  Lys  Lys  Ser  Gln  Leu  Gln  Ser  Glu  Leu  Gly  Val  Gln  Arg
               725                 730                 735

Ser  Gln  Thr  Ala  His  Leu  Thr  Ala  Arg  Glu  Ala  Gln  Leu  Val  Gly  Glu
               740                 745                 750

Val  Ala  His  Leu  Arg  Asp  Ala  Lys  Arg  Asn  Val  Glu  Glu  Glu  Leu  His
               755                 760                 765

Lys  Leu  Lys  Thr  Ala  Arg  Ser  Val  Asp  Asn  Ala  Gln  Met  Lys  Glu  Leu
     770                 775                 780

Gln  Glu  Gln  Val  Glu  Ala  Glu  Gln  Val  Phe  Ser  Thr  Leu  Tyr  Lys  Thr
785                 790                 795                      800

His  Ser  Asn  Glu  Leu  Lys  Glu  Glu  Leu  Glu  Glu  Lys  Ser  Arg  His  Ile
               805                 810                 815

Gln  Glu  Met  Glu  Glu  Glu  Arg  Glu  Ser  Leu  Val  His  Gln  Leu  Gln  Ile
               820                 825                 830
```

| Ala | Leu | Ala | Arg | Ala | Asp | Ser | Glu | Ala | Leu | Ala | Arg | Ser | Ile | Ala | Asp |
|-----|-----|-----|-----|-----|-----|-----|-----|-----|-----|-----|-----|-----|-----|-----|-----|
|     |     | 835 |     |     |     |     | 840 |     |     |     |     | 845 |     |     |     |

| Glu | Ser | Ile | Ala | Asp | Leu | Glu | Lys | Glu | Lys | Thr | Met | Lys | Glu | Leu | Glu |
|-----|-----|-----|-----|-----|-----|-----|-----|-----|-----|-----|-----|-----|-----|-----|-----|
|     | 850 |     |     |     |     | 855 |     |     |     |     | 860 |     |     |     |     |

| Leu | Lys | Glu | Leu | Leu | Asn | Lys | Asn | Arg | Thr | Glu | Leu | Ser | Gln | Lys | Asp |
|-----|-----|-----|-----|-----|-----|-----|-----|-----|-----|-----|-----|-----|-----|-----|-----|
| 865 |     |     |     |     | 870 |     |     |     |     | 875 |     |     |     |     | 880 |

| Ile | Ser | Ile | Ser | Ala | Leu | Arg | Glu | Arg | Glu | Asn | Glu | Gln | Lys | Lys | Leu |
|-----|-----|-----|-----|-----|-----|-----|-----|-----|-----|-----|-----|-----|-----|-----|-----|
|     |     |     |     | 885 |     |     |     |     | 890 |     |     |     |     | 895 |     |

| Leu | Glu | Gln | Ile |
|-----|-----|-----|-----|
|     |     |     | 900 |

( 2 ) INFORMATION FOR SEQ ID NO:63:

( i ) SEQUENCE CHARACTERISTICS:
    ( A ) LENGTH: 414 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 3..414

( x i ) SEQUENCE DESCRIPTION: SEQ ID NO:63:

| GA | GCT | GAT | GAG | AAT | GGA | AAT | GTG | ATT | AGC | ATT | ACT | GAT | GAA | AAT | GGA |  47 |
|----|-----|-----|-----|-----|-----|-----|-----|-----|-----|-----|-----|-----|-----|-----|-----|-----|
|    | Ala | Asp | Glu | Asn | Gly | Asn | Val | Ile | Ser | Ile | Thr | Asp | Glu | Asn | Gly |     |
|    |  1  |     |     |     |  5  |     |     |     |     | 10  |     |     |     |     | 15  |     |

| AAC | ATT | ATT | AGT | ACT | ACT | GAT | GAG | AAT | GGA | AAT | GTG | ATT | AGC | ATT | ACT |  95 |
|-----|-----|-----|-----|-----|-----|-----|-----|-----|-----|-----|-----|-----|-----|-----|-----|-----|
| Asn | Ile | Ile | Ser | Thr | Thr | Asp | Glu | Asn | Gly | Asn | Val | Ile | Ser | Ile | Thr |     |
|     |     |     |     | 20  |     |     |     |     | 25  |     |     |     |     | 30  |     |     |

| GAT | GAG | AAT | GGA | AAC | ATT | ATT | AGT | ACT | ACT | GAT | GAG | AAT | GGA | AAT | GTG | 143 |
|-----|-----|-----|-----|-----|-----|-----|-----|-----|-----|-----|-----|-----|-----|-----|-----|-----|
| Asp | Glu | Asn | Gly | Asn | Ile | Ile | Ser | Thr | Thr | Asp | Glu | Asn | Gly | Asn | Val |     |
|     |     |     | 35  |     |     |     |     | 40  |     |     |     |     | 45  |     |     |     |

| ATT | AGC | ATT | ACT | GAT | GAA | AAT | GGA | AAC | ATT | ATT | AGT | ACT | ACT | GAT | GAG | 191 |
|-----|-----|-----|-----|-----|-----|-----|-----|-----|-----|-----|-----|-----|-----|-----|-----|-----|
| Ile | Ser | Ile | Thr | Asp | Glu | Asn | Gly | Asn | Ile | Ile | Ser | Thr | Thr | Asp | Glu |     |
|     |     | 50  |     |     |     |     | 55  |     |     |     |     | 60  |     |     |     |     |

| AAT | GGA | AAT | GTG | ATT | AGC | ATT | ACT | GAT | GAG | AAT | GGA | AAT | GTG | ATT | AGC | 239 |
|-----|-----|-----|-----|-----|-----|-----|-----|-----|-----|-----|-----|-----|-----|-----|-----|-----|
| Asn | Gly | Asn | Val | Ile | Ser | Ile | Thr | Asp | Glu | Asn | Gly | Asn | Val | Ile | Ser |     |
|     | 65  |     |     |     |     | 70  |     |     |     |     | 75  |     |     |     |     |     |

| ATT | ACT | GAT | GAA | AAT | GGA | AAC | TCG | AAT | AGC | ACT | ACT | AGT | GTT | TTC | AAT | 287 |
|-----|-----|-----|-----|-----|-----|-----|-----|-----|-----|-----|-----|-----|-----|-----|-----|-----|
| Ile | Thr | Asp | Glu | Asn | Gly | Asn | Ser | Asn | Ser | Thr | Thr | Ser | Val | Phe | Asn |     |
| 80  |     |     |     |     | 85  |     |     |     |     | 90  |     |     |     |     | 95  |     |

| GAA | ACT | GAA | AAT | ATG | ACT | GGT | GCT | GCT | GAT | ACA | AAT | GAA | TAT | TCA | ATT | 335 |
|-----|-----|-----|-----|-----|-----|-----|-----|-----|-----|-----|-----|-----|-----|-----|-----|-----|
| Glu | Thr | Glu | Asn | Met | Thr | Gly | Ala | Ala | Asp | Thr | Asn | Glu | Tyr | Ser | Ile |     |
|     |     |     |     | 100 |     |     |     |     | 105 |     |     |     |     | 110 |     |     |

| GGT | TCT | ACT | GAC | GGA | AAT | GGA | AAT | TTT | ATA | AGT | ACT | TTT | AGT | GAT | CAT | 383 |
|-----|-----|-----|-----|-----|-----|-----|-----|-----|-----|-----|-----|-----|-----|-----|-----|-----|
| Gly | Ser | Thr | Asp | Gly | Asn | Gly | Asn | Phe | Ile | Ser | Thr | Phe | Ser | Asp | His |     |
|     |     |     | 115 |     |     |     |     | 120 |     |     |     |     | 125 |     |     |     |

| GAT | TAC | GTA | AGT | AAT | ACT | GAA | GAA | AAT | GAA | A |  |  |  |  |  | 414 |
|-----|-----|-----|-----|-----|-----|-----|-----|-----|-----|---|--|--|--|--|--|-----|
| Asp | Tyr | Val | Ser | Asn | Thr | Glu | Glu | Asn | Glu |   |  |  |  |  |  |     |
|     |     | 130 |     |     |     |     | 135 |     |     |   |  |  |  |  |  |     |

( 2 ) INFORMATION FOR SEQ ID NO:64:

( i ) SEQUENCE CHARACTERISTICS:
    ( A ) LENGTH: 137 amino acids
    ( B ) TYPE: amino acid
    ( D ) TOPOLOGY: linear ( i i ) MOLECULE TYPE: protein ( x i ) SEQUENCE DESCRIPTION: SEQ ID NO:64:

| Ala | Asp | Glu | Asn | Gly | Asn | Val | Ile | Ser | Ile | Thr | Asp | Glu | Asn | Gly | Asn |
|---|---|---|---|---|---|---|---|---|---|---|---|---|---|---|---|
| 1 | | | | 5 | | | | | 10 | | | | | 15 | |

| Ile | Ile | Ser | Thr | Thr | Asp | Glu | Asn | Gly | Asn | Val | Ile | Ser | Ile | Thr | Asp |
|---|---|---|---|---|---|---|---|---|---|---|---|---|---|---|---|
| | | | 20 | | | | | 25 | | | | | 30 | | |

| Glu | Asn | Gly | Asn | Ile | Ile | Ser | Thr | Thr | Asp | Glu | Asn | Gly | Asn | Val | Ile |
|---|---|---|---|---|---|---|---|---|---|---|---|---|---|---|---|
| | | 35 | | | | | 40 | | | | | 45 | | | |

| Ser | Ile | Thr | Asp | Glu | Asn | Gly | Asn | Ile | Ile | Ser | Thr | Thr | Asp | Glu | Asn |
|---|---|---|---|---|---|---|---|---|---|---|---|---|---|---|---|
| | 50 | | | | | 55 | | | | | 60 | | | | |

| Gly | Asn | Val | Ile | Ser | Ile | Thr | Asp | Glu | Asn | Gly | Asn | Val | Ile | Ser | Ile |
|---|---|---|---|---|---|---|---|---|---|---|---|---|---|---|---|
| 65 | | | | | 70 | | | | | 75 | | | | | 80 |

| Thr | Asp | Glu | Asn | Gly | Asn | Ser | Asn | Ser | Thr | Thr | Ser | Val | Phe | Asn | Glu |
|---|---|---|---|---|---|---|---|---|---|---|---|---|---|---|---|
| | | | | 85 | | | | | 90 | | | | | 95 | |

| Thr | Glu | Asn | Met | Thr | Gly | Ala | Ala | Asp | Thr | Asn | Glu | Tyr | Ser | Ile | Gly |
|---|---|---|---|---|---|---|---|---|---|---|---|---|---|---|---|
| | | | 100 | | | | | 105 | | | | | 110 | | |

| Ser | Thr | Asp | Gly | Asn | Gly | Asn | Phe | Ile | Ser | Thr | Phe | Ser | Asp | His | Asp |
|---|---|---|---|---|---|---|---|---|---|---|---|---|---|---|---|
| | | 115 | | | | | 120 | | | | | 125 | | | |

| Tyr | Val | Ser | Asn | Thr | Glu | Glu | Asn | Glu |
|---|---|---|---|---|---|---|---|---|
| | | 130 | | | | 135 | | |

(2) INFORMATION FOR SEQ ID NO:65:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..273

(xi) SEQUENCE DESCRIPTION: SEQ ID NO:65:

```
AT GAG AAT GGA AAT GTG ATT AGC TAT ACT GAT GAA AAT GGA AAC ATT        47
   Glu Asn Gly Asn Val Ile Ser Tyr Thr Asp Glu Asn Gly Asn Ile
   1               5                  10                 15

ATC AGT ACT ACT GAT GAG AAT GGA AAT GTG ATT AGC ATT ACT GAT GAA       95
Ile Ser Thr Thr Asp Glu Asn Gly Asn Val Ile Ser Ile Thr Asp Glu
            20                  25                  30

AAT GGA AAT GTG ATT AGC ATT ACT GAT GAA AAT GGA AAC ATT ATC AGT      143
Asn Gly Asn Val Ile Ser Ile Thr Asp Glu Asn Gly Asn Ile Ile Ser
                35                  40                  45

ACT ACT GAT GAG AAT GGA AAT GTG ATT AGC ATT ACT GAT GAA AAT GGA      191
Thr Thr Asp Glu Asn Gly Asn Val Ile Ser Ile Thr Asp Glu Asn Gly
            50                  55                  60

AAT GTG ATT AGC ATT ACT GAT GAA AAT GGA AAC ATT ATT AGT ACT ACT      239
Asn Val Ile Ser Ile Thr Asp Glu Asn Gly Asn Ile Ile Ser Thr Thr
        65                  70                  75

GAT GAG AAT GGA AAT GTG ATT AGC AAT ACT CGA    G                     273
Asp Glu Asn Gly Asn Val Ile Ser Asn Thr Arg
 80                  85                  90
```

(2) INFORMATION FOR SEQ ID NO:66:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO:66:

```
Glu  Asn  Gly  Asn  Val  Ile  Ser  Tyr  Thr  Asp  Glu  Asn  Gly  Asn  Ile  Ile
 1              5                        10                       15

Ser  Thr  Thr  Asp  Glu  Asn  Gly  Asn  Val  Ile  Ser  Ile  Thr  Asp  Glu  Asn
               20                        25                      30

Gly  Asn  Val  Ile  Ser  Ile  Thr  Asp  Glu  Asn  Gly  Asn  Ile  Ile  Ser  Thr
               35                        40                      45

Thr  Asp  Glu  Asn  Gly  Asn  Val  Ile  Ser  Ile  Thr  Asp  Glu  Asn  Gly  Asn
          50                        55                      60

Val  Ile  Ser  Ile  Thr  Asp  Glu  Asn  Gly  Asn  Ile  Ile  Ser  Thr  Thr  Asp
 65                       70                       75                      80

Glu  Asn  Gly  Asn  Val  Ile  Ser  Asn  Thr  Arg
               85                       90
```

( 2 ) INFORMATION FOR SEQ ID NO:67:

( i ) SEQUENCE CHARACTERISTICS:
        ( A ) LENGTH: 1704 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 24..1409

( x i ) SEQUENCE DESCRIPTION: SEQ ID NO:67:

```
CAGAAACCCG ACATTCTCAA AAT ATG GAA CCT CAA TCG CTG TCT TGG CAA            50
                         Met Glu Pro Gln Ser Leu Ser Trp Gln
                          1                   5

CTT CCG ACT CAA GTA GTT CAG CCA GTT TTT GAA CAA CAA ATG CAG ATT          98
Leu Pro Thr Gln Val Val Gln Pro Val Phe Glu Gln Gln Met Gln Ile
 10              15                  20                  25

CCT GGA TAT AAT ATG CAA ATT CAA TCT AAT TAT TAT CAA ATT CAC CCA         146
Pro Gly Tyr Asn Met Gln Ile Gln Ser Asn Tyr Tyr Gln Ile His Pro
             30                  35                  40

GAA ATG TTG GAT CCA AAT TTG AAC AAT CCT CAG CAG TTA ATG TTT AAT         194
Glu Met Leu Asp Pro Asn Leu Asn Asn Pro Gln Gln Leu Met Phe Asn
             45                  50                  55

TAT ATG CAA TTA CAA CAA TTG CAG GAA CTA CAA CAT TTA AGT CAA CAA         242
Tyr Met Gln Leu Gln Gln Leu Gln Glu Leu Gln His Leu Ser Gln Gln
         60                  65                  70

CAG CCA ATG CAT CAT GAA TTT GAA CAT CAT ATC CCC ATT CCA CAA GAA         290
Gln Pro Met His His Glu Phe Glu His His Ile Pro Ile Pro Gln Glu
     75                  80                  85

GCA ACT TCA ACT AAT TAC GGT CCA TCC GGA CAG TAT ATT ACT AGT GAC         338
Ala Thr Ser Thr Asn Tyr Gly Pro Ser Gly Gln Tyr Ile Thr Ser Asp
 90                  95                 100                 105

GCA ACA TCT TAT CAA TCA ATT GCC CAA CAA TTT GTA CCA CAA CCA CCA         386
Ala Thr Ser Tyr Gln Ser Ile Ala Gln Gln Phe Val Pro Gln Pro Pro
             110                 115                 120

ATT GAA ACT ACC ACC ACG AAA ATA CCT GAA ACT GAA ATT CAA ATT GGC         434
Ile Glu Thr Thr Thr Thr Lys Ile Pro Glu Thr Glu Ile Gln Ile Gly
             125                 130                 135

GTT TCG AAT CAA TAT GCC CAA AAT ATA ACT TAT AAT TCA AAT ATC AGT         482
Val Ser Asn Gln Tyr Ala Gln Asn Ile Thr Tyr Asn Ser Asn Ile Ser
         140                 145                 150

CCT GAA GTG ATT GGA TTC CGA GAA CAT TAT GTT GCG GAA CAG CCT TCT         530
Pro Glu Val Ile Gly Phe Arg Glu His Tyr Val Ala Glu Gln Pro Ser
     155                 160                 165
```

```
GGT GAC GTG CTT CAC AAA AGT CAT TTA ACA GAA CAA CCA GCA GAT AAA          578
Gly Asp Val Leu His Lys Ser His Leu Thr Glu Gln Pro Ala Asp Lys
170             175             180             185

AGC ACA CGT GGT GAT CAG GAA CCT GTT AGT GAG ACA GGC TCT GGT TTT          626
Ser Thr Arg Gly Asp Gln Glu Pro Val Ser Glu Thr Gly Ser Gly Phe
                190             195             200

TCG TAT GCA CAA ATT TTA TCA CAG GGA CTT AAG CCT ACC CAG CCA TCC          674
Ser Tyr Ala Gln Ile Leu Ser Gln Gly Leu Lys Pro Thr Gln Pro Ser
            205             210             215

AAC TCA GTT AAT TTG CTT GCA GAT CGA TCG AGA TCA CCT CTA GAT ACG          722
Asn Ser Val Asn Leu Leu Ala Asp Arg Ser Arg Ser Pro Leu Asp Thr
        220             225             230

AAA ACG AAA GAA AAT TAT AAA TCT CCT GGT CGT GTG CAG GAT ATC ACG          770
Lys Thr Lys Glu Asn Tyr Lys Ser Pro Gly Arg Val Gln Asp Ile Thr
    235             240             245

AAA ATA ATA GAT GAG AAA CAA AAG TCG TCA AAA GAC ACA GAG TGG CAT          818
Lys Ile Ile Asp Glu Lys Gln Lys Ser Ser Lys Asp Thr Glu Trp His
250             255             260             265

AAT AAG AAA GTG AAA GAA CAT AAA AAA GTG AAA GAT ATC AAA CCT GAT          866
Asn Lys Lys Val Lys Glu His Lys Lys Val Lys Asp Ile Lys Pro Asp
            270             275             280

TTC GAA TCT TCT CAA AGG AAT AAG AAA AGC AAG AAT ATT CCT AAG CAA          914
Phe Glu Ser Ser Gln Arg Asn Lys Lys Ser Lys Asn Ile Pro Lys Gln
        285             290             295

ATT GAA AAT ATC ACA CCT CAA CTT GAC AGC TTA CGA TCA CGA GAT ATA          962
Ile Glu Asn Ile Thr Pro Gln Leu Asp Ser Leu Arg Ser Arg Asp Ile
    300             305             310

GTA ATT AAG GGA GAA TTA CTA ACA AAA GAT ACT ACA AAA AGT TTA ACT         1010
Val Ile Lys Gly Glu Leu Leu Thr Lys Asp Thr Thr Lys Ser Leu Thr
315             320             325

ACT GTT AAT GTT GAT AGT GAA TTA GAT AGT GTA AAA CCT AAA GAT GAA         1058
Thr Val Asn Val Asp Ser Glu Leu Asp Ser Val Lys Pro Lys Asp Glu
330             335             340             345

AAA CCT GAA CCT TCT GAA CCT AGT AAA ACG TTT ATT GAT ACT TCA GTT         1106
Lys Pro Glu Pro Ser Glu Pro Ser Lys Thr Phe Ile Asp Thr Ser Val
            350             355             360

GCA AAG GAT GTT GAT AAT TCT ACA CAG GCG AAC CAT AAA AAG AAG AAA         1154
Ala Lys Asp Val Asp Asn Ser Thr Gln Ala Asn His Lys Lys Lys Lys
        365             370             375

AGT AAA TCT AAG CCG AGG AAA ACG GAA CCG GAA GAT GAA ATT GAA AAA         1202
Ser Lys Ser Lys Pro Arg Lys Thr Glu Pro Glu Asp Glu Ile Glu Lys
    380             385             390

GCT TTG AAA GAA ATT CAA GCT AGT GAG AAA AAA CTT ACG AAG TCT ATC         1250
Ala Leu Lys Glu Ile Gln Ala Ser Glu Lys Lys Leu Thr Lys Ser Ile
395             400             405

GAT AAC ATT GTG AAT AAA TTT AAT ACA CCA CTT GCT AGT GTT AAA GCC         1298
Asp Asn Ile Val Asn Lys Phe Asn Thr Pro Leu Ala Ser Val Lys Ala
410             415             420             425

GAT GAT TCC AAT TCT ACC AAG GAT AAT GTA CCA GCA AAG AAG AAA AAA         1346
Asp Asp Ser Asn Ser Thr Lys Asp Asn Val Pro Ala Lys Lys Lys Lys
            430             435             440

CCT TCG AAG TCA TCT GTT TCT TTA CCT GAG AAT GTA GTA CAA AAT CTA         1394
Pro Ser Lys Ser Ser Val Ser Leu Pro Glu Asn Val Val Gln Asn Leu
        445             450             455

TTG ATA CTA ACA       TAACTACTAG TAGCGACAAG ATTGAAAACA TGCCGCAACC       1446
Leu Ile Leu Thr
        460

GCAACCAAAA AGAGAAGATT TACAAGATGC AGCTAAGGAA GTATTGACTT CAATAGAGTC       1506

AGTAATGATG CAGTCTGTTG AGACTATTCC TATTACGAAG AAAAGAGTAA ATAAGAAAAA       1566
```

```
GAATACCACT CAACAGACGA AGGAATTTGT GGAACACGAA ATATGCGATA CATCAAAAAA    1626

TGAAACTTTA AAAAATATTG AAAAAGAATC GCATGAGAAT ATGGCTATAT TGCAAACAAG    1686

TCCGAAACCG CCACTAAG                                                  1704
```

( 2 ) INFORMATION FOR SEQ ID NO:68:

( i ) SEQUENCE CHARACTERISTICS:
        ( A ) LENGTH: 461 amino acids
        ( B ) TYPE: amino acid
        ( D ) TOPOLOGY: linear ( i i ) MOLECULE TYPE: protein ( x i ) SEQUENCE DESCRIPTION: SEQ ID NO:68:

```
Met Glu Pro Gln Ser Leu Ser Trp Gln Leu Pro Thr Gln Val Val Gln
 1               5                  10                  15

Pro Val Phe Glu Gln Met Gln Ile Pro Gly Tyr Asn Met Gln Ile
         20                  25                  30

Gln Ser Asn Tyr Tyr Gln Ile His Pro Glu Met Leu Asp Pro Asn Leu
         35                  40                  45

Asn Asn Pro Gln Gln Leu Met Phe Asn Tyr Met Gln Leu Gln Gln Leu
     50                  55                  60

Gln Glu Leu Gln His Leu Ser Gln Gln Gln Pro Met His His Glu Phe
65                  70                  75                  80

Glu His His Ile Pro Ile Pro Gln Glu Ala Thr Ser Thr Asn Tyr Gly
                 85                  90                  95

Pro Ser Gly Gln Tyr Ile Thr Ser Asp Ala Thr Ser Tyr Gln Ser Ile
             100                 105                 110

Ala Gln Gln Phe Val Pro Gln Pro Pro Ile Glu Thr Thr Thr Thr Lys
             115                 120                 125

Ile Pro Glu Thr Glu Ile Gln Ile Gly Val Ser Asn Gln Tyr Ala Gln
130                 135                 140

Asn Ile Thr Tyr Asn Ser Asn Ile Ser Pro Glu Val Ile Gly Phe Arg
145                 150                 155                 160

Glu His Tyr Val Ala Glu Gln Pro Ser Gly Asp Val Leu His Lys Ser
                 165                 170                 175

His Leu Thr Glu Gln Pro Ala Asp Lys Ser Thr Arg Gly Asp Gln Glu
             180                 185                 190

Pro Val Ser Glu Thr Gly Ser Gly Phe Ser Tyr Ala Gln Ile Leu Ser
             195                 200                 205

Gln Gly Leu Lys Pro Thr Gln Pro Ser Asn Ser Val Asn Leu Leu Ala
210                 215                 220

Asp Arg Ser Arg Ser Pro Leu Asp Thr Lys Thr Lys Glu Asn Tyr Lys
225                 230                 235                 240

Ser Pro Gly Arg Val Gln Asp Ile Thr Lys Ile Ile Asp Glu Lys Gln
                 245                 250                 255

Lys Ser Ser Lys Asp Thr Glu Trp His Asn Lys Lys Val Lys Glu His
             260                 265                 270

Lys Lys Val Lys Asp Ile Lys Pro Asp Phe Glu Ser Ser Gln Arg Asn
             275                 280                 285

Lys Lys Ser Lys Asn Ile Pro Lys Gln Ile Glu Asn Ile Thr Pro Gln
290                 295                 300

Leu Asp Ser Leu Arg Ser Arg Asp Ile Val Ile Lys Gly Glu Leu Leu
305                 310                 315                 320

Thr Lys Asp Thr Thr Lys Ser Leu Thr Thr Val Asn Val Asp Ser Glu
                 325                 330                 335
```

| | | | | | | | | | | | | | | |
|---|---|---|---|---|---|---|---|---|---|---|---|---|---|---|
| Leu | Asp | Ser | Val<br>340 | Lys | Pro | Lys | Asp | Glu<br>345 | Lys | Pro | Glu | Pro | Ser<br>350 | Glu | Pro |
| Ser | Lys | Thr<br>355 | Phe | Ile | Asp | Thr | Ser<br>360 | Val | Ala | Lys | Asp | Val<br>365 | Asp | Asn | Ser |
| Thr | Gln<br>370 | Ala | Asn | His | Lys<br>375 | Lys | Lys | Ser | Lys | Ser<br>380 | Lys | Pro | Arg | Lys |
| Thr<br>385 | Glu | Pro | Glu | Asp | Glu<br>390 | Ile | Glu | Lys | Ala | Leu<br>395 | Lys | Glu | Ile | Gln | Ala<br>400 |
| Ser | Glu | Lys | Lys | Leu<br>405 | Thr | Lys | Ser | Ile | Asp<br>410 | Asn | Ile | Val | Asn | Lys<br>415 | Phe |
| Asn | Thr | Pro | Leu<br>420 | Ala | Ser | Val | Lys<br>425 | Ala | Asp | Ser | Asn | Ser<br>430 | Thr | Lys |
| Asp | Asn | Val<br>435 | Pro | Ala | Lys | Lys | Lys<br>440 | Lys | Pro | Ser | Lys | Ser<br>445 | Ser | Val | Ser |
| Leu | Pro<br>450 | Glu | Asn | Val | Val | Gln<br>455 | Asn | Leu | Leu | Ile | Leu<br>460 | Thr |

(2) INFORMATION FOR SEQ ID NO:69:

(i) SEQUENCE CHARACTERISTICS:
        (A) LENGTH: 1758 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1758

(ix) FEATURE:
        (A) NAME/KEY: W = A or T
        (B) LOCATION: 1..1758
        (D) OTHER INFORMATION: /note= "Change A at 1136 to W;
            change Lys to Xaa, any aa (xi) SEQUENCE DESCRIPTION: SEQ ID NO:69:

| | | | | | | | | | | | | | | | | |
|---|---|---|---|---|---|---|---|---|---|---|---|---|---|---|---|---|
| CTA | GAG | ATG | GCT | AAA | TTT | CTG | ACG | GAA | ACA | TTA | GAC | GAC | ATG | ACT | CTA | 48 |
| Leu | Glu | Met | Ala | Lys | Phe | Leu | Thr | Glu | Thr | Leu | Asp | Asp | Met | Thr | Leu | |
| 1 | | | | 5 | | | | | 10 | | | | | 15 | | |
| CAA | CAC | AAA | GAT | CAC | AGA | TCA | GAA | TTG | GCT | AAA | GAG | TTT | TCA | ATT | TGG | 96 |
| Gln | His | Lys | Asp | His | Arg | Ser | Glu | Leu | Ala | Lys | Glu | Phe | Ser | Ile | Trp | |
| | | | 20 | | | | | 25 | | | | | 30 | | | |
| TTT | ACG | AAA | ATG | AGA | CAG | TCT | GGC | GCT | CAA | GCC | AGT | AAC | GAA | GAA | ATC | 144 |
| Phe | Thr | Lys | Met | Arg | Gln | Ser | Gly | Ala | Gln | Ala | Ser | Asn | Glu | Glu | Ile | |
| | | 35 | | | | | 40 | | | | | 45 | | | | |
| ATG | AAA | TTT | TCA | AAA | TTG | TTT | GAA | GAT | GAA | ATC | ACT | CTT | GAC | TCG | CTG | 192 |
| Met | Lys | Phe | Ser | Lys | Leu | Phe | Glu | Asp | Glu | Ile | Thr | Leu | Asp | Ser | Leu | |
| | 50 | | | | | 55 | | | | | 60 | | | | | |
| GCG | AGG | CCG | CAA | CTT | GTT | GCT | TTG | TGC | AGG | GTA | CTA | GAA | ATC | AGT | ACT | 240 |
| Ala | Arg | Pro | Gln | Leu | Val | Ala | Leu | Cys | Arg | Val | Leu | Glu | Ile | Ser | Thr | |
| 65 | | | | | 70 | | | | | 75 | | | | | 80 | |
| TTA | GGA | ACA | ACA | AAT | TTC | TTA | AGG | TTT | CAA | CTG | CGA | ATG | AAA | CTG | CGT | 288 |
| Leu | Gly | Thr | Thr | Asn | Phe | Leu | Arg | Phe | Gln | Leu | Arg | Met | Lys | Leu | Arg | |
| | | | | 85 | | | | | 90 | | | | | 95 | | |
| TCA | TTA | GCT | GCT | GAT | GAT | AAA | ATG | ATT | CAA | AAA | GAA | GGC | ATA | GTT | TCT | 336 |
| Ser | Leu | Ala | Ala | Asp | Asp | Lys | Met | Ile | Gln | Lys | Glu | Gly | Ile | Val | Ser | |
| | | | 100 | | | | | 105 | | | | | 110 | | | |
| ATG | ACT | TAT | TCG | GAG | GTG | CAA | CAG | GCC | TGC | AGA | GCT | CGT | GGA | ATG | CGA | 384 |
| Met | Thr | Tyr | Ser | Glu | Val | Gln | Gln | Ala | Cys | Arg | Ala | Arg | Gly | Met | Arg | |
| | | 115 | | | | | 120 | | | | | 125 | | | | |

```
GCT  TAT  GGT  ATG  CCT  GAA  CAT  AGG  TTG  AGG  AGG  CAA  TTG  GAA  GAC  TGG         432
Ala  Tyr  Gly  Met  Pro  Glu  His  Arg  Leu  Arg  Arg  Gln  Leu  Glu  Asp  Trp
     130                      135                      140

ATT  AAT  TTA  AGC  TTG  AAT  GAA  AAG  GTT  CCA  CCA  TCA  TTA  TTG  CTT  TTG         480
Ile  Asn  Leu  Ser  Leu  Asn  Glu  Lys  Val  Pro  Pro  Ser  Leu  Leu  Leu  Leu
145                      150                      155                      160

TCA  AGG  GCG  CTG  ATG  TTG  CCC  GAG  AAT  GTT  CCA  GTG  TCT  GAT  AAA  CTT         528
Ser  Arg  Ala  Leu  Met  Leu  Pro  Glu  Asn  Val  Pro  Val  Ser  Asp  Lys  Leu
               165                      170                      175

AAA  GCA  ACA  ATA  AAT  GCT  CTT  CCT  GAA  ACT  ATT  GTA  ACT  CAG  ACA  AAG         576
Lys  Ala  Thr  Ile  Asn  Ala  Leu  Pro  Glu  Thr  Ile  Val  Thr  Gln  Thr  Lys
          180                      185                      190

GCT  GCT  ATT  GGA  GAA  AGA  GAA  GGA  AAG  ATT  GAC  AAT  AAG  ACC  AAA  ATT         624
Ala  Ala  Ile  Gly  Glu  Arg  Glu  Gly  Lys  Ile  Asp  Asn  Lys  Thr  Lys  Ile
          195                      200                      205

GAG  GTC  ATC  AAA  GAG  GAA  GAA  CGC  AAA  ATT  CGC  GAA  GAG  CGC  CAA  GAA         672
Glu  Val  Ile  Lys  Glu  Glu  Glu  Arg  Lys  Ile  Arg  Glu  Glu  Arg  Gln  Glu
     210                      215                      220

GCA  CGT  GAG  GAA  GAG  GAA  CAA  CGC  AAG  CAA  GCC  GAA  CTT  GCT  CTT  AAT         720
Ala  Arg  Glu  Glu  Glu  Glu  Gln  Arg  Lys  Gln  Ala  Glu  Leu  Ala  Leu  Asn
225                      230                      235                      240

GCC  AGT  TCT  GCA  GCA  GCT  GAG  GCC  TCT  TCA  GCT  CAG  GAA  CTT  TTG  ATA         768
Ala  Ser  Ser  Ala  Ala  Ala  Glu  Ala  Ser  Ser  Ala  Gln  Glu  Leu  Leu  Ile
               245                      250                      255

GAT  ACA  GCT  CCT  GTA  ATA  GAT  GCA  GAA  AAG  ACA  CCA  AAG  GTG  GCA  ACA         816
Asp  Thr  Ala  Pro  Val  Ile  Asp  Ala  Glu  Lys  Thr  Pro  Lys  Val  Ala  Thr
          260                      265                      270

TCA  CCT  GTT  GAA  TCA  CCA  TTG  GCA  CCA  CCA  GAA  GTT  CTG  ATT  ATG  GGT         864
Ser  Pro  Val  Glu  Ser  Pro  Leu  Ala  Pro  Pro  Glu  Val  Leu  Ile  Met  Gly
          275                      280                      285

GCT  CCT  AAA  ACA  CCT  GTT  GCA  ACC  GAA  GTG  GAT  AAG  AAT  GCT  GAT  GAG         912
Ala  Pro  Lys  Thr  Pro  Val  Ala  Thr  Glu  Val  Asp  Lys  Asn  Ala  Asp  Glu
     290                      295                      300

GTG  GAA  TTC  ACC  AAG  AAA  GAT  CTT  GAG  GTT  GTT  GAA  GAT  GCA  TTG  GAT         960
Val  Glu  Phe  Thr  Lys  Lys  Asp  Leu  Glu  Val  Val  Glu  Asp  Ala  Leu  Asp
305                      310                      315                      320

ACA  CTA  TCG  AAA  GAC  AAA  AAT  AAT  TTG  GTG  ATT  GAA  AAG  GAA  GTT  ATT        1008
Thr  Leu  Ser  Lys  Asp  Lys  Asn  Asn  Leu  Val  Ile  Glu  Lys  Glu  Val  Ile
               325                      330                      335

AAA  GAC  ATT  AAG  GAA  GAA  ATT  GCT  GAT  TAC  CAA  GAA  GAT  GTA  GAA  GAA        1056
Lys  Asp  Ile  Lys  Glu  Glu  Ile  Ala  Asp  Tyr  Gln  Glu  Asp  Val  Glu  Glu
          340                      345                      350

TTG  AAA  GAA  GCC  ATA  GTT  GCT  GCT  GAG  AAA  CCA  AAG  GAT  GAG  ATA  AAA        1104
Leu  Lys  Glu  Ala  Ile  Val  Ala  Ala  Glu  Lys  Pro  Lys  Asp  Glu  Ile  Lys
          355                      360                      365

GAA  ACT  AAA  GGA  GCT  CAA  CGA  TTG  TTG  AAG  AWG  GTT  AAC  AAG  ATG  ATA        1152
Glu  Thr  Lys  Gly  Ala  Gln  Arg  Leu  Leu  Lys  Xaa  Val  Asn  Lys  Met  Ile
     370                      375                      380

ACG  AAA  ATG  GAT  ACT  GTT  GTA  CAA  GAA  ATT  GAA  AGC  AAA  GAA  TCT  GAG        1200
Thr  Lys  Met  Asp  Thr  Val  Val  Gln  Glu  Ile  Glu  Ser  Lys  Glu  Ser  Glu
385                      390                      395                      400

AAG  AAA  GCC  AAA  ACA  TTG  CCA  CTT  GAA  GCT  CCT  AGG  AGC  GCT  ACT  GAA        1248
Lys  Lys  Ala  Lys  Thr  Leu  Pro  Leu  Glu  Ala  Pro  Arg  Ser  Ala  Thr  Glu
               405                      410                      415

ACT  CAA  GAA  TTA  GAT  GTA  AGG  AAA  GAA  AGA  GGA  GAG  ATT  TTA  ATT  GAC        1296
Thr  Gln  Glu  Leu  Asp  Val  Arg  Lys  Glu  Arg  Gly  Glu  Ile  Leu  Ile  Asp
          420                      425                      430

GAA  TTA  ATG  GAC  GCT  ATT  AAG  AAA  GTT  AAA  AAT  GTG  CCA  GAC  GAA  AAT        1344
Glu  Leu  Met  Asp  Ala  Ile  Lys  Lys  Val  Lys  Asn  Val  Pro  Asp  Glu  Asn
     435                      440                      445
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| CGC | TTG | AAA | TTA | ATT | GAG | AAC | ATT | TTG | GGC | AGG | ATC | GAT | ACT | GAC | AAA | 1392 |
| Arg | Leu | Lys | Leu | Ile | Glu | Asn | Ile | Leu | Gly | Arg | Ile | Asp | Thr | Asp | Lys |      |
|     | 450 |     |     |     |     | 455 |     |     |     |     | 460 |     |     |     |     |      |
| GAT | AGG | CAT | ATC | AAA | GTT | GAA | GAT | GTA | TTG | AAG | GTT | ATT | GAC | ATT | GTG | 1440 |
| Asp | Arg | His | Ile | Lys | Val | Glu | Asp | Val | Leu | Lys | Val | Ile | Asp | Ile | Val |      |
| 465 |     |     |     |     | 470 |     |     |     |     | 475 |     |     |     |     | 480 |      |
| GAA | AAA | GAA | GAT | GGT | ATC | ATG | AGT | ACA | AAA | CAA | TTA | GAT | GAG | TTG | GTT | 1488 |
| Glu | Lys | Glu | Asp | Gly | Ile | Met | Ser | Thr | Lys | Gln | Leu | Asp | Glu | Leu | Val |      |
|     |     |     |     | 485 |     |     |     |     | 490 |     |     |     |     | 495 |     |      |
| CAG | CTT | TTG | AAA | AAG | GAG | GAA | GTT | ATT | GAA | TTG | GAA | GAA | AAG | AAA | GAA | 1536 |
| Gln | Leu | Leu | Lys | Lys | Glu | Glu | Val | Ile | Glu | Leu | Glu | Glu | Lys | Lys | Glu |      |
|     |     |     | 500 |     |     |     |     | 505 |     |     |     |     | 510 |     |     |      |
| AAG | CAA | GAG | TCT | CAA | CAG | AAA | AGT | TTT | GTA | CCA | CCA | AGT | GAA | ACT | TTG | 1584 |
| Lys | Gln | Glu | Ser | Gln | Gln | Lys | Ser | Phe | Val | Pro | Pro | Ser | Glu | Thr | Leu |      |
|     |     | 515 |     |     |     |     | 520 |     |     |     |     | 525 |     |     |     |      |
| CAT | CTT | GAA | TCA | TCA | CAG | CAG | AAG | AGT | ACA | GTT | CCT | AGC | TCG | GGA | CAT | 1632 |
| His | Leu | Glu | Ser | Ser | Gln | Gln | Lys | Ser | Thr | Val | Pro | Ser | Ser | Gly | His |      |
|     | 530 |     |     |     |     | 535 |     |     |     |     | 540 |     |     |     |     |      |
| GAA | GCT | AAG | GTG | TCC | GAA | GAT | GAC | TTA | AAT | GTT | AAA | AAT | AAA | AAT | TTG | 1680 |
| Glu | Ala | Lys | Val | Ser | Glu | Asp | Asp | Leu | Asn | Val | Lys | Asn | Lys | Asn | Leu |      |
| 545 |     |     |     |     | 550 |     |     |     |     | 555 |     |     |     |     | 560 |      |
| GAA | GAA | TCG | ACC | AAA | ACT | GAA | TGT | GGA | GCA | ATT | GAC | GAA | GAG | CAC | AGA | 1728 |
| Glu | Glu | Ser | Thr | Lys | Thr | Glu | Cys | Gly | Ala | Ile | Asp | Glu | Glu | His | Arg |      |
|     |     |     |     | 565 |     |     |     |     | 570 |     |     |     |     | 575 |     |      |
| AGA | GAG | CAT | TGC | CAG | TAC | CCA | GAC | ATT | ACA |     |     |     |     |     |     | 1758 |
| Arg | Glu | His | Cys | Gln | Tyr | Pro | Asp | Ile | Thr |     |     |     |     |     |     |      |
|     |     |     | 580 |     |     |     |     | 585 |     |     |     |     |     |     |     |      |

( 2 ) INFORMATION FOR SEQ ID NO:70:

( i ) SEQUENCE CHARACTERISTICS:
        ( A ) LENGTH: 586 amino acids
        ( B ) TYPE: amino acid
        ( D ) TOPOLOGY: linear ( i i ) MOLECULE TYPE: protein ( i x ) FEATURE:
        ( A ) NAME/KEY: Xaa = any amino acid
        ( B ) LOCATION: 379

( x i ) SEQUENCE DESCRIPTION: SEQ ID NO:70:

|     |     |     |     |     |     |     |     |     |     |     |     |     |     |     |
| --- | --- | --- | --- | --- | --- | --- | --- | --- | --- | --- | --- | --- | --- | --- |
| Leu | Glu | Met | Ala | Lys | Phe | Leu | Thr | Glu | Thr | Leu | Asp | Asp | Met | Thr | Leu |
| 1   |     |     |     | 5   |     |     |     |     | 10  |     |     |     |     | 15  |     |
| Gln | His | Lys | Asp | His | Arg | Ser | Glu | Leu | Ala | Lys | Glu | Phe | Ser | Ile | Trp |
|     |     |     | 20  |     |     |     |     | 25  |     |     |     |     | 30  |     |     |
| Phe | Thr | Lys | Met | Arg | Gln | Ser | Gly | Ala | Gln | Ala | Ser | Asn | Glu | Glu | Ile |
|     |     | 35  |     |     |     |     | 40  |     |     |     |     | 45  |     |     |     |
| Met | Lys | Phe | Ser | Lys | Leu | Phe | Glu | Asp | Glu | Ile | Thr | Leu | Asp | Ser | Leu |
|     | 50  |     |     |     |     | 55  |     |     |     |     | 60  |     |     |     |     |
| Ala | Arg | Pro | Gln | Leu | Val | Ala | Leu | Cys | Arg | Val | Leu | Glu | Ile | Ser | Thr |
| 65  |     |     |     |     | 70  |     |     |     |     | 75  |     |     |     |     | 80  |
| Leu | Gly | Thr | Thr | Asn | Phe | Leu | Arg | Phe | Gln | Leu | Arg | Met | Lys | Leu | Arg |
|     |     |     |     | 85  |     |     |     |     | 90  |     |     |     |     | 95  |     |
| Ser | Leu | Ala | Ala | Asp | Asp | Lys | Met | Ile | Gln | Lys | Glu | Gly | Ile | Val | Ser |
|     |     |     | 100 |     |     |     |     | 105 |     |     |     |     | 110 |     |     |
| Met | Thr | Tyr | Ser | Glu | Val | Gln | Gln | Ala | Cys | Arg | Ala | Arg | Gly | Met | Arg |
|     |     | 115 |     |     |     |     | 120 |     |     |     |     | 125 |     |     |     |
| Ala | Tyr | Gly | Met | Pro | Glu | His | Arg | Leu | Arg | Arg | Gln | Leu | Glu | Asp | Trp |
|     | 130 |     |     |     |     | 135 |     |     |     |     | 140 |     |     |     |     |

```
Ile  Asn  Leu  Ser  Leu  Asn  Glu  Lys  Val  Pro  Pro  Ser  Leu  Leu  Leu  Leu
145                 150                      155                          160

Ser  Arg  Ala  Leu  Met  Leu  Pro  Glu  Asn  Val  Pro  Val  Ser  Asp  Lys  Leu
                    165                 170                      175

Lys  Ala  Thr  Ile  Asn  Ala  Leu  Pro  Thr  Ile  Val  Thr  Gln  Thr  Lys
               180                 185                      190

Ala  Ala  Ile  Gly  Glu  Arg  Glu  Gly  Lys  Ile  Asp  Asn  Lys  Thr  Lys  Ile
               195                 200                      205

Glu  Val  Ile  Lys  Glu  Glu  Glu  Arg  Lys  Ile  Arg  Glu  Glu  Arg  Gln  Glu
          210                 215                      220

Ala  Arg  Glu  Glu  Glu  Glu  Gln  Arg  Lys  Gln  Ala  Glu  Leu  Ala  Leu  Asn
225                      230                 235                          240

Ala  Ser  Ser  Ala  Ala  Ala  Glu  Ala  Ser  Ser  Ala  Gln  Glu  Leu  Leu  Ile
               245                      250                          255

Asp  Thr  Ala  Pro  Val  Ile  Asp  Ala  Glu  Lys  Thr  Pro  Lys  Val  Ala  Thr
               260                 265                      270

Ser  Pro  Val  Glu  Ser  Pro  Leu  Ala  Pro  Glu  Val  Leu  Ile  Met  Gly
          275                 280                      285

Ala  Pro  Lys  Thr  Pro  Val  Ala  Thr  Glu  Val  Asp  Lys  Asn  Ala  Asp  Glu
290                      295                      300

Val  Glu  Phe  Thr  Lys  Lys  Asp  Leu  Glu  Val  Val  Glu  Asp  Ala  Leu  Asp
305                      310                      315                      320

Thr  Leu  Ser  Lys  Asp  Lys  Asn  Asn  Leu  Val  Ile  Glu  Lys  Glu  Val  Ile
                    325                      330                      335

Lys  Asp  Ile  Lys  Glu  Glu  Ile  Ala  Asp  Tyr  Gln  Glu  Asp  Val  Glu  Glu
               340                      345                 350

Leu  Lys  Glu  Ala  Ile  Val  Ala  Ala  Glu  Lys  Pro  Lys  Asp  Glu  Ile  Lys
          355                      360                 365

Glu  Thr  Lys  Gly  Ala  Gln  Arg  Leu  Leu  Lys  Xaa  Val  Asn  Lys  Met  Ile
     370                      375                 380

Thr  Lys  Met  Asp  Thr  Val  Val  Gln  Glu  Ile  Glu  Ser  Lys  Glu  Ser  Glu
385                      390                 395                          400

Lys  Lys  Ala  Lys  Thr  Leu  Pro  Leu  Glu  Ala  Pro  Arg  Ser  Ala  Thr  Glu
                    405                 410                      415

Thr  Gln  Glu  Leu  Asp  Val  Arg  Lys  Glu  Arg  Gly  Glu  Ile  Leu  Ile  Asp
               420                 425                      430

Glu  Leu  Met  Asp  Ala  Ile  Lys  Lys  Val  Lys  Asn  Val  Pro  Asp  Glu  Asn
               435                 440                 445

Arg  Leu  Lys  Leu  Ile  Glu  Asn  Ile  Leu  Gly  Arg  Ile  Asp  Thr  Asp  Lys
     450                 455                      460

Asp  Arg  His  Ile  Lys  Val  Glu  Asp  Val  Leu  Lys  Val  Ile  Asp  Ile  Val
465                      470                      475                      480

Glu  Lys  Glu  Asp  Gly  Ile  Met  Ser  Thr  Lys  Gln  Leu  Asp  Glu  Leu  Val
               485                      490                      495

Gln  Leu  Leu  Lys  Lys  Glu  Glu  Val  Ile  Glu  Leu  Glu  Glu  Lys  Lys  Glu
               500                 505                      510

Lys  Gln  Glu  Ser  Gln  Gln  Lys  Ser  Phe  Val  Pro  Pro  Ser  Glu  Thr  Leu
          515                 520                      525

His  Leu  Glu  Ser  Ser  Gln  Gln  Lys  Ser  Thr  Val  Pro  Ser  Ser  Gly  His
     530                      535                      540

Glu  Ala  Lys  Val  Ser  Glu  Asp  Asp  Leu  Asn  Val  Lys  Asn  Lys  Asn  Leu
545                      550                      555                      560

Glu  Glu  Ser  Thr  Lys  Thr  Glu  Cys  Gly  Ala  Ile  Asp  Glu  Glu  His  Arg
                    565                      570                      575
```

Arg Glu His Cys Gln Tyr Pro Asp Ile Thr
       580                     585

( 2 ) INFORMATION FOR SEQ ID NO:71:

( i ) SEQUENCE CHARACTERISTICS:
       ( A ) LENGTH: 293 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:71:

CCCGGGCTGC AGGAATTCGG CACGAGATGA GAATGGAAAT GTGATTAGCT ATACTGATGA      60

AAATGGAAAC ATTATCAGTA CTACTGATGA GAATGGAAAT GTGATTAGCA TTACTGATGA     120

AAATGGAAAT GTGATTAGCA TTACTGATGA AAATGGAAAC ATTATCAGTA CTACTGATGA     180

GAATGGAAAT GTGATTAGCA TTACTGATGA AAATGGAAAT GTGATTAGCA TTACTGATGA     240

AAATGGAAAC ATTATTAGTA CTACTGATGA GAATGGAAAT GTGATTAGCA ATA            293

( 2 ) INFORMATION FOR SEQ ID NO:72:

( i ) SEQUENCE CHARACTERISTICS:
       ( A ) LENGTH: 26 amino acids
       ( B ) TYPE: amino acid
       ( D ) TOPOLOGY: linear ( i i ) MOLECULE TYPE: protein ( x i ) SEQUENCE DESCRIPTION: SEQ ID NO:72:

Met Arg Gly Asn His Val Phe Leu Glu Asp Gly Met Ala Asp Met Thr
   1               5                   10                  15

Gly Gly Gln Gln Met Gly Arg Asp Leu Tyr
               20                  25

( 2 ) INFORMATION FOR SEQ ID NO:73:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: protein ( i x ) FEATURE:
       ( A ) NAME/KEY: Xaa = Tyr or Asp
       ( B ) LOCATION: 5

( x i ) SEQUENCE DESCRIPTION: SEQ ID NO:73:

Lys Tyr Arg Asn Xaa Xaa Thr Asn Asp Pro Gln Tyr
   1               5                   10

( 2 ) INFORMATION FOR SEQ ID NO:74:

( i ) SEQUENCE CHARACTERISTICS:
       ( A ) LENGTH: 27 amino acids
       ( B ) TYPE: amino acid
       ( D ) TOPOLOGY: linear ( i i ) MOLECULE TYPE: protein ( x i ) SEQUENCE DESCRIPTION: SEQ ID NO:74:

Glu Ile Lys Arg Asn Asp Arg Glu Pro Gly Asn Leu Ser Lys Ile Arg
   1               5                   10                  15

Thr Val Met Asp Lys Val Ile Lys Gln Thr Gln
             20                  25

( 2 ) INFORMATION FOR SEQ ID NO:75:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( i x ) FEATURE:
        ( A ) NAME/KEY: Xaa = Ala or His
        ( B ) LOCATION: 8

( i x ) FEATURE:
        ( A ) NAME/KEY: Xaa = Ala or His
        ( B ) LOCATION: 9

( x i ) SEQUENCE DESCRIPTION: SEQ ID NO:75:

Leu Lys Asp Asn Asp Ile Tyr Xaa Xaa Arg Asp Ile Asn Glu Ile Leu
1                5                   10                  15

Arg Val Leu Asp Pro Ser Lys
             20

( 2 ) INFORMATION FOR SEQ ID NO:76:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

Asn Tyr Gly Arg Val Gln Ile Glu Asp Tyr Thr Xaa Ser Asn His Lys
1                5                   10                  15

Asp Xaa Glu Glu Lys Asp Gln Ile Asn Gly Leu
             20                  25

( 2 ) INFORMATION FOR SEQ ID NO:77:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

Lys Tyr Arg Asn Xaa Tyr Thr Asn Asp Pro Gln Leu Lys Leu Leu Asp
1                5                   10                  15

Glu Gly ( 2 ) INFORMATION FOR SEQ ID NO:78:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:78:

Tyr Phe Asn Asp Gln Ile Lys Ser Val Met Glu Pro Xaa Val Phe Lys
1                5                   10                  15

```
            Tyr  Pro  Xaa  Ala  Xaa  Leu
                            20
```

( 2 ) INFORMATION FOR SEQ ID NO:79:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..270

( x i ) SEQUENCE DESCRIPTION: SEQ ID NO:79:

```
ATG  AAA  TTT  TTA  CTG  GCA  ATT  TGC  GTG  TTG  TGT  GTT  TTA  TTA  AAT  CAA        48
Met  Lys  Phe  Leu  Leu  Ala  Ile  Cys  Val  Leu  Cys  Val  Leu  Leu  Asn  Gln
  1                  5                      10                      15

GTA  TCT  ATG  TCA  AAA  ATG  GTC  ACT  GAA  AAG  TGT  AAG  TCA  GGT  GGA  AAT        96
Val  Ser  Met  Ser  Lys  Met  Val  Thr  Glu  Lys  Cys  Lys  Ser  Gly  Gly  Asn
                20                      25                      30

AAT  CCA  AGT  ACA  GAA  GAG  GTG  TCA  ATA  CCA  TCT  GGG  AAG  CTT  ACT  ATT       144
Asn  Pro  Ser  Thr  Glu  Glu  Val  Ser  Ile  Pro  Ser  Gly  Lys  Leu  Thr  Ile
            35                      40                      45

GAA  GAT  TTT  TGT  ATT  GGA  AAT  CAT  CAA  AGT  TGC  AAA  ATA  TTT  TAC  AAA       192
Glu  Asp  Phe  Cys  Ile  Gly  Asn  His  Gln  Ser  Cys  Lys  Ile  Phe  Tyr  Lys
       50                      55                      60

AGT  CAA  TGT  GGA  TTT  GGA  GGT  GGT  GCT  TGT  GGA  AAC  GGT  GGT  TCA  ACA       240
Ser  Gln  Cys  Gly  Phe  Gly  Gly  Gly  Ala  Cys  Gly  Asn  Gly  Gly  Ser  Thr
 65                      70                      75                      80

CGA  CCA  AAT  CAA  AAA  CAC  TGT  TAT  TGC  GAA                                     270
Arg  Pro  Asn  Gln  Lys  His  Cys  Tyr  Cys  Glu
                85                      90
```

( 2 ) INFORMATION FOR SEQ ID NO:80:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: protein ( x i ) SEQUENCE DESCRIPTION: SEQ ID NO:80:

```
Met  Lys  Phe  Leu  Leu  Ala  Ile  Cys  Val  Leu  Cys  Val  Leu  Leu  Asn  Gln
  1                  5                      10                      15

Val  Ser  Met  Ser  Lys  Met  Val  Thr  Glu  Lys  Cys  Lys  Ser  Gly  Gly  Asn
                20                      25                      30

Asn  Pro  Ser  Thr  Glu  Glu  Val  Ser  Ile  Pro  Ser  Gly  Lys  Leu  Thr  Ile
            35                      40                      45

Glu  Asp  Phe  Cys  Ile  Gly  Asn  His  Gln  Ser  Cys  Lys  Ile  Phe  Tyr  Lys
       50                      55                      60

Ser  Gln  Cys  Gly  Phe  Gly  Gly  Gly  Ala  Cys  Gly  Asn  Gly  Gly  Ser  Thr
 65                      70                      75                      80

Arg  Pro  Asn  Gln  Lys  His  Cys  Tyr  Cys  Glu
                85                      90
```

( 2 ) INFORMATION FOR SEQ ID NO:81:

( i ) SEQUENCE CHARACTERISTICS:
        ( A ) LENGTH: 471 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:81:

| | | | | | |
|---|---|---|---|---|---|
| ATGGTTTACG | AAAGTGACTT | TTACACGACC | CGTCGGCCCT | ACAGTCGTCC | GGCTTTGTCT | 60 |
| TCATACTCCG | TAACGGCACG | TCCAGAGCCG | GTTCCTTGGG | ACAAATTGCC | GTTCGTCCCC | 120 |
| CGTCCAAGTT | TGGTAGCAGA | TCCCATAACA | GCATTTTGCA | AGCGAAAACC | TCGCCGAGAA | 180 |
| GAAGTTGTTC | AAAAAGAGTC | CATTGTTCGA | AGGATCAATT | CTGCAGGAAT | TAAACCCAGC | 240 |
| CAGAGAGTTT | TATCGGCTCC | AATAAGAGAA | TACGAATCCC | CAAGGGACCA | GACCAGGCGT | 300 |
| AAAGTTTTGG | AAAGCGTCAG | AAGACAAGAA | GCTTTTCTGA | ACCAAGGAGG | AATTTGTCCA | 360 |
| TTGACCACCA | GAAATGATGA | CATGGATAGA | CTTCTACCCC | GTCTCCACAG | TTCACACACA | 420 |
| ACACCTTCTG | CGGATAGGAA | AGTTTTGTTG | ACCACTTTTC | ACAGAAGATA | C | 471 |

( 2 ) INFORMATION FOR SEQ ID NO:82:

( i ) SEQUENCE CHARACTERISTICS:
( A ) LENGTH: 1383 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:82:

| | | | | | |
|---|---|---|---|---|---|
| ATGGAACCTC | AATCGCTGTC | TTGGCAACTT | CCGACTCAAG | TAGTTCAGCC | AGTTTTTGAA | 60 |
| CAACAAATGC | AGATTCCTGG | ATATAATATG | CAAATTCAAT | CTAATTATTA | TCAAATTCAC | 120 |
| CCAGAAATGT | TGGATCCAAA | TTTGAACAAT | CCTCAGCAGT | TAATGTTTAA | TTATATGCAA | 180 |
| TTACAACAAT | TGCAGGAACT | ACAACATTTA | AGTCAACAAC | AGCCAATGCA | TCATGAATTT | 240 |
| GAACATCATA | TCCCCATTCC | ACAAGAAGCA | ACTTCAACTA | ATTACGGTCC | ATCCGGACAG | 300 |
| TATATTACTA | GTGACGCAAC | ATCTTATCAA | TCAATTGCCC | AACAATTTGT | ACCACAACCA | 360 |
| CCAATTGAAA | CTACCACCAC | GAAAATACCT | GAAACTGAAA | TTCAAATTGG | CGTTTCGAAT | 420 |
| CAATATGCCC | AAAATATAAC | TTATAATTCA | AATATCAGTC | CTGAAGTGAT | TGGATTCCGA | 480 |
| GAACATTATG | TTGCGGAACA | GCCTTCTGGT | GACGTGCTTC | ACAAAAGTCA | TTTAACAGAA | 540 |
| CAACCAGCAG | ATAAAAGCAC | ACGTGGTGAT | CAGGAACCTG | TTAGTGAGAC | AGGCTCTGGT | 600 |
| TTTTCGTATG | CACAAATTTT | ATCACAGGGA | CTTAAGCCTA | CCCAGCCATC | CAACTCAGTT | 660 |
| AATTTGCTTG | CAGATCGATC | GAGATCACCT | CTAGATACGA | AAACGAAAGA | AAATTATAAA | 720 |
| TCTCCTGGTC | GTGTGCAGGA | TATCACGAAA | ATAATAGATG | AGAAACAAAA | GTCGTCAAAA | 780 |
| GACACAGAGT | GGCATAATAA | GAAAGTGAAA | GAACATAAAA | AAGTGAAAGA | TATCAAACCT | 840 |
| GATTTCGAAT | CTTCTCAAAG | GAATAAGAAA | AGCAAGAATA | TTCCTAAGCA | AATTGAAAAT | 900 |
| ATCACACCTC | AACTTGACAG | CTTACGATCA | CGAGATATAG | TAATTAAGGG | AGAATTACTA | 960 |
| ACAAAAGATA | CTACAAAAAG | TTTAACTACT | GTTAATGTTG | ATAGTGAATT | AGATAGTGTA | 1020 |
| AAACCTAAAG | ATGAAAAACC | TGAACCTTCT | GAACCTAGTA | AAACGTTTAT | TGATACTTCA | 1080 |
| GTTGCAAAGG | ATGTTGATAA | TTCTACACAG | GCGAACCATA | AAAGAAGAA | AAGTAAATCT | 1140 |
| AAGCCGAGGA | AAACGGAACC | GGAAGATGAA | ATTGAAAAAG | CTTTGAAAGA | AATTCAAGCT | 1200 |
| AGTGAGAAAA | AACTTACGAA | GTCTATCGAT | AACATTGTGA | ATAAATTTAA | TACACCACTT | 1260 |
| GCTAGTGTTA | AAGCCGATGA | TTCCAATTCT | ACCAAGGATA | ATGTACCAGC | AAAGAAGAAA | 1320 |

| | | | | | | |
|---|---|---|---|---|---|---|
| AAACCTTCGA | AGTCATCTGT | TTCTTTACCT | GAGAATGTAG | TACAAAATCT | ATTGATACTA | 1380 |
| ACA | | | | | | 1383 |

( 2 ) INFORMATION FOR SEQ ID NO:83:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:83:

| | | | | | | |
|---|---|---|---|---|---|---|
| TTGGAAACAG | CTATGACCAT | GATTACCCCA | AGCTCGAAAG | TTAAVCCCTC | ACTHARAGGG | 60 |
| GAACAAAAGT | CTGGAGCTCC | ACCCGCGGAT | GGCGGCCGCB | TCTAGAACCT | AGTGGACTCC | 120 |
| CCCGGSGCTG | CAGGAATTCG | GGCACGAGCT | CCAGCTAGCC | ATATACATTC | ATCCAAAATG | 180 |
| AAGTTGSAAT | GTGTCCTACC | CGGCAACGGG | ATGCCAGAAA | TTGTKTCGAA | ATKTGTGGAC | 240 |
| GAGCACAAGC | TTCGTGTCTK | TCTATGAAAA | ACGTATGGGA | GCAGAAGTCG | AGGGCCGACA | 300 |
| TCCTCGGCGA | TGAATGGARA | GGTTATGTGC | TCCGA | | | 335 |

( 2 ) INFORMATION FOR SEQ ID NO:84:

( i ) SEQUENCE CHARACTERISTICS:
        ( A ) LENGTH: 396 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:84:

| | | | | | | |
|---|---|---|---|---|---|---|
| ATAGCTTTTA | ATATTTTAA | TTGATGTATT | GCTCAATGGT | GATTTCTGTT | TATTAAACTG | 60 |
| AGTTACCAAT | ATGCTCGCTT | CAATAGACAT | AGCAAATGAA | AGCATTCCGT | ATCCTCAAGC | 120 |
| GTTACCAAAC | TAACATTAAG | GAGTTAAATA | AATGTTGTTT | CCAATAAATA | TAATGGGAAA | 180 |
| AACATTTAAT | ATTTGTTCCA | ATTTGTATTT | ATTTTTACTA | CAATTATATA | CAATAAAATA | 240 |
| TTTTTATATA | TATTTTATAA | AGTTTATGAT | GCAGGAGAGA | AAATAATGTT | AAGAATATAG | 300 |
| GTAATGTGTA | TATATAAATG | TTTGACAAGC | ATGTTCTAGT | TAAATAATAA | ATACAATGTT | 360 |
| AAATCTACTT | AAAAAAAAAA | AAAAAAAAAA | AAAAAA | | | 396 |

( 2 ) INFORMATION FOR SEQ ID NO:85:

( i ) SEQUENCE CHARACTERISTICS:
        ( A ) LENGTH: 285 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:85:

| | | | | | | |
|---|---|---|---|---|---|---|
| GGAAAGCGAA | GAATGAAAAG | GGGAAACAAA | AAAAGAAAAG | ACGAAGGAGT | GGAGAGATAA | 60 |
| AACGGAGGCA | AAGAAGAAAA | TGAGGATGCA | AAAGAAAGGT | AATAAAAGAG | ATGAAAAGAA | 120 |
| GGAAAAAGGA | AATAAGAAAG | AAAGAGTGAG | GGAAAAATAA | AGACAGAGGC | GAAGCAAAAA | 180 |
| AGGAGGAGAA | ATAGAGATTA | AAAAAGAAAT | ACAGCGAAGA | AACCAGGAAA | GCGATAAAGA | 240 |
| AAAAAAAAGA | AAAAAAGAGA | GCAGTGAAAA | AAAAAAAAAA | AAAAA | | 285 |

( 2 ) INFORMATION FOR SEQ ID NO:86:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

```
CAGATATTTA CTAAAYATTG TGAAAYAAAT CATTTTCAAA ATGGTSTCCA AAGTGTTTGT        60

TGCTCTTGCC ATCAATGGCT TTATAGGGGG CTSCACAAGY CTTTTTTCGA ACAAGATGMC       120

GTCTTAGATA ASATSGTAGA TRACATCTCT GRCTSMATAT GAGAACARCA TTGSMAGAAT       180

TAGCCAAGGR TNGCRAAATT GATATGMTTS CYGCTGTAAT TCGAAAAA                    228
```

( 2 ) INFORMATION FOR SEQ ID NO:87:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..339

( x i ) SEQUENCE DESCRIPTION: SEQ ID NO:87:

```
CTT  CGT  GTC  AAC  CGC  TGG  GTC  AGA  CCT  GTT  ATT  GCT  ATG  CAC  CCA  ACC        48
Leu  Arg  Val  Asn  Arg  Trp  Val  Arg  Pro  Val  Ile  Ala  Met  His  Pro  Thr
 1              5                        10                       15

ATG  ACT  CTT  GCT  GAA  CGT  CTC  GGC  AAA  AAA  GCT  TTG  CGC  GAC  CAA  TAT        96
Met  Thr  Leu  Ala  Glu  Arg  Leu  Gly  Lys  Lys  Ala  Leu  Arg  Asp  Gln  Tyr
           20                       25                       30

GCT  CCC  GTT  TGC  TCC  ATT  GGA  CAA  CGT  AAC  ATC  AAC  ACC  TTT  GAC  AAC       144
Ala  Pro  Val  Cys  Ser  Ile  Gly  Gln  Arg  Asn  Ile  Asn  Thr  Phe  Asp  Asn
                35                       40                       45

ATG  ACC  TTC  CCC  GCT  CAA  TTC  GGA  AAA  TGC  TGG  CAC  GCT  TTG  TTG  CAA       192
Met  Thr  Phe  Pro  Ala  Gln  Phe  Gly  Lys  Cys  Trp  His  Ala  Leu  Leu  Gln
      50                       55                       60

ACT  GTT  CCC  CAA  AAG  TAT  TCC  GAA  GAA  CGT  GAA  TAC  AGC  GAA  GAA  CAA       240
Thr  Val  Pro  Gln  Lys  Tyr  Ser  Glu  Glu  Arg  Glu  Tyr  Ser  Glu  Glu  Gln
 65                       70                       75                       80

CAA  TAC  GAC  CGT  CAA  ATG  TCC  GTC  CTC  GTT  CGT  GAA  AAC  GGC  GAA  GAA       288
Gln  Tyr  Asp  Arg  Gln  Met  Ser  Val  Leu  Val  Arg  Glu  Asn  Gly  Glu  Glu
                85                       90                       95

AAA  AGA  CGT  TAT  GAT  TGT  CTT  GGG  CAA  CCG  TTA  CAA  CAA  TTG  AAT  TGC       336
Lys  Arg  Arg  Tyr  Asp  Cys  Leu  Gly  Gln  Pro  Leu  Gln  Gln  Leu  Asn  Cys
               100                      105                      110

AAT                                                                                  339
Asn
```

( 2 ) INFORMATION FOR SEQ ID NO:88:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:88:

| Leu | Arg | Val | Asn | Arg | Trp | Val | Arg | Pro | Val | Ile | Ala | Met | His | Pro | Thr |
|---|---|---|---|---|---|---|---|---|---|---|---|---|---|---|---|
| 1 | | | | 5 | | | | | 10 | | | | | 15 | |

| Met | Thr | Leu | Ala | Glu | Arg | Leu | Gly | Lys | Lys | Ala | Leu | Arg | Asp | Gln | Tyr |
|---|---|---|---|---|---|---|---|---|---|---|---|---|---|---|---|
| | | | 20 | | | | | 25 | | | | | 30 | | |

| Ala | Pro | Val | Cys | Ser | Ile | Gly | Gln | Arg | Asn | Ile | Asn | Thr | Phe | Asp | Asn |
|---|---|---|---|---|---|---|---|---|---|---|---|---|---|---|---|
| | | 35 | | | | | 40 | | | | | 45 | | | |

| Met | Thr | Phe | Pro | Ala | Gln | Phe | Gly | Lys | Cys | Trp | His | Ala | Leu | Leu | Gln |
|---|---|---|---|---|---|---|---|---|---|---|---|---|---|---|---|
| | 50 | | | | | 55 | | | | | 60 | | | | |

| Thr | Val | Pro | Gln | Lys | Tyr | Ser | Glu | Glu | Arg | Glu | Tyr | Ser | Glu | Glu | Gln |
|---|---|---|---|---|---|---|---|---|---|---|---|---|---|---|---|
| 65 | | | | | 70 | | | | 75 | | | | | 80 | |

| Gln | Tyr | Asp | Arg | Gln | Met | Ser | Val | Leu | Val | Arg | Glu | Asn | Gly | Glu | Glu |
|---|---|---|---|---|---|---|---|---|---|---|---|---|---|---|---|
| | | | | 85 | | | | | 90 | | | | | 95 | |

| Lys | Arg | Arg | Tyr | Asp | Cys | Leu | Gly | Gln | Pro | Leu | Gln | Gln | Leu | Asn | Cys |
|---|---|---|---|---|---|---|---|---|---|---|---|---|---|---|---|
| | | | 100 | | | | | 105 | | | | | 110 | | |

Asn (2) INFORMATION FOR SEQ ID NO:89:

(i) SEQUENCE CHARACTERISTICS:
        (A) LENGTH: 493 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..390

(xi) SEQUENCE DESCRIPTION: SEQ ID NO:89:

| TCC | AGC | TCC | TCC | AGC | TCC | AGC | AGT | GAC | TCT | TCC | AGC | TCC | AGC | AGC | TCT | 48 |
|---|---|---|---|---|---|---|---|---|---|---|---|---|---|---|---|---|
| Ser | Ser | Ser | Ser | Ser | Ser | Ser | Ser | Asp | Ser | Ser | Ser | Ser | Ser | Ser | Ser | |
| 1 | | | | 5 | | | | | 10 | | | | | 15 | | |

| TCC | TCT | TCC | AGC | TCC | AGC | AGC | TCC | TCT | TCT | GAA | TCT | TCC | GAA | GAA | AAA | 96 |
|---|---|---|---|---|---|---|---|---|---|---|---|---|---|---|---|---|
| Ser | Ser | Ser | Ser | Ser | Ser | Ser | Ser | Ser | Ser | Glu | Ser | Ser | Glu | Glu | Lys | |
| | | | 20 | | | | | 25 | | | | | 30 | | | |

| ACC | TCC | CAC | AAA | AAA | TCC | GAA | AAG | AAG | GAA | CAC | AAA | TCC | TGC | TCC | ATC | 144 |
|---|---|---|---|---|---|---|---|---|---|---|---|---|---|---|---|---|
| Thr | Ser | His | Lys | Lys | Ser | Glu | Lys | Lys | Glu | His | Lys | Ser | Cys | Ser | Ile | |
| | | 35 | | | | | 40 | | | | | 45 | | | | |

| AAG | AAG | CAA | GTA | CAA | TTC | GTA | GAA | AAA | GAC | GGT | AAA | CTC | TGC | TTC | AGC | 192 |
|---|---|---|---|---|---|---|---|---|---|---|---|---|---|---|---|---|
| Lys | Lys | Gln | Val | Gln | Phe | Val | Glu | Lys | Asp | Gly | Lys | Leu | Cys | Phe | Ser | |
| | 50 | | | | | 55 | | | | | 60 | | | | | |

| ATC | CGT | CCC | TTG | GCC | GCT | TGC | CAA | AAA | CAC | TGC | AAA | GCC | ACT | GAA | ACC | 240 |
|---|---|---|---|---|---|---|---|---|---|---|---|---|---|---|---|---|
| Ile | Arg | Pro | Leu | Ala | Ala | Cys | Gln | Lys | His | Cys | Lys | Ala | Thr | Glu | Thr | |
| 65 | | | | 70 | | | | | 75 | | | | | 80 | | |

| ACT | CAA | ATG | GAA | GTC | GAA | GTA | TAC | TGC | CCC | TCT | GGC | AGC | CTT | GCT | GAA | 288 |
|---|---|---|---|---|---|---|---|---|---|---|---|---|---|---|---|---|
| Thr | Gln | Met | Glu | Val | Glu | Val | Tyr | Cys | Pro | Ser | Gly | Ser | Leu | Ala | Glu | |
| | | | 85 | | | | | 90 | | | | | 95 | | | |

| CTT | TAC | AAA | CAA | AAG | ATC | CTT | AAG | GGA | GCC | AAC | CCC | GAC | TTG | AGC | GAC | 336 |
|---|---|---|---|---|---|---|---|---|---|---|---|---|---|---|---|---|
| Leu | Tyr | Lys | Gln | Lys | Ile | Leu | Lys | Gly | Ala | Asn | Pro | Asp | Leu | Ser | Asp | |
| | | 100 | | | | | 105 | | | | | 110 | | | | |

| AAG | ACT | CCT | TCC | AGA | ATC | TTG | AAA | TTC | AAG | GTT | CCC | AAA | GCT | TGC | ACC | 384 |
|---|---|---|---|---|---|---|---|---|---|---|---|---|---|---|---|---|
| Lys | Thr | Pro | Ser | Arg | Ile | Leu | Lys | Phe | Lys | Val | Pro | Lys | Ala | Cys | Thr | |
| | | 115 | | | | | 120 | | | | | 125 | | | | |

| GCT | TAC | TAAATCTGAA | ATAAATTACA | TGGATTAGTT | CATTTCTGAT | GTAGTGCAAT | 440 |
|---|---|---|---|---|---|---|---|
| Ala | Tyr | | | | | | |
| | 130 | | | | | | |

| TAGTTCGATA | ATAAATTATT | CAATGAGCAT | TTAAAAAAAA | AAAAAAAAA | AAC | 493 |
|---|---|---|---|---|---|---|

(2) INFORMATION FOR SEQ ID NO:90:

( i ) SEQUENCE CHARACTERISTICS:
- ( A ) LENGTH: 130 amino acids
- ( B ) TYPE: amino acid
- ( D ) TOPOLOGY: linear ( i i ) MOLECULE TYPE: protein ( x i ) SEQUENCE DESCRIPTION: SEQ ID NO:90:

| Ser | Ser | Ser | Ser | Ser | Ser | Ser | Ser | Asp | Ser | Ser | Ser | Ser | Ser | Ser |
|-----|-----|-----|-----|-----|-----|-----|-----|-----|-----|-----|-----|-----|-----|-----|
| 1   |     |     |     | 5   |     |     |     | 10  |     |     |     |     |     | 15  |
| Ser | Ser | Ser | Ser | Ser | Ser | Ser | Ser | Ser | Ser | Glu | Ser | Ser | Glu | Glu | Lys |
|     |     |     | 20  |     |     |     |     | 25  |     |     |     |     | 30  |     |
| Thr | Ser | His | Lys | Lys | Ser | Glu | Lys | Lys | Glu | His | Lys | Ser | Cys | Ser | Ile |
|     |     |     | 35  |     |     |     | 40  |     |     |     |     | 45  |     |     |
| Lys | Lys | Gln | Val | Gln | Phe | Val | Glu | Lys | Asp | Gly | Lys | Leu | Cys | Phe | Ser |
|     |     | 50  |     |     |     | 55  |     |     |     |     | 60  |     |     |     |
| Ile | Arg | Pro | Leu | Ala | Ala | Cys | Gln | Lys | His | Cys | Lys | Ala | Thr | Glu | Thr |
| 65  |     |     |     |     | 70  |     |     |     |     | 75  |     |     |     |     | 80  |
| Thr | Gln | Met | Glu | Val | Glu | Val | Tyr | Cys | Pro | Ser | Gly | Ser | Leu | Ala | Glu |
|     |     |     |     | 85  |     |     |     |     | 90  |     |     |     |     | 95  |     |
| Leu | Tyr | Lys | Gln | Lys | Ile | Leu | Lys | Gly | Ala | Asn | Pro | Asp | Leu | Ser | Asp |
|     |     |     | 100 |     |     |     |     | 105 |     |     |     |     | 110 |     |     |
| Lys | Thr | Pro | Ser | Arg | Ile | Leu | Lys | Phe | Lys | Val | Pro | Lys | Ala | Cys | Thr |
|     |     |     | 115 |     |     |     | 120 |     |     |     |     | 125 |     |     |     |
| Ala | Tyr |
|     |     |
|     | 130 |

( 2 ) INFORMATION FOR SEQ ID NO:91:

( i ) SEQUENCE CHARACTERISTICS:
- ( A ) LENGTH: 306 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:91:

```
GTAGTGCCAT  CATTCGTAAA  CSTTYTGACG  GTKGGGCGCT  GTATWGGTGC  TGCCTGGAAA        60
TTGCATCGAT  GCACTWCCGT  GTCGGGCGCA  WATAGTGCKK  TGGSCCCTGT  CTGMTTATAG       120
ACATTCAGGG  CGCSGGSAKT  AGCCATGTTC  ATGGCTCMCA  AWMTGCATTC  ACAGTGGGGT       180
CACATTTCAG  TCGCATGATT  KMTCAARTTA  GTATMWGADA  TATATTTTTA  TCATACTAAG       240
TAGTGAGCDA  ATAACACGCG  ARWWACRAAC  ACCGAATATC  TTKAGTTTTT  GCACAGATAT       300
KTGTAA                                                                       306
```

( 2 ) INFORMATION FOR SEQ ID NO:92:

( i ) SEQUENCE CHARACTERISTICS:
- ( A ) LENGTH: 490 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:92:

```
ACCGGATACG  TTGCCAATGA  CTACGTCACC  ACCAATGTTG  TTTCCACTCC  AGTTACTGGA        60
TACACCACCG  GACATCTTGC  TAATGACTAC  GTCACCACCA  ATGTTGTATC  CACTCCAGTT       120
ACTGGATACA  CCACCGGACA  TCTTGCCAAT  GACTACGTCA  CCACCAACGT  AGTTTCCGCA       180
```

| CCAGTCACCA | CTGGATACAC | CACTGGCTAT | ACCACCGGTA | ATGTCGGATA | CACCACCGGA | 240 |
| GTTACTGGTT | ACACCAACGG | AGTTAGTGGA | TATACCAATG | GACTTAATGG | TTATACCACT | 300 |
| GGTAGCTATG | TCAGCTCCCC | AGGATACACT | TCTTCTGGAC | TTGTCAACGT | TTTCTAGATT | 360 |
| TATGATTTCG | TCTGCCCTCA | ATGATGATGA | CCACACTTTT | TACTTTTTAT | GATATTTGGA | 420 |
| AAAAATAAAT | AACTGGAAGA | ATATATAATA | ATTTCAAAAT | AAAAAAAAAA | AAAAAAAAA | 480 |
| CTCGAGGGGG | | | | | | 490 |

(2) INFORMATION FOR SEQ ID NO:93:

(i) SEQUENCE CHARACTERISTICS:
                (A) LENGTH: 616 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:93:

| AAAAAATCGA | AAGAAGGCGT | AAAACCAAAA | TGGGCACAGA | AGGATATTCG | GGATTTTAGT | 60 |
| GATGCCGACA | TGGAGAGGTT | ACTGGATCAA | TGGGAAGAAG | ATGAAGACCC | CCTTCCAGAA | 120 |
| GACGAATTGC | CCGAACATCT | CAGACCTGAT | CCAAGATCG | ACATAAGCAA | CATCGATATG | 180 |
| AGCAATCCCB | AAAACATACT | AAAGGCTTCC | AAAAAAGGCA | AGACTTTGAT | GGCATTCGTA | 240 |
| CAAGTCAGTG | GAAATCCAAC | ACAAGAAGAA | GCCGAAACCA | TCACTAAATT | GTGGCAAGGC | 300 |
| AGTCTATGGA | ATAGTCATAT | ACAAGCCGAA | AGATATATGG | TTAGCGATGA | CAGGGCTATA | 360 |
| TTTATGTTTA | AAGATGGTTC | TCAAGCTTGG | CCTGCTAAAG | ACTTTTTAGT | GGAACAAGAA | 420 |
| AGGTGTAAAG | ATGTTACAAT | TGAAAATAAA | ATATATCCTG | GTAAATATTC | TTCGACTAAA | 480 |
| GAAGAATTAT | AATATAATAT | ATTATAATTA | TAATCTATAA | AATAGATTTG | AAATTCTACA | 540 |
| TTCATGATCT | ACTATGTATG | ATATTAATTT | ATTAAAAATA | ATGTTTTTC | AAGTAAAAAA | 600 |
| AAAAAAAAAA | AAAAAA | | | | | 616 |

(2) INFORMATION FOR SEQ ID NO:94:

(i) SEQUENCE CHARACTERISTICS:
                (A) LENGTH: 475 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:94:

| CTCGTGCGGG | ACAGATATAG | GACCGGATTC | GTTAATTGAT | TTGAGTGAAG | TGGCTTCTGG | 60 |
| TGGTTCTGAT | ATTGACACAA | AATTTTCCAA | TTTAAAAATA | GATAAAAGC | CTGTTGCAAC | 120 |
| TTCACAACAA | GGAATTGATG | AATTTGATAT | GTTTGCACAA | TCGAGAAACA | TTTCTAGTGA | 180 |
| GGGATCAACC | AGTGCTATGA | AGGAAGGACA | CGGTTTGGAC | TTATTATCAA | ATACACATAA | 240 |
| AAATGTACCA | CCAACAATTC | CACAAGCCGG | ACAACTTCCA | AGGGATTCTG | AGTTTGATGA | 300 |
| AATTGCTGCT | TGGCTTGATG | AAAAGGTTGA | AGACAAAGCC | CAAGTTCCCG | AAGACAGTAT | 360 |
| TACAAGCAGT | GAATTTGATA | AATTCCTGGC | AGAACGGGCA | GCTGTTGCTG | AAACTTTGCC | 420 |
| AAATATTCCA | CCGACTACAC | AAAGTAATCA | TTCAAATATT | GAAGCAAACG | ATAAA | 475 |

(2) INFORMATION FOR SEQ ID NO:95:

( i ) SEQUENCE CHARACTERISTICS:
   ( A ) LENGTH: 295 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:95:

| | | | | | | |
|---|---|---|---|---|---|---|
| CCGGCACGGG | AGGTAGTGAC | GAAAAATAAC | GATACGGGAC | TCATCCGAGG | CCCCGTAATC | 60 |
| GGAATGAGTA | CACTTTAAAT | CCTTTAACGA | GGATCTATTA | GAGGGCCAGT | CTGTGTGCCA | 120 |
| GCAGCCGCGG | TAATTCCAGC | TCTAATAGCG | TATATTAAAG | TTGTTGCGGT | TAAAAAGCTC | 180 |
| GTAGTTGAAT | CTGTGTCCCA | CACTGTYGGT | TCACCGCTCG | CGGTGTTCAA | CTGGCATGTC | 240 |
| TGTGGGACGT | CCTACCGGTG | GGCTTAGCCC | GTCAAAGGC | GGCCCAACTC | AAAAT | 295 |

( 2 ) INFORMATION FOR SEQ ID NO:96:

( i ) SEQUENCE CHARACTERISTICS:
      ( A ) LENGTH: 372 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:96:

| | | | | | | |
|---|---|---|---|---|---|---|
| CTGACTAATC | CCAGGACTCC | TTTATCCTGT | TTGCGCAATG | TCGATACCCA | TCTCACAATG | 60 |
| GTTAATGATT | TATCGGCTAA | ACAGAAGAGT | CCTAAGAAGG | TTGTTAAAGG | TGTTTCTAGA | 120 |
| ATACCGACTT | TTAGACCCAA | GGCTATGAAT | GCTGATGTTG | AGAATTTTGA | TTCGATGAGG | 180 |
| TGCGATGTTT | GGRACAAAGA | CACCAGTGTT | GTTATATAAT | TACTAAAGCA | ATCCACATGT | 240 |
| AGCTAATTTT | TTTTTTACAA | TTTTATTTGT | AACTATGTGT | ATTTATATGA | ATTCTTGTGG | 300 |
| AATATAATTT | TAAGTTTTTA | AATGAAATAT | AGATATTATT | CTAAAAAAAA | AAAACAAAAA | 360 |
| AAAAAAAAAA | AA | | | | | 372 |

( 2 ) INFORMATION FOR SEQ ID NO:97:

( i ) SEQUENCE CHARACTERISTICS:
      ( A ) LENGTH: 252 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:97:

| | | | | | | |
|---|---|---|---|---|---|---|
| GGATTCGGCA | CGAGAATTTA | TTAAGCGCAT | TATTTGCAAG | TGTAATTTGC | TCCTTTAACG | 60 |
| CGGAAGTACA | AAATCGAATC | GTTGGTGGCA | ATGATGTAAG | TATTTCAAAA | ATTGGGTGGC | 120 |
| AAGTATCTAT | TCAAAGTAAT | AACCAACATT | TCTGTGGTGG | TTCAATCATT | GCTAAAGATT | 180 |
| GGGTACTGAC | TTCTTCTCAA | TGCGTCGTGG | ACAAACAAAG | TCCACCGAAG | GATTTAACTG | 240 |
| TTCGTGTTGG | AA | | | | | 252 |

( 2 ) INFORMATION FOR SEQ ID NO:98:

( i ) SEQUENCE CHARACTERISTICS:
      ( A ) LENGTH: 613 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:98:

| | | | | | |
|---|---|---|---|---|---|
| ATTCCTGCTG | TTAATAGTAC | TAATGCAGTA | ATTGCTGCHA | GCTGCTGCAC | AGAGGTTTTT | 60 |
| AAAATGGCAA | CAAGTTGTTA | CACCCACATG | AACAACTACA | TGGTATTCAA | TGATACCGAT | 120 |
| GGGATTTATA | CATATACTTA | CGAAGCTGAA | AGAAACCTG | ACTGTTTAGC | TTGTTCACAA | 180 |
| ATTCCAAAAA | CTATAGAAGT | TTCTAATCCT | GAAAATATGA | CTCTCCAAGA | CTTGATTACT | 240 |
| TTGTTGTGTG | AAGGGGCTGA | ATATCAAATG | AAGAGCCCAG | GTATTGTAGC | CTCAATCGAA | 300 |
| GGCAAAAACA | AAACCTTATA | CATGTCAACA | GTAGCAAGTA | TAGAAGAAAA | GACTAAACAG | 360 |
| AATCTAACAA | AGTCTCTAAA | AGAATTAAAT | CTAGAAAATG | GAATGGAACT | GATGGTTGCA | 420 |
| GATGTGACGA | CACCAAACAC | AATATTACTT | AAATTAAAAT | ATAAGAATGT | AATTGAAAAC | 480 |
| GATGTTGAGA | TGACTTGATA | TTTACTTAAA | AATGTTATCT | TACAATAATT | GATAATTTAT | 540 |
| ATTTAATACT | TTTGGAACTT | TGTATTTAAT | GATAATAAAT | TATTATAAGA | ATTAAAAAAA | 600 |
| AAAAAAAAAA | AAA | | | | | 613 |

( 2 ) INFORMATION FOR SEQ ID NO:99:

( i ) SEQUENCE CHARACTERISTICS:
        ( A ) LENGTH: 538 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..538

( x i ) SEQUENCE DESCRIPTION: SEQ ID NO:99:

```
TT GAT ATT TGC TCT GTT GAG GGT GCC TTA GGA TTT TTA GTG GAA ATG        47
   Asp Ile Cys Ser Val Glu Gly Ala Leu Gly Phe Leu Val Glu Met
    1               5                  10                  15

TTA AAA TAT AAG GCC CCA AGT AAA ACT CTA GCT ATT GTA GAG AAT GCT       95
Leu Lys Tyr Lys Ala Pro Ser Lys Thr Leu Ala Ile Val Glu Asn Ala
                    20                  25                  30

GGT GGA ATA TTA CGA AAT GTA TCT AGT CAT ATA GCC CTT AGA GAG GAC      143
Gly Gly Ile Leu Arg Asn Val Ser Ser His Ile Ala Leu Arg Glu Asp
                35                  40                  45

TAC AGA GAA ATA CTT CGA CAT CAT AAT TGC TTA ACA ATA TTA CTA CAA      191
Tyr Arg Glu Ile Leu Arg His His Asn Cys Leu Thr Ile Leu Leu Gln
            50                  55                  60

CAA TTA AAA TCA CCA AGC CTC ATA ATT GTC AGT AAT GCT TGT GGG ACA      239
Gln Leu Lys Ser Pro Ser Leu Ile Ile Val Ser Asn Ala Cys Gly Thr
        65                  70                  75

TTA TGG AAT TTA TCT GCT AGG AAT TCA ACA GAT CAA CAA TTT TTA TGG      287
Leu Trp Asn Leu Ser Ala Arg Asn Ser Thr Asp Gln Gln Phe Leu Trp
    80                  85                  90                  95

GAG AAT GGT GCT GTC CCT TTA TTA AGA AGT TTG ATA TAT TCT AAG CAT      335
Glu Asn Gly Ala Val Pro Leu Leu Arg Ser Leu Ile Tyr Ser Lys His
                    100                 105                 110

AAA ATG ATA TCT ATG GGA TCA AGT GCA GCT CTC AAA AAT TTG TTA AAT      383
Lys Met Ile Ser Met Gly Ser Ser Ala Ala Leu Lys Asn Leu Leu Asn
                115                 120                 125

GCA AAA CCT GAG TGC ATC AAT TTC TTA AGT GAT TCT TCT TCT AAA GGA      431
Ala Lys Pro Glu Cys Ile Asn Phe Leu Ser Asp Ser Ser Ser Lys Gly
            130                 135                 140
```

```
GTT  CCA  AAT  CTA  ACT  ACA  TTG  GGT  GTA  AGA  AAA  CAA  AAA  TCT  CTA  CAT       479
Val  Pro  Asn  Leu  Thr  Thr  Leu  Gly  Val  Arg  Lys  Gln  Lys  Ser  Leu  His
     145                      150                      155

GAG  TTA  ATA  GAT  CAA  AAT  CTT  TCA  GAA  ACT  TGT  GAT  AAT  ATA  GAT  AGT       527
Glu  Leu  Ile  Asp  Gln  Asn  Leu  Ser  Glu  Thr  Cys  Asp  Asn  Ile  Asp  Ser
160                      165                      170                      175

GTG  GCC  GCT  AA                                                                    538
Val  Ala  Ala
```

( 2 ) INFORMATION FOR SEQ ID NO:100:

( i ) SEQUENCE CHARACTERISTICS:
        ( A ) LENGTH: 178 amino acids
        ( B ) TYPE: amino acid
        ( D ) TOPOLOGY: linear ( i i ) MOLECULE TYPE: protein ( x i ) SEQUENCE DESCRIPTION: SEQ ID NO:100:

```
Asp  Ile  Cys  Ser  Val  Glu  Gly  Ala  Leu  Gly  Phe  Leu  Val  Glu  Met  Leu
1                   5                        10                      15

Lys  Tyr  Lys  Ala  Pro  Ser  Lys  Thr  Leu  Ala  Ile  Val  Glu  Asn  Ala  Gly
               20                       25                      30

Gly  Ile  Leu  Arg  Asn  Val  Ser  Ser  His  Ile  Ala  Leu  Arg  Glu  Asp  Tyr
          35                        40                       45

Arg  Glu  Ile  Leu  Arg  His  His  Asn  Cys  Leu  Thr  Ile  Leu  Leu  Gln  Gln
     50                        55                       60

Leu  Lys  Ser  Pro  Ser  Leu  Ile  Ile  Val  Ser  Asn  Ala  Cys  Gly  Thr  Leu
65                       70                       75                       80

Trp  Asn  Leu  Ser  Ala  Arg  Asn  Ser  Thr  Asp  Gln  Gln  Phe  Leu  Trp  Glu
                    85                       90                       95

Asn  Gly  Ala  Val  Pro  Leu  Leu  Arg  Ser  Leu  Ile  Tyr  Ser  Lys  His  Lys
                    100                      105                      110

Met  Ile  Ser  Met  Gly  Ser  Ser  Ala  Ala  Leu  Lys  Asn  Leu  Asn  Ala
          115                      120                      125

Lys  Pro  Glu  Cys  Ile  Asn  Phe  Leu  Ser  Asp  Ser  Ser  Lys  Gly  Val
     130                      135                      140

Pro  Asn  Leu  Thr  Thr  Leu  Gly  Val  Arg  Lys  Gln  Lys  Ser  Leu  His  Glu
145                      150                      155                      160

Leu  Ile  Asp  Gln  Asn  Leu  Ser  Glu  Thr  Cys  Asp  Asn  Ile  Asp  Ser  Val
                    165                      170                      175

Ala  Ala
```

( 2 ) INFORMATION FOR SEQ ID NO:101:

( i ) SEQUENCE CHARACTERISTICS:
        ( A ) LENGTH: 432 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..388

( x i ) SEQUENCE DESCRIPTION: SEQ ID NO:101:

```
GTT  CTT  CTT  AAA  CAG  TTG  GAC  TCT  GGA  TTG  TTA  CTT  GTT  ACA  GGT  CCC       48
Val  Leu  Leu  Lys  Gln  Leu  Asp  Ser  Gly  Leu  Leu  Leu  Val  Thr  Gly  Pro
1                   5                        10                      15
```

| | | | | | | | | | | | | | | | |
|---|---|---|---|---|---|---|---|---|---|---|---|---|---|---|---|
| TTC | TTA | ATC | AAT | GCA | TGC | CCA | TTG | CGT | CGC | ATT | TCC | CAA | AAC | TAT | GTC | 96
| Phe | Leu | Ile | Asn | Ala | Cys | Pro | Leu | Arg | Arg | Ile | Ser | Gln | Asn | Tyr | Val |
| | | 20 | | | | | 25 | | | | | 30 | | | |
| ATT | GCC | ACC | TCT | ACC | CGA | TTA | GAC | GTT | AGT | GGA | GTT | AAA | TTA | CCA | GAA | 144
| Ile | Ala | Thr | Ser | Thr | Arg | Leu | Asp | Val | Ser | Gly | Val | Lys | Leu | Pro | Glu |
| | | 35 | | | | | 40 | | | | | 45 | | | |
| CAC | ATC | AAT | GAT | GAT | TAT | TTC | AAA | AGG | CAA | AAG | AAC | AAG | CGT | GCA | AAG | 192
| His | Ile | Asn | Asp | Asp | Tyr | Phe | Lys | Arg | Gln | Lys | Asn | Lys | Arg | Ala | Lys |
| | 50 | | | | | 55 | | | | | 60 | | | | |
| AAA | GAG | GAA | GGT | GAT | ATT | TTT | GCT | GCC | AAG | AAA | GAG | GCT | TAT | AAA | CCA | 240
| Lys | Glu | Glu | Gly | Asp | Ile | Phe | Ala | Ala | Lys | Lys | Glu | Ala | Tyr | Lys | Pro |
| 65 | | | | | 70 | | | | | 75 | | | | | 80 |
| ACT | GAG | CAA | AGG | AAG | AAT | GAC | CAA | AAG | CTT | GTA | GAC | AAA | ATG | GTT | TTA | 288
| Thr | Glu | Gln | Arg | Lys | Asn | Asp | Gln | Lys | Leu | Val | Asp | Lys | Met | Val | Leu |
| | | | | 85 | | | | | 90 | | | | | 95 | |
| GGA | GTA | ATC | AAG | AAG | CAC | CCA | GAC | CAC | AAA | CTT | TTG | TAT | ACA | TAT | TTG | 336
| Gly | Val | Ile | Lys | Lys | His | Pro | Asp | His | Lys | Leu | Leu | Tyr | Thr | Tyr | Leu |
| | | | 100 | | | | | 105 | | | | | 110 | | |
| TCA | GCT | ATG | TTT | GGT | TTG | AAA | TCT | TCC | CAA | TAT | CCA | CAT | CGT | ATG | AAG | 384
| Ser | Ala | Met | Phe | Gly | Leu | Lys | Ser | Ser | Gln | Tyr | Pro | His | Arg | Met | Lys |
| | | 115 | | | | | 120 | | | | | 125 | | | |

TTC T  AAATACTATA TTCATAAAAT AAATTGAACT TCTCAAAAAA AAAA            432
Phe ( 2 ) INFORMATION FOR SEQ ID NO:102:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( x i ) SEQUENCE DESCRIPTION: SEQ ID NO:102:

| | | | | | | | | | | | | | | |
|---|---|---|---|---|---|---|---|---|---|---|---|---|---|---|
| Val | Leu | Leu | Lys | Gln | Leu | Asp | Ser | Gly | Leu | Leu | Leu | Val | Thr | Gly | Pro |
| 1 | | | | 5 | | | | | 10 | | | | | 15 | |
| Phe | Leu | Ile | Asn | Ala | Cys | Pro | Leu | Arg | Arg | Ile | Ser | Gln | Asn | Tyr | Val |
| | | | 20 | | | | | 25 | | | | | 30 | | |
| Ile | Ala | Thr | Ser | Thr | Arg | Leu | Asp | Val | Ser | Gly | Val | Lys | Leu | Pro | Glu |
| | | | 35 | | | | | 40 | | | | | 45 | | |
| His | Ile | Asn | Asp | Asp | Tyr | Phe | Lys | Arg | Gln | Lys | Asn | Lys | Arg | Ala | Lys |
| | 50 | | | | | 55 | | | | | 60 | | | | |
| Lys | Glu | Glu | Gly | Asp | Ile | Phe | Ala | Ala | Lys | Lys | Glu | Ala | Tyr | Lys | Pro |
| 65 | | | | | 70 | | | | | 75 | | | | | 80 |
| Thr | Glu | Gln | Arg | Lys | Asn | Asp | Gln | Lys | Leu | Val | Asp | Lys | Met | Val | Leu |
| | | | | 85 | | | | | 90 | | | | | 95 | |
| Gly | Val | Ile | Lys | Lys | His | Pro | Asp | His | Lys | Leu | Leu | Tyr | Thr | Tyr | Leu |
| | | | 100 | | | | | 105 | | | | | 110 | | |
| Ser | Ala | Met | Phe | Gly | Leu | Lys | Ser | Ser | Gln | Tyr | Pro | His | Arg | Met | Lys |
| | | 115 | | | | | 120 | | | | | 125 | | | |

Phe ( 2 ) INFORMATION FOR SEQ ID NO:103:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
  ( A ) NAME/KEY: misc_feature
  ( B ) LOCATION: 1..20
  ( D ) OTHER INFORMATION: /label=primer ( x i ) SEQUENCE DESCRIPTION: SEQ ID NO:103:

TGRTTTCCWA TRAARTCTTC                                                                                           20

( 2 ) INFORMATION FOR SEQ ID NO:104:

( i ) SEQUENCE CHARACTERISTICS:
    ( A ) LENGTH: 225 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:104:

GAATTCGGCA CGAGTGAAAT TCAATATTTT GTTTTACATT AAATTTTTCA AATTCGATAT        60

GAAATTTTTA CTGGCAATTT GCGTGTTGTG TGTTTTATTA AATCAAGTAT CTATGTCAAA       120

AATGGTCACT GAAAAGTGTA AGTCAGGTGG AAATAATCCA AGTACAGAAG AGGTGTCAAT       180

ACCATCTGGG AAGCTTACTA TTGAAGATTT TTGTATTGGA AATCA                      225

( 2 ) INFORMATION FOR SEQ ID NO:105:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..15
    ( D ) OTHER INFORMATION: /label=primer ( x i ) SEQUENCE DESCRIPTION: SEQ ID NO:105:

AATTCGGCAC GAGTG                                                                                                15

( 2 ) INFORMATION FOR SEQ ID NO:106:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..26
    ( D ) OTHER INFORMATION: /label=primer ( x i ) SEQUENCE DESCRIPTION: SEQ ID NO:106:

AGTGGATCCG TCAAAAATGG TCACTG                                                                                    26

( 2 ) INFORMATION FOR SEQ ID NO:107:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

```
( i x ) FEATURE:
        ( A ) NAME/KEY: misc_feature
        ( B ) LOCATION: 1..28
        ( D ) OTHER INFORMATION: /label=primer ( x i ) SEQUENCE DESCRIPTION: SEQ ID NO:107:

CCGGAATTCG  GTTATTCGCA  ATAACAGT                                                    2 8
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A formulation comprising at least one isolated ectoparasite saliva protein, wherein said ectoparasite saliva protein comprises at least a portion of an amino acid sequence, wherein said portion is encoded by a nucleic acid molecule that hybridizes under stringent hybridization conditions with a nucleic acid molecule that encodes a flea saliva protein present in a flea saliva extract selected from the group consisting of FS-1, FS-2 and FS-3 flea saliva extracts, wherein said formulation is substantially free of non-saliva ectoparasite proteins.

2. The formulation of claim 1, wherein said flea saliva protein is selected from the group consisting of fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), and fspN(O).

3. The formulation of claim 1, wherein said flea saliva protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:88, SEQ ID NO:90, SEQ ID NO:100, and SEQ ID NO:102.

4. The formulation of claim 1, wherein said ectoparasite is selected from the group consisting of fleas, flies, mosquitoes, ticks, mites, lice, spiders, ants and true bugs.

5. The formulation of claim 1, wherein said ectoparasite comprises a flea.

6. The formulation of claim 5, wherein said flea is of a species selected from the group consisting of *Ctenocephalides canis* and *Ctenocephalides felis*.

7. The formulation of claim 1, wherein said formulation comprises a flea saliva extract selected from the group consisting of FS-1 flea saliva extract, FS-2 flea saliva extract, FS-3 flea saliva extract and mixtures thereof.

8. The formulation of claim 1, wherein said formulation comprises at least a portion of at least one flea saliva protein selected from the group consisting of fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), and fspN(O).

9. The formulation of claim 1, wherein said ectoparasite saliva protein is selected from the group consisting of fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), fspN(O) and mixtures thereof.

10. The formulation of claim 1, wherein said formulation is produced by a process comprising:
  (a) collecting ectoparasite saliva products on a collection means within a saliva collection apparatus containing ectoparasites, said apparatus comprising:
    (i) a housing operatively connected to a chamber, said chamber having an ambient temperature warmer than said housing thereby forming a temperature differential between said housing and said chamber, said housing being capable of retaining ectoparasites; and
    (ii) an interface between said housing and said chamber, said interface comprising ((a)) a means capable of collecting at least a portion of saliva products deposited by ectoparasites retained in said apparatus and ((b)) a barrier means capable of substantially preventing contaminating material from contacting said collection means, wherein said temperature differential attracts ectoparasites retained in said housing to attempt to feed through said barrier means and collection means and, thereby, deposit saliva products on said collection means; and
  (b) extracting said products from said collection means to form said formulation.

11. The formulation of claim 10, wherein the ambient temperature in said chamber ranges from about 20° C. to about 45° C. and the ambient temperature in said housing ranges from about 5° C. to about 35° C.

12. The formulation of claim 10, wherein the relative humidity in said chamber ranges from about 50% relative humidity to about 100% relative humidity and the relative humidity in said housing ranges from about 40% relative humidity to about 60% relative humidity.

13. The formulation of claim 1, wherein said formulation is produced by a process comprising:
  (a) collecting ectoparasite saliva products on a collection means within a saliva collection apparatus containing ectoparasites, said apparatus comprising:

(i) a housing operatively connected to a chamber, said chamber having an ambient temperature warmer than said housing thereby forming a temperature differential between said housing and said chamber, said housing being capable of retaining ectoparasites; and (ii) an interface between said housing and said chamber, said interface comprising ((a)) a means capable of collecting at least a portion of saliva products deposited by ectoparasites retained in said apparatus and ((b)) a barrier means capable of substantially preventing contaminating material from contacting said collection means, wherein said temperature differential attracts ectoparasites retained in said housing to attempt to feed through said barrier means and collection means and, thereby, deposit saliva products on said collection means;

(b) extracting said products from said collection means with a solution to form an ectoparasite extract;

(c) fractionating said ectoparasite extract to obtain separated peak fractions; and (d) recovering at least one of said peak fractions substantially free of the remaining fractions to obtain said formulation.

14. The formulation of claim 13, wherein separated peak fractions obtained in step (c) comprise a fractionation profile as depicted in FIG. 2.

15. The formulation of claim 1, wherein said ectoparasite saliva protein is produced by a process comprising culturing a recombinant cell transformed with at least one nucleic acid molecule encoding at least one of said ectoparasite saliva proteins to produce said formulation.

16. The formulation of claim 1, wherein said formulation is used to identify animals susceptible to or having allergic dermatitis.

17. The formulation of claim 16, wherein said allergic dermatitis is selected from the group consisting of flea allergy dermatitis, mosquito allergy dermatitis and Culicoides allergy dermatitis.

18. A formulation comprising at least one isolated ectoparasite saliva protein, wherein said ectoparasite saliva protein comprises at least a portion of an amino acid sequence, wherein said portion is encoded by a nucleic acid molecule capable of hybridizing under stringent conditions with a nucleic acid molecule that encodes a flea saliva protein represented as a protein peak in FIG. 2, wherein said formulation is substantially free of non-saliva ectoparasite proteins.

19. The formulation of claim 18, wherein said formulation is substantially free of contaminating material.

20. The formulation of claim 19, wherein said contaminating material comprises material selected from the group consisting of blood proteins, fecal material, larval culture medium, and mixtures thereof.

21. The formulation of claim 18, wherein said peak is selected from the group consisting of peak A, peak B, peak C, peak D, peak E, peak F, peak G, peak H, peak I, peak J, peak K, peak L, peak M and peak N.

22. The formulation of claim 18, wherein said formulation is used to identify animals susceptible to or having allergic dermatitis.

23. A formulation comprising at least one isolated ectoparasite saliva product substantially free of contaminating material, said formulation being produced by a process comprising:

(a) collecting ectoparasite saliva products on a collection means within a saliva collection apparatus containing ectoparasites, said apparatus comprising:

(i) a housing operatively connected to a chamber, said chamber having an ambient temperature warmer than said housing thereby forming a temperature differential between said housing and said chamber, said housing being capable of retaining ectoparasites; and (ii) an interface between said housing and said chamber, said interface comprising ((a)) a means capable of collecting at least a portion of saliva products deposited by ectoparasites retained in said apparatus and ((b)) a barrier means capable of substantially preventing contaminating material from contacting said collection means, wherein said temperature differential attracts ectoparasites retained in said housing to attempt to feed through said barrier means and collection means and, thereby, deposit saliva products on said collection means; and (b) extracting said saliva products from said collection means to obtain said formulation.

24. The formulation of claim 23, wherein said ectoparasite comprises a flea.

25. The formulation of claim 23, wherein said formulation is selected from the group consisting of FS-1 flea saliva extract, FS-2 flea saliva extract, FS-3 flea saliva extract and mixtures thereof.

26. The formulation of claim 23, wherein said process further comprises fractionating said extracted saliva products produced in step (b) to obtain separated peak fractions of ectoparasite saliva proteins and recovering at least one of said peak fractions substantially free of the remaining fractions.

27. The formulation of claim 23, wherein said separated peak fractions comprise a fractionation profile as depicted in FIG. 2.

28. The formulation of claim 23, wherein said contaminating material comprises material selected from the group consisting of blood proteins, fecal material, larval culture medium and mixtures thereof.

29. The formulation of claim 23, wherein said formulation comprises less than about 50 percent of said contaminating material.

30. The formulation of claim 23, wherein said formulation comprises less than about 10 percent of said contaminating material.

31. The formulation of claim 23, wherein said formulation is used to identify animals susceptible to or having allergic dermatitis.

32. A therapeutic composition for treating allergic dermatitis comprising a formulation comprising at least one isolated ectoparasite saliva protein, wherein said ectoparasite saliva protein comprises at least a portion of an amino acid sequence, wherein said portion is encoded by a nucleic acid molecule that hybridizes under stringent hybridization conditions with a nucleic acid molecule that encodes a flea saliva protein present in a flea saliva extract selected from the group consisting of FS-1, FS-2 and FS-3 flea saliva extracts, wherein said formulation is substantially free of non-saliva ectoparasite proteins.

33. The composition of claim 32, wherein said allergic dermatitis is selected from the group consisting of flea allergy dermatitis, mosquito allergy dermatitis and Culicoides allergy dermatitis.

34. The composition of claim 32, wherein said allergic dermatitis comprises flea allergy dermatitis.

35. The composition of claim 32, wherein said formulation is selected from the group consisting of flea saliva extract FS-1, flea saliva extract FS-2, flea saliva extract FS-3 and mixtures thereof.

36. The composition of claim 32, wherein said formulation comprises at least a portion of at least one flea saliva protein selected from the group consisting of fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), and fspN(O).

37. The composition of claim 32, wherein said formulation comprises at least a portion of at least one flea saliva protein selected from the group consisting of fspE, fspF, fspG1, fspG2, fspG3, fspG4, fspH, fspI, fspJ1, fspJ2, fspK, fspL1, fspL2, fspM1, fspM2, fspN1, fspN2 and fspN3.

38. The composition of claim 32, wherein said formulation comprises at least a portion of at least one flea saliva protein selected from the group consisting of fspG1, fspG2, fspG3, fspG4, fspH, fspM1, fspM2, fspN1, fspN2 and fspN3.

39. The composition of claim 32, wherein said composition further comprises at least one component selected from the group consisting of an excipient, an adjuvant and a carrier.

40. The composition of claim 32, wherein said composition comprises a controlled release composition.

41. A formulation comprising at least one isolated ectoparasite saliva protein, wherein said ectoparasite saliva protein comprises at least a portion of an amino acid sequence, wherein said portion is encoded by a nucleic acid molecule that hybridizes under stringent hybridization conditions with a nucleic acid molecule that encodes a flea saliva protein present in a flea saliva extract selected from the group consisting of FS-1, FS-2 and FS-3 flea saliva extracts, wherein said formulation is produced by a process selected from the group consisting of: (a) culturing a recombinant cell transformed with at least one nucleic acid molecule encoding at least one of said ectoparasite saliva proteins to produce said formulation; and (b) a process comprising:

(i) collecting ectoparasite saliva products on a collection means within a saliva collection apparatus containing ectoparasites, said apparatus comprising:

((a)) a housing operatively connected to a chamber, said chamber having an ambient temperature warmer than said housing thereby forming a temperature differential between said housing and said chamber, said housing being capable of retaining ectoparasites; and ((b)) an interface between said housing and said chamber, said interface comprising ((i)) a means capable of collecting at least a portion of saliva products deposited by ectoparasites retained in said apparatus and ((ii)) a barrier means capable of substantially preventing contaminating material from contacting said collection means, wherein said temperature differential attracts ectoparasites retained in said housing to attempt to feed through said barrier means and collection means and, thereby, deposit saliva products on said collection means; and (ii) extracting said saliva products from said collection means to obtain said formulation.

* * * * *